(12) United States Patent
Loew et al.

(10) Patent No.: US 12,134,654 B2
(45) Date of Patent: Nov. 5, 2024

(54) MULTISPECIFIC MOLECULES AND USES THEREOF

(71) Applicant: MARENGO THERAPEUTICS, INC., Cambridge, MA (US)

(72) Inventors: Andreas Loew, Boston, MA (US); Brian Edward Vash, Cambridge, MA (US); Stephanie J. Maiocco, Arlington, MA (US)

(73) Assignee: MARENGO THERAPEUTICS, INC., Cambridge, MA (US)

( * ) Notice: Subject to any disclaimer, the term of this patent is extended or adjusted under 35 U.S.C. 154(b) by 391 days.

(21) Appl. No.: 16/605,936

(22) PCT Filed: Apr. 19, 2018

(86) PCT No.: PCT/US2018/028315
§ 371 (c)(1),
(2) Date: Oct. 17, 2019

(87) PCT Pub. No.: WO2018/195283
PCT Pub. Date: Oct. 25, 2018

(65) Prior Publication Data
US 2020/0071417 A1    Mar. 5, 2020

Related U.S. Application Data

(60) Provisional application No. 62/487,061, filed on Apr. 19, 2017.

(51) Int. Cl.
| | | |
|---|---|---|
| *A61K 39/395* | (2006.01) | |
| *A61P 35/00* | (2006.01) | |
| *C07K 5/00* | (2006.01) | |
| *C07K 16/28* | (2006.01) | |
| *C07K 16/30* | (2006.01) | |

(52) U.S. Cl.
CPC .......... *C07K 16/3061* (2013.01); *A61P 35/00* (2018.01); *C07K 16/2827* (2013.01); *C07K 16/2866* (2013.01); *C07K 16/2893* (2013.01); *C07K 16/2896* (2013.01); *C07K 2317/31* (2013.01); *C07K 2317/52* (2013.01); *C07K 2317/76* (2013.01)

(58) Field of Classification Search
CPC ............ C07K 16/3061; C07K 16/2827; C07K 16/2866; C07K 16/2893; C07K 16/2896; C07K 2317/31; C07K 2317/52; C07K 2317/76; C07K 16/28; A61P 35/00; A61K 2039/505; A61K 2039/507
See application file for complete search history.

(56) References Cited

U.S. PATENT DOCUMENTS

| | | |
|---|---|---|
| 4,816,567 A | 3/1989 | Cabilly et al. |
| 5,223,409 A | 6/1993 | Ladner et al. |
| 5,225,539 A | 7/1993 | Winter |
| 5,585,089 A | 12/1996 | Queen et al. |
| 5,624,821 A | 4/1997 | Winter et al. |
| 5,648,260 A | 7/1997 | Winter et al. |
| 5,693,761 A | 12/1997 | Queen et al. |
| 5,693,762 A | 12/1997 | Queen et al. |
| 5,731,116 A | 3/1998 | Matsuo et al. |
| 5,811,097 A | 9/1998 | Allison et al. |
| 6,312,689 B1 * | 11/2001 | LaRosa .................... A61P 31/12 424/143.1 |
| 7,476,724 B2 | 1/2009 | Dennis et al. |
| 7,501,121 B2 | 3/2009 | Tchistiakova et al. |
| 7,943,743 B2 | 5/2011 | Korman et al. |
| 8,008,449 B2 | 8/2011 | Korman et al. |
| 8,354,509 B2 | 1/2013 | Carven et al. |
| 8,552,156 B2 | 10/2013 | Takayanagi et al. |
| 8,609,089 B2 | 12/2013 | Langermann et al. |
| 9,068,002 B2 | 6/2015 | Prinz et al. |
| 9,522,196 B2 | 12/2016 | Matsuyama et al. |
| 2004/0009530 A1 | 1/2004 | Wilson et al. |
| 2005/0152898 A1 | 7/2005 | Carr et al. |
| 2010/0028330 A1 | 2/2010 | Collins et al. |
| 2011/0150892 A1 | 6/2011 | Thudium et al. |
| 2012/0039906 A1 | 2/2012 | Olive |
| 2012/0114649 A1 | 5/2012 | Langermann et al. |
| 2012/0258107 A1 | 10/2012 | Graversen et al. |
| 2013/0344070 A1 * | 12/2013 | Huang .................... A61P 35/02 530/387.3 |
| 2014/0044728 A1 | 2/2014 | Takayanagi et al. |

(Continued)

FOREIGN PATENT DOCUMENTS

| | | |
|---|---|---|
| EP | 0125023 A1 | 11/1984 |
| EP | 0171496 A2 | 2/1986 |

(Continued)

OTHER PUBLICATIONS

Xiang Zheng et al: "Redirecting tumor-associated macrophages to become tumoricidal effectors as a novel strategy for cancer therapy", Oncotarget, vol. 8, No. 29, Apr. 12, 2017, pp. 48436-48452,XP055482407, DOI: 10.18632/oncotarget.17061 (Year: 2017).*
Zheng (Oncotarget, 2017, vol. 8, (No. 29), pp. 48436-48452., published Apr. 12, 2017) (Year: 2017).*
Ryder (PLoS One. 2013;8(1):e54302. doi: 10.1371/journal.pone.0054302., published Jan. 23, 2013) (Year: 2013).*
Invivogen (Immunoglobulin G Review, InvivoGen, published 2011) (Year: 2011).*
Pradel (Mol Cancer Ther. Dec. 2016;15(12):3077-3086., published Aug. 31, 2016) (Year: 2016).*

(Continued)

*Primary Examiner* — Meera Natarajan
(74) *Attorney, Agent, or Firm* — Wilson Sonsini Goodrich & Rosati

(57) ABSTRACT

Multispecific molecules targeting tumor associated macrophages (TAMs) or myeloid derived suppressor cells (MDSCs) and methods of using the same, are disclosed.

12 Claims, 12 Drawing Sheets

Specification includes a Sequence Listing.

(56) References Cited

U.S. PATENT DOCUMENTS

| | | | |
|---|---|---|---|
| 2014/0363426 A1* | 12/2014 | Moore | C07K 16/00 435/69.6 |
| 2016/0060347 A1 | 3/2016 | Herrmann et al. | |
| 2016/0220669 A1 | 8/2016 | Hoves et al. | |
| 2016/0326254 A1 | 11/2016 | Wong et al. | |

FOREIGN PATENT DOCUMENTS

| | | |
|---|---|---|
| EP | 0173494 A2 | 3/1986 |
| EP | 0184187 A2 | 6/1986 |
| EP | 0388151 A1 | 9/1990 |
| EP | 0519596 A1 | 12/1992 |
| EP | 2581113 A1 | 4/2013 |
| EP | 3108897 A1 | 12/2016 |
| GB | 2188638 A | 10/1987 |
| JP | 2009532399 A | 9/2009 |
| JP | 2015527978 A | 9/2015 |
| WO | WO-8601533 A1 | 3/1986 |
| WO | WO-8702671 A1 | 5/1987 |
| WO | WO-9002809 A1 | 3/1990 |
| WO | WO-9100906 A1 | 1/1991 |
| WO | WO-9110741 A1 | 7/1991 |
| WO | WO-9117271 A1 | 11/1991 |
| WO | WO-9201047 A1 | 1/1992 |
| WO | WO-9203917 A1 | 3/1992 |
| WO | WO-9203918 A1 | 3/1992 |
| WO | WO-9209690 A2 | 6/1992 |
| WO | WO-9215679 A1 | 9/1992 |
| WO | WO-9218619 A1 | 10/1992 |
| WO | WO-9220791 A1 | 11/1992 |
| WO | WO-9301288 A1 | 1/1993 |
| WO | WO-9404678 A1 | 3/1994 |
| WO | 1997031949 A1 | 9/1997 |
| WO | WO-9856915 A2 | 12/1998 |
| WO | WO-9945110 A1 | 9/1999 |
| WO | WO-0034784 A1 | 6/2000 |
| WO | WO-0060070 A1 | 10/2000 |
| WO | 2001057226 A1 | 8/2001 |
| WO | WO-0164942 A1 | 9/2001 |
| WO | WO-0178653 A2 | 10/2001 |
| WO | WO-2006121168 A1 | 11/2006 |
| WO | 2007005874 A2 | 1/2007 |
| WO | 2009026303 A1 | 2/2009 |
| WO | WO-2009101611 A1 | 8/2009 |
| WO | WO-2009114335 A2 | 9/2009 |
| WO | 2010021697 A2 | 2/2010 |
| WO | WO-2010019570 A2 | 2/2010 |
| WO | WO-2010027827 A2 | 3/2010 |
| WO | 2010077634 A1 | 7/2010 |
| WO | 2011070024 A1 | 6/2011 |
| WO | WO-2011066342 A2 | 6/2011 |
| WO | 2011106528 A1 | 9/2011 |
| WO | 2011107553 A1 | 9/2011 |
| WO | WO-2011109789 A2 | 9/2011 |
| WO | 2011123381 A1 | 10/2011 |
| WO | 2011131407 A1 | 10/2011 |
| WO | WO-2011140249 A2 | 11/2011 |
| WO | WO-2011155607 A1 | 12/2011 |
| WO | 2013079174 A1 | 6/2013 |
| WO | 2013087699 A1 | 6/2013 |
| WO | 2013169264 A1 | 11/2013 |
| WO | 2013192596 A2 | 12/2013 |
| WO | WO-2014008218 A1 | 1/2014 |
| WO | 2014170317 A1 | 10/2014 |
| WO | WO-2015036511 A1 | 3/2015 |
| WO | WO-2015118175 A2 | 8/2015 |
| WO | WO-2015200089 A1 | 12/2015 |
| WO | WO-2016069727 A1 | 5/2016 |
| WO | 2016106180 A1 | 6/2016 |
| WO | WO-2016168149 A1 | 10/2016 |
| WO | 2016196612 A1 | 12/2016 |
| WO | 2016207312 A1 | 12/2016 |
| WO | WO-2017091429 A1 | 6/2017 |
| WO | 2017165464 A1 | 9/2017 |
| WO | WO-2018195283 A1 | 10/2018 |
| WO | WO-2019113464 A1 | 6/2019 |
| WO | WO-2020069372 A1 | 4/2020 |

OTHER PUBLICATIONS

Vidarsson (Front. Immunol. 5:520., published Oct. 20, 2014) (Year: 2014).*

Rudnick SI, Adams GP. Affinity and avidity in antibody-based tumor targeting. Cancer Biother Radiopharm. Apr. 2009;24(2):155-61. doi: 10.1089/cbr.2009.0627. PMID: 19409036; PMCID: PMC2902227. (Year: 2009).*

Young PA, Morrison SL, Timmerman JM. Antibody-cytokine fusion proteins for treatment of cancer: engineering cytokines for improved efficacy and safety. Semin Oncol. Oct. 2014;41(5):623-36. doi: 10.1053/j.seminoncol.2014.08.002. Epub Aug. 12, 2014. PMID: 25440607; PMCID: PMC4354941. (Year: 2014).*

Jarantow SW, Bushey BS, Pardinas JR, Boakye K, Lacy ER, Sanders R, Sepulveda MA, Moores SL, Chiu ML. Impact of Cell-surface Antigen Expression on Target Engagement and Function of an Epidermal Growth Factor Receptor × c-MET Bispecific Antibody. J Biol Chem. Oct. 9, 2015;290(41):24689-704. (Year: 2015).*

MacDonald KP et al., An antibody against the colony-stimulating factor 1 receptor depletes the resident subset of monocytes and tissue-and tumor-associated macrophages but does not inhibit inflammation. Blood. Nov. 11, 2010;116(19):3955-63. doi: 10.1182/blood-2010-02-266296. Epub Aug. 3, 2010. (Year: 2010).*

Abdel-Wahab et al., "Primary myelofibrosis: update on definition, pathogenesis, and treatment," Annu Rev Med (2009) vol. 60, pp. 233-245.

Agostinis et al., "Photodynamic therapy of cancer: an update," CA Cancer J Clin (2011) vol. 61 pp. 250-281.

Agrawal et al., "Experimental therapeutics for patients with myeloproliferative neoplasias," Cancer (2011) vol. 117, No. 4, pp. 662-676.

Brass et al., "Using mouse genomics to understand idiopathic interstitial fibrosis," Proc Am Thorac Soc (2007) vol. 4, pp. 92-100.

Green et al., "Comparative Pathology of Environmental Lung Disease: An Overview," Toxicologic Pathology (2007) vol. 35, pp. 136-147.

International Search Report and Written Opinion issued in International Application No. PCT/US2018/028315, mailed Jun. 28, 2018.

Liu et al., "The origin and function of tumor-associated macrophages," Cellular & Molecular Immunology (2015) vol. 12, four pages.

Mack et al., "Expression and Characterization of the Chemokine Receptors CCR2 and CCR5 in Mice," The Journal of Immunology (2001) vol. 166, pp. 4697-4704.

Noy et al. "Tumor-Associated Macrophages: From Mechanisms to Therapy" Immunity (2014) vol. 41, pp. 49-61.

Paramothayan et al., "Treatments for pulmonary sarcoidosis," Respir Med (2008) vol. 102 pp. 1-9.

Quatromoni et al., "Tumor-associated macrophages: function, phenotype, and link to prognosis in human lung cancer," Am J Transl Res (2012) vol. 4, No. 4, pp. 376-389.

Steele et al., "Genetic predisposition to respiratory diseases: infiltrative lung diseases," Respiration (2007) vol. 74, pp. 601-608.

Ugel et al., "Tumor-induced myeloid deviation: when myeloid-derived suppressor cells meet tumor-associated macrophages," J Clin Invest (2015) vol. 125, No. 9, pp. 3365-3376.

Varricchio et al., "Pathological interactions between hematopoietic stem cells and their niche revealed by mouse models of primary myelofibrosis," Expert Rev Hematol (2009) vol. 2, No. 3, pp. 315-334.

Zheng et al., "Redirecting tumor-associated macrophages to become tumoricidal effectors as a novel strategy for cancer therapy," Oncotarget (20217) vol. 8, No. 29, pp. 48436-48452.

"Abdel-Wahab, O.I. et al., "Primary Myelofibrosis: Update on Definition, Pathogens, and Treatment", Annu. Rev. Med, 2009, vol. 60, pp. 233-245".

Al-Lazikani, B. et al., "Standard Conformations for Canonical Structures of Immunoglobulins", J. Mol. Biol., 1997, vol. 273, pp. 927-948.

(56) References Cited

OTHER PUBLICATIONS

Altschul, S. et al, "Basic Local Alignment Search Tool", J. Mol Biol., 1990, vol. 215, pp. 403-410.

Altschul, S. et al., "Gapped BLAST and PSI-BLAST: a new generation of protein database search programs", Nucleic Acids Research, 1997, vol. 25, No. 17, pp. 3389-3402.

"Antoniou, K.M. et al., "Scleroderma lung disease: evolving understanding in light of newer studies", Curr Opin Rheumatol, 2008, vol. 20, No. 6, pp. 686-691".

Ayyar et al.: Coming-of-Age of Antibodies in Cancer Therapeutics. Trends Pharmacol Sci. 37(12):1009-1028 (2016).

Barbas, C.F. et al, "Assembly of combinatorial antibody libraries on phage surfaces: The gene III site", PNAS, 1991, vol. 88, pp. 7978-7982.

Beidler, C.B. et al., "Cloning and high level expression of a chimeric antibody with specificity for human carcinoembryonic antigen", J. Immuno, 1988, vol. 141, pp. 4053-4060.

Better, M. et al., "*Escherichia coli* Secretion of an Active Chimeric Antibody Fragment", Science, 1988, vol. 240, No. 4855, pp. 1041-1043.

Bird, R. et al., "Single-Chain Antigen-Binding Proteins", Science, 1988, vol. 242, No. 4877, pp. 423-426.

Bruggemann, M. et al., Designer Mice: The Production of Human Antibody Repertoires in Transgenic Animals, Terhorst C. Malavasi F, Albertini A (eds): Generation of Antibodies by Cell and Gene Immortalization, Year Immunol, 1993, vol. 7, pp. 33-40.

Bruggemann, M. et al., "Human antibody production in transgenic mice: expression from 100kb of the human IgH locus", Eur J. Immunol, 1991, vol. 21, pp. 1323-1326.

"Catane, R et al., "Pulmonary toxicity after radiation and bleomycin: a review", Int J Radiat Oncol Biol Phys, 1979, vol. 5, pp. 1513-1518".

Chothia, C. et al., "Canonical Structures for the Hypervariable Regions of Immunoglobulins", J. Mol. Biol, 1987, vol. 196, pp. 901-917.

Clackson, T. et al., "Making antibody fragments using phage display libraries", Nature, 1991, vol. 352, pp. 624-628.

Colcher, D. et al., "Single-Chain Antibodies in Pancreatic Cancer", Ann Ny Acad Sci, 1999, vol. 880, pp. 263-280.

Coloma, J. et al, "Design and production of novel tetravalent bispecific antibodies", Nature Biotech, 1997, vol. 15, pp. 159-163.

"Du Bois, R.M. et al., "Genetic factors in pulmonary fibrotic disorders", Semin Respir Crit Care Med, 2006, vol. 27, No. 6, pp. 581-588".

Eissler et al.: Regulation of myeloid cells by activated T cells determines the efficacy of PD-1 blockade. Oncoimmunology 5(12):e1232222 doi:10.1080/2162402X.2016.1232222 [1-12](2016).

Fuchs, P. et al., "Targeting Recombinant Antibodies to the surface of *Escherichia coli*: Fusion to the Peptidoglycan associated Lipoprotein", Nature Publishing Group, 1991, vol. 9, No. 12, pp. 1369-1372.

Garrard, L. et al., "FAB Assembly and Enrichment in a Monovalent Phage Display System", Nature Publishing Group, 1991, vol. 9, pp. 1373-1377.

Gotwals et al.: Prospects for combining targeted and conventional cancer therapy with immunotherapy. Nat Rev Cancer 17(5):286-301 (2017).

Gram, H. et al., In vitro selection and affinity maturation of antibodies from a naïve combinatorial immunoglobulin library, PNAS, 1992, vol. 89, pp. 3576-3580.

Green, L.L. et al, "Antigen-specific human monoclonal antibodies from mice engineered with human Ig heavy and light chain YACS", Nature Genet, 1994, vol. 7, pp. 13-21.

Griffiths, A.D. et al., "Human anti-self antibodies with high specificity from phage display libraries", The EMBO Journal, 1993, vol. 12, No. 2, pp. 725-734.

Hamid, O. et al., "Safety and Tumor Responses with Lambrolizumab (Anti-PD-1) in Melanoma", The New England Journal of Medicine, 2013, vol. 369, No. 2, pp. 134-144.

Hawkins, R. et al., "Selection of phage antibodies by binding affinity. Mimicking affinity maturation", J. Mol. Biol., 1992, vol. 226, No. 3, pp. 889-896.

Hay, B. et al., "Bacteriophage cloning and *Escherichia coli* expression of a human IgM Fab" Hum Antibodies Hybridomas, 1992, vol. 3, No. 2, pp. 81-85.

Hoogenboom, H.R. et al., "Multi-subunit proteins on the surface of filamentous phage: methodologies for displaying antibody (Fab) heavy and light chains", Nuc Acid Res, 1991, vol. 19, No. 15, pp. 4133-4137.

Huse, W. et al., "Generation of a large combinatorial library of the immunoglobulin repertoire in phage lambda" Science, 1989, vol. 246, No. 4935, pp. 1275-1281.

Huston, J. et al., "Protein engineering of antibody binding sites: Recovery of specific activity in an anti-digoxin single-chain Fv analogue produces in *Escherichia coli*", Proc Natl Acad Sci, 1988, vol. 85, pp. 5879-5883.

Jamieson T. et al., "Inhibition of CXCR2 profoundly suppresses inflammation-driven and spontaneous tumorigenesis", J Clin Invest, 2012, vol. 122, No. 9, pp. 3127-3144.

Japanese Patent Application No. 2019-556886 Office Action dated Feb. 14, 2022.

Japanese Patent Application No. 2019-556886 Office Action dated Nov. 4, 2022.

Jones, P. T. et al., "Replacing the complementarity-determining regions in a human antibody with those from a mouse", Nature, 1986, vol. 321, No. 29, pp. 522-525.

Leslie, K.O. et al., "Pulmonary Pathology of the Rheumatic Diseases", Semin Respir Crit Care Med, 2007, vol. 28, No. 4, pp. 369-378.

Li, P. et al., "Design and synthesis of paclitaxel conjugated with an ErbB2-recognizing peptide, EC-1", Biopolymers, 2007, vol. 87, No. 4, pp. 225-230.

Liu, A. et al., "Production of a mouse-human chimeric monoclonal antibody to CD20 with potent Fc-dependent biologic activity", J Immunol, 1987, vol. 139, No. 10, pp. 3521-3526.

Liu, A.Y. et al., "Chimeric mouse-human IgG1 antibody that can mediate lysis of cancer cells", PNAS, 1987, vol. 84, pp. 3439-3443.

Liu, D.Z. et al, "Synthesis of 2'-paclitaxel 2-glucopyranosyl succinate for specific targeted delivery to cancer cells", Bioorganic & Medicinal Chemistry Letters, 2007, vol. 17, pp. 617-620.

Lobuglio, A. et al., "Phase I Clinical Trial of CO17-1A Monoclonal Antibody", Hybridoma, 1986, vol. 5, No. 1, pp. S117-S123.

Lonberg, N. et al., "Antigen-specific human antibodies from mice comprising four distinct genetic modifications", Nature, 1994, vol. 368, pp. 856-859.

Manji et al.: Current and Emerging Therapies in Metastatic Pancreatic Cancer. Clin Cancer Res. 23(7):1670-1678 (2017).

Mao et al.: Targeting Suppressive Myeloid Cells Potentiates Checkpoint Inhibitors to Control Spontaneous Neuroblastoma. Clin Cancer Res. 22(15):3849-3859 (2016).

Martin, A. et al., "Chapter 3: Protein Sequence and Structure Analysis of Antibody Variable Domains", In: Antibody Engineering Lab Manual (Ed: Duebel, S. and Kontermann, R., Springer-Verlag, Heidelberg), 2010, vol. 2, pp. 33-51.

Martin, F. et al., "The affinity-selection of a minibody polypeptide inhibitor of human interleukin-6", EMBO J., 1994, vol. 13, No. 22, pp. 5303-5309.

McConnell, S.J. et al., "Tendamistat as a scaffold for conformationally constrained phage peptide libraries", J Mol Biol, 1995, vol. 250, No. 4, pp. 460-470.

Meyers, E. et al., "Optimal alignments in linear space", CABIOS, 1988, vol. 4, No. 1, pp. 11-17.

Morrison, Sherie L., "Transfectomas provide novel chimeric antibodies", Science, 1985, vol. 229, No. 4719, pp. 1202-1207.

Morrison, S.L. et al, "Chimeric human antibody molecules: Mouse antigen-binding domains with human constant region domains", Proc Natl Acad Sci, 1984, vol. 81, pp. 6851-6855.

Needleman, S. et al, "A General Method Applicable to the Search for Similarities in the Amino Acid Sequence of Two Proteins", J. Mol. Biol., 1970, vol. 48, pp. 444-453.

(56) References Cited

OTHER PUBLICATIONS

Ngambenjawong et al.: Progress in tumor-associated macrophage (TAM)-targeted therapeutics. Adv Drug Deliv Rev. 114:206-221 (2017).

Nishimura, Y. et al., "Recombinant Human-Mouse Chimeric Monoclonal Antibody Specific for Common Acute Lymphocytic Leukemia Antigen", Canc. Res, 1987, vol. 47, pp. 999-1005.

Oi, V. et al., "Chimeric Antibodies", BioTechniques, 1986, vol. 4, No. 3, pp. 214-221.

Pardoll, D.M., "The blockade of immune checkpoints in cancer immunotherapy", Nat Rev Cancer, 2012, Vo. 12, pp. 252-264.

PCT/US2018/064506 International Preliminary Report on Patentability dated Jun. 9, 2020.

PCT/US2018/064506 International Search Report and Written Opinion dated Mar. 6, 2019.

PCT/US2019/053544 International Preliminary Report on Patentability dated Mar. 23, 2021.

PCT/US2019/053544 International Search Report and Written Opinion dated Feb. 17, 2020.

Rakita, L. et al., "Amidarone pulmonary toxicity", Am Heart J., 1983, vol. 106, No. 4, pp. 906-916.

Ridgway, J. et al, Knobs-into holes engineering of antibody CH3 domains for heavy chain heterodimerization, Protein Engineering, 1996, vol. 9, No. 7. pp. 617-621.

Rosenberg, S. et al., "Use of Tumor-Infiltrating Lymphocytes and Interleukin-2 in the Immunotherapy of Patients with Metastatic Melanoma", New Eng J of Med, 1988, vol. 319, pp. 1676-1680.

Saleh, M.N. et al, "A phase II trial of murine monoclonal antibody 17-1A and interferon-γ: clinical and immunological data", Cancer Immunol Immunother, 1990, vol. 32, pp. 185-190.

Shaw, D. et al., "Mouse/human chimeric antibodies to a tumor-associated antigen: biologic activity of the four human IgG subclasses", Journal of the National Cancer Institute, 1988, vol. 80, No. 19. pp. 1553-1559.

Spiess, C. et al, "Alternative molecular formats and therapeutic applications for bispecific antibodies", Molecular Immunology, vol. 67, pp. 95-106.

Strohl: Current progress in innovative engineered antibodies. Protein Cell. 9(1):86-120 (2018).

Sun, L.K. et al., "Chimeric antibody with human constant regions and mouse variable regions directed against carcinoma-associated antigen 17-1A", PNAS, 1987, vol. 84, pp. 214-218.

Thorpe, P. E., "Vascular Targeting Agents as Cancer Therapeutics", Clinc Cancer Res, 2004, vol. 10, pp. 415-427.

Tramontano, A. et al., "The making of the minibody: An engineered β-protein for the display of conformationally constrained peptides", Journal of Molecular Recognition, 1994, vol. 7, pp. 9-24.

Tuaillon, N. et al, Human immunoglobulin heavy-chain minilocus recombination in transgenic mice: Gene-segment use in μ and γ transcripts, PNAS, 1993, vol. 90, pp. 3720-3724.

Twohig, K.J, et al., "Pulmonary effects of cytotoxic agents other than bleomycin", Clin Chest Med, 1990, vol. 11, No. 1, pp. 31-54.

Verhoeyen, M. et al., "Reshaping Human Antibodies: Grafting an Antilysozyme Activity", Science, 1988, vol. 239, pp. 1534-1536.

Weidel, U. et al, "The Intriguing Options of Mulitspecific Antibody Formats for Treatment of Cancer", Cancer Genomics & Proteomics, 2013, vol. 1, pp. 1-18.

Swigris, J.J. et al., "Pulmonary and Thrombotic Manifestations of Systemic Lupus Erythematosus*", Chest, 2008, vol. 133, No. 1, pp. 271-280.

Wood, C. R. et al., "The synthesis and in vivo assembly of functional antibodies in yeast", Nature Publishing Group, 1985, vol. 314, No. 4, pp. 446-449.

Zhu et al.: CSF1/CSF1R blockade reprograms tumor-infiltrating macrophages and improves response to T-cell checkpoint immunotherapy in pancreatic cancer models. Cancer Res. 74(18):5057-5069 (2014).

\* cited by examiner

SEQUENCE LISTING

```
<160> NUMBER OF SEQ ID NOS: 116

<210> SEQ ID NO 1
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 1
caggtccagc tgcaagagtc tggccctgga ctggttcagc cctctcagac cctgtctctg      60
acctgtaccg tgtccggctt ctccctgacc gacttctctg tgcactgggt ccgacagcct     120
ccaggcaaag gactggaatg gatgggcaga atcagatccg agggcaacac cgactacaac     180
agcgccctga gtcccggct gtctatcagc agagacacct ccaagagcca ggtgttcctg      240
aagatgaact ccctgcagac cgaggacacc gccatctatt tctgcaccag aggcgacatc     300
ctcggcttcg gctattgggg acagggcgtg atggtcaccg ttagctct                  348

<210> SEQ ID NO 2
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 2
gacatcgtga tgacccagtc tccactgtcc gtgtctgtga ccctggcga gtctgcctcc       60 atctcctgca gatcctccaa gagcctgctg cacttcaagg gcatcacctt cgtgtactgg     120
tatctgcaga agcccggcca gtctcctcag ctgctgatct tcagaatgtc cagcctggcc     180
```

```
tctggcgtgc cgatagatt ttctggctcc ggctccgaga cagacttcac cctgaagatc    240
tccagagtgg aagccgagga cgtgggcacc tactattgtg ccagctgct ggaaaacccc    300 tacacctttg gcgctggcac caagctggaa ctgaag                             336
```

<210> SEQ ID NO 3
<211> LENGTH: 294
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 3

```
gctcagacca ccgctcctag cgtgtaccct ttggctcctg gctgtggcga caccacctct    60
tctacagtga ccctgggctg tctggtcaag ggctactttc ctgagcctgt gaccgtgacc    120
tggaactctg gtgccctgtc ctccgacgtg cacacctttc cagctgtgct gcagtccggc    180
ctgtacaccc tgacatcctc cgtgacctct tccacctggc ctagccagac cgtgacatgc    240
aatgtggctc accctgcctc cagcaccaag gtggacaaga aggtggaacg gcgg          294
```

<210> SEQ ID NO 4
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 4

```
agagctgacg ctgccctac cgtgtctatc ttccctccat ccatggaaca gctgacctct    60
ggcggagcta ccgtcgtgtg cttcgtgaac aacttctacc ctcgggacat ctccgtgaag   120
tggaagatcg acggctctga gcagcgagat ggcgtgctgg attctgtgac cgaccaggac   180
tccaaggaca gcacctactc catgtctagc accctgagcc tgaccaaggt ggaatacgag   240
cggcacaacc tgtatacctg cgaggtggtg cacaagacct ccagctctcc cgtggtcaag   300
tccttcaacc ggaacgagtg c                                             321
```

<210> SEQ ID NO 5
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 5

```
caggtccagt tgcagcagtc tggcgctgag ctggtcaagc ctggatcctc cgtgaagatc    60
tcctgcaagg cctccggcta caccttcacc tccaacttca tgcactggat caagcagcag   120
cccggcaacg gcctggaatg gatcggatgg atctatcctg cgacggcga caccgagtac   180 aaccagaagt tcaacggcaa ggctaccctg accgccgaca gtcctcttc caccgcttac   240 atgcagctgt ccagcctgac ctctgaggac tccgccgtgt acttctgcgc cgtgaattat   300
ggcggctacg tgctggatgc ttggggccaa ggcgcttctg tgacagtgtc ctct         354
```

<210> SEQ ID NO 6
<211> LENGTH: 309

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 6
gccgagacaa ccgctcctag cgtttaccct ctggctcctg cacagccct gaagtccaac      60 tctatggtca ccctgggctg cctggtcaag ggctactttc ctgagcctgt gaccgtgacc    120
tggaactctg gtgctctgtc tagcggcgtg cacacctttc cagctgtgct gcagagcggc    180
ctgtacaccc tgacatctag cgtgaccgtg ccttccagca cctggtctag tcaggctgtg    240
acctgcaacg tggcccatcc tgcctcttct accaaggtgg acaagaaaat cgtgcccaga    300
gagtgcaac                                                            309

<210> SEQ ID NO 7
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 7
gagatcgtgc tgacccagtc tcctaccacc atggctgcta gccctggcga gaaagtgaca     60
attacctgcc gggcctcctc ctccaccaac tacatgtcct ggtatcagca gaagtccggc    120
gcctctccta agccttggat ctacgagaca tccaagctgg cctctggcgt gcccgataga    180
ttttccggct ctggctccgg cacctcctac agcttcacca tctccagcat ggaaacagag    240
gacgccgcca cctactactg ccaccagtgg tcatctaccc tctgaccctt tggcagcggc    300
accaagctgg aaatcaag                                                  318

<210> SEQ ID NO 8
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 8
agagctgacg ccgctcctac cgtgtctatc ttccctccat ccatggaaca gctgacctcc     60
ggcggagcta ccgtcgtgtg tttcgtgaac aacttctacc ctcgggacat ctccgtgaag    120
tggaagatcg acggctctga gcagcgagat ggcgtgctgg attctgtgac cgaccaggac    180
tccaaggaca gcacctactc catgtctagc accctgagcc tgaccaaggt ggaatacgag    240
cggcacaacc tgtatacctg cgaggtggtg cacaagacct ccagctctcc cgtggtcaag    300
tccttcaacc ggaacgagtg c                                              321

<210> SEQ ID NO 9
<211> LENGTH: 684
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 9

| | | | | | |
|---|---|---|---|---|---|
| accattaagc | cttgtcctcc | atgcaagtgc | cccgctccta | atctgctcgg | aggcccttcc | 60 |
| gtgttcatct | ttccacctaa | gatcaaggac | gtgctgatga | tctccctgtc | tcctatcgtg | 120 |
| acctgcgtgg | tggtggacgt | gtccgaggat | gatcctgacg | tgcagatcag | ttggttcgtg | 180 |
| aacaacgtgg | aagtgcacac | cgctcagacc | cagacacaca | gagaggacta | caactctacc | 240 |
| ctgagagtgg | tgtctgccct | gcctatccag | catcaggact | ggatgtccgg | caaagaattc | 300 |
| aagtgcaaag | tgaacaacaa | ggacctgcct | gctccaatcg | agcggaccat | ctctaagcct | 360 |
| aagggctctg | tcagggcccc | tcaggtgtac | gttctgcctc | cttgcgagga | agagatgacc | 420 |
| aagaaacaag | tgacactgtg | tgtgcatggtc | acagacttca | tgcccgagga | catctacgtg | 480 |
| gaatggacca | acaacggcaa | gaccgagctg | aactacaaga | acaccgagcc | tgtgctggac | 540 |
| tccgacggct | cctacttcat | gtactccaag | ctgcgcgtcg | agaagaagaa | ctgggtcgag | 600 |
| agaaactcct | actcctgctc | cgtggtgcac | gagggcctgc | acaatcacca | caccaccaag | 660 |
| tccttctctc | ggaccctgg | caag | | | | 684 |

<210> SEQ ID NO 10
<211> LENGTH: 684
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 10

| | | | | | |
|---|---|---|---|---|---|
| accatcaagc | cctgtcctcc | atgcaagtgc | cccgctccta | atctgctcgg | aggcccttcc | 60 |
| gtgttcatct | tcccacctaa | gatcaaggac | gtgctgatga | tctccctgtc | tcctatcgtg | 120 |
| acctgcgtgg | tggtggacgt | gtccgaggat | gatcctgacg | tgcagatcag | ttggttcgtg | 180 |
| aacaacgtgg | aagtgcacac | cgctcagacc | cagacacaca | gagaggacta | caacagcacc | 240 |
| ctgagagtgg | tgtctgccct | gccaatccag | caccaggatt | ggatgtccgg | caaagaattc | 300 |
| aagtgcaaag | tgaacaacaa | ggacctgcct | gctccaatcg | agcggaccat | ctctaagcct | 360 |
| aagggctctg | tgcgggctcc | ccaagtttgt | gttctgcctc | cacctgagga | agagatgacc | 420 |
| aagaaacaag | tgaccctgtc | ttgtgccgtg | accgacttca | tgcccgagga | catctacgtg | 480 |
| gaatggacca | acaatggcaa | gaccgagctg | aactacaaga | acaccgagcc | tgtgctggac | 540 |
| tccgacggct | cctacttcat | ggtgtctaag | ctgcgcgtcg | agaagaagaa | ctgggtcgag | 600 |
| agaaactcct | actcctgctc | cgtggtgcac | gagggcctgc | acaatcacca | caccaccaag | 660 |
| tccttctctc | ggaccctgg | caag | | | | 684 |

<210> SEQ ID NO 11
<211> LENGTH: 474
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 11

| | | | | | |
|---|---|---|---|---|---|
| gaggtgcagc | tggttgaatc | tggcggagga | ctggttaagc | ctggcggctc | tctgagactg | 60 |
| tcttgtgccg | cttctggctt | caccttctcc | gcctacgcca | tgaactgggt | ccgacaggct | 120 |
| cctggcaaag | gcctggaatg | ggtcggaaga | atccggacca | agaacaacaa | ctacgccacc | 180 |

| | |
|---|---|
| tactacgccg actccgtgaa ggaccggttc accatctctc gggacgactc caagaacacc | 240 |
| ctgtacctgc agatgaactc cctgaaaacc gaggacaccg ccgtgtacta ctgcaccacc | 300 |
| ttctacggca atggcgtgtg gggacagggc acactggtta ccgtttcttc cgcctccacc | 360 |
| aagggaccct ctgtgtttcc tctggctccc tccagcaagt ctacctctgg tggaacagct | 420 |
| gccctgggct gcctggtcaa ggattacttt cctgagcctg tgaccgtgtc ctgg | 474 |

<210> SEQ ID NO 12
<211> LENGTH: 309
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 12

| | |
|---|---|
| gcttctacca agggacccag cgtgttccct ctggctcctt ccagcaagtc tacctctggc | 60 |
| ggaacagctg ctctgggctg cctggtcaag gactactttc ctgagcctgt gaccgtgtct | 120 |
| tggaactctg gcgctctgac atccggcgtg cacacatttc cagctgtgct gcagtcctcc | 180 |
| ggcctgtact ctctgtcctc tgtcgtgacc gtgccttcca gctctctggg aacccagacc | 240 |
| tacatctgca atgtgaacca caagccttcc aacaccaagg tggacaagag agtggaaccc | 300 |
| aagtcctgc | 309 |

<210> SEQ ID NO 13
<211> LENGTH: 681
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 13

| | |
|---|---|
| gataagaccc acacatgtcc tccatgccct gccctgagc tgctgggcgg accttccgtg | 60 |
| ttcctgttcc ctccaaagcc caaggacacc ctgatgatca cccggacccc tgaagtgacc | 120 |
| tgcgtggtgg tggatgtgtc ccacgaggat cccgaagtga agttcaattg gtacgtggac | 180 |
| ggcgtggaag tgcacaacgc caagaccaag cccagagagg aacagtacaa cagcacctac | 240 |
| cgggtggtgt ccgtgctgac cgtgctgcat caggactggc tgaacggcaa agagtacaag | 300 |
| tgcaaggtgt ccaacaaggc cctgcctgcc cctatcgaga aaaccatcag caaggccaag | 360 |
| ggccagcccc gcgaacctca ggtgtacaca ctgcctccct gccgggaaga tgatgaccaag | 420 |
| aaccaggtgt ccctgtggtg cctggtcaag ggcttctacc cctccgatat cgccgtggaa | 480 |
| tgggagagca acggccagcc cgagaacaac tacaagacca cccctcccgt gctggacagc | 540 |
| gacggcagct ccttcctgta ctccaaactg accgtggaca gagccggtgtg gcagcagggc | 600 |
| aatgtgttca gctgtagcgt gatgcacgag gccctgcaca accactacac ccagaagtcc | 660 |
| ctgagcctgt ctcctggcaa a | 681 |

<210> SEQ ID NO 14
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 14

```
gacgtggtca tgacacagag ccctctgtct ctgcccgtga cattgggaca gcctgcctcc      60
atctcctgca gtcctctca gtccctgctg gactctgacg gcaagacctt cctgaactgg     120
ttccagcagc ggcctggcca gtctcctaga aggctgatct acctggtgtc caagctggat    180
tctggcgtgc ccgacagatt ctccggctct ggctctggca ccgacttcac cctgaagatc    240
tccagagtgg aagccgagga cgtgggcgtg tactactgtt ggcagggcac ccactttcca    300
tacaccttcg gccagggcac cagactggaa atcaag                              336
```

<210> SEQ ID NO 15
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 15

```
agaacagtgg ccgctccttc cgtgttcatc ttcccaccct ccgacgagca gctgaagtcc      60
ggcaccgctt ctgtcgtgtg cctgctcaac aacttctacc ctcgggaagc caaggtgcag    120
tggaaggtgg acaacgccct gcagtccggc aactcccagg aatccgtcac cgagcaggac    180
tccaaggaca gcacctactc cctgtcctcc accctgaccc tgtccaaggc cgactacgag    240
aagcacaagg tgtacgcctg cgaagtgacc caccagggcc tgagcagccc cgtgaccaag    300
tccttcaacc ggggcgagtg c                                              321
```

<210> SEQ ID NO 16
<211> LENGTH: 342
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 16

```
gaagtgcagc tggttcagtc tggcgccgaa gtgaagaaac tggcgcctc tgtgaaggtg       60 tcctgcaagg cttctggcta cacctttacc ggctaccaca tgcactgggt ccgacaggct    120
ccaggacaag gcttggaatg gatgggctgg atcaaccca actccggcgt gaccaaatac     180
gcccagaaat tccagggcag agtgaccatg accagagaca cctccatcaa caccgcctac    240
atggaactgt cccggctgag attcgacgac accgacgtgt actactgtgc caccggcggc    300
tttggctatt ggggagaggg aacactggtc accgtgtcct cc                        342
```

<210> SEQ ID NO 17
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 17

```
ctgcccgtgt tgacccagcc tcctagcgtt tccaagggcc tgagacagac cgccacactg      60
acctgtaccg gcaactctaa caacgtgggc aatcagggcg ctgcctggtt gcagcagcat    120
```

```
cagggacagc ctccaaagct gctgtcctac cggaaccaca acagacctag cggcgtgtcc     180
gagcggttca gcccttctag atctggcgac acctccagcc tgaccatcac tggactgcag     240
cctgaggacg aggccgacta ctattgtctg gcctgggaca gctccctgcg ggcctttgtt     300
tttggcaccg gcaccaagct gaccgtgctg                                      330

<210> SEQ ID NO 18
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 18
ggacaaccta aggccaatcc taccgtgaca ctgttccctc catcctccga ggaactgcag      60
gccaacaagg ctaccctcgt gtgcctgatc tccgactttt accctggcgc tgtgaccgtg     120
gcctggaagg ctgatggatc tcctgtgaag ctggcgtgg aaaccaccaa gccttccaag      180
cagtccaaca caaatacgc cgcctcctcc tacctgtctc tgaccctga acagtggaag       240 tcccaccggt cctacagctg ccaagtgacc catgagggct ccaccgtgga aaagaccgtg     300
gctcctaccg agtgctcc                                                   318

<210> SEQ ID NO 19
<211> LENGTH: 372
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 19
caggtgcagc tggttcagtc tggcgccgaa gtgaagaaac ctggcgcctc tgtgaaggtg      60
tcctgcaagg cttccggcta caccttctcc agctactaca tgcactgggt ccgacaggcc     120
cctggacaag gattggagtg gatgggcatc atcaacccct ctggcggcaa cacctcttac     180
gcccagaaat tccagggcag agtgaccatg accagagaca cctccaccag caccgtgtac     240
atggaactgt ccagcctgag atccgaggac accgccgtgt actactgtgc cagaggcgga     300
taccagctgc ctcacggtag agccagagcc ttcgatatgt ggggccaggg cacaatggtc     360
accgtgtcct ct                                                         372

<210> SEQ ID NO 20
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 20
gccatcagaa tgacccagtc tccactgagc ctgcctgtga cattgggcca gcctgcctct      60
atctcctgca cctcctctca gtctctggtg tacagagatg gcaccaccta cctgaactgg     120
ttccagcaga ggcctggcca gtctcctaga cggctgatct acaaggtgtc caacagagac     180
tctggcgtgc ccgacagatt caccggctct ggctctggcc ccacattcac cctgaccatc     240
```

```
tccagagtgg aagccgagga cgtgggcatc tactactgta tgcagggcac ccactggcct    300
ctgacctttg gccagggaac aaaggtggaa atcaag                              336
```

<210> SEQ ID NO 21
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 21

```
gaggtgcagc tggttgaatc tggcggagga ttggttcagc ctggcggctc tctgagactg     60
tcttgtgtgg cctctggctt caccttctcc gactactgga tgtcctgggt ccgacaggct    120
cctggcaaag gactggaatg ggtcgccaac atcaagaaag acggctccgt gaactactac    180
gtggactccg tgaagggcag attcaccatc tctcgggaca cgccaagaa ctccctgtac     240 ctgcagatga cagcctgag agccgaggac accgccgtgt actactgcac cagattcgat    300
tactggggcc agggcaccct ggtcacagtg tcctct                              336
```

<210> SEQ ID NO 22
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 22

```
caggctggct tgacccagcc tcctagcgtt tccaagggcc tgagacagac cgccacactg     60
acctgtaccg gcaactctaa caacgtgggc aatcagggcg ctgcctggtt gcagcagcat    120
cagggacatc ctccaaagct gctgttctac cggaacaaca acagagcctc cggcatctcc    180
gagcggctgt ctgcttctag atccggcaat accgccagcc tgaccatcac tggactgcag    240
cctgaggacg aggccgacta ctattgcctg acctgggact cctctctgtc cgtggtggtt    300
tttggcggag gcaccaagct gacagtgctg                                     330
```

<210> SEQ ID NO 23
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 23

```
caggtgcagc tggttcagtc tggcgccgaa gtgaagaaac ctggcgcctc tgtgaaggtg     60
tcctgcaagg cttccggcta caccttacc agctacgaca tctcctgggt ccgacaggct    120
cctggacaag gcttggaatg gatgggcgtg atctggaccg atggcggcac caattacgcc    180
cagaaactgc agggcagagt gaccatgacc accgacacct ctaccctccac cgcctacatg    240 gaactgcggt ccctgagatc tgacgacacc gccgtgtact actgcgccag agatcagcgg    300
ctgtacttcg atgtgtgggg ccagggcaca accgtgacag tgtcctct                 348
```

<210> SEQ ID NO 24
<211> LENGTH: 318

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 24
gacatccaga tgacccagtc tccatcctct ctgtccgcct ctgtgggcga cagagtgacc    60
atcacctgta gagcctccga ggacgtgaac acctacgtgt cctggtatca gcagaagccc   120
ggcaaggctc ccaagctgct gatctacgcc gcctctaaca gatacaccgg cgtgccctct   180
agattctccg gctctggctc tggcaccgac tttacccctg aatctccag cctgcagcct    240
gaggacttcg ccacctacta ctgccagcag tccttcagct accccacctt tggccagggc   300
accaagctgg aaatcaag                                                  318

<210> SEQ ID NO 25
<211> LENGTH: 681
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 25
gataagaccc acacctgtcc tccctgccct gcccctgaac tgctgggcgg acctagcgtg    60
ttcctgttcc ctccaaagcc caaggacacc ctgatgatca gccggacccc tgaagtgacc   120
tgcgtggtgg tggatgtgtc ccacgaggat cccgaagtga agttcaattg gtacgtggac   180
ggcgtggaag tgcacaacgc caagaccaag cccagagagg aacagtacaa cagcacctac   240
cgggtggtgt ccgtgctgac cgtgctgcac caggactggc tgaacggcaa agagtacaag   300
tgcaaggtgt ccaacaaggc cctgccagcc cctatcgaga aaaccatcag caaggccaag   360
ggccagccta gagagcctca ggtctgcacc ctgcctccca gccgggaaga gatgaccaag   420
aaccaggtgt ccctgagctg cgccgtgaag ggcttctacc cctccgatat cgccgtggaa   480
tgggagagca acggccagcc cgagaacaac tacaagacca cccctcccgt gctggacagc   540
gacggcagct tcttcctggt gtccaaactg accgtggaca gagccggtg gcagcagggc    600
aatgtgttca gctgtagcgt gatgcacgag gccctgcaca accactacac ccagaagtct   660
ctgagcctga gccctggcaa a                                              681

<210> SEQ ID NO 26
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 26
caggtgcagc tggttcagtc tggcgccgaa gtgaagaaac ctggctcctc cgtgaaggtg    60
tcctgcaagg cttctggcta cacctttacc gacaactaca tgatctgggt ccgacaggct   120
cctggacagg gacttgagtg gatgggcgac atcaaccctt acaacggcgg caccaccttc   180
aaccagaaat tcaagggcag agtgaccatc accgccgaca gtctacctc caccgcctac   240
atggaactgt ccagcctgag atctgaggac accgccgtgt actactgcgc cagagagtcc   300
```

```
ccttacttct ccaacctgta cgtgatggac tactggggcc agggcacact ggtcacagtg    360
tcctct                                                               366

<210> SEQ ID NO 27
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 27
gagatcgtgc tgacccagtc tcctgccaca ctgtcactgt ctccaggcga gagagctacc     60
ctgtcctgca aggcttctca gtccgtggac tacgacggcg acaactacat gaactggtat    120
cagcagaagc ccggccaggc tcctagactg ctgatctacg ccgcctccaa cctggaatct    180
ggcatccccg ctagattctc cggctctggc tctggcacag actttaccct gaccatctcc    240
agcctggaac ctgaggactt cgccgtgtac tactgccacc tgtccaacga ggacctgtcc    300
acatttggcg gaggcaccaa ggtggaaatc aag                                 333

<210> SEQ ID NO 28
<211> LENGTH: 1392
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 28
atggaaaccg acacactgct gctgtgggtg ctgctcttgt gggtgccagg atctacagga     60
caggtccagc tgcaagagtc tggccctgga ctggttcagc cctctcagac cctgtctctg    120
acctgtaccg tgtccggctt ctccctgacc gacttctctg tgcactgggt ccgacagcct    180
ccaggcaaag gactggaatg gatgggcaga atcagatccg agggcaacac cgactacaac    240
agcgccctga gtcccggct gtctatcagc agagacacct ccaagagcca ggtgttcctg    300
aagatgaact ccctgcagac cgaggacacc gccatctatt tctgcaccag aggcgacatc    360
ctcggcttcg ctattgggg acagggcgtg atggtcaccg ttagctctgc tcagaccacc    420
gctcctagcg tgtaccctt ggctcctggc tgtggcgaca ccacctcttc tacagtgacc    480
ctgggctgtc tggtcaaggg ctactttcct gagcctgtga ccgtgacctg aactctggt    540 gccctgtcct ccgacgtgca cacctttcca gctgtgctgc agtccggcct gtacaccctg    600
acatcctccg tgacctcttc cacctggcct agccagaccg tgacatgcaa tgtggctcac    660
cctgcctcca gcaccaaggt ggacaagaag gtggaacggc ggaccattaa gccttgtcct    720
ccatgcaagt gccccgctcc taatctgctc ggaggcccctt ccgtgttcat ctttccacct    780
aagatcaagg acgtgctgat gatctccctg tctcctatcg tgacctgcgt ggtggtggac    840
gtgtccgagg atgatcctga cgtgcagatc agttggttcg tgaacaacgt ggaagtgcac    900
accgctcaga cccagacaca cagagaggac tacaactcta ccctgagagt ggtgtctgcc    960
ctgcctatcc agcatcagga ctggatgtcc ggcaaagaat tcaagtgcaa agtgaacaac   1020
aaggacctgc ctgctccaat cgagcggacc atctctaagc ctaagggctc tgtcagggcc   1080
cctcaggtgt acgttctgcc tccttgcgag gaagagatga ccaagaaaca agtgacactg   1140
tggtgcatgg tcacagactt catgcccgag gacatctacg tggaatggac caacaacggc   1200
```

```
aagaccgagc tgaactacaa gaacaccgag cctgtgctgg actccgacgg ctcctacttc    1260
atgtactcca agctgcgcgt cgagaagaag aactgggtcg agagaaactc ctactcctgc    1320
tccgtggtgc acgagggcct gcacaatcac cacaccacca agtccttctc tcggacccct    1380
ggcaagtgat ga                                                        1392
```

```
<210> SEQ ID NO 29
<211> LENGTH: 723
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 29
```

```
atggaaaccg acacactgct gctgtgggtg ctgctcttgt gggtgccagg atctaccggc     60
gacatcgtga tgacccagtc tccactgtcc gtgtctgtga cccctggcga gtctgcctcc    120
atctcctgca gatcctccaa gagcctgctg cacttcaagg gcatcacctt cgtgtactgg    180
tatctgcaga agcccggcca gtctcctcag ctgctgatct tcagaatgtc cagcctggcc    240
tctggcgtgc ccgatagatt ttctggctcc ggctccgaga cagacttcac cctgaagatc    300
tccagagtgg aagccgagga cgtgggcacc tactattgtg ccagctgctg gaaaaacccc    360
tacacctttg gcgctggcac caagctggaa ctgaagagag ctgacgctgc ccctaccgtg    420
tctatcttcc ctccatccat ggaacagctg acctctggcg gagctaccgt cgtgtgcttc    480
gtgaacaact ctaccctcg ggacatctcc gtgaagtgga agatcgacgg ctctgagcag    540
cgagatggcg tgctggattc tgtgaccgac caggactcca aggacagcac ctactccatg    600
tctagcaccc tgagcctgac caaggtggaa tacgagcggc acaacctgta tacctgcgag    660
gtggtgcaca agacctccag ctctcccgtg gtcaagtcct tcaaccggaa cgagtgctga    720
tga                                                                  723
```

```
<210> SEQ ID NO 30
<211> LENGTH: 1413
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 30
```

```
atggaaaccg acacactgct gctgtgggtg ctgctcttgt gggtgccagg atctacagga     60
caggtccagt tgcagcagtc tggcgctgag ctggtcaagc ctggatcctc cgtgaagatc    120
tcctgcaagg cctccggcta caccttcacc tccaacttca tgcactggat caagcagcag    180
cccggcaacg gcctggaatg gatcggatgg atctatcctg cgacggcga caccgagtac    240 aaccagaagt tcaacggcaa ggctaccctg accgccgaca gtcctcttc caccgcttac    300 atgcagctgt ccagcctgac ctctgaggac tccgccgtgt acttctgcgc cgtgaattat    360
ggcggctacg tgctggatgc ttggggccaa ggcgcttctg tgacagtgtc ctctgccgag    420
acaaccgctc ctagcgttta ccctctggct cctggcacag ccctgaagtc caactctatg    480
gtcaccctgg gctgcctggt caagggctac tttcctgagc ctgtgaccgt gacctggaac    540
tctggtgctc tgtctagcgg cgtgcacacc tttccagctg tgctgcagag cggcctgtac    600
```

| | |
|---|---|
| accctgacat ctagcgtgac cgtgccttcc agcacctggt ctagtcaggc tgtgacctgc | 660 |
| aacgtggccc atcctgcctc ttctaccaag gtggacaaga aaatcgtgcc agagagtgc | 720 |
| aacaccatca agccctgtcc tccatgcaag tgccccgctc ctaatctgct cggaggccct | 780 |
| tccgtgttca tcttcccacc taagatcaag gacgtgctga tgatctccct gtctcctatc | 840 |
| gtgacctgcg tggtggtgga cgtgtccgag gatgatcctg acgtgcagat cagttggttc | 900 |
| gtgaacaacg tggaagtgca caccgctcag acccagacac acagagagga ctacaacagc | 960 |
| accctgagag tggtgtctgc cctgccaatc cagcaccagg attggatgtc cggcaaagaa | 1020 |
| ttcaagtgca aagtgaacaa caaggacctg cctgctccaa tcgagcggac catctctaag | 1080 |
| cctaagggct ctgtgcgggc tccccaagtt tgtgttctgc ctccacctga ggaagagatg | 1140 |
| accaagaaac aagtgaccct gtcttgtgcc gtgaccgact tcatgcccga ggacatctac | 1200 |
| gtggaatgga ccaacaatgg caagaccgag ctgaactaca agaacaccga gcctgtgctg | 1260 |
| gactccgacg gctcctactt catggtgtct aagctgcgcg tcgagaagaa gaactgggtc | 1320 |
| gagagaaact cctactcctg ctccgtggtg cacgagggcc tgcacaatca ccacaccacc | 1380 |
| aagtccttct ctcggacccc tggcaagtga tga | 1413 |

<210> SEQ ID NO 31
<211> LENGTH: 705
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 31

| | |
|---|---|
| atggaaaccg acacactgct gctgtgggtg ctgctcttgt gggtgccagg atctacaggc | 60 |
| gagatcgtgc tgacccagtc tcctaccacc atggctgcta gccctggcga gaaagtgaca | 120 |
| attacctgcc gggcctcctc ctccaccaac tacatgtcct ggtatcagca gaagtccggc | 180 |
| gcctctccta agccttggat ctacgagaca tccaagctgg cctctggcgt gcccgataga | 240 |
| ttttccggct ctggctccgg cacctcctac agcttcacca tctccagcat ggaaacagag | 300 |
| gacgccgcca cctactactg ccaccagtgg tcatctaccc ctctgacctt tggcagcggc | 360 |
| accaagctgg aaatcaagag agctgacgcc gctcctaccg tgtctatctt ccctccatcc | 420 |
| atggaacagc tgacctccgg cggagctacc gtcgtgtgtt tcgtgaacaa cttctaccct | 480 |
| cgggacatct ccgtgaagtg gaagatcgac ggctctgagc agcgagatgg cgtgctggat | 540 |
| tctgtgaccg accaggactc caaggacagc acctactcca tgtctagcac cctgagcctg | 600 |
| accaaggtgg aatacgagcg gcacaacctg tatacctgcg aggtggtgca caagacctcc | 660 |
| agctctcccg tggtcaagtc cttcaaccgg aacgagtgct gatga | 705 |

<210> SEQ ID NO 32
<211> LENGTH: 1407
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 32

| | |
|---|---|
| atggaaaccg acacactgct gctgtgggtg ctgctcttgt gggtgccagg atctacaggc | 60 |
| gaggtgcagc tggttgaatc tggcggagga ctggttaagc ctggcggctc tctgagactg | 120 |

```
tcttgtgccg cttctggctt caccttctcc gcctacgcca tgaactgggt ccgacaggct    180
cctggcaaag gcctggaatg ggtcggaaga atccggacca agaacaacaa ctacgccacc    240
tactacgccg actccgtgaa ggaccggttc accatctctc gggacgactc caagaacacc    300
ctgtacctgc agatgaactc cctgaaaacc gaggacaccg ccgtgtacta ctgcaccacc    360
ttctacggca atggcgtgtg gggacagggc acactggtta ccgtttcttc cgcctccacc    420
aagggacccc tgtgtttcc tctggctccc tccagcaagt ctacctctgg tggaacagct    480
gccctgggct gcctggtcaa ggattacttt cctgagcctg tgaccgtgtc ctggaactct    540
ggcgctctga catctggcgt gcacaccttt ccagctgtgc tgcagtcctc tggcctgtac    600
tctctgtcct ccgtcgtgac cgtgccttct agctctctgg cacccagac ctacatctgc    660 aatgtgaacc acaagccttc caacaccaag gtggacaaga gagtggaacc caagtcctgc    720
gacaagaccc acacctgtcc tccatgtcct gctccagaac tgctcggcgg accttccgtg    780
ttcctgtttc ctccaaagcc taaggacacc ctgatgatct ctcggacccc tgaagtgacc    840
tgcgtggtgg tggatgtgtc tcacgaggat cccgaagtga agttcaattg gtacgtggac    900
ggcgtggaag tgcacaacgc caagaccaag cctagagagg aacagtacaa ctccacctac    960
agagtggtgt ccgtgctgac cgtgctgcac caggattggc tgaacggcaa agagtacaag   1020
tgcaaggtgt ccaacaaggc cctgcctgct cctatcgaaa agaccatctc caaggccaag   1080
ggccagccta gggaaccca ggtttacacc ctgcctccat gccgggaaga tgaccaag     1140 aatcaggtgt ccctgtggtg cctcgtgaag ggcttctacc cttccgatat cgccgtggaa   1200
tgggagagca atggccagcc tgagaacaac tacaagacaa cccctcctgt gctggactcc   1260
gacggctcat tcttcctgta ctccaagctg acagtggaca gtccagatg gcagcagggc   1320 aacgtgttct cctgctccgt gatgcacgag gccctgcaca atcactacac ccagaagtcc   1380
ctgtctctgt cccctggcaa gtgatga                                       1407
```

<210> SEQ ID NO 33
<211> LENGTH: 723
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 33

```
atggaaaccg acacactgct gctgtgggtg ctgctcttgt gggtgccagg atctacaggc     60
gacgtggtca tgacacagag ccctctgtct ctgcccgtga cattgggaca gcctgcctcc    120
atctcctgca gtcctctca gtccctgctg gactctgacg gcaagacctt cctgaactgg    180
ttccagcagc ggcctggcca gtctcctaga aggctgatct acctggtgtc caagctggat    240
tctggcgtgc ccgacagatt ctccggctct ggctctggca ccgacttcac cctgaagatc    300
tccagagtgg aagccgagga cgtgggcgtg tactactgtt ggcagggcac ccactttcca    360
tacaccttcg gccagggcac cagactggaa atcaagagaa ccgtggccgc tccttccgtg    420
ttcatcttcc caccttccga cgagcagctg aagtccggca gcttctgt cgtgtgcctg    480 ctgaacaact tctaccctcg ggaagccaag gtgcagtgga aggtggacaa tgccctgcag    540
tccggcaact cccaagagtc tgtgaccgag caggactcca aggacagcac ctacagcctg    600
tccagcacac tgaccctgtc caaggccgac tacgagaagc acaaggtgta cgcctgcgaa    660
```

| | |
|---|---|
| gtgacccatc agggcctgtc tagccctgtg accaagtctt tcaaccgggg cgagtgctga | 720 |
| tga | 723 |

<210> SEQ ID NO 34
<211> LENGTH: 1398
<212> TYPE: DNA
<213> ORGANISM: Artificial Sequence
<220> FEATURE:
<221> NAME/KEY: source
<223> OTHER INFORMATION: /note="Description of Artificial Sequence:
        Synthetic polynucleotide"

<400> SEQUENCE: 34

| | |
|---|---|
| atggaaaccg acacactgct gctgtgggtg ctgctcttgt gggtgccagg atctacaggc | 60 |
| gaagtgcagc tggttcagtc tggcgccgaa gtgaagaaac tggcgcctc tgtgaaggtg | 120 |
| tcctgcaagg cttctggcta cacctttacc ggctaccaca tgcactgggt ccgacaggct | 180 |
| ccaggacaag gcttggaatg gatgggctgg atcaacccca actccggcgt gaccaaatac | 240 |
| gcccagaaat tccagggcag agtgaccatg accagagaca cctccatcaa caccgcctac | 300 |
| atggaactgt cccggctgag attcgacgac accgacgtgt actactgtgc caccggcggc | 360 |
| tttggctatt ggggagaggg aacactggtc accgtgtcct ccgcttctac caagggaccc | 420 |
| tccgtgtttc ctctggctcc ttccagcaag tctacctccg gtgaacagc tgctctgggc | 480 |
| tgcctggtca aggactactt tcctgagcct gtgaccgtgt cttggaactc tggcgctctg | 540 |
| acatccggcg tgcacacctt ccagctgtg ctgcaatcct ccggcctgta ctctctgtcc | 600 |
| tccgtcgtga ccgtgccttc tagctctctg ggcacccaga cctacatctg caatgtgaac | 660 |
| cacaagcctt ccaacaccaa ggtggacaag agagtggaac ccaagtcctg cgacaagacc | 720 |
| cacacctgtc ctccatgtcc tgctccagaa ctgctcggcg gaccttctgt gttcctgttt | 780 |
| cctccaaagc ctaaggacac cctgatgatc tctcggaccc ctgaagtgac ctgcgtggtg | 840 |
| gtggatgtgt ctcacgagga cccagaagtg aagttcaatt ggtacgtgga cggcgtggaa | 900 |
| gtgcacaacg ccaagaccaa gcctagagag gaacagtaca actccaccta cagagtggtg | 960 |
| tccgtgctga ccgtgctgca ccaggattgg ctgaacggca agagtacaa gtgcaaggtg | 1020 |
| tccaacaagg ccctgcctgc tcctatcgaa aagaccatct ccaaggccaa gggccagcct | 1080 |
| agggaacccc aggtttacac cctgcctcca tgccgggaag atgaccaa gaaccaggtg | 1140 |
| tccctgtggt gcctcgtgaa gggcttctac ccttccgata tcgccgtgga atgggagagc | 1200 |
| aatggccagc ctgagaacaa ctacaagaca cccctcctg tgctggactc cgacggctca | 1260 |
| ttcttcctgt actccaagct gacagtggac aagtccagat ggcagcaggg caacgtgttc | 1320 |
| tcctgctccg tgatgcacga ggccctgcac aatcactaca cacagaagtc cctgtctctg | 1380 |
| tcccctggca agtgatga | 1398 |

<210> SEQ ID NO 35
<211> LENGTH: 714
<212> TYPE: DNA
<213> ORGANISM: Artificial Sequence
<220> FEATURE:
<221> NAME/KEY: source
<223> OTHER INFORMATION: /note="Description of Artificial Sequence:
        Synthetic polynucleotide"

<400> SEQUENCE: 35

| | |
|---|---|
| atggaaaccg acacactgct gctgtgggtg ctgctcttgt gggtgccagg atctacagga | 60 |
| ctgcccgtgt tgacccagcc tcctagcgtt tccaagggcc tgagacagac cgccacactg | 120 |

| | |
|---|---|
| acctgtaccg gcaactctaa caacgtgggc aatcagggcg ctgcctggtt gcagcagcat | 180 |
| cagggacagc ctccaaagct gctgtcctac cggaaccaca acagacctag cggcgtgtcc | 240 |
| gagcggttca gcccttctag atctggcgac acctccagcc tgaccatcac tggactgcag | 300 |
| cctgaggacg aggccgacta ctattgtctg gcctgggaca gctccctgcg ggcctttgtt | 360 |
| tttggcaccg gcaccaagct gaccgtgctg gacaaccta aggccaatcc taccgtgaca | 420 |
| ctgttccctc catcctccga ggaactgcag gccaacaagg ctaccctcgt gtgcctgatc | 480 |
| tccgactttt accctggcgc tgtgaccgtg gcctggaagg ctgatggatc tcctgtgaag | 540 |
| gctggcgtgg aaaccaccaa gccttccaag cagtccaaca caaatacgc cgcctcctcc | 600 |
| tacctgtctc tgacccctga acagtggaag tcccaccggt cctacagctg ccaagtgacc | 660 |
| catgagggct ccaccgtgga aaagaccgtg gctcctaccg agtgctcctg atga | 714 |

<210> SEQ ID NO 36
<211> LENGTH: 1428
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 36

| | |
|---|---|
| atggaaaccg acacactgct gctgtgggtg ctgctcttgt gggtgccagg atctacagga | 60 |
| caggtgcagc tggttcagtc tggcgccgaa gtgaagaaac ctggcgcctc tgtgaaggtg | 120 |
| tcctgcaagg cttccggcta caccttctcc agctactaca tgcactgggt ccgacaggcc | 180 |
| cctggacaag gattggagtg gatgggcatc atcaacccct ctggcggcaa cacctcttac | 240 |
| gcccagaaat tccagggcag agtgaccatg accagagaca cctccaccag caccgtgtac | 300 |
| atggaactgt ccagcctgag atccgaggac accgccgtgt actactgtgc cagaggcgga | 360 |
| taccagctgc ctcacggtag agccagagcc ttcgatatgt ggggccaggg cacaatggtc | 420 |
| accgtgtcct ctgcttccac caagggaccc tctgtgttcc ctctggctcc ttccagcaag | 480 |
| tccacatccg gtgaacagc tgctctgggc tgcctggtca aggactactt cctgagcct | 540 |
| gtgaccgtgt cttggaactc tggcgctctg acatccggcg tgcacacatt tccagctgtg | 600 |
| ctgcagtcct ccggcctgta ctctctgtcc tctgtcgtga ccgtgccttc cagctctctg | 660 |
| ggaacccaga cctacatctg caatgtgaac cacaagcctt ccaacaccaa ggtggacaag | 720 |
| agagtggaac ccaagtcctg cgacaagacc cacacctgtc caccatgtcc tgctccagaa | 780 |
| ctgctcggcg gaccttccgt gttcctgttt cctccaaagc ctaaggacac cctgatgatc | 840 |
| tctcggaccc ctgaagtgac ctgcgtggtg gtggatgtgt cccacgagga cccagaagtg | 900 |
| aagttcaatt ggtacgtgga cggcgtggaa gtgcacaacg ccaagaccaa gcctagagag | 960 |
| gaacagtaca actccaccta cagagtggtg tccgtgctga ccgtgctgca ccaggattgg | 1020 |
| ctgaacggca agagtacaa gtgcaaggtg tccaacaagg ccctgcctgc tcctatcgaa | 1080 |
| aagaccatct ccaaggccaa gggccagcct agggaacccc aggtttacac cctgcctcca | 1140 |
| tgccgggaag agatgaccaa gaaccaggtg tccctgtggt gctcgtgaa gggcttctac | 1200 |
| ccttccgata tcgccgtgga atgggagagc aatggccagc cagagaacaa ctacaagaca | 1260 |
| acccctcctg tgctggactc cgacggctca ttcttcctgt actccaagct gacagtggac | 1320 |
| aagtccagat ggcagcaggg caacgtgttc tcctgctccg tgatgcacga ggccctgcac | 1380 | aatcactaca cacagaagtc cctgtctctg tccctggca agtgatga            1428

<210> SEQ ID NO 37
<211> LENGTH: 723
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 37

```
atggaaaccg acacactgct gctgtgggtg ctgctcttgt gggtgccagg atctaccggc      60
gccatcagaa tgacccagtc tccactgagc ctgcctgtga cattgggcca gcctgcctct     120
atctcctgca cctcctctca gtctctggta tacagagatg gcaccaccta cctgaactgg     180
ttccagcaga ggcctggcca gtctcctaga cggctgatct acaaggtgtc aacagagac     240
tctggcgtgc ccgacagatt caccggctct ggctctggca ccacattcac cctgaccatc     300
tccagagtgg aagccgagga cgtggcatc tactactgta gcagggcac ccactggcct      360
ctgacctttg gcagggaac aaaggtggaa atcaagcgga ccgtggccgc tccttccgtg     420
ttcatcttcc caccttccga cgagcagctg aagtctggca gcctctgt cgtgtgcctg      480
ctgaacaact tctaccctcg ggaagccaag gtgcagtgga aggtggacaa tgccctgcag     540
tccggcaact cccaagagtc tgtgaccgag caggactcca aggacagcac ctacagcctg     600
tcctccacac tgaccctgtc caaggccgac tacgagaagc acaaggtgta cgcctgcgaa     660
gtgacccatc agggcctgtc tagccctgtg accaagtctt tcaaccgggg cgagtgctga     720
tga                                                                   723
```

<210> SEQ ID NO 38
<211> LENGTH: 1392
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 38

```
atggaaaccg acacactgct gctgtgggtg ctgctcttgt gggtgccagg atctacaggc      60
gaggtgcagc tggttgaatc tggcggagga ttggttcagc ctggcggctc tctgagactg     120
tcttgtgtgg cctctggctt caccttctcc gactactgga tgtcctgggt ccgacaggct     180
cctggcaaag gactggaatg ggtcgccaac atcaagaaag acggctccgt gaactactac     240
gtggactccg tgaagggcag attcaccatc tctcgggaca cgccaagaa ctccctgtac     300
ctgcagatga acagcctgag agccgaggac accgccgtgt actactgcac cagattcgat     360
tactggggcc agggcaccct ggtcacagtg tcctctgctt ctaccaaggg accagcgtg      420
ttccctctgg ctccttccag caagtctacc tctggcggaa cagctgctct gggctgcctg     480
gtcaaggact actttcctga gcctgtgacc gtgtcctgga ctctggcgc tctgacatct      540
ggcgtgcaca ccttttccagc tgtgctgcag tcctccggcc tgtactctct gtcctctgtc     600
gtgaccgtgc cttccagctc tctgggaacc cagacctaca tctgcaatgt gaaccacaag     660
ccttccaaca ccaaggtgga caagagagtg gaacccaagt cctgcgacaa gacccacacc     720
tgtcctccat gtcctgctcc agaactgctc ggcggacctt ccgtgttcct gtttcctcca     780
aagcctaagg acaccctgat gatctctcgg accctgaag tgacctgcgt ggtggtggat     840
```

```
gtgtctcacg aggatcccga agtgaagttc aattggtacg tggacggcgt ggaagtgcac    900
aatgccaaga ccaagcctag agaggaacag tacaactcca cctacagagt ggtgtccgtg    960
ctgaccgtgc tgcaccagga ttggctgaac ggcaaagagt acaagtgcaa ggtgtccaac   1020
aaggccctgc ctgctcctat cgaaaagacc atctccaagg ccaagggcca gcctagggaa   1080
ccccaggttt acaccctgcc tccatgccgg gaagagatga ccaagaacca ggtgtccctg   1140
tggtgcctgg ttaagggctt ctaccccctcc gatatcgccg tggaatggga gtctaatggc   1200
cagccagaga caactacaa gacaaccccct cctgtgctgg actccgacgg ctcattcttc   1260
ctgtactcca agctgacagt ggacaagtcc agatggcagc agggcaacgt gttctcctgc   1320
tccgtgatgc acgaggccct gcacaatcac tacacccaga gtccctgtc tctgtccct   1380 ggcaagtgat ga                                                       1392
```

<210> SEQ ID NO 39
<211> LENGTH: 714
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 39

```
atggaaaccg acacactgct gctgtgggtg ctgctcttgt gggtgccagg atctacagga     60
caggctggct tgacccagcc tcctagcgtt tccaagggcc tgagacagac cgccacactg    120
acctgtaccg gcaactctaa caacgtgggc aatcagggcg ctgcctggtt gcagcagcat    180
cagggacatc ctccaaagct gctgttctac cggaacaaca acagagcctc cggcatctcc    240
gagcggctgt ctgcttctag atccggcaat accgccagct gaccatcac tggactgcag    300 cctgaggacg aggccgacta ctattgcctg acctgggact cctctctgtc cgtggtggtt    360
tttggcggag gcaccaagct gacagtgctg gacagcctta aggccaatcc taccgtgaca    420
ctgttccctc catcctccga ggaactgcag gccaacaagg ctaccctcgt gtgcctgatc    480
tccgactttt accctggcgc tgtgaccgtg gcctggaagc tgatggatc tcctgtgaag    540 gctggcgtgg aaaccaccaa gccttccaag cagtccaaca caaatacgc cgcctcctcc    600 tacctgtctc tgaccctga acagtggaag tcccaccggt cctacagctg ccaagtgacc    660
catgagggct ccaccgtgga aaagaccgtg gctcctaccg agtgctcctg atga         714
```

<210> SEQ ID NO 40
<211> LENGTH: 1404
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 40

```
atggaaaccg acacactgct gctgtgggtg ctgctcttgt gggtgccagg atctacagga     60
caggtgcagc tggttcagtc tggcgccgaa gtgaagaaac tggcgcctc tgtgaaggtg    120 tcctgcaagg cttccggcta cacctttacc agctacgaca tctcctgggt ccgacaggct    180
cctggacaag gcttggaatg gatgggcgta atctggaccg atggcggcac caattacgcc    240
cagaaactgc agggcagagt gaccatgacc accgacacct ctacctccac cgcctacatg    300
```

```
gaactgcggt ccctgagatc tgacgacacc gccgtgtact actgcgccag agatcagcgg      360
ctgtacttcg atgtgtgggg ccagggcaca accgtgacag tgtcctctgc ttccaccaag      420
ggacccagcg tttccctct ggctccatcc tccaagtcta cctctggcgg aacagctgct      480
ctgggctgcc tggtcaagga ctactttcct gagcctgtga ccgtgtcctg gaactctggc     540
gctctgacat ctggcgtgca cacattccct gctgtgctgc agtcctccgg cctgtactct     600
ctgtcctctg tggttaccgt gccttcctct agcctgggca cccagaccta catctgcaat     660
gtgaaccaca agccttccaa caccaaggtg gacaagagag tggaacccaa gtcctgcgac     720
aagacccaca cctgtccacc atgtcctgct ccagaactgc tcggcggacc ttccgtgttc     780
ctgtttcctc caaagcctaa ggacaccctg atgatctctc ggaccctga agtgacctgc      840 gtggtggtgg atgtgtctca cgaggaccca gaagtgaagt tcaattggta cgtggacggc     900
gtggaagtgc acaacgccaa gaccaagcct agagaggaac agtacaactc cacctacaga     960
gtggtgtccg tgctgaccgt gctgcaccag gattggctga acggcaaaga gtacaagtgc    1020
aaggtgtcca caaggccct gcctgctcct atcgaaaaga ccatctccaa ggccaagggc     1080
cagcctcggg aacctcaagt ctgtaccctg cctcctagcc gggaagagat gaccaagaac    1140
caggtgtccc tgagctgcgc cgtgaagggc ttctaccctt ctgatatcgc cgtggaatgg    1200
gagagcaacg gccagcctga gaacaactac aagacaaccc ctcctgtgct ggactccgac    1260
ggctcattct cctggtgtc caagctgaca gtggacaagt ccagatggca gcagggcaac    1320
gtgttctcct gctccgtgat gcacgaggcc ctgcacaatc actacacaca gaagtccctg    1380
tctctgtccc ctggcaagtg atga                                             1404
```

<210> SEQ ID NO 41  
<211> LENGTH: 705  
<212> TYPE: DNA  
<213> ORGANISM: Artificial Sequence  
<220> FEATURE:  
<221> NAME/KEY: source  
<223> OTHER INFORMATION: /note="Description of Artificial Sequence: Synthetic polynucleotide"

<400> SEQUENCE: 41

```
atggaaaccg acacactgct gctgtgggtg ctgctcttgt gggtgccagg atctaccggc      60
gacatccaga tgacccagtc tccatcctct ctgtccgcct ctgtgggcga cagagtgacc      120
atcacctgta gagcctccga ggacgtgaac acctacgtgt cctggtatca gcagaagccc     180
ggcaaggctc ccaagctgct gatctacgcc gcctctaaca gataccaccg cgtgccctct     240
agattctccg gctctggctc tggcaccgac tttaccctga caatctccag cctgcagcct     300
gaggacttcg ccacctacta ctgccagcag tccttcagct accccacctt tggccagggc     360
accaagctgg aaatcaagcg gacagtggcc gctccttccg tgttcatctt cccaccttcc     420
gacgagcagc tgaagtccgg cacagcttct gtcgtgtgcc tgctgaacaa cttctaccct     480
cgggaagcca aggtgcagtg gaaggtggac aatgccctgc agtccggcaa ctcccaagag     540
tctgtgaccg agcaggactc caaggacagc acctacagcc tgtcctccac actgaccctg     600
tccaaggccg actacgagaa gcacaaggtg tacgcctgcg aagtgaccca tcagggcctg     660
tctagccctg tgaccaagtc tttcaaccgg ggcgagtgct gatga                     705
```

<210> SEQ ID NO 42  
<211> LENGTH: 1422  
<212> TYPE: DNA  
<213> ORGANISM: Artificial Sequence
<220> FEATURE:
<221> NAME/KEY: source
<223> OTHER INFORMATION: /note="Description of Artificial Sequence:
       Synthetic polynucleotide"

<400> SEQUENCE: 42

| | | | | | |
|---|---|---|---|---|---|
| atggaaaccg | acacactgct | gctgtgggtg | ctgctcttgt | gggtgccagg | atctacagga | 60 |
| caggtgcagc | tggttcagtc | tggcgccgaa | gtgaagaaac | ctggctcctc | cgtgaaggtg | 120 |
| tcctgcaagg | cttctggcta | cacctttacc | gacaactaca | tgatctgggt | ccgacaggct | 180 |
| cctggacagg | gacttgagtg | gatgggcgac | atcaacccTT | acaacggcgg | caccaccttc | 240 |
| aaccagaaat | tcaagggcag | agtgaccatc | accgccgaca | gtctacctc | caccgcctac | 300 |
| atggaactgt | ccagcctgag | atctgaggac | accgccgtgt | actactgcgc | cagagagtcc | 360 |
| ccttacttct | ccaacctgta | cgtgatggac | tactggggcc | agggcacact | ggtcacagtg | 420 |
| tcctctgctt | ccaccaaggg | acccagcgtt | ttccctctgg | ctccatcctc | caagtccacc | 480 |
| tctggtggaa | cagctgctct | gggctgcctg | gtcaaggact | actttcctga | gcctgtgacc | 540 |
| gtgtcctgga | actctggcgc | tctgacatct | ggcgtgcaca | cctttccagc | tgtgctgcag | 600 |
| tcctccggcc | tgtactctct | gtcctctgtc | gtgaccgtgc | cttccagctc | tctgggaacc | 660 |
| cagacctaca | tctgcaatgt | gaaccacaag | ccttccaaca | ccaaggtcga | caagagagtg | 720 |
| gaacccaagt | cctgcgacaa | gacccacacc | tgtccacctt | gtcctgctcc | agaactgctc | 780 |
| ggcggacctt | ccgtgttcct | gtttcctcca | agcctaagg | acaccctgat | gatctctcgg | 840 |
| acccctgaag | tgacctgcgt | ggtggtggat | gtgtctcacg | aggacccaga | agtgaagttc | 900 |
| aattggtacg | tggacggcgt | ggaagtgcac | aacgccaaga | ccaagcctag | agaggaacag | 960 |
| tacaactcca | cctacagagt | ggtgtccgtg | ctgaccgtgc | tgcaccagga | ttggctgaac | 1020 |
| ggcaaagagt | acaagtgcaa | ggtgtccaac | aaggccctgc | ctgctcctat | cgaaaagacc | 1080 |
| atctccaagg | ccaagggcca | gcctcgggaa | cctcaagtct | gtaccctgcc | tcctagccgg | 1140 |
| gaagagatga | ccaagaacca | ggtgtccctg | agctgcgccg | tgaagggctt | ctacccttct | 1200 |
| gatatcgccg | tggaatggga | gagcaacggc | cagccagaga | caactacaa | gacaacccct | 1260 |
| cctgtgctgg | actccgacgg | ctcattcttc | ctggtgtcca | agctgacagt | ggacaagtcc | 1320 |
| agatggcagc | agggcaacgt | gttctcctgc | tccgtgatgc | acgaggccct | gcacaatcac | 1380 |
| tacacacaga | agtctctgtc | tctgagcccc | ggcaagtgat | ga | | 1422 |

<210> SEQ ID NO 43
<211> LENGTH: 720
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic polynucleotide"

<400> SEQUENCE: 43

| | | | | | |
|---|---|---|---|---|---|
| atggaaaccg | acacactgct | gctgtgggtg | ctgctcttgt | gggtgccagg | atctacaggc | 60 |
| gagatcgtgc | tgacccagtc | tcctgccaca | ctgtcactgt | ctccaggcga | gagagctacc | 120 |
| ctgtcctgca | aggcttctca | gtccgtgac | tacgacggcg | acaactacat | gaactggtat | 180 |
| cagcagaagc | ccggccaggc | tcctagactg | ctgatctacg | ccgcctccaa | cctggaatct | 240 |
| ggcatccccg | ctagattctc | cggctctggc | tctggcacag | actttaccct | gaccatctcc | 300 |
| agcctggaac | ctgaggactt | cgccgtgtac | tactgccacc | tgtccaacga | ggacctgtcc | 360 |

```
acatttggcg gaggcaccaa ggtggaaatc aagcggacag tggccgctcc ttccgtgttc    420
atcttcccac cttccgacga gcagctgaag tctggcaccg cttctgtcgt gtgcctgctg    480
aacaacttct accctcggga agccaaggtg cagtggaagg tggacaatgc cctgcagtcc    540
ggcaactccc aagagtctgt gaccgagcag gactccaagg acagcaccta cagcctgtcc    600
tccacactga ccctgtccaa ggccgactac gagaagcaca aggtgtacgc ctgcgaagtg    660
acccatcagg gcctgtctag ccctgtgacc aagtctttca accggggcga gtgctgatga    720
```

```
<210> SEQ ID NO 44
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44
```

Gln Val Gln Leu Gln Glu Ser Gly Pro Gly Leu Val Gln Pro Ser Gln
1               5                   10                  15

Thr Leu Ser Leu Thr Cys Thr Val Ser Gly Phe Ser Leu Thr Asp Phe
            20                  25                  30

Ser Val His Trp Val Arg Gln Pro Pro Gly Lys Gly Leu Glu Trp Met
        35                  40                  45

Gly Arg Ile Arg Ser Glu Gly Asn Thr Asp Tyr Asn Ser Ala Leu Lys
    50                  55                  60

Ser Arg Leu Ser Ile Ser Arg Asp Thr Ser Lys Ser Gln Val Phe Leu
65                  70                  75                  80

Lys Met Asn Ser Leu Gln Thr Glu Asp Thr Ala Ile Tyr Phe Cys Thr
                85                  90                  95

Arg Gly Asp Ile Leu Gly Phe Gly Tyr Trp Gly Gln Gly Val Met Val
            100                 105                 110

Thr Val Ser Ser
        115

```
<210> SEQ ID NO 45
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45
```

Asp Ile Val Met Thr Gln Ser Pro Leu Ser Val Ser Val Thr Pro Gly
1               5                   10                  15

Glu Ser Ala Ser Ile Ser Cys Arg Ser Ser Lys Ser Leu Leu His Phe
            20                  25                  30

Lys Gly Ile Thr Phe Val Tyr Trp Tyr Leu Gln Lys Pro Gly Gln Ser
        35                  40                  45

Pro Gln Leu Leu Ile Phe Arg Met Ser Ser Leu Ala Ser Gly Val Pro
    50                  55                  60

Asp Arg Phe Ser Gly Ser Gly Ser Glu Thr Asp Phe Thr Leu Lys Ile
65                  70                  75                  80

Ser Arg Val Glu Ala Glu Asp Val Gly Thr Tyr Tyr Cys Gly Gln Leu
                85                  90                  95

Leu Glu Asn Pro Tyr Thr Phe Gly Ala Gly Thr Lys Leu Glu Leu Lys

<210> SEQ ID NO 46
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 46

```
Ala Gln Thr Thr Ala Pro Ser Val Tyr Pro Leu Ala Pro Gly Cys Gly
1               5                   10                  15

Asp Thr Thr Ser Ser Thr Val Thr Leu Gly Cys Leu Val Lys Gly Tyr
            20                  25                  30

Phe Pro Glu Pro Val Thr Val Thr Trp Asn Ser Gly Ala Leu Ser Ser
        35                  40                  45

Asp Val His Thr Phe Pro Ala Val Leu Gln Ser Gly Leu Tyr Thr Leu
    50                  55                  60

Thr Ser Ser Val Thr Ser Ser Thr Trp Pro Ser Gln Thr Val Thr Cys
65                  70                  75                  80

Asn Val Ala His Pro Ala Ser Ser Thr Lys Val Asp Lys Lys Val Glu
                85                  90                  95

Arg Arg
```

<210> SEQ ID NO 47
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 47

```
Arg Ala Asp Ala Ala Pro Thr Val Ser Ile Phe Pro Pro Ser Met Glu
1               5                   10                  15

Gln Leu Thr Ser Gly Gly Ala Thr Val Val Cys Phe Val Asn Asn Phe
            20                  25                  30

Tyr Pro Arg Asp Ile Ser Val Lys Trp Lys Ile Asp Gly Ser Glu Gln
        35                  40                  45

Arg Asp Gly Val Leu Asp Ser Val Thr Asp Gln Asp Ser Lys Asp Ser
    50                  55                  60

Thr Tyr Ser Met Ser Ser Thr Leu Ser Leu Thr Lys Val Glu Tyr Glu
65                  70                  75                  80

Arg His Asn Leu Tyr Thr Cys Glu Val Val His Lys Thr Ser Ser Ser
                85                  90                  95

Pro Val Val Lys Ser Phe Asn Arg Asn Glu Cys
            100                 105
```

<210> SEQ ID NO 48
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 48

Gln Val Gln Leu Gln Gln Ser Gly Ala Glu Leu Val Lys Pro Gly Ser
1               5                   10                  15

Ser Val Lys Ile Ser Cys Lys Ala Ser Gly Tyr Thr Phe Thr Ser Asn
            20                  25                  30

Phe Met His Trp Ile Lys Gln Gln Pro Gly Asn Gly Leu Glu Trp Ile
            35                  40                  45

Gly Trp Ile Tyr Pro Gly Asp Gly Asp Thr Glu Tyr Asn Gln Lys Phe
        50                  55                  60

Asn Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Phe Cys
            85                  90                  95

Ala Val Asn Tyr Gly Gly Tyr Val Leu Asp Ala Trp Gly Gln Gly Ala
            100                 105                 110

Ser Val Thr Val Ser Ser
            115

<210> SEQ ID NO 49
<211> LENGTH: 103
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Ala Glu Thr Thr Ala Pro Ser Val Tyr Pro Leu Ala Pro Gly Thr Ala
1               5                   10                  15

Leu Lys Ser Asn Ser Met Val Thr Leu Gly Cys Leu Val Lys Gly Tyr
            20                  25                  30

Phe Pro Glu Pro Val Thr Val Thr Trp Asn Ser Gly Ala Leu Ser Ser
            35                  40                  45

Gly Val His Thr Phe Pro Ala Val Leu Gln Ser Gly Leu Tyr Thr Leu
        50                  55                  60

Thr Ser Ser Val Thr Val Pro Ser Ser Thr Trp Ser Ser Gln Ala Val
65                  70                  75                  80

Thr Cys Asn Val Ala His Pro Ala Ser Ser Thr Lys Val Asp Lys Lys
            85                  90                  95

Ile Val Pro Arg Glu Cys Asn
            100

<210> SEQ ID NO 50
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Glu Ile Val Leu Thr Gln Ser Pro Thr Thr Met Ala Ala Ser Pro Gly
1               5                   10                  15

Glu Lys Val Thr Ile Thr Cys Arg Ala Ser Ser Ser Thr Asn Tyr Met
            20                  25                  30

Ser Trp Tyr Gln Gln Lys Ser Gly Ala Ser Pro Lys Pro Trp Ile Tyr
            35                  40                  45

Glu Thr Ser Lys Leu Ala Ser Gly Val Pro Asp Arg Phe Ser Gly Ser

```
                    50                  55                  60
Gly Ser Gly Thr Ser Tyr Ser Phe Thr Ile Ser Ser Met Glu Thr Glu
 65                  70                  75                  80

Asp Ala Ala Thr Tyr Tyr Cys His Gln Trp Ser Ser Thr Pro Leu Thr
                     85                  90                  95

Phe Gly Ser Gly Thr Lys Leu Glu Ile Lys
                100                 105

<210> SEQ ID NO 51
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Arg Ala Asp Ala Ala Pro Thr Val Ser Ile Phe Pro Pro Ser Met Glu
  1               5                  10                  15

Gln Leu Thr Ser Gly Gly Ala Thr Val Val Cys Phe Val Asn Asn Phe
                 20                  25                  30

Tyr Pro Arg Asp Ile Ser Val Lys Trp Lys Ile Asp Gly Ser Glu Gln
             35                  40                  45

Arg Asp Gly Val Leu Asp Ser Val Thr Asp Gln Asp Ser Lys Asp Ser
 50                  55                  60

Thr Tyr Ser Met Ser Ser Thr Leu Ser Leu Thr Lys Val Glu Tyr Glu
 65                  70                  75                  80

Arg His Asn Leu Tyr Thr Cys Glu Val Val His Lys Thr Ser Ser Ser
                 85                  90                  95

Pro Val Val Lys Ser Phe Asn Arg Asn Glu Cys
                100                 105

<210> SEQ ID NO 52
<211> LENGTH: 228
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

Thr Ile Lys Pro Cys Pro Pro Cys Lys Cys Pro Ala Pro Asn Leu Leu
  1               5                  10                  15

Gly Gly Pro Ser Val Phe Ile Phe Pro Pro Lys Ile Lys Asp Val Leu
                 20                  25                  30

Met Ile Ser Leu Ser Pro Ile Val Thr Cys Val Val Val Asp Val Ser
             35                  40                  45

Glu Asp Asp Pro Asp Val Gln Ile Ser Trp Phe Val Asn Asn Val Glu
 50                  55                  60

Val His Thr Ala Gln Thr Gln Thr His Arg Glu Asp Tyr Asn Ser Thr
 65                  70                  75                  80

Leu Arg Val Val Ser Ala Leu Pro Ile Gln His Gln Asp Trp Met Ser
                 85                  90                  95

Gly Lys Glu Phe Lys Cys Lys Val Asn Asn Lys Asp Leu Pro Ala Pro
                100                 105                 110

Ile Glu Arg Thr Ile Ser Lys Pro Lys Gly Ser Val Arg Ala Pro Gln
             115                 120                 125
```

```
Val Tyr Val Leu Pro Pro Cys Glu Glu Met Thr Lys Lys Gln Val
    130                 135                 140

Thr Leu Trp Cys Met Val Thr Asp Phe Met Pro Glu Asp Ile Tyr Val
145                 150                 155                 160

Glu Trp Thr Asn Asn Gly Lys Thr Glu Leu Asn Tyr Lys Asn Thr Glu
                165                 170                 175

Pro Val Leu Asp Ser Asp Gly Ser Tyr Phe Met Tyr Ser Lys Leu Arg
            180                 185                 190

Val Glu Lys Lys Asn Trp Val Glu Arg Asn Ser Tyr Ser Cys Ser Val
        195                 200                 205

Val His Glu Gly Leu His Asn His His Thr Thr Lys Ser Phe Ser Arg
    210                 215                 220

Thr Pro Gly Lys
225

<210> SEQ ID NO 53
<211> LENGTH: 228
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

Thr Ile Lys Pro Cys Pro Pro Cys Lys Cys Pro Ala Pro Asn Leu Leu
1               5                   10                  15

Gly Gly Pro Ser Val Phe Ile Phe Pro Pro Lys Ile Lys Asp Val Leu
            20                  25                  30

Met Ile Ser Leu Ser Pro Ile Val Thr Cys Val Val Val Asp Val Ser
        35                  40                  45

Glu Asp Asp Pro Asp Val Gln Ile Ser Trp Phe Val Asn Asn Val Glu
    50                  55                  60

Val His Thr Ala Gln Thr Gln Thr His Arg Glu Asp Tyr Asn Ser Thr
65                  70                  75                  80

Leu Arg Val Val Ser Ala Leu Pro Ile Gln His Gln Asp Trp Met Ser
                85                  90                  95

Gly Lys Glu Phe Lys Cys Lys Val Asn Asn Lys Asp Leu Pro Ala Pro
            100                 105                 110

Ile Glu Arg Thr Ile Ser Lys Pro Lys Gly Ser Val Arg Ala Pro Gln
        115                 120                 125

Val Cys Val Leu Pro Pro Pro Glu Glu Met Thr Lys Lys Gln Val
    130                 135                 140

Thr Leu Ser Cys Ala Val Thr Asp Phe Met Pro Glu Asp Ile Tyr Val
145                 150                 155                 160

Glu Trp Thr Asn Asn Gly Lys Thr Glu Leu Asn Tyr Lys Asn Thr Glu
                165                 170                 175

Pro Val Leu Asp Ser Asp Gly Ser Tyr Phe Met Val Ser Lys Leu Arg
            180                 185                 190

Val Glu Lys Lys Asn Trp Val Glu Arg Asn Ser Tyr Ser Cys Ser Val
        195                 200                 205

Val His Glu Gly Leu His Asn His His Thr Thr Lys Ser Phe Ser Arg
    210                 215                 220

Thr Pro Gly Lys
225
```

<210> SEQ ID NO 54
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 54

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ala Tyr
            20                  25                  30

Ala Met Asn Trp Val Arg Gln Ala Pro Gly Lys Gly Leu Glu Trp Val
        35                  40                  45

Gly Arg Ile Arg Thr Lys Asn Asn Tyr Ala Thr Tyr Tyr Ala Asp
    50                  55                  60

Ser Val Lys Asp Arg Phe Thr Ile Ser Arg Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Phe Tyr Gly Asn Gly Val Trp Gly Gln Gly Thr Leu
            100                 105                 110

Val Thr Val Ser Ser
        115

<210> SEQ ID NO 55
<211> LENGTH: 103
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 55

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys
            100

<210> SEQ ID NO 56
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:

```
<221> NAME/KEY: VARIANT
<222> LOCATION: (227)..(227)
<223> OTHER INFORMATION: /replace=" "
<220> FEATURE:
<221> NAME/KEY: MISC_FEATURE
<222> LOCATION: (1)..(227)
<223> OTHER INFORMATION: /note="Variant residues given in the sequence
      have no preference with respect to those in the annotations
      for variant positions"
```

<400> SEQUENCE: 56

| | | | | | | | | | | | | | | | |
|---|---|---|---|---|---|---|---|---|---|---|---|---|---|---|---|
| Asp | Lys | Thr | His | Thr | Cys | Pro | Pro | Cys | Pro | Ala | Pro | Glu | Leu | Leu | Gly |
| 1 | | | | 5 | | | | | 10 | | | | | 15 | |
| Gly | Pro | Ser | Val | Phe | Leu | Phe | Pro | Pro | Lys | Pro | Lys | Asp | Thr | Leu | Met |
| | | | 20 | | | | | 25 | | | | | 30 | | |
| Ile | Ser | Arg | Thr | Pro | Glu | Val | Thr | Cys | Val | Val | Val | Asp | Val | Ser | His |
| | | | 35 | | | | | 40 | | | | | 45 | | |
| Glu | Asp | Pro | Glu | Val | Lys | Phe | Asn | Trp | Tyr | Val | Asp | Gly | Val | Glu | Val |
| | | 50 | | | | | 55 | | | | | 60 | | | |
| His | Asn | Ala | Lys | Thr | Lys | Pro | Arg | Glu | Glu | Gln | Tyr | Asn | Ser | Thr | Tyr |
| 65 | | | | | 70 | | | | | 75 | | | | | 80 |
| Arg | Val | Val | Ser | Val | Leu | Thr | Val | Leu | His | Gln | Asp | Trp | Leu | Asn | Gly |
| | | | | 85 | | | | | 90 | | | | | 95 | |
| Lys | Glu | Tyr | Lys | Cys | Lys | Val | Ser | Asn | Lys | Ala | Leu | Pro | Ala | Pro | Ile |
| | | | 100 | | | | | 105 | | | | | 110 | | |
| Glu | Lys | Thr | Ile | Ser | Lys | Ala | Lys | Gly | Gln | Pro | Arg | Glu | Pro | Gln | Val |
| | | | 115 | | | | | 120 | | | | | 125 | | |
| Tyr | Thr | Leu | Pro | Pro | Cys | Arg | Glu | Glu | Met | Thr | Lys | Asn | Gln | Val | Ser |
| | | 130 | | | | | 135 | | | | | 140 | | | |
| Leu | Trp | Cys | Leu | Val | Lys | Gly | Phe | Tyr | Pro | Ser | Asp | Ile | Ala | Val | Glu |
| 145 | | | | | 150 | | | | | 155 | | | | | 160 |
| Trp | Glu | Ser | Asn | Gly | Gln | Pro | Glu | Asn | Asn | Tyr | Lys | Thr | Thr | Pro | Pro |
| | | | | 165 | | | | | 170 | | | | | 175 | |
| Val | Leu | Asp | Ser | Asp | Gly | Ser | Phe | Phe | Leu | Tyr | Ser | Lys | Leu | Thr | Val |
| | | | 180 | | | | | 185 | | | | | 190 | | |
| Asp | Lys | Ser | Arg | Trp | Gln | Gln | Gly | Asn | Val | Phe | Ser | Cys | Ser | Val | Met |
| | | 195 | | | | | 200 | | | | | 205 | | | |
| His | Glu | Ala | Leu | His | Asn | His | Tyr | Thr | Gln | Lys | Ser | Leu | Ser | Leu | Ser |
| | 210 | | | | | 215 | | | | | 220 | | | | |
| Pro | Gly | Lys | | | | | | | | | | | | | |
| 225 | | | | | | | | | | | | | | | |

```
<210> SEQ ID NO 57
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 57

| | | | | | | | | | | | | | | | |
|---|---|---|---|---|---|---|---|---|---|---|---|---|---|---|---|
| Asp | Val | Val | Met | Thr | Gln | Ser | Pro | Leu | Ser | Leu | Pro | Val | Thr | Leu | Gly |
| 1 | | | | 5 | | | | | 10 | | | | | 15 | |
| Gln | Pro | Ala | Ser | Ile | Ser | Cys | Lys | Ser | Ser | Gln | Ser | Leu | Leu | Asp | Ser |
| | | | 20 | | | | | 25 | | | | | 30 | | |
| Asp | Gly | Lys | Thr | Phe | Leu | Asn | Trp | Phe | Gln | Gln | Arg | Pro | Gly | Gln | Ser |
| | | | 35 | | | | | 40 | | | | | 45 | | |
| Pro | Arg | Arg | Leu | Ile | Tyr | Leu | Val | Ser | Lys | Leu | Asp | Ser | Gly | Val | Pro |

```
                      50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                     85                  90                  95

Thr His Phe Pro Tyr Thr Phe Gly Gln Gly Thr Arg Leu Glu Ile Lys
                    100                 105                 110

<210> SEQ ID NO 58
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

Arg Thr Val Ala Ala Pro Ser Val Phe Ile Phe Pro Pro Ser Asp Glu
  1               5                  10                  15

Gln Leu Lys Ser Gly Thr Ala Ser Val Val Cys Leu Leu Asn Asn Phe
                 20                  25                  30

Tyr Pro Arg Glu Ala Lys Val Gln Trp Lys Val Asp Asn Ala Leu Gln
             35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
                100                 105

<210> SEQ ID NO 59
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 59

Glu Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Gly Tyr
                 20                  25                  30

His Met His Trp Val Arg Gln Ala Pro Gly Gln Gly Leu Glu Trp Met
             35                  40                  45

Gly Trp Ile Asn Pro Asn Ser Gly Val Thr Lys Tyr Ala Gln Lys Phe
 50                  55                  60

Gln Gly Arg Val Thr Met Thr Arg Asp Thr Ser Ile Asn Thr Ala Tyr
 65                  70                  75                  80

Met Glu Leu Ser Arg Leu Arg Phe Asp Asp Thr Asp Val Tyr Tyr Cys
                 85                  90                  95

Ala Thr Gly Gly Phe Gly Tyr Trp Gly Glu Gly Thr Leu Val Thr Val
                100                 105                 110

Ser Ser
```

```
<210> SEQ ID NO 60
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 60

Leu Pro Val Leu Thr Gln Pro Pro Ser Val Ser Lys Gly Leu Arg Gln
1               5                   10                  15

Thr Ala Thr Leu Thr Cys Thr Gly Asn Ser Asn Asn Val Gly Asn Gln
            20                  25                  30

Gly Ala Ala Trp Leu Gln Gln His Gln Gly Gln Pro Pro Lys Leu Leu
        35                  40                  45

Ser Tyr Arg Asn His Asn Arg Pro Ser Gly Val Ser Glu Arg Phe Ser
    50                  55                  60

Pro Ser Arg Ser Gly Asp Thr Ser Leu Thr Ile Thr Gly Leu Gln
65                  70                  75                  80

Pro Glu Asp Glu Ala Asp Tyr Tyr Cys Leu Ala Trp Asp Ser Ser Leu
                85                  90                  95

Arg Ala Phe Val Phe Gly Thr Gly Thr Lys Leu Thr Val Leu
            100                 105                 110

<210> SEQ ID NO 61
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 61

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 62
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 62

Gln Val Gln Leu Val Gln Ser Gly Ala Glu Val Lys Lys Pro Gly Ala
```

```
1               5                   10                  15
Ser Val Lys Val Ser Cys Lys Ala Ser Gly Tyr Thr Phe Ser Ser Tyr
                20                  25                  30

Tyr Met His Trp Val Arg Gln Ala Pro Gly Gln Gly Leu Glu Trp Met
        35                  40                  45

Gly Ile Ile Asn Pro Ser Gly Asn Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Gln Leu Pro His Gly Arg Ala Arg Ala Phe Asp
                100                 105                 110

Met Trp Gly Gln Gly Thr Met Val Thr Val Ser Ser
                115                 120
```

<210> SEQ ID NO 63
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 63

```
Ala Ile Arg Met Thr Gln Ser Pro Leu Ser Leu Pro Val Thr Leu Gly
1               5                   10                  15

Gln Pro Ala Ser Ile Ser Cys Thr Ser Ser Gln Ser Leu Val Tyr Arg
                20                  25                  30

Asp Gly Thr Thr Tyr Leu Asn Trp Phe Gln Gln Arg Pro Gly Gln Ser
            35                  40                  45

Pro Arg Arg Leu Ile Tyr Lys Val Ser Asn Arg Asp Ser Gly Val Pro
    50                  55                  60

Asp Arg Phe Thr Gly Ser Gly Ser Gly Thr Asp Phe Thr Leu Thr Ile
65                  70                  75                  80

Ser Arg Val Glu Ala Glu Asp Val Gly Ile Tyr Tyr Cys Met Gln Gly
                85                  90                  95

Thr His Trp Pro Leu Thr Phe Gly Gln Gly Thr Lys Val Glu Ile Lys
                100                 105                 110
```

<210> SEQ ID NO 64
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 64

```
Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Asp Tyr
                20                  25                  30

Trp Met Ser Trp Val Arg Gln Ala Pro Gly Lys Gly Leu Glu Trp Val
            35                  40                  45

Ala Asn Ile Lys Lys Asp Gly Ser Val Asn Tyr Val Asp Ser Val
    50                  55                  60
```

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Thr Arg Phe Asp Tyr Trp Gly Gln Gly Thr Leu Val Thr Val Ser Ser
            100                 105                 110
```

<210> SEQ ID NO 65
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 65

```
Gln Ala Gly Leu Thr Gln Pro Pro Ser Val Ser Lys Gly Leu Arg Gln
 1               5                  10                  15

Thr Ala Thr Leu Thr Cys Thr Gly Asn Ser Asn Asn Val Gly Asn Gln
                 20                  25                  30

Gly Ala Ala Trp Leu Gln Gln His Gln Gly His Pro Pro Lys Leu Leu
             35                  40                  45

Phe Tyr Arg Asn Asn Asn Arg Ala Ser Gly Ile Ser Glu Arg Leu Ser
 50                  55                  60

Ala Ser Arg Ser Gly Asn Thr Ala Ser Leu Thr Ile Thr Gly Leu Gln
 65                  70                  75                  80

Pro Glu Asp Glu Ala Asp Tyr Tyr Cys Leu Thr Trp Asp Ser Ser Leu
                 85                  90                  95

Ser Val Val Val Phe Gly Gly Gly Thr Lys Leu Thr Val Leu
            100                 105                 110
```

<210> SEQ ID NO 66
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 66

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                 20                  25                  30

Asp Ile Ser Trp Val Arg Gln Ala Pro Gly Gln Gly Leu Glu Trp Met
             35                  40                  45

Gly Val Ile Trp Thr Asp Gly Gly Thr Asn Tyr Ala Gln Lys Leu Gln
 50                  55                  60

Gly Arg Val Thr Met Thr Thr Asp Thr Ser Thr Ser Thr Ala Tyr Met
 65                  70                  75                  80

Glu Leu Arg Ser Leu Arg Ser Asp Asp Thr Ala Val Tyr Tyr Cys Ala
                 85                  90                  95

Arg Asp Gln Arg Leu Tyr Phe Asp Val Trp Gly Gln Gly Thr Thr Val
            100                 105                 110

Thr Val Ser Ser
            115
```

```
<210> SEQ ID NO 67
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Val Asn Thr Tyr
            20                  25                  30

Val Ser Trp Tyr Gln Gln Lys Pro Gly Lys Ala Pro Lys Leu Leu Ile
        35                  40                  45

Tyr Ala Ala Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Phe Ser Tyr Pro Thr
                85                  90                  95

Phe Gly Gln Gly Thr Lys Leu Glu Ile Lys
            100                 105

<210> SEQ ID NO 68
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (227)..(227)
<223> OTHER INFORMATION: /replace=" "
<220> FEATURE:
<221> NAME/KEY: MISC_FEATURE
<222> LOCATION: (1)..(227)
<223> OTHER INFORMATION: /note="Variant residues given in the sequence
      have no preference with respect to those in the annotations
      for variant positions"

<400> SEQUENCE: 68

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125
```

```
Cys Thr Leu Pro Pro Ser Arg Glu Glu Met Thr Lys Asn Gln Val Ser
        130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
                180                 185                 190

Asp Lys Ser Arg Trp Gln Gln Gly Asn Val Phe Ser Cys Ser Val Met
                195                 200                 205

His Glu Ala Leu His Asn His Tyr Thr Gln Lys Ser Leu Ser Leu Ser
210                 215                 220

Pro Gly Lys
225

<210> SEQ ID NO 69
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Asn
                20                  25                  30

Tyr Met Ile Trp Val Arg Gln Ala Pro Gly Gln Gly Leu Glu Trp Met
            35                  40                  45

Gly Asp Ile Asn Pro Tyr Asn Gly Gly Thr Thr Phe Asn Gln Lys Phe
        50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ser Pro Tyr Phe Ser Asn Leu Tyr Val Met Asp Tyr Trp
                100                 105                 110

Gly Gln Gly Thr Leu Val Thr Val Ser Ser
            115                 120

<210> SEQ ID NO 70
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 70

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Gln Ser Val Asp Tyr Asp
                20                  25                  30

Gly Asp Asn Tyr Met Asn Trp Tyr Gln Gln Lys Pro Gly Gln Ala Pro
            35                  40                  45

Arg Leu Leu Ile Tyr Ala Ala Ser Asn Leu Glu Ser Gly Ile Pro Ala
```

```
                    50                  55                  60
Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys His Leu Ser Asn
                 85                  90                  95

Glu Asp Leu Ser Thr Phe Gly Gly Gly Thr Lys Val Glu Ile Lys
            100                 105                 110
```

<210> SEQ ID NO 71
<211> LENGTH: 442
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 71

```
Gln Val Gln Leu Gln Glu Ser Gly Pro Gly Leu Val Gln Pro Ser Gln
 1               5                  10                  15

Thr Leu Ser Leu Thr Cys Thr Val Ser Gly Phe Ser Leu Thr Asp Phe
             20                  25                  30

Ser Val His Trp Val Arg Gln Pro Pro Gly Lys Gly Leu Glu Trp Met
         35                  40                  45

Gly Arg Ile Arg Ser Glu Gly Asn Thr Asp Tyr Asn Ser Ala Leu Lys
     50                  55                  60

Ser Arg Leu Ser Ile Ser Arg Asp Thr Ser Lys Ser Gln Val Phe Leu
 65                  70                  75                  80

Lys Met Asn Ser Leu Gln Thr Glu Asp Thr Ala Ile Tyr Phe Cys Thr
                 85                  90                  95

Arg Gly Asp Ile Leu Gly Phe Gly Tyr Trp Gly Gln Gly Val Met Val
            100                 105                 110

Thr Val Ser Ser Ala Gln Thr Thr Ala Pro Ser Val Tyr Pro Leu Ala
        115                 120                 125

Pro Gly Cys Gly Asp Thr Thr Ser Ser Thr Val Thr Leu Gly Cys Leu
    130                 135                 140

Val Lys Gly Tyr Phe Pro Glu Pro Val Thr Val Thr Trp Asn Ser Gly
145                 150                 155                 160

Ala Leu Ser Ser Asp Val His Thr Phe Pro Ala Val Leu Gln Ser Gly
                165                 170                 175

Leu Tyr Thr Leu Thr Ser Ser Val Thr Ser Ser Thr Trp Pro Ser Gln
            180                 185                 190

Thr Val Thr Cys Asn Val Ala His Pro Ala Ser Ser Thr Lys Val Asp
        195                 200                 205

Lys Lys Val Glu Arg Arg Thr Ile Lys Pro Cys Pro Pro Cys Lys Cys
    210                 215                 220

Pro Ala Pro Asn Leu Leu Gly Gly Pro Ser Val Phe Ile Phe Pro Pro
225                 230                 235                 240

Lys Ile Lys Asp Val Leu Met Ile Ser Leu Ser Pro Ile Val Thr Cys
                245                 250                 255

Val Val Val Asp Val Ser Glu Asp Asp Pro Asp Val Gln Ile Ser Trp
            260                 265                 270

Phe Val Asn Asn Val Glu Val His Thr Ala Gln Thr Gln Thr His Arg
        275                 280                 285

Glu Asp Tyr Asn Ser Thr Leu Arg Val Val Ser Ala Leu Pro Ile Gln
    290                 295                 300
```

His Gln Asp Trp Met Ser Gly Lys Glu Phe Lys Cys Lys Val Asn Asn
305                 310                 315                 320

Lys Asp Leu Pro Ala Pro Ile Glu Arg Thr Ile Ser Lys Pro Lys Gly
            325                 330                 335

Ser Val Arg Ala Pro Gln Val Tyr Val Leu Pro Pro Cys Glu Glu Glu
        340                 345                 350

Met Thr Lys Lys Gln Val Thr Leu Trp Cys Met Val Thr Asp Phe Met
    355                 360                 365

Pro Glu Asp Ile Tyr Val Glu Trp Thr Asn Asn Gly Lys Thr Glu Leu
370                 375                 380

Asn Tyr Lys Asn Thr Glu Pro Val Leu Asp Ser Asp Gly Ser Tyr Phe
385                 390                 395                 400

Met Tyr Ser Lys Leu Arg Val Glu Lys Lys Asn Trp Val Glu Arg Asn
            405                 410                 415

Ser Tyr Ser Cys Ser Val Val His Glu Gly Leu His Asn His His Thr
        420                 425                 430

Thr Lys Ser Phe Ser Arg Thr Pro Gly Lys
    435                 440

<210> SEQ ID NO 72
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72

Asp Ile Val Met Thr Gln Ser Pro Leu Ser Val Ser Val Thr Pro Gly
1               5                   10                  15

Glu Ser Ala Ser Ile Ser Cys Arg Ser Ser Lys Ser Leu Leu His Phe
            20                  25                  30

Lys Gly Ile Thr Phe Val Tyr Trp Tyr Leu Gln Lys Pro Gly Gln Ser
        35                  40                  45

Pro Gln Leu Leu Ile Phe Arg Met Ser Ser Leu Ala Ser Gly Val Pro
    50                  55                  60

Asp Arg Phe Ser Gly Ser Gly Ser Glu Thr Asp Phe Thr Leu Lys Ile
65                  70                  75                  80

Ser Arg Val Glu Ala Glu Asp Val Gly Thr Tyr Tyr Cys Gly Gln Leu
                85                  90                  95

Leu Glu Asn Pro Tyr Thr Phe Gly Ala Gly Thr Lys Leu Glu Leu Lys
            100                 105                 110

Arg Ala Asp Ala Ala Pro Thr Val Ser Ile Phe Pro Pro Ser Met Glu
        115                 120                 125

Gln Leu Thr Ser Gly Gly Ala Thr Val Val Cys Phe Val Asn Asn Phe
    130                 135                 140

Tyr Pro Arg Asp Ile Ser Val Lys Trp Lys Ile Asp Gly Ser Glu Gln
145                 150                 155                 160

Arg Asp Gly Val Leu Asp Ser Val Thr Asp Gln Asp Ser Lys Asp Ser
                165                 170                 175

Thr Tyr Ser Met Ser Ser Thr Leu Ser Leu Thr Lys Val Glu Tyr Glu
            180                 185                 190

Arg His Asn Leu Tyr Thr Cys Glu Val Val His Lys Thr Ser Ser Ser
        195                 200                 205

```
Pro Val Val Lys Ser Phe Asn Arg Asn Glu Cys
    210                 215

<210> SEQ ID NO 73
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 73

Gln Val Gln Leu Gln Gln Ser Gly Ala Glu Leu Val Lys Pro Gly Ser
1               5                   10                  15

Ser Val Lys Ile Ser Cys Lys Ala Ser Gly Tyr Thr Phe Thr Ser Asn
            20                  25                  30

Phe Met His Trp Ile Lys Gln Gln Pro Gly Asn Gly Leu Glu Trp Ile
        35                  40                  45

Gly Trp Ile Tyr Pro Gly Asp Gly Asp Thr Gly Tyr Asn Gln Lys Phe
    50                  55                  60

Asn Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Val Asn Tyr Gly Gly Tyr Val Leu Asp Ala Trp Gly Gln Gly Ala
            100                 105                 110

Ser Val Thr Val Ser Ser Ala Glu Thr Thr Ala Pro Ser Val Tyr Pro
        115                 120                 125

Leu Ala Pro Gly Thr Ala Leu Lys Ser Asn Ser Met Val Thr Leu Gly
    130                 135                 140

Cys Leu Val Lys Gly Tyr Phe Pro Glu Pro Val Thr Val Thr Trp Asn
145                 150                 155                 160

Ser Gly Ala Leu Ser Ser Gly Val His Thr Phe Pro Ala Val Leu Gln
                165                 170                 175

Ser Gly Leu Tyr Thr Leu Thr Ser Ser Val Thr Val Pro Ser Ser Thr
            180                 185                 190

Trp Ser Ser Gln Ala Val Thr Cys Asn Val Ala His Pro Ala Ser Ser
        195                 200                 205

Thr Lys Val Asp Lys Lys Ile Val Pro Arg Glu Cys Asn Thr Ile Lys
    210                 215                 220

Pro Cys Pro Pro Cys Lys Cys Pro Ala Pro Asn Leu Leu Gly Gly Pro
225                 230                 235                 240

Ser Val Phe Ile Phe Pro Pro Lys Ile Lys Asp Val Leu Met Ile Ser
                245                 250                 255

Leu Ser Pro Ile Val Thr Cys Val Val Val Asp Val Ser Glu Asp Asp
            260                 265                 270

Pro Asp Val Gln Ile Ser Trp Phe Val Asn Asn Val Glu Val His Thr
        275                 280                 285

Ala Gln Thr Gln Thr His Arg Glu Asp Tyr Asn Ser Thr Leu Arg Val
    290                 295                 300

Val Ser Ala Leu Pro Ile Gln His Gln Asp Trp Met Ser Gly Lys Glu
305                 310                 315                 320

Phe Lys Cys Lys Val Asn Asn Lys Asp Leu Pro Ala Pro Ile Glu Arg
                325                 330                 335

Thr Ile Ser Lys Pro Lys Gly Ser Val Arg Ala Pro Gln Val Cys Val
```

```
                    340                 345                 350
Leu Pro Pro Pro Glu Glu Met Thr Lys Lys Gln Val Thr Leu Ser
            355                 360                 365

Cys Ala Val Thr Asp Phe Met Pro Glu Asp Ile Tyr Val Glu Trp Thr
370                 375                 380

Asn Asn Gly Lys Thr Glu Leu Asn Tyr Lys Asn Thr Glu Pro Val Leu
385                 390                 395                 400

Asp Ser Asp Gly Ser Tyr Phe Met Val Ser Lys Leu Arg Val Glu Lys
                405                 410                 415

Lys Asn Trp Val Glu Arg Asn Ser Tyr Ser Cys Ser Val Val His Glu
            420                 425                 430

Gly Leu His Asn His His Thr Thr Lys Ser Phe Ser Arg Thr Pro Gly
            435                 440                 445

Lys

<210> SEQ ID NO 74
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 74

Glu Ile Val Leu Thr Gln Ser Pro Thr Thr Met Ala Ala Ser Pro Gly
1               5                   10                  15

Glu Lys Val Thr Ile Thr Cys Arg Ala Ser Ser Ser Thr Asn Tyr Met
            20                  25                  30

Ser Trp Tyr Gln Gln Lys Ser Gly Ala Ser Pro Lys Pro Trp Ile Tyr
        35                  40                  45

Glu Thr Ser Lys Leu Ala Ser Gly Val Pro Asp Arg Phe Ser Gly Ser
    50                  55                  60

Gly Ser Gly Thr Ser Tyr Ser Phe Thr Ile Ser Ser Met Glu Thr Glu
65                  70                  75                  80

Asp Ala Ala Thr Tyr Tyr Cys His Gln Trp Ser Ser Thr Pro Leu Thr
                85                  90                  95

Phe Gly Ser Gly Thr Lys Leu Glu Ile Lys Arg Ala Asp Ala Ala Pro
            100                 105                 110

Thr Val Ser Ile Phe Pro Pro Ser Met Glu Gln Leu Thr Ser Gly Gly
        115                 120                 125

Ala Thr Val Val Cys Phe Val Asn Asn Phe Tyr Pro Arg Asp Ile Ser
    130                 135                 140

Val Lys Trp Lys Ile Asp Gly Ser Glu Gln Arg Asp Gly Val Leu Asp
145                 150                 155                 160

Ser Val Thr Asp Gln Asp Ser Lys Asp Ser Thr Tyr Ser Met Ser Ser
                165                 170                 175

Thr Leu Ser Leu Thr Lys Val Glu Tyr Glu Arg His Asn Leu Tyr Thr
            180                 185                 190

Cys Glu Val Val His Lys Thr Ser Ser Ser Pro Val Val Lys Ser Phe
        195                 200                 205

Asn Arg Asn Glu Cys
    210

<210> SEQ ID NO 75
<211> LENGTH: 447
```

-continued

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (447)..(447)
<223> OTHER INFORMATION: /replace=" "
<220> FEATURE:
<221> NAME/KEY: MISC_FEATURE
<222> LOCATION: (1)..(447)
<223> OTHER INFORMATION: /note="Variant residues given in the sequence
      have no preference with respect to those in the annotations
      for variant positions"

<400> SEQUENCE: 75

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ala Tyr
            20                  25                  30

Ala Met Asn Trp Val Arg Gln Ala Pro Gly Lys Gly Leu Glu Trp Val
        35                  40                  45

Gly Arg Ile Arg Thr Lys Asn Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Phe Tyr Gly Asn Gly Val Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320
```

-continued

```
Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
        340                 345                 350

Pro Cys Arg Glu Glu Met Thr Lys Asn Gln Val Ser Leu Trp Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
            435                 440                 445

<210> SEQ ID NO 76
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 76

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Phe Leu Asn Trp Phe Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gln Gly Thr Arg Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

-continued

```
<210> SEQ ID NO 77
<211> LENGTH: 444
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (444)..(444)
<223> OTHER INFORMATION: /replace=" "
<220> FEATURE:
<221> NAME/KEY: MISC_FEATURE
<222> LOCATION: (1)..(444)
<223> OTHER INFORMATION: /note="Variant residues given in the sequence
      have no preference with respect to those in the annotations
      for variant positions"

<400> SEQUENCE: 77

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

His Met His Trp Val Arg Gln Ala Pro Gly Gln Gly Leu Glu Trp Met
        35                  40                  45

Gly Trp Ile Asn Pro Asn Ser Gly Val Thr Lys Tyr Ala Gln Lys Phe
    50                  55                  60

Gln Gly Arg Val Thr Met Thr Arg Asp Thr Ser Ile Asn Thr Ala Tyr
65                  70                  75                  80

Met Glu Leu Ser Arg Leu Arg Phe Asp Asp Thr Asp Val Tyr Tyr Cys
                85                  90                  95

Ala Thr Gly Gly Phe Gly Tyr Trp Gly Glu Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Arg Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
```

```
              305                 310                 315                 320
        Ser Asn Lys Ala Leu Pro Ala Pro Ile Glu Lys Thr Ile Ser Lys Ala
                        325                 330                 335

Lys Gly Gln Pro Arg Glu Pro Gln Val Tyr Thr Leu Pro Pro Cys Arg
                        340                 345                 350

Glu Glu Met Thr Lys Asn Gln Val Ser Leu Trp Cys Leu Val Lys Gly
                        355                 360                 365

Phe Tyr Pro Ser Asp Ile Ala Val Glu Trp Glu Ser Asn Gly Gln Pro
                        370                 375                 380

Glu Asn Asn Tyr Lys Thr Thr Pro Pro Val Leu Asp Ser Asp Gly Ser
        385                 390                 395                 400

Phe Phe Leu Tyr Ser Lys Leu Thr Val Asp Lys Ser Arg Trp Gln Gln
                        405                 410                 415

Gly Asn Val Phe Ser Cys Ser Val Met His Glu Ala Leu His Asn His
                        420                 425                 430

Tyr Thr Gln Lys Ser Leu Ser Leu Ser Pro Gly Lys
                        435                 440

<210> SEQ ID NO 78
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 78

Leu Pro Val Leu Thr Gln Pro Pro Ser Val Ser Lys Gly Leu Arg Gln
1               5                   10                  15

Thr Ala Thr Leu Thr Cys Thr Gly Asn Ser Asn Asn Val Gly Asn Gln
                20                  25                  30

Gly Ala Ala Trp Leu Gln Gln His Gln Gly Gln Pro Pro Lys Leu Leu
            35                  40                  45

Ser Tyr Arg Asn His Asn Arg Pro Ser Gly Val Ser Glu Arg Phe Ser
    50                  55                  60

Pro Ser Arg Ser Gly Asp Thr Ser Ser Leu Thr Ile Thr Gly Leu Gln
65                  70                  75                  80

Pro Glu Asp Glu Ala Asp Tyr Tyr Cys Leu Ala Trp Asp Ser Ser Leu
                85                  90                  95

Arg Ala Phe Val Phe Gly Thr Gly Thr Lys Leu Thr Val Leu Gly Gln
                100                 105                 110

Pro Lys Ala Asn Pro Thr Val Thr Leu Phe Pro Pro Ser Ser Glu Glu
            115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
    195                 200                 205

Thr Val Ala Pro Thr Glu Cys Ser
            210                 215
```

```
<210> SEQ ID NO 79
<211> LENGTH: 454
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (454)..(454)
<223> OTHER INFORMATION: /replace=" "
<220> FEATURE:
<221> NAME/KEY: MISC_FEATURE
<222> LOCATION: (1)..(454)
<223> OTHER INFORMATION: /note="Variant residues given in the sequence
      have no preference with respect to those in the annotations
      for variant positions"

<400> SEQUENCE: 79
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Asn Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Gln Leu Pro His Gly Arg Ala Arg Ala Phe Asp
            100                 105                 110

Met Trp Gly Gln Gly Thr Met Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

```
Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
            325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Cys Arg Glu Glu Met Thr Lys Asn
            355                 360                 365

Gln Val Ser Leu Trp Cys Leu Val Lys Gly Phe Tyr Pro Ser Asp Ile
            370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
            405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
            435                 440                 445

Ser Leu Ser Pro Gly Lys
            450

<210> SEQ ID NO 80
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 80

Ala Ile Arg Met Thr Gln Ser Pro Leu Ser Leu Pro Val Thr Leu Gly
1               5                   10                  15

Gln Pro Ala Ser Ile Ser Cys Thr Ser Ser Gln Ser Leu Val Tyr Arg
            20                  25                  30

Asp Gly Thr Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Thr Gly Ser Gly Ser Gly Thr Thr Phe Thr Leu Thr Ile
65                  70                  75                  80

Ser Arg Val Glu Ala Glu Asp Val Gly Ile Tyr Tyr Cys Met Gln Gly
            85                  90                  95

Thr His Trp Pro Leu Thr Phe Gly Gln Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
            130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
            180                 185                 190
```

```
Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 81
<211> LENGTH: 442
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (442)..(442)
<223> OTHER INFORMATION: /replace=" "
<220> FEATURE:
<221> NAME/KEY: MISC_FEATURE
<222> LOCATION: (1)..(442)
<223> OTHER INFORMATION: /note="Variant residues given in the sequence
      have no preference with respect to those in the annotations
      for variant positions"

<400> SEQUENCE: 81

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Asp Tyr
            20                  25                  30

Trp Met Ser Trp Val Arg Gln Ala Pro Gly Lys Gly Leu Glu Trp Val
        35                  40                  45

Ala Asn Ile Lys Lys Asp Gly Ser Val Asn Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Arg Phe Asp Tyr Trp Gly Gln Gly Thr Leu Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Arg Val Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270
```

Tyr Val Asp Gly Val Glu Val His Asn Ala Lys Thr Lys Pro Arg Glu
            275                 280                 285
Glu Gln Tyr Asn Ser Thr Tyr Arg Val Val Ser Val Leu Thr Val Leu
        290                 295                 300
His Gln Asp Trp Leu Asn Gly Lys Glu Tyr Lys Cys Lys Val Ser Asn
305                 310                 315                 320
Lys Ala Leu Pro Ala Pro Ile Glu Lys Thr Ile Ser Lys Ala Lys Gly
                325                 330                 335
Gln Pro Arg Glu Pro Gln Val Tyr Thr Leu Pro Pro Cys Arg Glu Glu
            340                 345                 350
Met Thr Lys Asn Gln Val Ser Leu Trp Cys Leu Val Lys Gly Phe Tyr
        355                 360                 365
Pro Ser Asp Ile Ala Val Glu Trp Glu Ser Asn Gly Gln Pro Glu Asn
            370                 375                 380
Asn Tyr Lys Thr Thr Pro Pro Val Leu Asp Ser Asp Gly Ser Phe Phe
385                 390                 395                 400
Leu Tyr Ser Lys Leu Thr Val Asp Lys Ser Arg Trp Gln Gln Gly Asn
                405                 410                 415
Val Phe Ser Cys Ser Val Met His Glu Ala Leu His Asn His Tyr Thr
            420                 425                 430
Gln Lys Ser Leu Ser Leu Ser Pro Gly Lys
        435                 440

<210> SEQ ID NO 82
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 82

Gln Ala Gly Leu Thr Gln Pro Pro Ser Val Ser Lys Gly Leu Arg Gln
1               5                   10                  15
Thr Ala Thr Leu Thr Cys Thr Gly Asn Ser Asn Asn Val Gly Asn Gln
            20                  25                  30
Gly Ala Ala Trp Leu Gln Gln His Gln Gly His Pro Pro Lys Leu Leu
        35                  40                  45
Phe Tyr Arg Asn Asn Asn Arg Ala Ser Gly Ile Ser Glu Arg Leu Ser
    50                  55                  60
Ala Ser Arg Ser Gly Asn Thr Ala Ser Leu Thr Ile Thr Gly Leu Gln
65                  70                  75                  80
Pro Glu Asp Glu Ala Asp Tyr Tyr Cys Leu Thr Trp Asp Ser Ser Leu
                85                  90                  95
Ser Val Val Val Phe Gly Gly Gly Thr Lys Leu Thr Val Leu Gly Gln
            100                 105                 110
Pro Lys Ala Asn Pro Thr Val Thr Leu Phe Pro Pro Ser Ser Glu Glu
        115                 120                 125
Leu Gln Ala Asn Lys Ala Thr Leu Val Cys Leu Ile Ser Asp Phe Tyr
    130                 135                 140
Pro Gly Ala Val Thr Val Ala Trp Lys Ala Asp Gly Ser Pro Val Lys
145                 150                 155                 160
Ala Gly Val Glu Thr Thr Lys Pro Ser Lys Gln Ser Asn Asn Lys Tyr
                165                 170                 175
Ala Ala Ser Ser Tyr Leu Ser Leu Thr Pro Glu Gln Trp Lys Ser His

```
                180              185                  190
Arg Ser Tyr Ser Cys Gln Val Thr His Glu Gly Ser Thr Val Glu Lys
        195                 200                 205

Thr Val Ala Pro Thr Glu Cys Ser
        210                 215

<210> SEQ ID NO 83
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (446)..(446)
<223> OTHER INFORMATION: /replace=" "
<220> FEATURE:
<221> NAME/KEY: MISC_FEATURE
<222> LOCATION: (1)..(446)
<223> OTHER INFORMATION: /note="Variant residues given in the sequence
      have no preference with respect to those in the annotations
      for variant positions"

<400> SEQUENCE: 83

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Ser Trp Val Arg Gln Ala Pro Gly Gln Gly Leu Glu Trp Met
        35                  40                  45

Gly Val Ile Trp Thr Asp Gly Gly Thr Asn Tyr Ala Gln Lys Leu Gln
    50                  55                  60

Gly Arg Val Thr Met Thr Thr Asp Thr Ser Thr Ser Thr Ala Tyr Met
65                  70                  75                  80

Glu Leu Arg Ser Leu Arg Ser Asp Asp Thr Ala Val Tyr Tyr Cys Ala
                85                  90                  95

Arg Asp Gln Arg Leu Tyr Phe Asp Val Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
```

```
              260                 265                 270
Lys Phe Asn Trp Tyr Val Asp Gly Val Glu Val His Asn Ala Lys Thr
            275                 280                 285
Lys Pro Arg Glu Glu Gln Tyr Asn Ser Thr Tyr Arg Val Val Ser Val
        290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
Lys Ala Lys Gly Gln Pro Arg Glu Pro Gln Val Cys Thr Leu Pro Pro
                340                 345                 350
Ser Arg Glu Glu Met Thr Lys Asn Gln Val Ser Leu Ser Cys Ala Val
            355                 360                 365
Lys Gly Phe Tyr Pro Ser Asp Ile Ala Val Glu Trp Glu Ser Asn Gly
        370                 375                 380
Gln Pro Glu Asn Asn Tyr Lys Thr Thr Pro Pro Val Leu Asp Ser Asp
385                 390                 395                 400
Gly Ser Phe Phe Leu Val Ser Lys Leu Thr Val Asp Lys Ser Arg Trp
                405                 410                 415
Gln Gln Gly Asn Val Phe Ser Cys Ser Val Met His Glu Ala Leu His
                420                 425                 430
Asn His Tyr Thr Gln Lys Ser Leu Ser Leu Ser Pro Gly Lys
                435                 440                 445

<210> SEQ ID NO 84
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84

Asp Ile Gln Met Thr Gln Ser Pro Ser Ser Leu Ser Ala Ser Val Gly
1               5                   10                  15
Asp Arg Val Thr Ile Thr Cys Arg Ala Ser Glu Asp Val Asn Thr Tyr
                20                  25                  30
Val Ser Trp Tyr Gln Gln Lys Pro Gly Lys Ala Pro Lys Leu Leu Ile
            35                  40                  45
Tyr Ala Ala Ser Asn Arg Tyr Thr Gly Val Pro Ser Arg Phe Ser Gly
        50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Phe Ser Tyr Pro Thr
                85                  90                  95
Phe Gly Gln Gly Thr Lys Leu Glu Ile Lys Arg Thr Val Ala Ala Pro
            100                 105                 110
Ser Val Phe Ile Phe Pro Pro Ser Asp Glu Gln Leu Lys Ser Gly Thr
        115                 120                 125
Ala Ser Val Val Cys Leu Leu Asn Asn Phe Tyr Pro Arg Glu Ala Lys
    130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
```

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 85
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (452)..(452)
<223> OTHER INFORMATION: /replace=" "
<220> FEATURE:
<221> NAME/KEY: MISC_FEATURE
<222> LOCATION: (1)..(452)
<223> OTHER INFORMATION: /note="Variant residues given in the sequence
      have no preference with respect to those in the annotations
      for variant positions"

<400> SEQUENCE: 85

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Asn
            20                  25                  30

Tyr Met Ile Trp Val Arg Gln Ala Pro Gly Gln Gly Leu Glu Trp Met
        35                  40                  45

Gly Asp Ile Asn Pro Tyr Asn Gly Gly Thr Thr Phe Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ser Pro Tyr Phe Ser Asn Leu Tyr Val Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

```
Met Ile Ser Arg Thr Pro Glu Val Thr Cys Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Cys Thr Leu Pro Pro Ser Arg Glu Glu Met Thr Lys Asn Gln Val
            355                 360                 365

Ser Leu Ser Cys Ala Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Val Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
            435                 440                 445

Ser Pro Gly Lys
    450

<210> SEQ ID NO 86
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 86

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Gln Ser Val Asp Tyr Asp
            20                  25                  30

Gly Asp Asn Tyr Met Asn Trp Tyr Gln Gln Lys Pro Gly Gln Ala Pro
        35                  40                  45

Arg Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys His Leu Ser Asn
                85                  90                  95

Glu Asp Leu Ser Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140
```

```
Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 87
<211> LENGTH: 972
<212> TYPE: PRT
<213> ORGANISM: Homo sapiens

<400> SEQUENCE: 87

Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
                20                  25                  30

Lys Pro Gly Ala Thr Val Thr Leu Arg Cys Val Gly Asn Gly Ser Val
            35                  40                  45

Glu Trp Asp Gly Pro Pro Ser Pro His Trp Thr Leu Tyr Ser Asp Gly
50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
            100                 105                 110

Gln Glu Val Val Val Phe Glu Asp Gln Asp Ala Leu Leu Pro Cys Leu
        115                 120                 125

Leu Thr Asp Pro Val Leu Glu Ala Gly Val Ser Leu Val Arg Val Arg
130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
            180                 185                 190

Leu Lys Val Gln Lys Val Ile Pro Gly Pro Pro Ala Leu Thr Leu Val
        195                 200                 205

Pro Ala Glu Leu Val Arg Ile Arg Gly Glu Ala Ala Gln Ile Val Cys
210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
            260                 265                 270

Ala Gly Asn Tyr Ser Cys Val Ala Ser Asn Val Gln Gly Lys His Ser
        275                 280                 285

Thr Ser Met Phe Phe Arg Val Val Glu Ser Ala Tyr Leu Asn Leu Ser
290                 295                 300
```

```
Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
            340                 345                 350

Asn Ala Thr Thr Lys Asp Thr Tyr Arg His Thr Phe Thr Leu Ser Leu
                355                 360                 365

Pro Arg Leu Lys Pro Ser Glu Ala Gly Arg Tyr Ser Phe Leu Ala Arg
        370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415

Leu Leu Cys Ala Ala Ser Gly Tyr Pro Gln Pro Asn Val Thr Trp Leu
            420                 425                 430

Gln Cys Ser Gly His Thr Asp Arg Cys Asp Glu Ala Gln Val Leu Gln
        435                 440                 445

Val Trp Asp Asp Pro Tyr Pro Glu Val Leu Ser Gln Glu Pro Phe His
    450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala His Thr His Pro Pro Asp Glu
            500                 505                 510

Phe Leu Phe Thr Pro Val Val Ala Cys Met Ser Ile Met Ala Leu
        515                 520                 525

Leu Leu Leu Leu Leu Leu Leu Leu Tyr Lys Tyr Lys Gln Lys Pro
    530                 535                 540

Lys Tyr Gln Val Arg Trp Lys Ile Ile Glu Ser Tyr Glu Gly Asn Ser
545                 550                 555                 560

Tyr Thr Phe Ile Asp Pro Thr Gln Leu Pro Tyr Asn Glu Lys Trp Glu
                565                 570                 575

Phe Pro Arg Asn Asn Leu Gln Phe Gly Lys Thr Leu Gly Ala Gly Ala
            580                 585                 590

Phe Gly Lys Val Val Glu Ala Thr Ala Phe Gly Leu Gly Lys Glu Asp
        595                 600                 605

Ala Val Leu Lys Val Ala Val Lys Met Leu Lys Ser Thr Ala His Ala
    610                 615                 620

Asp Glu Lys Glu Ala Leu Met Ser Glu Leu Lys Ile Met Ser His Leu
625                 630                 635                 640

Gly Gln His Glu Asn Ile Val Asn Leu Leu Gly Ala Cys Thr His Gly
                645                 650                 655

Gly Pro Val Leu Val Ile Thr Glu Tyr Cys Cys Tyr Gly Asp Leu Leu
            660                 665                 670

Asn Phe Leu Arg Arg Lys Ala Glu Ala Met Leu Gly Pro Ser Leu Ser
        675                 680                 685

Pro Gly Gln Asp Pro Glu Gly Gly Val Asp Tyr Lys Asn Ile His Leu
    690                 695                 700

Glu Lys Lys Tyr Val Arg Arg Asp Ser Gly Phe Ser Ser Gln Gly Val
705                 710                 715                 720
```

```
Asp Thr Tyr Val Glu Met Arg Pro Val Ser Thr Ser Ser Asn Asp Ser
            725                 730                 735

Phe Ser Glu Gln Asp Leu Asp Lys Glu Asp Gly Arg Pro Leu Glu Leu
        740                 745                 750

Arg Asp Leu Leu His Phe Ser Ser Gln Val Ala Gln Gly Met Ala Phe
        755                 760                 765

Leu Ala Ser Lys Asn Cys Ile His Arg Asp Val Ala Ala Arg Asn Val
770                 775                 780

Leu Leu Thr Asn Gly His Val Ala Lys Ile Gly Asp Phe Gly Leu Ala
785                 790                 795                 800

Arg Asp Ile Met Asn Asp Ser Asn Tyr Ile Val Lys Gly Asn Ala Arg
            805                 810                 815

Leu Pro Val Lys Trp Met Ala Pro Glu Ser Ile Phe Asp Cys Val Tyr
        820                 825                 830

Thr Val Gln Ser Asp Val Trp Ser Tyr Gly Ile Leu Leu Trp Glu Ile
        835                 840                 845

Phe Ser Leu Gly Leu Asn Pro Tyr Pro Gly Ile Leu Val Asn Ser Lys
850                 855                 860

Phe Tyr Lys Leu Val Lys Asp Gly Tyr Gln Met Ala Gln Pro Ala Phe
865                 870                 875                 880

Ala Pro Lys Asn Ile Tyr Ser Ile Met Gln Ala Cys Trp Ala Leu Glu
            885                 890                 895

Pro Thr His Arg Pro Thr Phe Gln Gln Ile Cys Ser Phe Leu Gln Glu
        900                 905                 910

Gln Ala Gln Glu Asp Arg Arg Glu Arg Asp Tyr Thr Asn Leu Pro Ser
        915                 920                 925

Ser Ser Arg Ser Gly Gly Ser Gly Ser Ser Ser Glu Leu Glu Glu
930                 935                 940

Glu Ser Ser Ser Glu His Leu Thr Cys Cys Glu Gln Gly Asp Ile Ala
945                 950                 955                 960

Gln Pro Leu Leu Gln Pro Asn Asn Tyr Gln Phe Cys
            965                 970

<210> SEQ ID NO 88
<211> LENGTH: 306
<212> TYPE: PRT
<213> ORGANISM: Homo sapiens

<400> SEQUENCE: 88

Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
            20                  25                  30

Lys Pro Gly Ala Thr Val Thr Leu Arg Cys Val Gly Asn Gly Ser Val
        35                  40                  45

Glu Trp Asp Gly Pro Pro Ser Pro His Trp Thr Leu Tyr Ser Asp Gly
    50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
            100                 105                 110

Gln Glu Val Val Val Phe Glu Asp Gln Asp Ala Leu Leu Pro Cys Leu
        115                 120                 125
```

```
Leu Thr Asp Pro Val Leu Glu Ala Gly Val Ser Leu Val Arg Val Arg
            130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
            180                 185                 190

Leu Lys Val Gln Lys Val Ile Pro Gly Pro Ala Leu Thr Leu Val
        195                 200                 205

Pro Ala Glu Leu Val Arg Ile Arg Gly Glu Ala Ala Gln Ile Val Cys
        210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
            260                 265                 270

Ala Gly Asn Tyr Ser Cys Val Ala Ser Asn Val Gln Gly Lys His Ser
        275                 280                 285

Thr Ser Met Phe Phe Arg Val Val Gly Thr Pro Ser Pro Ser Leu Cys
290                 295                 300

Pro Ala
305

<210> SEQ ID NO 89
<211> LENGTH: 374
<212> TYPE: PRT
<213> ORGANISM: Homo sapiens

<400> SEQUENCE: 89

Met Leu Ser Thr Ser Arg Ser Arg Phe Ile Arg Asn Thr Asn Glu Ser
1               5                   10                  15

Gly Glu Glu Val Thr Thr Phe Phe Asp Tyr Asp Tyr Gly Ala Pro Cys
            20                  25                  30

His Lys Phe Asp Val Lys Gln Ile Gly Ala Gln Leu Leu Pro Pro Leu
        35                  40                  45

Tyr Ser Leu Val Phe Ile Phe Gly Phe Val Gly Asn Met Leu Val Val
    50                  55                  60

Leu Ile Leu Ile Asn Cys Lys Lys Leu Lys Cys Leu Thr Asp Ile Tyr
65                  70                  75                  80

Leu Leu Asn Leu Ala Ile Ser Asp Leu Leu Phe Leu Ile Thr Leu Pro
                85                  90                  95

Leu Trp Ala His Ser Ala Ala Asn Glu Trp Val Phe Gly Asn Ala Met
            100                 105                 110

Cys Lys Leu Phe Thr Gly Leu Tyr His Ile Gly Tyr Phe Gly Gly Ile
        115                 120                 125

Phe Phe Ile Ile Leu Leu Thr Ile Asp Arg Tyr Leu Ala Ile Val His
    130                 135                 140

Ala Val Phe Ala Leu Lys Ala Arg Thr Val Thr Phe Gly Val Val Thr
145                 150                 155                 160

Ser Val Ile Thr Trp Leu Val Ala Val Phe Ala Ser Val Pro Gly Ile
                165                 170                 175

Ile Phe Thr Lys Cys Gln Lys Glu Asp Ser Val Tyr Val Cys Gly Pro
```

```
            180                 185                 190
Tyr Phe Pro Arg Gly Trp Asn Asn Phe His Thr Ile Met Arg Asn Ile
            195                 200                 205

Leu Gly Leu Val Leu Pro Leu Ile Met Val Ile Cys Tyr Ser Gly
            210                 215                 220

Ile Leu Lys Thr Leu Leu Arg Cys Arg Asn Glu Lys Lys Arg His Arg
225                 230                 235                 240

Ala Val Arg Val Ile Phe Thr Ile Met Ile Val Tyr Phe Leu Phe Trp
                245                 250                 255

Thr Pro Tyr Asn Ile Val Ile Leu Leu Asn Thr Phe Gln Glu Phe Phe
                260                 265                 270

Gly Leu Ser Asn Cys Glu Ser Thr Ser Gln Leu Asp Gln Ala Thr Gln
            275                 280                 285

Val Thr Glu Thr Leu Gly Met Thr His Cys Cys Ile Asn Pro Ile Ile
            290                 295                 300

Tyr Ala Phe Val Gly Glu Lys Phe Arg Ser Leu Phe His Ile Ala Leu
305                 310                 315                 320

Gly Cys Arg Ile Ala Pro Leu Gln Lys Pro Val Cys Gly Gly Pro Gly
                325                 330                 335

Val Arg Pro Gly Lys Asn Val Lys Val Thr Thr Gln Gly Leu Leu Asp
                340                 345                 350

Gly Arg Gly Lys Gly Lys Ser Ile Gly Arg Ala Pro Glu Ala Ser Leu
            355                 360                 365

Gln Asp Lys Glu Gly Ala
            370

<210> SEQ ID NO 90
<211> LENGTH: 360
<212> TYPE: PRT
<213> ORGANISM: Homo sapiens

<400> SEQUENCE: 90

Met Leu Ser Thr Ser Arg Ser Arg Phe Ile Arg Asn Thr Asn Glu Ser
1               5                   10                  15

Gly Glu Glu Val Thr Thr Phe Phe Asp Tyr Asp Tyr Gly Ala Pro Cys
                20                  25                  30

His Lys Phe Asp Val Lys Gln Ile Gly Ala Gln Leu Leu Pro Pro Leu
            35                  40                  45

Tyr Ser Leu Val Phe Ile Phe Gly Phe Val Gly Asn Met Leu Val Val
50                  55                  60

Leu Ile Leu Ile Asn Cys Lys Lys Leu Lys Cys Leu Thr Asp Ile Tyr
65                  70                  75                  80

Leu Leu Asn Leu Ala Ile Ser Asp Leu Leu Phe Leu Ile Thr Leu Pro
                85                  90                  95

Leu Trp Ala His Ser Ala Ala Asn Glu Trp Val Phe Gly Asn Ala Met
            100                 105                 110

Cys Lys Leu Phe Thr Gly Leu Tyr His Ile Gly Tyr Phe Gly Gly Ile
            115                 120                 125

Phe Phe Ile Ile Leu Leu Thr Ile Asp Arg Tyr Leu Ala Ile Val His
130                 135                 140

Ala Val Phe Ala Leu Lys Ala Arg Thr Val Thr Phe Gly Val Val Thr
145                 150                 155                 160

Ser Val Ile Thr Trp Leu Val Ala Val Phe Ala Ser Val Pro Gly Ile
                165                 170                 175
```

-continued

```
Ile Phe Thr Lys Cys Gln Lys Glu Asp Ser Val Tyr Val Cys Gly Pro
            180                 185                 190

Tyr Phe Pro Arg Gly Trp Asn Asn Phe His Thr Ile Met Arg Asn Ile
        195                 200                 205

Leu Gly Leu Val Leu Pro Leu Leu Ile Met Val Ile Cys Tyr Ser Gly
    210                 215                 220

Ile Leu Lys Thr Leu Leu Arg Cys Arg Asn Glu Lys Lys Arg His Arg
225                 230                 235                 240

Ala Val Arg Val Ile Phe Thr Ile Met Ile Val Tyr Phe Leu Phe Trp
                245                 250                 255

Thr Pro Tyr Asn Ile Val Ile Leu Leu Asn Thr Phe Gln Glu Phe Phe
            260                 265                 270

Gly Leu Ser Asn Cys Glu Ser Thr Ser Gln Leu Asp Gln Ala Thr Gln
        275                 280                 285

Val Thr Glu Thr Leu Gly Met Thr His Cys Cys Ile Asn Pro Ile Ile
    290                 295                 300

Tyr Ala Phe Val Gly Glu Lys Phe Arg Arg Tyr Leu Ser Val Phe Phe
305                 310                 315                 320

Arg Lys His Ile Thr Lys Arg Phe Cys Lys Gln Cys Pro Val Phe Tyr
                325                 330                 335

Arg Glu Thr Val Asp Gly Val Thr Ser Thr Asn Thr Pro Ser Thr Gly
            340                 345                 350

Glu Gln Glu Val Ser Ala Gly Leu
        355                 360

<210> SEQ ID NO 91
<211> LENGTH: 360
<212> TYPE: PRT
<213> ORGANISM: Homo sapiens

<400> SEQUENCE: 91

Met Glu Asp Phe Asn Met Glu Ser Asp Ser Phe Glu Asp Phe Trp Lys
1               5                   10                  15

Gly Glu Asp Leu Ser Asn Tyr Ser Tyr Ser Ser Thr Leu Pro Pro Phe
            20                  25                  30

Leu Leu Asp Ala Ala Pro Cys Glu Pro Glu Ser Leu Glu Ile Asn Lys
        35                  40                  45

Tyr Phe Val Val Ile Ile Tyr Ala Leu Val Phe Leu Leu Ser Leu Leu
    50                  55                  60

Gly Asn Ser Leu Val Met Leu Val Ile Leu Tyr Ser Arg Val Gly Arg
65                  70                  75                  80

Ser Val Thr Asp Val Tyr Leu Leu Asn Leu Ala Leu Ala Asp Leu Leu
                85                  90                  95

Phe Ala Leu Thr Leu Pro Ile Trp Ala Ala Ser Lys Val Asn Gly Trp
            100                 105                 110

Ile Phe Gly Thr Phe Leu Cys Lys Val Val Ser Leu Leu Lys Glu Val
        115                 120                 125

Asn Phe Tyr Ser Gly Ile Leu Leu Leu Ala Cys Ile Ser Val Asp Arg
    130                 135                 140

Tyr Leu Ala Ile Val His Ala Thr Arg Thr Leu Thr Gln Lys Arg Tyr
145                 150                 155                 160

Leu Val Lys Phe Ile Cys Leu Ser Ile Trp Gly Leu Ser Leu Leu Leu
                165                 170                 175

Ala Leu Pro Val Leu Leu Phe Arg Arg Thr Val Tyr Ser Ser Asn Val
            180                 185                 190
```

-continued

```
Ser Pro Ala Cys Tyr Glu Asp Met Gly Asn Asn Thr Ala Asn Trp Arg
        195                 200                 205

Met Leu Leu Arg Ile Leu Pro Gln Ser Phe Gly Phe Ile Val Pro Leu
    210                 215                 220

Leu Ile Met Leu Phe Cys Tyr Gly Phe Thr Leu Arg Thr Leu Phe Lys
225                 230                 235                 240

Ala His Met Gly Gln Lys His Arg Ala Met Arg Val Ile Phe Ala Val
                245                 250                 255

Val Leu Ile Phe Leu Leu Cys Trp Leu Pro Tyr Asn Leu Val Leu Leu
            260                 265                 270

Ala Asp Thr Leu Met Arg Thr Gln Val Ile Gln Glu Thr Cys Glu Arg
            275                 280                 285

Arg Asn His Ile Asp Arg Ala Leu Asp Ala Thr Glu Ile Leu Gly Ile
        290                 295                 300

Leu His Ser Cys Leu Asn Pro Leu Ile Tyr Ala Phe Ile Gly Gln Lys
305                 310                 315                 320

Phe Arg His Gly Leu Leu Lys Ile Leu Ala Ile His Gly Leu Ile Ser
                325                 330                 335

Lys Asp Ser Leu Pro Lys Asp Ser Arg Pro Ser Phe Val Gly Ser Ser
            340                 345                 350

Ser Gly His Thr Ser Thr Thr Leu
        355                 360

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98
```

```
<400> SEQUENCE: 98

000

<210> SEQ ID NO 99
<400> SEQUENCE: 99

000

<210> SEQ ID NO 100
<400> SEQUENCE: 100

000

<210> SEQ ID NO 101
<400> SEQUENCE: 101

000

<210> SEQ ID NO 102
<400> SEQUENCE: 102

000

<210> SEQ ID NO 103
<400> SEQUENCE: 103

000

<210> SEQ ID NO 104
<400> SEQUENCE: 104

000

<210> SEQ ID NO 105
<400> SEQUENCE: 105

000

<210> SEQ ID NO 106
<400> SEQUENCE: 106

000

<210> SEQ ID NO 107
<400> SEQUENCE: 107

000

<210> SEQ ID NO 108
<400> SEQUENCE: 108

000

<210> SEQ ID NO 109
<211> LENGTH: 121
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 109

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Leu Ala Phe Asp Tyr Trp Gly
            100                 105                 110

Gln Gly Thr Leu Val Thr Val Ser Ser
        115                 120

<210> SEQ ID NO 110
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 110

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys
            100                 105

<210> SEQ ID NO 111
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 111

Glu Val Gln Leu Val Glu Ser Gly Gly Gly Leu Val Gln Pro Gly Gly
1               5                   10                  15
```

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
            115

<210> SEQ ID NO 112
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 112

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys
            100                 105

<210> SEQ ID NO 113
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 113

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
    50                  55                  60

Lys Gly Arg Phe Thr Ile Ser Arg Asp Asn Ser Lys Asn Thr Leu Tyr

```
                65                  70                  75                  80
Leu Gln Met Asn Ser Leu Arg Ala Glu Asp Thr Ala Val Tyr Tyr Cys
                        85                  90                  95

Ala Arg Ile Lys Leu Gly Thr Val Thr Val Asp Tyr Trp Gly Gln
                100                 105                 110

Gly Thr Leu Val Thr Val Ser Ser
        115                 120
```

<210> SEQ ID NO 114
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 114

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu
                100                 105                 110
```

<210> SEQ ID NO 115
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 115
atggaaaccg acacactgct gctgtgggtg ctgctcttgt gggtgccagg atctacagga     60

<210> SEQ ID NO 116
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 116

```
Met Glu Thr Asp Thr Leu Leu Leu Trp Val Leu Leu Leu Trp Val Pro
1               5                   10                  15

Gly Ser Thr Gly
            20
```

MULTISPECIFIC MOLECULES AND USES THEREOF

RELATED APPLICATIONS

This application is a U.S. National Phase Application under 35 U.S.C. § 371 of International Application No. PCT/US2018/028315 filed Apr. 19, 2018, which claims priority to U.S. Ser. No. 62/487,061 filed Apr. 19, 2017, the contents of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Apr. 18, 2018, is named E2070-7005WO_SL.txt and is 158,210 bytes in size.

BACKGROUND

Multispecific molecules targeting tumor associated macrophages (TAMs) or myeloid derived suppressor cells (MDSCs) and methods of using the same, are disclosed.

SUMMARY OF THE INVENTION

The disclosure relates, inter alia, to novel multispecific molecules comprising: (i) a first immunosuppressive myeloid cell (IMC) binding moiety (e.g., a first tumor associated macrophage (TAM) binding moiety; or a first myeloid derived suppressor cell (MDSC) binding moiety) (e.g., an antibody molecule); and (ii) a second IMC binding moiety (e.g., a first TAM binding moiety; or a second MDSC binding moiety) (e.g., an antibody molecule), wherein the first and the second IMC (e.g., TAM or MDSC) binding moieties are different. Without being bound by theory, the multispecific molecules disclosed herein are expected to deplete TAMs and/or MDSCs. Accordingly, provided herein are, inter alia, multispecific molecules (e.g., multispecific antibody molecules) that include the aforesaid moieties, nucleic acids encoding the same, methods of producing the aforesaid molecules, and methods of treating a cancer using the aforesaid molecules.

In one aspect, provided herein are isolated multispecific, e.g., a bispecific, molecules, comprising: (i) a first immunosuppressive myeloid cell (IMC) binding moiety (e.g., a first tumor associated macrophage (TAM) binding moiety; or a first myeloid derived suppressor cell (MDSC) binding moiety) (e.g., an antibody molecule); and (ii) a second IMC binding moiety (e.g., a second TAM binding moiety; or a second MDSC binding moiety) (e.g., an antibody molecule), wherein the first and the second IMC (e.g., TAM or MDSC) binding moieties are different. In some embodiments, the first and the second IMC (e.g., TAM or MDSC) binding moieties bind to different epitopes. In some embodiments, the first and the second IMC (e.g., TAM or MDSC) binding moieties bind to different antigens.

In some embodiments, the first IMC binding moiety is a first MDSC binding moiety; and the second IMC binding moiety is a second MDSC binding moiety. In some embodiments, the first IMC binding moiety is a first TAM binding moiety; and the second IMC binding moiety is a second TAM binding moiety. In some embodiments, the first TAM binding moiety binds to CSF1R, CCR2, CXCR2, CD86, CD163, CX3CR1, MARCO, CD204, CD52, folate receptor beta, or PD-L1; and the second TAM binding moiety binds to CCR2, CSF1R, CXCR2, CD86, CD163, CX3CR1, MARCO, CD204, CD52, folate receptor beta, or PD-L1. In some embodiments, the first TAM binding moiety binds to CSF1R, CCR2, CXCR2, or PD-L1 (e.g., human CSF1R, CCR2, CXCR2, or PD-L1) and the second TAM binding moiety binds to CCR2, CSF1R, CXCR2, or PD-L1 (e.g., human CCR2, CSF1R, CXCR2, or PD-L1). In some embodiments, the first TAM binding moiety binds to CSF1R and the second TAM binding moiety binds to CCR2. In some embodiments, the first TAM binding moiety binds to CSF1R and the second TAM binding moiety binds to CXCR2. In some embodiments, the first TAM binding moiety binds to CCR2 and the second TAM binding moiety binds to CXCR2. In some embodiments, the first TAM binding moiety binds to CSF1R and the second TAM binding moiety binds to PD-L1. In some embodiments, the first TAM binding moiety binds to CCR2 and the second TAM binding moiety binds to PD-L1. In some embodiments, the first TAM binding moiety binds to CXCR2 and the second TAM binding moiety binds to PD-L1.

In some embodiments, the first TAM binding moiety binds to CSF1R, CCR2, CXCR2, or PD-L1 with a dissociation constant of less than about 10 nM, and more typically, 10-100 pM; and the second TAM binding moiety binds to CCR2, CSF1R, CXCR2, or PD-L1 with a dissociation constant of less than about 10 nM, and more typically, 10-100 pM. In some embodiments, the first TAM binding moiety binds to a conformational or a linear epitope on CSF1R, CCR2, CXCR2, or PD-L1; and the second TAM binding moiety binds to a conformational or a linear epitope on CCR2, CSF1R, CXCR2, or PD-L1.

In some embodiments, the multispecific molecule comprises at least two non-contiguous polypeptide chains. In some embodiments, the first IMC binding moiety comprises a first anti-IMC antibody molecule and/or the second IMC binding moiety comprises a second anti-IMC antibody molecule. In some embodiments, the first anti-IMC antibody molecule and the second anti-IMC antibody molecule are, independently, a full antibody (e.g., an antibody that includes at least one, and preferably two, complete heavy chains, and at least one, and preferably two, complete light chains), or an antigen-binding fragment (e.g., a Fab, F(ab')2, Fv, a scFv, a single domain antibody, or a diabody (dAb)).

In some embodiments, the first anti-IMC antibody molecule and/or the second anti-IMC antibody molecule comprises a heavy chain constant region chosen from IgG1, IgG2, IgG3, or IgG4, or a fragment thereof.

In some embodiments, the first anti-IMC antibody molecule and/or the second anti-IMC antibody molecule comprises a light chain constant region chosen from the light chain constant regions of kappa or lambda, or a fragment thereof. In some embodiments, the first anti-IMC antibody molecule comprises a kappa light chain constant region, or a fragment thereof, and the second anti-IMC antibody molecule comprises a lambda light chain constant region, or a fragment thereof. In some embodiments, the first anti-IMC antibody molecule comprises a lambda light chain constant region, or a fragment thereof, and the second anti-IMC antibody molecule comprises a kappa light chain constant region, or a fragment thereof. In some embodiments, the first anti-IMC antibody molecule and the second anti-IMC antibody molecule have a common light chain variable region.

In some embodiments the multispecific molecule further comprises a heavy chain constant region (e.g., an Fc region) chosen from the heavy chain constant regions of IgG1, IgG2, and IgG4, more particularly, the heavy chain constant region of human IgG1, IgG2 or IgG4. In some embodiments, the heavy chain constant region (e.g., an Fc region) is linked to, e.g., covalently linked to, one or both of the first anti-IMC antibody molecule and the second anti-IMC antibody molecule. In some embodiments, the heavy chain constant region (e.g., an Fc region) is altered, e.g., mutated, to increase or decrease one or more of: Fc receptor binding, antibody glycosylation, the number of cysteine residues, effector cell function, or complement function. In some embodiments, an interface of a first and second heavy chain constant regions (e.g., Fc region) is altered, e.g., mutated, to increase or decrease dimerization, e.g., relative to a non-engineered interface. In some embodiments, the dimerization of the heavy chain constant region (e.g., Fc region) is enhanced by providing an Fc interface of a first and a second Fc region with one or more of: a paired cavity-protuberance ("knob-in-a hole"), an electrostatic interaction, or a strand-exchange, such that a greater ratio of heteromultimer:homomultimer forms, e.g., relative to a non-engineered interface. In some embodiments, the heavy chain constant region (e.g., Fc region) comprises an amino acid substitution at a position chosen from one or more of 347, 349, 350, 351, 366, 368, 370, 392, 394, 395, 397, 398, 399, 405, 407, or 409, e.g., of the Fc region of human IgG1, numbered based on the Eu numbering system. In some embodiments, the heavy chain constant region (e.g., Fc region) comprises an amino acid substitution chosen from: T366S, L368A, or Y407V (e.g., corresponding to a cavity or hole), or T366W (e.g., corresponding to a protuberance or knob), or a combination thereof, numbered based on the Eu numbering system.

In some embodiments, the heavy chain constant region (e.g., an Fc region) comprises one or more mutations that increase or decrease one or more of: Fc receptor binding, antibody glycosylation, the number of cysteine residues, effector cell function, or complement function, relative to a naturally-existing heavy chain constant region. In some embodiments, the first anti-IMC antibody molecule comprises a first heavy chain constant region (e.g., a first Fc region) and the second anti-IMC antibody molecule comprises a second heavy chain constant region (e.g., a second Fc region), wherein the first heavy chain constant region comprises one or more mutations that increase heterodimerization of the first heavy chain constant region and the second heavy chain constant region, relative to a naturally-existing heavy chain constant region, and/or wherein the second heavy chain constant region comprises one or more mutations that increase heterodimerization of the second heavy chain constant region and the first heavy chain constant region, relative to a naturally-existing heavy chain constant region. In some embodiments, the first and the second heavy chain constant regions (e.g., first and second Fc regions) comprise one or more of: a paired cavity-protuberance ("knob-in-a hole"), an electrostatic interaction, or a strand-exchange, such that a greater ratio of heteromultimer:homomultimer forms, e.g., relative to naturally-existing heavy chain constant regions. In some embodiments, the first and/or second heavy chain constant region (e.g., a first and/or second Fc region, e.g., a first and/or second IgG1 Fc region) comprises an amino acid substitution at a position chosen from one or more of 347, 349, 350, 351, 366, 368, 370, 392, 394, 395, 397, 398, 399, 405, 407, or 409, numbered based on the Eu numbering system. In some embodiments, the first and/or second heavy chain constant region (e.g., a first and/or second Fc region, e.g., a first and/or second IgG1 Fc region) comprises an amino acid substitution chosen from: T366S, L368A, Y407V, or Y349C (e.g., corresponding to a cavity or hole), or T366W or S354C (e.g., corresponding to a protuberance or knob), or a combination thereof, numbered based on the Eu numbering system.

In some embodiments, the multispecific molecule further comprises a linker, e.g., a linker between one or more of: the first anti-IMC antibody molecule and the second anti-IMC antibody molecule, the first anti-IMC antibody molecule and the heavy chain constant region (e.g., the Fc region), or the second anti-IMC antibody molecule and the heavy chain constant region. In some embodiments, the linker is chosen from: a cleavable linker, a non-cleavable linker, a peptide linker, a flexible linker, a rigid linker, a helical linker, or a non-helical linker. In some embodiments, the linker is a peptide linker. In some embodiments, the peptide linker comprises Gly and Ser.

In some embodiments, the heavy chain constant region (e.g., Fc region) induces antibody dependent cellular cytotoxicity (ADCC).

In some embodiments, the first or the second TAM binding moiety is an antibody molecule that binds to CSF1R and comprises one, two, or three CDRs from the heavy chain variable region sequence of: SEQ ID NO: 48, SEQ ID NO: 66, or SEQ ID NO: 69, or a closely related CDR, e.g., CDRs which have at least one amino acid alteration, but not more than two, three or four alterations (e.g., substitutions, deletions, or insertions, e.g., conservative substitutions) from a CDR of SEQ ID NO: 48, SEQ ID NO: 66, or SEQ ID NO: 69; and/or comprises one, two, or three CDRs from the light chain variable region sequence of: SEQ ID NO: 50, SEQ ID NO: 67, or SEQ ID NO: 70, or a closely related CDR, e.g., CDRs which have at least one amino acid alteration, but not more than two, three or four alterations (e.g., substitutions, deletions, or insertions, e.g., conservative substitutions) from a CDR of SEQ ID NO: 50, SEQ ID NO: 67, or SEQ ID NO: 70. In some embodiments, the antibody molecule that binds to CSF1R comprises the heavy chain variable region sequence of: SEQ ID NO: 48, SEQ ID NO: 66, or SEQ ID NO: 69, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 48, SEQ ID NO: 66, or SEQ ID NO: 69; and/or comprises the light chain variable region sequence of: SEQ ID NO: 50, SEQ ID NO: 67, or SEQ ID NO: 70, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 50, SEQ ID NO: 67, or SEQ ID NO: 70.

In some embodiments, the first or the second TAM binding moiety is an antibody molecule that binds to CCR2 and comprises one, two, or three CDRs from the heavy chain variable region sequence of: SEQ ID NO: 44, SEQ ID NO: 54, SEQ ID NO: 59, SEQ ID NO: 62, SEQ ID NO: 64, or a closely related CDR, e.g., CDRs which have at least one amino acid alteration, but not more than two, three or four alterations (e.g., substitutions, deletions, or insertions, e.g., conservative substitutions) from a CDR of SEQ ID NO: 44, SEQ ID NO: 54, SEQ ID NO: 59, SEQ ID NO: 62, SEQ ID NO: 64; and/or comprises one, two, or three CDRs from the light chain variable region sequence of: SEQ ID NO: 45, SEQ ID NO: 57, SEQ ID NO: 60, SEQ ID NO: 63, SEQ ID NO: 65, or a closely related CDR, e.g., CDRs which have at least one amino acid alteration, but not more than two, three or four alterations (e.g., substitutions, deletions, or insertions, e.g., conservative substitutions) from a CDR of SEQ ID NO: 45, SEQ ID NO: 57, SEQ ID NO: 60, SEQ ID NO: 63, SEQ ID NO: 65. In some embodiments, the antibody molecule that binds to CCR2 comprises the heavy chain variable region sequence of: SEQ ID NO: 44, SEQ ID NO: 54, SEQ ID NO: 59, SEQ ID NO: 62, SEQ ID NO: 64, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 44, SEQ ID NO: 54, SEQ ID NO: 59, SEQ ID NO: 62, SEQ ID NO: 64; and/or comprises the light chain variable region sequence of: SEQ ID NO: 45, SEQ ID NO: 57, SEQ ID NO: 60, SEQ ID NO: 63, SEQ ID NO: 65, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 45, SEQ ID NO: 57, SEQ ID NO: 60, SEQ ID NO: 63, SEQ ID NO: 65.

In one embodiment, the first TAM binding moiety is an antibody molecule that binds to CCR2 and comprises one, two, or three CDRs from the heavy chain variable region sequence of: SEQ ID NO: 44, or a closely related CDR, e.g., CDRs which have at least one amino acid alteration, but not more than two, three or four alterations (e.g., substitutions, deletions, or insertions, e.g., conservative substitutions) from a CDR of SEQ ID NO: 44; and/or comprises one, two, or three CDRs from the light chain variable region sequence of: SEQ ID NO: 45, or a closely related CDR, e.g., CDRs which have at least one amino acid alteration, but not more than two, three or four alterations (e.g., substitutions, deletions, or insertions, e.g., conservative substitutions) from a CDR of SEQ ID NO: 45; and the second TAM binding moiety is an antibody molecule that binds to CSF1R and comprises one, two, or three CDRs from the heavy chain variable region sequence of: SEQ ID NO: 48, or a closely related CDR, e.g., CDRs which have at least one amino acid alteration, but not more than two, three or four alterations (e.g., substitutions, deletions, or insertions, e.g., conservative substitutions) from a CDR of SEQ ID NO: 48; and/or comprises one, two, or three CDRs from the light chain variable region sequence of: SEQ ID NO: 50, or a closely related CDR, e.g., CDRs which have at least one amino acid alteration, but not more than two, three or four alterations (e.g., substitutions, deletions, or insertions, e.g., conservative substitutions) from a CDR of SEQ ID NO: 50.

In one embodiment, the first TAM binding moiety is an antibody molecule that binds to CCR2 and comprises one, two, or three CDRs from the heavy chain variable region sequence of: SEQ ID NO: 54, or a closely related CDR, e.g., CDRs which have at least one amino acid alteration, but not more than two, three or four alterations (e.g., substitutions, deletions, or insertions, e.g., conservative substitutions) from a CDR of SEQ ID NO: 54; and/or comprises one, two, or three CDRs from the light chain variable region sequence of: SEQ ID NO: 57, or a closely related CDR, e.g., CDRs which have at least one amino acid alteration, but not more than two, three or four alterations (e.g., substitutions, deletions, or insertions, e.g., conservative substitutions) from a CDR of SEQ ID NO: 57; and the second TAM binding moiety is an antibody molecule that binds to CSF1R and comprises one, two, or three CDRs from the heavy chain variable region sequence of: SEQ ID NO: 66, or a closely related CDR, e.g., CDRs which have at least one amino acid alteration, but not more than two, three or four alterations (e.g., substitutions, deletions, or insertions, e.g., conservative substitutions) from a CDR of SEQ ID NO: 66; and/or comprises one, two, or three CDRs from the light chain variable region sequence of: SEQ ID NO: 67, or a closely related CDR, e.g., CDRs which have at least one amino acid alteration, but not more than two, three or four alterations (e.g., substitutions, deletions, or insertions, e.g., conservative substitutions) from a CDR of SEQ ID NO: 67.

In one embodiment, the first TAM binding moiety is an antibody molecule that binds to CCR2 and comprises one, two, or three CDRs from the heavy chain variable region sequence of: SEQ ID NO: 54, or a closely related CDR, e.g., CDRs which have at least one amino acid alteration, but not more than two, three or four alterations (e.g., substitutions, deletions, or insertions, e.g., conservative substitutions) from a CDR of SEQ ID NO: 54; and/or comprises one, two, or three CDRs from the light chain variable region sequence of: SEQ ID NO: 57, or a closely related CDR, e.g., CDRs which have at least one amino acid alteration, but not more than two, three or four alterations (e.g., substitutions, deletions, or insertions, e.g., conservative substitutions) from a CDR of SEQ ID NO: 57; and the second TAM binding moiety is an antibody molecule that binds to CSF1R and comprises one, two, or three CDRs from the heavy chain variable region sequence of: SEQ ID NO: 69, or a closely related CDR, e.g., CDRs which have at least one amino acid alteration, but not more than two, three or four alterations (e.g., substitutions, deletions, or insertions, e.g., conservative substitutions) from a CDR of SEQ ID NO: 69; and/or comprises one, two, or three CDRs from the light chain variable region sequence of: SEQ ID NO: 70, or a closely related CDR, e.g., CDRs which have at least one amino acid alteration, but not more than two, three or four alterations (e.g., substitutions, deletions, or insertions, e.g., conservative substitutions) from a CDR of SEQ ID NO: 70.

In one embodiment, the first TAM binding moiety is an antibody molecule that binds to CCR2 and comprises one, two, or three CDRs from the heavy chain variable region sequence of: SEQ ID NO: 59, or a closely related CDR, e.g., CDRs which have at least one amino acid alteration, but not more than two, three or four alterations (e.g., substitutions, deletions, or insertions, e.g., conservative substitutions) from a CDR of SEQ ID NO: 59; and/or comprises one, two, or three CDRs from the light chain variable region sequence of: SEQ ID NO: 60, or a closely related CDR, e.g., CDRs which have at least one amino acid alteration, but not more than two, three or four alterations (e.g., substitutions, deletions, or insertions, e.g., conservative substitutions) from a CDR of SEQ ID NO: 60; and the second TAM binding moiety is an antibody molecule that binds to CSF1R and comprises one, two, or three CDRs from the heavy chain variable region sequence of: SEQ ID NO: 66, or a closely related CDR, e.g., CDRs which have at least one amino acid alteration, but not more than two, three or four alterations (e.g., substitutions, deletions, or insertions, e.g., conservative substitutions) from a CDR of SEQ ID NO: 66; and/or comprises one, two, or three CDRs from the light chain variable region sequence of: SEQ ID NO: 67, or a closely related CDR, e.g., CDRs which have at least one amino acid alteration, but not more than two, three or four alterations (e.g., substitutions, deletions, or insertions, e.g., conservative substitutions) from a CDR of SEQ ID NO: 67.

In one embodiment, the first TAM binding moiety is an antibody molecule that binds to CCR2 and comprises one, two, or three CDRs from the heavy chain variable region sequence of: SEQ ID NO: 59, or a closely related CDR, e.g., CDRs which have at least one amino acid alteration, but not more than two, three or four alterations (e.g., substitutions, deletions, or insertions, e.g., conservative substitutions) from a CDR of SEQ ID NO: 59; and/or comprises one, two, or three CDRs from the light chain variable region sequence of: SEQ ID NO: 60, or a closely related CDR, e.g., CDRs which have at least one amino acid alteration, but not more than two, three or four alterations (e.g., substitutions, deletions, or insertions, e.g., conservative substitutions) from a CDR of SEQ ID NO: 60; and the second TAM binding moiety is an antibody molecule that binds to CSF1R and comprises one, two, or three CDRs from the heavy chain variable region sequence of: SEQ ID NO: 69, or a closely related CDR, e.g., CDRs which have at least one amino acid alteration, but not more than two, three or four alterations (e.g., substitutions, deletions, or insertions, e.g., conservative substitutions) from a CDR of SEQ ID NO: 69; and/or comprises one, two, or three CDRs from the light chain variable region sequence of: SEQ ID NO: 70, or a closely related CDR, e.g., CDRs which have at least one amino acid alteration, but not more than two, three or four alterations (e.g., substitutions, deletions, or insertions, e.g., conservative substitutions) from a CDR of SEQ ID NO: 70.

In one embodiment, the first TAM binding moiety is an antibody molecule that binds to CCR2 and comprises one, two, or three CDRs from the heavy chain variable region sequence of: SEQ ID NO: 62, or a closely related CDR, e.g., CDRs which have at least one amino acid alteration, but not more than two, three or four alterations (e.g., substitutions, deletions, or insertions, e.g., conservative substitutions) from a CDR of SEQ ID NO: 62; and/or comprises one, two, or three CDRs from the light chain variable region sequence of: SEQ ID NO: 63, or a closely related CDR, e.g., CDRs which have at least one amino acid alteration, but not more than two, three or four alterations (e.g., substitutions, deletions, or insertions, e.g., conservative substitutions) from a CDR of SEQ ID NO: 63; and the second TAM binding moiety is an antibody molecule that binds to CSF1R and comprises one, two, or three CDRs from the heavy chain variable region sequence of: SEQ ID NO: 66, or a closely related CDR, e.g., CDRs which have at least one amino acid alteration, but not more than two, three or four alterations (e.g., substitutions, deletions, or insertions, e.g., conservative substitutions) from a CDR of SEQ ID NO: 66; and/or comprises one, two, or three CDRs from the light chain variable region sequence of: SEQ ID NO: 67, or a closely related CDR, e.g., CDRs which have at least one amino acid alteration, but not more than two, three or four alterations (e.g., substitutions, deletions, or insertions, e.g., conservative substitutions) from a CDR of SEQ ID NO: 67.

In one embodiment, the first TAM binding moiety is an antibody molecule that binds to CCR2 and comprises one, two, or three CDRs from the heavy chain variable region sequence of: SEQ ID NO: 62, or a closely related CDR, e.g., CDRs which have at least one amino acid alteration, but not more than two, three or four alterations (e.g., substitutions, deletions, or insertions, e.g., conservative substitutions) from a CDR of SEQ ID NO: 62; and/or comprises one, two, or three CDRs from the light chain variable region sequence of: SEQ ID NO: 63, or a closely related CDR, e.g., CDRs which have at least one amino acid alteration, but not more than two, three or four alterations (e.g., substitutions, deletions, or insertions, e.g., conservative substitutions) from a CDR of SEQ ID NO: 63; and the second TAM binding moiety is an antibody molecule that binds to CSF1R and comprises one, two, or three CDRs from the heavy chain variable region sequence of: SEQ ID NO: 69, or a closely related CDR, e.g., CDRs which have at least one amino acid alteration, but not more than two, three or four alterations (e.g., substitutions, deletions, or insertions, e.g., conservative substitutions) from a CDR of SEQ ID NO: 69; and/or comprises one, two, or three CDRs from the light chain variable region sequence of: SEQ ID NO: 70, or a closely related CDR, e.g., CDRs which have at least one amino acid alteration, but not more than two, three or four alterations (e.g., substitutions, deletions, or insertions, e.g., conservative substitutions) from a CDR of SEQ ID NO: 70.

In one embodiment, the first TAM binding moiety is an antibody molecule that binds to CCR2 and comprises one, two, or three CDRs from the heavy chain variable region sequence of: SEQ ID NO: 64, or a closely related CDR, e.g., CDRs which have at least one amino acid alteration, but not more than two, three or four alterations (e.g., substitutions, deletions, or insertions, e.g., conservative substitutions) from a CDR of SEQ ID NO: 64; and/or comprises one, two, or three CDRs from the light chain variable region sequence of: SEQ ID NO: 65, or a closely related CDR, e.g., CDRs which have at least one amino acid alteration, but not more than two, three or four alterations (e.g., substitutions, deletions, or insertions, e.g., conservative substitutions) from a CDR of SEQ ID NO: 65; and the second TAM binding moiety is an antibody molecule that binds to CSF1R and comprises one, two, or three CDRs from the heavy chain variable region sequence of: SEQ ID NO: 66, or a closely related CDR, e.g., CDRs which have at least one amino acid alteration, but not more than two, three or four alterations (e.g., substitutions, deletions, or insertions, e.g., conservative substitutions) from a CDR of SEQ ID NO: 66; and/or comprises one, two, or three CDRs from the light chain variable region sequence of: SEQ ID NO: 67, or a closely related CDR, e.g., CDRs which have at least one amino acid alteration, but not more than two, three or four alterations (e.g., substitutions, deletions, or insertions, e.g., conservative substitutions) from a CDR of SEQ ID NO: 67.

In one embodiment, the first TAM binding moiety is an antibody molecule that binds to CCR2 and comprises one, two, or three CDRs from the heavy chain variable region sequence of: SEQ ID NO: 64, or a closely related CDR, e.g., CDRs which have at least one amino acid alteration, but not more than two, three or four alterations (e.g., substitutions, deletions, or insertions, e.g., conservative substitutions) from a CDR of SEQ ID NO: 64; and/or comprises one, two, or three CDRs from the light chain variable region sequence of: SEQ ID NO: 65, or a closely related CDR, e.g., CDRs which have at least one amino acid alteration, but not more than two, three or four alterations (e.g., substitutions, deletions, or insertions, e.g., conservative substitutions) from a CDR of SEQ ID NO: 65; and the second TAM binding moiety is an antibody molecule that binds to CSF1R and comprises one, two, or three CDRs from the heavy chain variable region sequence of: SEQ ID NO: 69, or a closely related CDR, e.g., CDRs which have at least one amino acid alteration, but not more than two, three or four alterations (e.g., substitutions, deletions, or insertions, e.g., conservative substitutions) from a CDR of SEQ ID NO: 69; and/or comprises one, two, or three CDRs from the light chain variable region sequence of: SEQ ID NO: 70, or a closely related CDR, e.g., CDRs which have at least one amino acid alteration, but not more than two, three or four alterations (e.g., substitutions, deletions, or insertions, e.g., conservative substitutions) from a CDR of SEQ ID NO: 70.

In one embodiment, the first TAM binding moiety is an antibody molecule that binds to CCR2 and comprises the heavy chain variable region sequence of: SEQ ID NO: 44, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 44; and/or comprises the light chain variable region sequence of: SEQ ID NO: 45, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 45; and the second TAM binding moiety is an antibody molecule that binds to CSF1R and comprises the heavy chain variable region sequence of: SEQ ID NO: 48, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 48; and/or comprises the light chain variable region sequence of: SEQ ID NO: 50, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 50.

In one embodiment, the first TAM binding moiety is an antibody molecule that binds to CCR2 and comprises the heavy chain variable region sequence of: SEQ ID NO: 54, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 54; and/or comprises the light chain variable region sequence of: SEQ ID NO: 57, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 57; and the second TAM binding moiety is an antibody molecule that binds to CSF1R and comprises the heavy chain variable region sequence of: SEQ ID NO: 66, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 66; and/or comprises the light chain variable region sequence of: SEQ ID NO: 67, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 67.

In one embodiment, the first TAM binding moiety is an antibody molecule that binds to CCR2 and comprises the heavy chain variable region sequence of: SEQ ID NO: 54, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 54; and/or comprises the light chain variable region sequence of: SEQ ID NO: 57, or a an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 57; and the second TAM binding moiety is an antibody molecule that binds to CSF1R and comprises the heavy chain variable region sequence of: SEQ ID NO: 69, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 69; and/or comprises the light chain variable region sequence of: SEQ ID NO: 70, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 70.

In one embodiment, the first TAM binding moiety is an antibody molecule that binds to CCR2 and comprises the heavy chain variable region sequence of: SEQ ID NO: 59, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 59; and/or comprises the light chain variable region sequence of: SEQ ID NO: 60, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 60; and the second TAM binding moiety is an antibody molecule that binds to CSF1R and comprises the heavy chain variable region sequence of: SEQ ID NO: 66, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 66; and/or comprises the light chain variable region sequence of: SEQ ID NO: 67, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 67.

In one embodiment, the first TAM binding moiety is an antibody molecule that binds to CCR2 and comprises the heavy chain variable region sequence of: SEQ ID NO: 59, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 59; and/or comprises the light chain variable region sequence of: SEQ ID NO: 60, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 60; and the second TAM binding moiety is an antibody molecule that binds to CSF1R and comprises the heavy chain variable region sequence of: SEQ ID NO: 69, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 69; and/or comprises the light chain variable region sequence of: SEQ ID NO: 70, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 70.

In one embodiment, the first TAM binding moiety is an antibody molecule that binds to CCR2 and comprises the heavy chain variable region sequence of: SEQ ID NO: 62, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 62; and/or comprises the light chain variable region sequence of: SEQ ID NO: 63, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 63; and the second TAM binding moiety is an antibody molecule that binds to CSF1R and comprises the heavy chain variable region sequence of: SEQ ID NO: 66, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 66; and/or comprises the light chain variable region sequence of: SEQ ID NO: 67, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 67.

In one embodiment, the first TAM binding moiety is an antibody molecule that binds to CCR2 and comprises the heavy chain variable region sequence of: SEQ ID NO: 62, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 62; and/or comprises the light chain variable region sequence of: SEQ ID NO: 63, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 63; and the second TAM binding moiety is an antibody molecule that binds to CSF1R and comprises the heavy chain variable region sequence of: SEQ ID NO: 69, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 69; and/or comprises the light chain variable region sequence of: SEQ ID NO: 70, an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 70.

In one embodiment, the first TAM binding moiety is an antibody molecule that binds to CCR2 and comprises the heavy chain variable region sequence of: SEQ ID NO: 64, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 64; and/or comprises the light chain variable region sequence of: SEQ ID NO: 65, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 65; and the second TAM binding moiety is an antibody molecule that binds to CSF1R and comprises the heavy chain variable region sequence of: SEQ ID NO: 66, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 66; and/or comprises the light chain variable region sequence of: SEQ ID NO: 67, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 67.

In one embodiment, the first TAM binding moiety is an antibody molecule that binds to CCR2 and comprises the heavy chain variable region sequence of: SEQ ID NO: 64, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 64; and/or comprises the light chain variable region sequence of: SEQ ID NO: 65, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 65; and the second TAM binding moiety is an antibody molecule that binds to CSF1R and comprises the heavy chain variable region sequence of: SEQ ID NO: 69, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 69; and/or comprises the light chain variable region sequence of: SEQ ID NO: 70, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 70.

In some embodiments, the first or the second TAM binding moiety is an antibody molecule that binds to PD-L1 and comprises one, two, or three CDRs from the heavy chain variable region sequence of: SEQ ID NO: 109, SEQ ID NO: 111, or SEQ ID NO: 113, or a closely related CDR, e.g., CDRs which have at least one amino acid alteration, but not more than two, three or four alterations (e.g., substitutions, deletions, or insertions, e.g., conservative substitutions) from a CDR of SEQ ID NO: 109, SEQ ID NO: 111, or SEQ ID NO: 113; and/or comprises one, two, or three CDRs from the light chain variable region sequence of: SEQ ID NO: 110, SEQ ID NO: 112, or SEQ ID NO: 114, or a closely related CDR, e.g., CDRs which have at least one amino acid alteration, but not more than two, three or four alterations (e.g., substitutions, deletions, or insertions, e.g., conservative substitutions) from a CDR of SEQ ID NO: 110, SEQ ID NO: 112, or SEQ ID NO: 114. In some embodiments, the antibody molecule that binds to PD-L1 comprises the heavy chain variable region sequence of: SEQ ID NO: 109, SEQ ID NO: 111, or SEQ ID NO: 113, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 109, SEQ ID NO: 111, or SEQ ID NO: 113); and/or comprises the light chain variable region sequence of: SEQ ID NO: 110, SEQ ID NO: 112, or SEQ ID NO: 114, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 110, SEQ ID NO: 112, or SEQ ID NO: 114).

In some embodiments, (i) the first IMC binding moiety binds to a first antigen (e.g., CSF1R, CCR2, CXCR2, CD86, CD163, CX3CR1, MARCO, CD204, CD52, folate receptor beta, or PD-L1) monovalently, and/or (ii) the second IMC binding moiety binds to a second antigen (e.g., CCR2, CSF1R, CXCR2, CD86, CD163, CX3CR1, MARCO, CD204, CD52, folate receptor beta, or PD-L1) monovalently, wherein the first antigen is different from the second antigen.

In some embodiments, (i) the multispecific molecule binds to a first antigen (e.g., CSF1R, CCR2, CXCR2, CD86, CD163, CX3CR1, MARCO, CD204, CD52, folate receptor beta, or PD-L1) monovalently, and/or (ii) the multispecific molecule binds to a second antigen (e.g., CCR2, CSF1R, CXCR2, CD86, CD163, CX3CR1, MARCO, CD204, CD52, folate receptor beta, or PD-L1) monovalently, wherein the first antigen is different from the second antigen.

In some embodiments, (i) the multispecific molecule inhibits a first antigen in the presence of a second antigen, optionally wherein the multispecific molecule reduces an activity of the first antigen in a cell, e.g., by at least 40, 50, 60, 70, 80, or 90%, when the cell expresses both the first antigen and the second antigen on the cell surface, and/or (ii) the multispecific molecule does not inhibit or does not substantially inhibit the first antigen in the absence of the second antigen, optionally wherein the multispecific molecule does not reduce an activity of the first antigen, or does not reduce an activity of the first antigen by more than 2, 4, 6, 8, 10, or 15%, when the cell expresses the first antigen but not the second antigen on the cell surface.

In some embodiments, (i) the multispecific molecule inhibits a second antigen in the presence of a first antigen, optionally wherein the multispecific molecule reduces an activity of the second antigen in a cell, e.g., by at least 40, 50, 60, 70, 80, or 90%, when the cell expresses both the first antigen and the second antigen on the cell surface, and/or (ii) the multispecific molecule does not inhibit or does not substantially inhibit the second antigen in the absence of the first antigen, optionally wherein the multispecific molecule does not reduce an activity of the second antigen, or does not reduce an activity of the second antigen by more than 2, 4, 6, 8, 10, or 15%, when the cell expresses the second antigen but not the first antigen on the cell surface.

In some embodiments, the multispecific molecule further comprises one or more additional binding moieties (e.g., a third binding moiety, a fourth binding moiety, (e.g., a trispecific or a tetraspecific molecule). In some embodiments, the multispecific molecule further comprises one or more additional binding moieties (e.g., a third binding moiety, a fourth binding moiety, (e.g., a trispecific or a tetraspecific molecule). In some embodiments, the multispecific molecule comprises a third TAM binding moiety (e.g., an antibody molecule), wherein the third TAM binding moiety is different from the first and the second TAM binding moieties. In some embodiments, the first TAM binding moiety binds to human CSF1R, the second TAM binding moiety binds to human CCR2, and the third TAM binding moiety binds to CXCR2.

In some embodiments, the multispecific molecule comprises a third binding moiety (e.g., antibody molecule) that is a tumor targeting moiety. In some embodiments, the tumor targeting moiety binds to PD-L1, mesothelin, CD47, ganglioside 2 (GD2), prostate stem cell antigen (PSCA), prostate specific membrane antigen (PMSA), prostate-specific antigen (PSA), carcinoembryonic antigen (CEA), Ron Kinase, c-Met, Immature laminin receptor, TAG-72, BING-4, Calcium-activated chloride channel 2, Cyclin-B1, 9D7, Ep-CAM, EphA3, Her2/neu, Telomerase, SAP-1, Survivin, NY-ESO-1/LAGE-1, PRAME, SSX-2, Melan-A/MART-1, Gp100/pmel17, Tyrosinase, TRP-1/-2, MC1R, β-catenin, BRCA1/2, CDK4, CML66, Fibronectin, p53, Ras, TGF-B receptor, AFP, ETA, MAGE, MUC-1, CA-125, BAGE, GAGE, NY-ESO-1, β-catenin, CDK4, CDC27, CD47, α actinin-4, TRP1/gp75, TRP2, gp100, Melan-A/MART1, gangliosides, WT1, EphA3, Epidermal growth factor receptor (EGFR), CD20, MART-2, MART-1, MUC1, MUC2, MUM1, MUM2, MUM3, NA88-1, NPM, OA1, OGT, RCC, RUI1, RUI2, SAGE, TRG, TRP1, TSTA, Folate receptor alpha, L1-CAM, CAIX, EGFRvIII, gpA33, GD3, GM2, VEGFR, Intergrins (Integrin alphaVbeta3, Integrin alpha5Beta1), Carbohydrates (Le), IGF1R, EPHA3, TRAILR1, TRAILR2, or RANKL.

In some embodiments, the multispecific molecule is a bispecific molecule comprising a first and a second non-contiguous polypeptides, wherein: (i) the first polypeptide includes, e.g., in the N- to C-orientation, the first TAM binding moiety (e.g., an antibody molecule (e.g., a first portion of a first antigen domain, e.g., a first VH-CH1 of a Fab molecule)), that binds to, e.g., a first TAM antigen, e.g., CSF1R, CCR2, CXCR2, or PD-L1, connected, optionally via a linker to, a first domain that promotes association between the first and the second polypeptide (e.g., a first immunoglobulin constant domain (e.g., a first Fc molecule as described herein); (ii) the second polypeptide includes, e.g., in the N- to C-orientation, the second TAM binding moiety (e.g., an antibody molecule, e.g., a scFv that binds to, e.g., a second TAM antigen, e.g., CCR2, CSF1R, CXCR2, or PD-L1)), connected, optionally, via a linker to, a second domain that promotes association between the first and the second polypeptide (e.g., a second immunoglobulin constant domain (e.g., a second Fc molecule as described herein); and (iii) the third polypeptide includes, e.g., in the N- to C-orientation, a second portion of the first antigen domain, e.g., a first VL-CL of the Fab, that binds to the first TAM antigen, e.g., wherein the third polypeptide associates non-covalently to the first polypeptide; and (iv) the fourth polypeptide includes, e.g., in the N- to C-orientation, a second portion of the second antigen domain, e.g., a second VL-CL of the Fab, that binds to the second TAM antigen, e.g., wherein the fourth polypeptide associates non-covalently to the second polypeptide. In some embodiments, the first and the second polypeptides are homo- or heterodimers.

In some embodiments, the multispecific molecule is a bispecific molecule, wherein:
  (i) the first TAM binding moiety (e.g., a binding moiety that binds to a first TAM antigen, e.g., CSF1R, CCR2, or CXCR2) comprises a first and a second non-contiguous polypeptides, and
  (ii) the second TAM binding moiety (e.g., a binding moiety that binds to a second TAM antigen, e.g., CSF1R, CCR2, or CXCR2) comprises a third and a fourth non-contiguous polypeptides, wherein:
    (a) the first polypeptide comprises, e.g., in the N- to C-orientation, a first VH, a first CH1, connected, optionally via a linker, to a first domain (e.g., a first Fc region) that promotes association between the first and the third polypeptides,
    (b) the second polypeptide comprises, e.g., in the N- to C-orientation, a first VL and a first CL,
    (c) the third polypeptide comprises, e.g., in the N- to C-orientation, a second VH, a second CH1, connected, optionally via a linker, to a second domain (e.g., a second Fc region) that promotes association between the first and the third polypeptides, and
    (d) the fourth polypeptide comprises, e.g., in the N- to C-orientation, a second VL and a second CL. In some embodiments, the first and the second domains (e.g., the first and the second Fc regions) form a homo- or heterodimer.

In one aspect, the invention provides an isolated multispecific, e.g., a bispecific, molecule, comprising (i) an anti-CSF1R binding moiety (e.g., an anti-CSF1R antibody molecule); and (ii) an anti-CCR2 binding moiety (e.g., an anti-CCR2 antibody molecule). Without wishing to be bound by theory, the anti-CSF1R/anti-CCR2 multispecific molecule may preferentially bind to a CSF1R-positive, CCR2-positive cell relative to a CSF1R-positve, CCR2-negative cell, or a CSF1R-negative, CCR2-positive cell. Exemplary CSF1R-positive, CCR2-positive cell include, but are not limited to, tumor-associated macrophages (TAMs) and myeloid derived suppressor cells (MDSCs). Exemplary CSF1R-positive, CCR2-negative cells include, but are not limited to, tissue-resident macrophages (e.g., Kupffer cells), and Langerhans cells. Exemplary CSF1R-negative, CCR2-positive cells include, but are not limited to, T cells (e.g., activated T cells, e.g., activated CD4+ and/or CD8+ T cells), NK cells, and neutrophils. Without wishing to be bound by theory, the anti-CSF1R/anti-CCR2 multispecific molecule may preferentially bind to CSF1R-positive, CCR2-positive cells (e.g., pro-tumorigenic TAMs or MDSCs) relative to CSF1R-positve, CCR2-negative cells (e.g., tissue-resident macrophages (e.g., Kupffer cells), or Langerhans cells), or CSF1R-negative, CCR2-positive cells (e.g., activated T cells or NK cells).

In some embodiments, the anti-CSF1R/anti-CCR2 multispecific molecule, when it binds to a target cell, may induce antibody-dependent cellular cytotoxicity (ADCC) or complement-dependent cytotoxicity (CDC) of the target cell. In some embodiments, the anti-CSF1R/anti-CCR2 multispecific molecule may preferentially bind to and reduce the number of immunosuppressive myeloid cells in the tumor microenvironment (e.g., TAMs or MDSCs), while sparing homeostatic myeloid cells (e.g., tissue-resident macrophages (e.g., Kupffer cells)) and other anti-tumor immune cells (e.g., activated T cells and NK cells). Depletion of homeostatic myeloid cells may be partially responsible for adverse events in patients receiving anti-CSF1R antibody therapies.

In some embodiments, the multispecific molecule has one or more (e.g., 1, 2, 3, 4, 5, 6, 7, 8, 9, 10, 11, 12, 13, or more) of the following properties:
  (i) the multispecific molecule preferentially binds to a CSF1R-positive, CCR2-positive cell relative to a CSF1R-positve, CCR2-negative cell, or a CSF1R-negative, CCR2-positive cell, e.g., the binding of the multispecific molecule to the CSF1R-positive, CCR2-positive cell is at least 2, 4, 6, 8, 10, 15, 20, or 25-fold stronger than the binding of the multispecific molecule to the CSF1R-positve, CCR2-negative cell, or the CSF1R-negative, CCR2-positive cell, e.g., as measured using a flow cytometry analysis, e.g., as measured using methods described in Example 2 with respect to FIG. 1;
  (ii) the multispecific molecule preferentially binds to a CSF1R-positive, CCR2-positive cell relative to a CSF1R-positve, CCR2-negative cell, e.g., the EC50 of the multispecific molecule for binding to a CSF1R-positive, CCR2-positive cell is no more than 60, 50, 40, 30, 20, or 10% of the EC50 of the multispecific molecule for binding to a CSF1R-positve, CCR2-negative cell, e.g., as measured using a flow cytometry analysis, e.g., as measured using methods described in Example 2 with respect to FIG. 1;
  (iii) the multispecific molecule preferentially binds to a CSF1R-positive, CCR2-positive cell relative to a CSF1R-negative, CCR2-positive cell, e.g., the EC50 of the multispecific molecule for binding to a CSF1R-positive, CCR2-positive cell is no more than 50, 40, 30, 20, 10, or 5% of the EC50 of the multispecific molecule for binding to a CSF1R-negative, CCR2-positive cell, e.g., as measured using a flow cytometry analysis, e.g., as measured using methods described in Example 2 with respect to FIG. 1;
  (iv) the multispecific molecule preferentially binds to tumor-associated macrophages (TAMs) or myeloid derived suppressor cells (MDSCs) relative to T cells, NK cells, neutrophils, tissue-resident macrophages (e.g., Kupffer cells), or Langerhans cells, e.g., the binding of the multispecific molecule to TAMs or MDSCs is at least 2, 4, 6, 8, 10, 15, 20, or 25-fold stronger than the binding of the multispecific molecule to T cells, NK cells, neutrophils, tissue-resident macrophages (e.g., Kupffer cells), or Langerhans cells, e.g., as measured using a flow cytometry analysis, e.g., as measured using methods described in Example 6 with respect to FIG. 5;
  (v) the multispecific molecule inhibits monocyte migration, e.g., monocyte chemoattractant protein 1 (MCP1)-induced monocyte migration, e.g., reduces MCP1-induced monocyte migration by at least 40, 50, 60, or 70%, e.g., as measured using a transwell plate migration assay, e.g., as measured using methods described in Example 3 with respect to FIG. 2;
  (vi) the multispecific molecule inhibits the proliferation of macrophages, e.g., bone marrow-derived macrophages, e.g., CSF-1-induced proliferation of bone marrow-derived macrophages, e.g., reduces CSF-1-induced proliferation of bone marrow-derived macrophages by at least 50, 60, 70, or 80%, e.g., as measured using a cell proliferation MTT assay, e.g., as measured using methods described in Example 4 with respect to FIG. 3B;

(vii) the multispecific molecule does not inhibit or does not substantially inhibit the differentiation of monocytes, e.g., bone marrow-derived monocytes, e.g., CSF-1-induced differentiation of bone marrow-derived monocytes, e.g., does not reduce CSF-1-induced differentiation of bone marrow-derived monocytes by more than 2, 4, 6, 8, or 10%, e.g., as measured using a flow cytometry analysis, e.g., as measured using methods described in Example 5 with respect to FIG. 4;

(viii) the multispecific molecule depletes suppressive myeloid cells, e.g., TAMs or MDSCs, e.g., reduces the number of suppressive myeloid cells, e.g., TAMs or MDSCs, by at least 80, 85, 90, 95, 99, or 99.5%, in vivo, e.g., as measured using a flow cytometry analysis, e.g., as measured using methods described in Example 7 with respect to FIG. 6;

(ix) the multispecific molecule does not deplete or does not substantially deplete tissue-resident macrophages, e.g., Kupffer cells, e.g., does not reduce the number of tissue-resident macrophages, e.g., Kupffer cells, by more than 4, 6, 8, 10, or 15%, in vivo, e.g., as measured using an immunohistochemistry analysis, e.g., as measured using methods described in Example 8 with respect to FIGS. 7B and 7D;

(x) the multispecific molecule does not inhibit or does not substantially inhibit CSF-1 dependent cell survival of CSF1R-positive, CCR2-negative cells, e.g., does not reduce CSF-1 dependent cell survival of CSF1R-positive, CCR2-negative cells by more than 5, 10, or 15%, e.g., as measured using a cell viability MTT assay, e.g., as measured using methods described in Example 9 with respect to FIG. 8A;

(xi) the multispecific molecule increases CD8+ T cell tumor infiltration in vivo, e.g., increases % CD8+ T cells in CD3+ T cells in tumor by at least 1.5, 2, or 2.5-fold, e.g., as measured using a flow cytometry analysis, e.g., as measured using methods described in Example 10 with respect to FIG. 9;

(xii) the multispecific molecule reduces Treg frequency in tumor in vivo, e.g., reduces Treg frequency in tumor by at least 15, 20, 25, or 30%, e.g., as measured using a flow cytometry analysis, e.g., as measured using methods described in Example 11 with respect to FIG. 10A;

(xiii) the multispecific molecule increases the CD8+ T cell/Treg ratio in tumor in vivo, e.g., increases the CD8+ T cell/Treg ratio in tumor by at least 2.5, 3, 3.5, 4, or 4.5-fold, e.g., as measured using a flow cytometry analysis, e.g., as measured using methods described in Example 11 with respect to FIG. 10B; or (xiv) the multispecific molecule reduces tumor growth and/or increases survival of a tumor-bearing animal, e.g., as measured using methods described in Example 12 with respect to FIGS. 11A and 11B.

In some embodiments, the multispecific molecule preferentially binds to a CSF1R-positive, CCR2-positive cell relative to a CSF1R-positve, CCR2-negative cell, or a CSF1R-negative, CCR2-positive cell, e.g., the binding of the multispecific molecule to the CSF1R-positive, CCR2-positive cell is at least 2, 4, 6, 8, 10, 15, 20, or 25-fold stronger than the binding of the multispecific molecule to the CSF1R-positve, CCR2-negative cell, or the CSF1R-negative, CCR2-positive cell, e.g., as measured using a flow cytometry analysis, e.g., as measured using methods described in Example 2 with respect to FIG. 1.

In some embodiments, the multispecific molecule preferentially binds to a CSF1R-positive, CCR2-positive cell relative to a CSF1R-positve, CCR2-negative cell, e.g., the EC50 of the multispecific molecule for binding to a CSF1R-positive, CCR2-positive cell is no more than 60, 50, 40, 30, 20, or 10% of the EC50 of the multispecific molecule for binding to a CSF1R-positve, CCR2-negative cell, e.g., as measured using a flow cytometry analysis, e.g., as measured using methods described in Example 2 with respect to FIG. 1.

In some embodiments, the multispecific molecule preferentially binds to a CSF1R-positive, CCR2-positive cell relative to a CSF1R-negative, CCR2-positive cell, e.g., the EC50 of the multispecific molecule for binding to a CSF1R-positive, CCR2-positive cell is no more than 50, 40, 30, 20, 10, or 5% of the EC50 of the multispecific molecule for binding to a CSF1R-negative, CCR2-positive cell, e.g., as measured using a flow cytometry analysis, e.g., as measured using methods described in Example 2 with respect to FIG. 1.

In some embodiments, the multispecific molecule preferentially binds to tumor-associated macrophages (TAMs) or myeloid derived suppressor cells (MDSCs) relative to T cells, NK cells, neutrophils, tissue-resident macrophages (e.g., Kupffer cells), or Langerhans cells, e.g., the binding of the multispecific molecule to TAMs or MDSCs is at least 2, 4, 6, 8, 10, 15, 20, or 25-fold stronger than the binding of the multispecific molecule to T cells, NK cells, neutrophils, tissue-resident macrophages (e.g., Kupffer cells), or Langerhans cells, e.g., as measured using a flow cytometry analysis, e.g., as measured using methods described in Example 6 with respect to FIG. 5.

In some embodiments, the multispecific molecule inhibits monocyte migration, e.g., monocyte chemoattractant protein 1 (MCP1)-induced monocyte migration, e.g., reduces MCP1-induced monocyte migration by at least 40, 50, 60, or 70%, e.g., as measured using a transwell plate migration assay, e.g., as measured using methods described in Example 3 with respect to FIG. 2.

In some embodiments, the multispecific molecule inhibits the proliferation of macrophages, e.g., bone marrow-derived macrophages, e.g., CSF-1-induced proliferation of bone marrow-derived macrophages, e.g., reduces CSF-1-induced proliferation of bone marrow-derived macrophages by at least 50, 60, 70, or 80%, e.g., as measured using a cell proliferation MTT assay, e.g., as measured using methods described in Example 4 with respect to FIG. 3B.

In some embodiments, the multispecific molecule does not inhibit or does not substantially inhibit the differentiation of monocytes, e.g., bone marrow-derived monocytes, e.g., CSF-1-induced differentiation of bone marrow-derived monocytes, e.g., does not reduce CSF-1-induced differentiation of bone marrow-derived monocytes by more than 2, 4, 6, 8, or 10%, e.g., as measured using a flow cytometry analysis, e.g., as measured using methods described in Example 5 with respect to FIG. 4.

In some embodiments, the multispecific molecule depletes suppressive myeloid cells, e.g., TAMs or MDSCs, e.g., reduces the number of suppressive myeloid cells, e.g., TAMs or MDSCs, by at least 80, 85, 90, 95, 99, or 99.5%, in vivo, e.g., as measured using a flow cytometry analysis, e.g., as measured using methods described in Example 7 with respect to FIG. 6.

In some embodiments, the multispecific molecule does not deplete or does not substantially deplete tissue-resident macrophages, e.g., Kupffer cells, e.g., does not reduce the number of tissue-resident macrophages, e.g., Kupffer cells, by more than 4, 6, 8, 10, or 15%, in vivo, e.g., as measured using an immunohistochemistry analysis, e.g., as measured using methods described in Example 8 with respect to FIGS. 7B and 7D.

In some embodiments, the multispecific molecule does not inhibit or does not substantially inhibit CSF-1 dependent cell survival of CSF1R-positive, CCR2-negative cells, e.g., does not reduce CSF-1 dependent cell survival of CSF1R-positive, CCR2-negative cells by more than 5, 10, or 15%, e.g., as measured using a cell viability MTT assay, e.g., as measured using methods described in Example 9 with respect to FIG. 8A.

In some embodiments, the multispecific molecule increases CD8+ T cell tumor infiltration in vivo, e.g., increases % CD8+ T cells in CD3+ T cells in tumor by at least 1.5, 2, or 2.5-fold, e.g., as measured using a flow cytometry analysis, e.g., as measured using methods described in Example 10 with respect to FIG. 9.

In some embodiments, the multispecific molecule reduces Treg frequency in tumor in vivo, e.g., reduces Treg frequency in tumor by at least 15, 20, 25, or 30%, e.g., as measured using a flow cytometry analysis, e.g., as measured using methods described in Example 11 with respect to FIG. 10A.

In some embodiments, the multispecific molecule increases the CD8+ T cell/Treg ratio in tumor in vivo, e.g., increases the CD8+ T cell/Treg ratio in tumor by at least 2.5, 3, 3.5, 4, or 4.5-fold, e.g., as measured using a flow cytometry analysis, e.g., as measured using methods described in Example 11 with respect to FIG. 10B.

In some embodiments, the multispecific molecule reduces tumor growth and/or increases survival of a tumor-bearing animal, e.g., as measured using methods described in Example 12 with respect to FIGS. 11A and 11B.

In some embodiments, the anti-CSF1R binding moiety and the anti-CCR2 binding moiety are, independently, a full antibody (e.g., an antibody that includes at least one, and preferably two, complete heavy chains, and at least one, and preferably two, complete light chains), or an antigen-binding fragment (e.g., a Fab, F(ab')2, Fv, a scFv, a single domain antibody, or a diabody (dAb)). In some embodiments, the anti-CSF1R binding moiety and/or the anti-CCR2 binding moiety comprises a heavy chain constant region chosen from IgG1, IgG2, IgG3, or IgG4, or a fragment thereof. In some embodiments, the anti-CSF1R binding moiety and/or the anti-CCR2 binding moiety comprises a heavy chain constant region that can mediate antibody-dependent cellular cytotoxicity (ADCC) or complement-dependent cytotoxicity (CDC). In some embodiments, the anti-CSF1R binding moiety comprises a first heavy chain constant region (e.g., a first Fc region) and the anti-CCR2 binding moiety comprises a second heavy chain constant region (e.g., a second Fc region), wherein the first heavy chain constant region comprises one or more mutations that increase heterodimerization of the first heavy chain constant region and the second heavy chain constant region, relative to a naturally-existing heavy chain constant region, and/or wherein the second heavy chain constant region comprises one or more mutations that increase heterodimerization of the second heavy chain constant region and the first heavy chain constant region, relative to a naturally-existing heavy chain constant region. In some embodiments, the anti-CSF1R binding moiety and/or the anti-CCR2 binding moiety comprises a light chain constant region chosen from the light chain constant regions of kappa or lambda, or a fragment thereof. In some embodiments, the anti-CSF1R binding moiety comprises a kappa light chain constant region, or a fragment thereof, and the anti-CCR2 binding moiety comprises a lambda light chain constant region, or a fragment thereof. In some embodiments, the anti-CSF1R binding moiety comprises a lambda light chain constant region, or a fragment thereof, and the anti-CCR2 binding moiety comprises a kappa light chain constant region, or a fragment thereof. In some embodiments, the anti-CSF1R binding moiety and the anti-CCR2 binding moiety have a common light chain variable region. In some embodiments, the multispecific molecule further comprises a heavy chain constant region (e.g., an Fc region) chosen from the heavy chain constant regions of IgG1, IgG2, and IgG4, more particularly, the heavy chain constant region of human IgG1, IgG2 or IgG4. In some embodiments, the multispecific molecule further comprises a heavy chain constant region that can mediate antibody-dependent cellular cytotoxicity (ADCC) or complement-dependent cytotoxicity (CDC).

In some embodiments, the multispecific molecule comprises an anti-CSF1R antibody molecule and an anti-CCR2 antibody molecule, wherein:
(i) the anti-CSF1R antibody molecule comprises a first polypeptide and a second polypeptide, wherein the first polypeptide comprises a first light chain variable region (VL) and a first light chain constant region (CL), and the second polypeptide comprises a first heavy chain variable region (VH), a first heavy chain constant region 1 (CH1), and optionally, a first CH2 and a first CH3, and
(ii) the anti-CCR2 antibody molecule comprises a third polypeptide and a fourth polypeptide, wherein the third polypeptide comprises a second VL and a second CL, and the fourth polypeptide comprises a second VH, a second CH1, and optionally, a second CH2 and a second CH3.

In some embodiments, (i) the anti-CSF1R antibody molecule binds to CSF1R monovalently, and/or (ii) the anti-CCR2 antibody molecule binds to CCR2 monovalently. In some embodiments, the multispecific molecule binds to CSF1R monovalently, and/or binds to CCR2 monovalently. In some embodiments, the multispecific molecule binds to CSF1R monovalently, and binds to CCR2 monovalently.

In some embodiments,
(i) the multispecific molecule inhibits CSF1R in the presence of CCR2, optionally wherein the multispecific molecule reduces an activity of CSF1R (e.g., CSF1R signaling, e.g., CSF1-induced CSF1R signaling) in a cell, e.g., by at least 40, 50, 60, 70, 80, or 90%, when the cell expresses both CSF1R and CCR2 on the cell surface, and/or
(ii) the multispecific molecule does not inhibit or does not substantially inhibit CSF1R in the absence of CCR2, optionally wherein the multispecific molecule does not reduce an activity of CSF1R (e.g., CSF1R signaling, e.g., CSF1-induced CSF1R signaling), or does not reduce an activity of CSF1R by more than 2, 4, 6, 8, 10, or 15%, when the cell expresses CSF1R but not CCR2 on the cell surface.

In some embodiments,
(i) the multispecific molecule inhibits CCR2 in the presence of CSF1R, optionally wherein the multispecific molecule reduces an activity of CCR2 in a cell, e.g., by at least 40, 50, 60, 70, 80, or 90%, when the cell expresses both CCR2 and CSF1R on the cell surface, and/or
(ii) the multispecific molecule does not inhibit or does not substantially inhibit CCR2 in the absence of CSF1R, optionally wherein the multispecific molecule does not reduce an activity of CCR2, or does not reduce an activity of CCR2 by more than 2, 4, 6, 8, 10, or 15%, when the cell expresses CCR2 but not CSF1R on the cell surface.

In one aspect, this invention provides an isolated multispecific, e.g., a bispecific, molecule, comprising:
(i) a first binding moiety that binds to a molecule that mediates the trafficking of monocytes, e.g., inflammatory monocytes, e.g., Ly6C$^{Hi}$ CCR2+ CX3CR1$^{Lo}$ inflammatory monocytes, optionally wherein the first binding moiety binds to CCR2; and
(ii) a second binding moiety that binds to a molecule that mediates the maturation and/or survival of monocytes and/or macrophages at an inflamed tissue, optionally wherein the second binding moiety binds to CSF1R.

In one aspect, this invention provides an isolated multispecific, e.g., a bispecific, molecule, comprising:
(i) a first binding moiety that reduces recruitment of inflammatory monocytes to tumor, optionally wherein the first binding moiety binds to and/or inhibits CCR2; and
(ii) a second binding moiety that reduces maturation and/or survival of monocytes and/or macrophages in the tumor microenvironment, optionally wherein the second binding moiety binds to and/or inhibits CSF1R.

In one aspect, this invention provides an isolated multispecific, e.g., a bispecific, molecule, comprising (i) an anti-CSF1R binding moiety (e.g., an anti-CSF1R antibody molecule); and (ii) an anti-PD-L1 binding moiety (e.g., an anti-PD-L1 antibody molecule).

In some embodiments of the aforementioned aspects and embodiments, the multispecific molecule further comprises one or more additional binding moieties (e.g., a third binding moiety, a fourth binding moiety, (e.g., a trispecific or a tetraspecific molecule), optionally wherein the third binding moiety is a third IMC binding moiety or a tumor targeting moiety. In some embodiments, the tumor targeting moiety is a tumor targeting moiety disclosed in WO2017165464, e.g., pages 108-118 of WO2017165464, herein incorporated by reference in its entirety.

In some embodiments of the aforementioned aspects and embodiments, the multispecific molecule further comprises an immune cell engager chosen from a T cell engager, an NK cell engager, a B cell engager, a dendritic cell engager, or a macrophage cell engager. In some embodiment, the immune cell engager is an immune cell engager disclosed in WO2017165464, e.g., pages 119-131 of WO2017165464, herein incorporated by reference in its entirety. In some embodiments, the immune cell engager binds to and activates an immune cell, e.g., an effector cell. In some embodiments, the immune cell engager binds to, but does not activate, an immune cell, e.g., an effector cell.

In some embodiments, the immune cell engager is a T cell engager, e.g., a T cell engager that mediates binding to and activation of a T cell, or a T cell engager that mediates binding to but not activation of a T cell. In some embodiments, the T cell engager binds to CD3, TCRα, TCRβ, TCRγ, TCRζ, ICOS, CD28, CD27, HVEM, LIGHT, CD40, 4-1BB, OX40, DR3, GITR, CD30, TIM1, SLAM, CD2, or CD226, e.g., the T cell engager is an anti-CD3 antibody molecule.

In some embodiments, the immune cell engager is an NK cell engager, e.g., an NK cell engager that mediates binding to and activation of an NK cell, or an NK cell engager that mediates binding to but not activation of an NK cell. In some embodiments, the NK cell engager is chosen from an antibody molecule, e.g., an antigen binding domain, or ligand that binds to (e.g., activates): NKp30, NKp40, NKp44, NKp46, NKG2D, DNAM1, DAP10, CD16 (e.g., CD16a, CD16b, or both), CRTAM, CD27, PSGL1, CD96, CD100 (SEMA4D), NKp80, CD244 (also known as SLAMF4 or 2B4), SLAMF6, SLAMF7, KIR2DS2, KIR2DS4, KIR3DS1, KIR2DS3, KIR2DS5, KIR2DS1, CD94, NKG2C, NKG2E, or CD160.

In some embodiments, the immune cell engager is a B cell engager, e.g., a CD40L, an OX40L, or a CD70 ligand, or an antibody molecule that binds to OX40, CD40 or CD70. In some embodiments, the immune cell engager is a macrophage cell engager, e.g., a CD2 agonist; a CD40L; an OX40L; an antibody molecule that binds to OX40, CD40 or CD70; an agonist of a Toll-like receptor (TLR) (e.g., a TLR4, e.g., a constitutively active TLR4 (caTLR4) or a TLR9 agonist); CD47; or a STING agonist.

In some embodiments, the immune cell engager is a dendritic cell engager, e.g., a CD2 agonist, an OX40 antibody, an OX40L, 41BB agonist, a Toll-like receptor agonist or a fragment thereof (e.g., a TLR4, e.g., a constitutively active TLR4 (caTLR4)), CD47 agonist, or a STING agonist.

In some embodiments of the aforementioned aspects and embodiments, the multispecific molecule further comprises a cytokine molecule. In some embodiments, the cytokine molecule is chosen from interleukin-2 (IL-2), interleukin-7 (IL-7), interleukin-12 (IL-12), interleukin-15 (IL-15), interleukin-18 (IL-18), interleukin-21 (IL-21), or interferon gamma, or a fragment or variant thereof, or a combination of any of the aforesaid cytokines. In some embodiments, the cytokine molecule is a cytokine molecule disclosed in WO2017165464, e.g., pages 108-118 of WO2017165464, herein incorporated by reference in its entirety.

In some embodiments of the aforementioned aspects and embodiments, the multispecific molecule further comprises a stromal modifying moiety. In some embodiments, the stromal modifying moiety causes one or more of: decreases the level or production of a stromal or extracellular matrix (ECM) component; decreases tumor fibrosis; increases interstitial tumor transport; improves tumor perfusion; expands the tumor microvasculature; decreases interstitial fluid pressure (IFP) in a tumor; or decreases or enhances penetration or diffusion of an agent, e.g., a cancer therapeutic or a cellular therapy, into a tumor or tumor vasculature. In some embodiments, the stromal modifying moiety is a stromal modifying moiety disclosed in WO2017165464, e.g., pages 131-136 of WO2017165464, herein incorporated by reference in its entirety.

In another aspect, provided herein are isolated nucleic acid molecules encoding the multispecific molecule (e.g., antibody) of any one of the preceding claims.

In another aspect, provided herein are isolated nucleic acid molecules, which comprises the nucleotide sequence encoding any of the multispecific molecules described herein, or a nucleotide sequence substantially homologous thereto (e.g., at least 95% to 99.9% identical thereto).

In another aspect, provided herein are vectors, e.g., expression vectors, comprising one or more of the nucleic acid molecules described herein.

In another aspect, provided herein are cells, e.g., host cells, comprising the nucleic acid molecule described herein or the vector described herein.

In another aspect, provided herein are methods of making, e.g., producing, the multispecific molecules described herein, comprising culturing the cell, e.g., the host cell, described herein, under suitable conditions, e.g., conditions suitable for gene expression and/or heterodimerization.

In another aspect, provided herein are pharmaceutical compositions comprising the multispecific molecule described herein and a pharmaceutically acceptable carrier, excipient, or stabilizer.

In another aspect, provided herein are methods of treating a hyperproliferative disorder, a cancer, a fibrotic disorder or condition, an inflammatory disorder or condition, or an autoimmune disorder. In one embodiment, the disorder is a hyperproliferative disorder, e.g., a hyperproliferative connective tissue disorder (e.g., a hyperproliferative fibrotic disease). In one embodiment, the fibrotic (e.g., hyperproliferative fibrotic) disease is multisystemic or organ-specific. Exemplary fibrotic diseases include, but are not limited to, multisystemic (e.g., systemic sclerosis, multifocal fibrosclerosis, sclerodermatous graft-versus-host disease in bone marrow transplant recipients, nephrogenic systemic fibrosis, scleroderma), and organ-specific disorders (e.g., fibrosis of the lung, liver, heart, kidney, pancreas, skin and other organs). In other embodiments, the fibrotic disease is chosen from liver fibrosis (e.g., liver cirrhosis, NASH, and other conditions described herein), pulmonary fibrosis (e.g., IPF), renal fibrosis, or fibrosis of the bone marrow (e.g., myelofibrosis).

In another aspect, provided herein are methods of treating a cancer in a subject, comprising administering to the subject in need thereof the multispecific molecule described herein, wherein the multispecific molecule is administered in an amount effective to treat the cancer.

In another aspect, provided herein are method of treating a cancer in a subject, comprising administering to the subject in need thereof the multispecific molecule described herein, wherein the multispecific molecule is administered in an amount effective to reduce the number of TAMs (e.g., the number of TAMs in or near a tumor in the subject), inhibit the proliferation of TAMs (e.g., the proliferation of TAMs in or near a tumor in the subject), or reduce or inhibit macrophage infiltration into a tumor in the subject.

In another aspect, provided herein are methods of treating a cancer in a subject by reducing a portion of a population of TAMs, comprising administering to the subject in need thereof the multispecific molecule described herein, wherein the multispecific molecule is administered in an amount effective to inhibit or deplete a portion of the population of TAMs.

In another aspect, provided herein are methods of reducing the proliferation of a portion of a population of TAMs in a subject (e.g., in a subject having cancer, e.g., a solid tumor), comprising, administering to the subject in need thereof the multispecific molecule described herein, wherein the multispecific molecule is administered in an amount effective to reduce the proliferation of a portion of the population of TAMs.

In another aspect, provided herein are methods of inhibiting or depleting a portion of a population of TAMs in a subject having a cancer (e.g., a tumor), comprising administering to the subject the multispecific molecule described herein, wherein the multispecific molecule is administered in an amount effective to reduce the number of tumor infiltrating macrophages, inhibit the proliferation of tumor infiltrating macrophages, or reduce macrophage infiltration into a tumor.

In some embodiments, the cancer is a solid tumor cancer or a metastatic lesion. In some embodiments, the solid tumor cancer is one or more of pancreatic cancer (e.g., pancreatic adenocarcinoma), breast cancer, colorectal cancer, lung cancer (e.g., small or non-small cell lung cancer), skin cancer (e.g., melanoma), ovarian cancer, liver cancer, or brain cancer (e.g., glioma). In some embodiments, the cancer is characterized as containing TAMs, is associated with the presence of TAMs, TAMs are in and/or form part of the cancer (e.g., tumor), or TAMs have been detected in or near the solid tumor.

In some embodiments, the methods further comprise identifying the presence of TAMs in or near the cancer (e.g., tumor) in the subject. In some embodiments, the TAMs express CXCR2 and CCR2, CCR2 and CSF1R, CSF1R and CXCR2, or CCR2, CXCR2, and CSF1R.

In some embodiments, the methods further comprise administering a second therapeutic treatment. In some embodiments, the second therapeutic treatment comprises a therapeutic agent (e.g., a chemotherapeutic agent, a biologic agent, hormonal therapy), radiation, or surgery. In some embodiments, the therapeutic agent is selected from: a chemotherapeutic agent, or a biologic agent. In some embodiments, the therapeutic agent is a checkpoint inhibitor. In some embodiments, the check point inhibitor is selected from the group consisting of an anti-CTLA4 antibody, an anti-PD1 antibody (e.g., Nivolumab, Pembrolizumab or Pidilizumab), an anti-PD-L1 antibody, an anti-PD-L2 antibody, an anti-TIM3 antibody, an anti-LAG3 antibody, an anti-CD160 antibody, an anti-2B4 antibody, an anti-CD80 antibody, an anti-CD86 antibody, an anti-B7-H3 (CD276) antibody, an anti-B7-H4 (VTCN1) antibody, an anti-HVEM (TNFRSF14 or CD270) antibody, an anti-BTLA antibody, an anti-KIR antibody, an anti-MHC class I antibody, an anti-MHC class II antibody, an anti-GALS antibody, an anti-VISTA antibody, an anti-BTLA antibody, an anti-TIGIT antibody, an anti-LAIR1 antibody, and an anti-A2aR antibody.

In another aspect, provided herein are methods of treating a cancer in a subject, comprising administering to the subject in need thereof the multispecific molecule described herein, wherein the multispecific molecule is administered in an amount effective to reduce the number of MDSCs (e.g., the number of MDSCs in or near a tumor in the subject), inhibit the proliferation of MDSCs (e.g., the number of MDSCs in or near a tumor in the subject), or reduce or inhibit MDSC infiltration into a tumor in the subject.

In another aspect, provided herein are methods of treating a cancer in a subject by reducing a portion of a population of MDSCs, comprising administering to the subject in need thereof the multispecific molecule described herein, wherein the multispecific molecule is administered in an amount effective to inhibit or deplete a portion of the population of MDSCs.

In another aspect, provided herein are methods of reducing the proliferation of a portion of a population of MDSCs in a subject (e.g., in a subject having cancer, e.g., a solid tumor), comprising, administering to the subject in need thereof the multispecific molecule described herein, wherein the multispecific molecule is administered in an amount effective to reduce the proliferation of a portion of the population of MDSCs.

In another aspect, provided herein are methods of inhibiting or depleting a portion of a population of MDSCs in a subject having a cancer (e.g., a tumor), comprising administering to the subject the multispecific molecule described herein, wherein the multispecific molecule is administered in an amount effective to reduce the number of MDSCs, inhibit the proliferation of MDSCs, or reduce MDSC infiltration into a tumor.

In some embodiments, the cancer is a solid tumor cancer or a metastatic lesion. In some embodiments, the solid tumor cancer is one or more of pancreatic cancer (e.g., pancreatic adenocarcinoma), breast cancer, colorectal cancer, lung cancer (e.g., small or non-small cell lung cancer), skin cancer (e.g., melanoma), ovarian cancer, liver cancer, or brain cancer (e.g., glioma). In some embodiments, the cancer is characterized as containing MDSCs, is associated with the presence of MDSCs, MDSCs are in and/or form part of the cancer (e.g., tumor), or MDSCs have been detected in or near the solid tumor. In some embodiments, the methods further comprise identifying the presence of MDSCs in or near the cancer (e.g., tumor) in the subject.

In some embodiments, the methods further comprise administering a second therapeutic treatment. In some embodiments, the second therapeutic treatment comprises a therapeutic agent (e.g., a chemotherapeutic agent, a biologic agent, hormonal therapy), radiation, or surgery. In some embodiments, the therapeutic agent is selected from: a chemotherapeutic agent, or a biologic agent. In some embodiments, the therapeutic agent is a checkpoint inhibitor. In some embodiments, the check point inhibitor is selected from the group consisting of an anti-CTLA4 antibody, an anti-PD1 antibody (e.g., Nivolumab, Pembrolizumab or Pidilizumab), an anti-PD-L1 antibody, an anti-PD-L2 antibody, an anti-TIM3 antibody, an anti-LAG3 antibody, an anti-CD160 antibody, an anti-2B4 antibody, an anti-CD80 antibody, an anti-CD86 antibody, an anti-B7-H3 (CD276) antibody, an anti-B7-H4 (VTCN1) antibody, an anti-HVEM (TNFRSF14 or CD270) antibody, an anti-BTLA antibody, an anti-KIR antibody, an anti-MHC class I antibody, an anti-MHC class II antibody, an anti-GALS antibody, an anti-VISTA antibody, an anti-BTLA antibody, an anti-TIGIT antibody, an anti-LAIR1 antibody, and an anti-A2aR antibody.

In one aspect, provided herein are methods of treating a fibrotic disease or disorder in a subject in need thereof, comprising administering to the subject an effective amount of a multispecific molecule disclosed herein, thereby treating the fibrotic disease or disorder. In some embodiments, the fibrotic disease or disorder is a fibrotic disease or disorder of the lung, the liver, the heart or vasculature, the kidney, the pancreas, the skin, the gastrointestinal tract, the bone marrow or a hematopoietic tissue, the nervous system, the eye, or a combination thereof. In some embodiments, the fibrotic disease or disorder is lung fibrosis (e.g., Idiopathic pulmonary fibrosis (IPF)) or liver fibrosis (e.g., Nonalcoholic steatohepatitis (NASH)).

In some embodiments, treatment of a fibrotic condition includes reducing or inhibiting one or more of: formation or deposition of tissue fibrosis; reducing the size, cellularity (e.g., fibroblast or immune cell numbers), composition; or cellular content, of a fibrotic lesion; reducing the collagen or hydroxyproline content, of a fibrotic lesion; reducing expression or activity of a fibrogenic protein; reducing fibrosis associated with an inflammatory response; decreasing weight loss associated with fibrosis; or increasing survival.

In some embodiments, the fibrotic disease or disorder is primary fibrosis. In one embodiment, the fibrotic disease or disorder is idiopathic. In other embodiments, the fibrotic disease or disorder is associated with (e.g., is secondary to) a disease (e.g., an infectious disease, an inflammatory disease, an autoimmune disease, a malignant or cancerous disease, and/or a connective disease); a toxin; an insult (e.g., an environmental hazard (e.g., asbestos, coal dust, polycyclic aromatic hydrocarbons), cigarette smoking, a wound); a medical treatment (e.g., surgical incision, chemotherapy or radiation), or a combination thereof.

In one aspect, provided herein are methods of treating a liver disease or disorder in a subject in need thereof, comprising administering to the subject an effective amount of a multispecific molecule disclosed herein, thereby treating the liver disease or disorder. In some embodiments, the liver disease or disorder is a fibrotic disorder or connective tissue disorder affecting the function or physiology of the liver. In one embodiment, the fibrotic disorder or connective tissue disorder can be systemic (affecting the whole body), multi-organ, or organ-specific (e.g., liver-specific). Examples of fibrotic liver disorders include, but are not limited to, liver fibrosis (hepatic fibrosis), liver cirrhosis, and any disorder associated with accumulation of extracellular matrix proteins, e.g., collagen, in the liver, liver scarring, and/or abnormal hepatic vasculature. In one embodiment, the liver disease or disorder is liver cirrhosis. Liver cirrhosis is considered to be an end stage of liver fibrosis, involving regenerative nodules (as a result of repair processes), and is typically accompanied with the distortion of the hepatic vasculature. In other embodiments, the liver disease or disorder is a liver cancer. Examples of liver cancers include, but are not limited to, hepatocellular carcinoma (HCC), primary liver cell carcinoma, hepatoma, fibrolamellar carcinoma, focal nodular hyperplasia, cholangiosarcoma, intrahepatic bile duct cancer, angiosarcoma or hemangiosarcoma, hepatic adenoma, hepatic hemangiomas, hepatic hamartoma, hepatoblastoma, infantile hemangioendothelialoma, mixed tumors of the liver, tumors of mesenchymal tissue, and sarcoma of the liver. Liver cancers can also be associated with metastasis of non-liver cancers, such as breast cancer, colorectal cancer, esophageal cancer, kidney or renal cancer, lung cancer, ovarian cancer, pancreatic cancer, rectal cancer, skin cancer (e.g., melanoma), gastric or stomach cancer (including gastrointestinal cancer), and uterine cancer. In one embodiment, the liver disease or disorder is HCC. In certain embodiments, the liver disease or disorder is caused by one or more insults including, but not limited to, liver inflammation or damage; viral (e.g., chronic viral) infection (e.g., hepatitis B, hepatitis C virus, hepatitis A virus, hepatitis D virus (hepatitis delta virus), hepatitis E virus, Epstein-Barr adenovirus, or cytomegalovirus; or parasitic infection, such as schistosomiasis); alcoholism; fatty liver disease; metabolic disorders (e.g., hemachromatosis, diabetes, obesity, hypertension, dyslipidemia, galactosemia, or glycogen storage disease); autoimmune disorders (e.g., autoimmune hepatitis (AIH), autoimmune liver disease, lupoid hepatitis, systemic lupus erythematosus, primary biliary cirrhosis (PBC), scleroderma, or systemic scerlosis); inflammatory liver disorders (e.g., steatohepatitis, primary sclerosing cholangitis (PSC), ulcerative colitis, Crohn's disease, inflammatory bowel disease); inherited or congenital liver disease (e.g., Wilson's disease, Gilbert's disease, Byler syndrome, Greenland-Eskimo familial cholestasis, Zellweger's syndrome, Alagilles syndrome (ALGS), progressive familial intrahepatic cholestasis (PFIC), alpha 1-antitrypsin deficiency, cystic fibrosis, Indian childhood cirrhosis, or hereditary hemochromatosis); and liver injury (e.g., drug toxicity, alcoholism, ischemia, malnutrition, or physical trauma). In one embodiment, the liver disease or disorder is fatty liver (or FLD), alcoholic liver disease, non-alcoholic fatty liver disease (NAFLD), non-alcoholic steatohepatitis (NASH), alcoholic steatohepatitis, simple steatosis, Reye's syndrome, and any disorder associated with abnormal retention of lipids in liver cells.

In one aspect, provided herein are methods of treating an inflammatory disorder or condition in a subject in need thereof, comprising administering to the subject an effective amount of a multispecific molecule disclosed herein, thereby treating the inflammatory disorder or condition. In one embodiment, the inflammatory disorder or condition is an inflammatory disorder or condition in the kidney. In one embodiment, the inflammatory disorder or condition is Lupus nephritis.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the invention will be apparent from the following detailed description and claims.

BRIEF DESCRIPTION OF THE DRAWINGS

In FIG. 1, percent fluorescence (%) is plotted against antibody concentrations tested.

FIG. 3A is a pair of flow cytometry plots showing the staining of bone marrow cells with an anti-CCR2 antibody and an anti-CSF1R antibody at day 0 or day 4 of cell culture in the presence of mCSF1. In FIG. 3B, % proliferation is plotted for each condition tested. All antibodies were tested at 15 µg/ml.

FIG. 5 is a panel of histograms showing staining of CD206+ macrophages, M-MDSCs, neutrophils, or CD3+ T cells using UniTI-01.

FIGS. 7A and 7B are immunohistochemistry graphs of tumor and liver tissues, respectively, stained with the antibody F4/80. FIGS. 7C and 7D are graphs showing % F4/80 positive area for tumor and liver tissues, respectively.

In FIG. 8A, cell viability is plotted against the antibody concentrations tested for the anti-CCR2/anti-CSF1R bispecific antibody UniTI-01, a bivalent monospecific anti-CSF1R antibody (aCSF1R), or a monovalent monospecific anti-CSF1R antibody (mono-aCSF1R). FIG. 8B is a pair of flow cytometry plots showing the staining of NFS-60 cells with an anti-CCR2 antibody and an anti-CSF1R antibody, or the staining of NFS-60 cells with an isotype control antibody.

FIG. 9 is a graph showing % CD8+ T cells in CD3+ T cells in tumors under indicated treatments.

FIG. 10A is a graph showing % FOXP3+ cells in CD4+ T cells in tumors under indicated treatments. In FIG. 10B, the CD8+ T cell/Treg ratio in tumors is plotted for each treatment.

FIG. 11A is a panel of graphs showing tumor volumes for each treatment. FIG. 11B is a graph showing percent survival under indicated treatments.

DETAILED DESCRIPTION OF THE INVENTION

Figure 1:
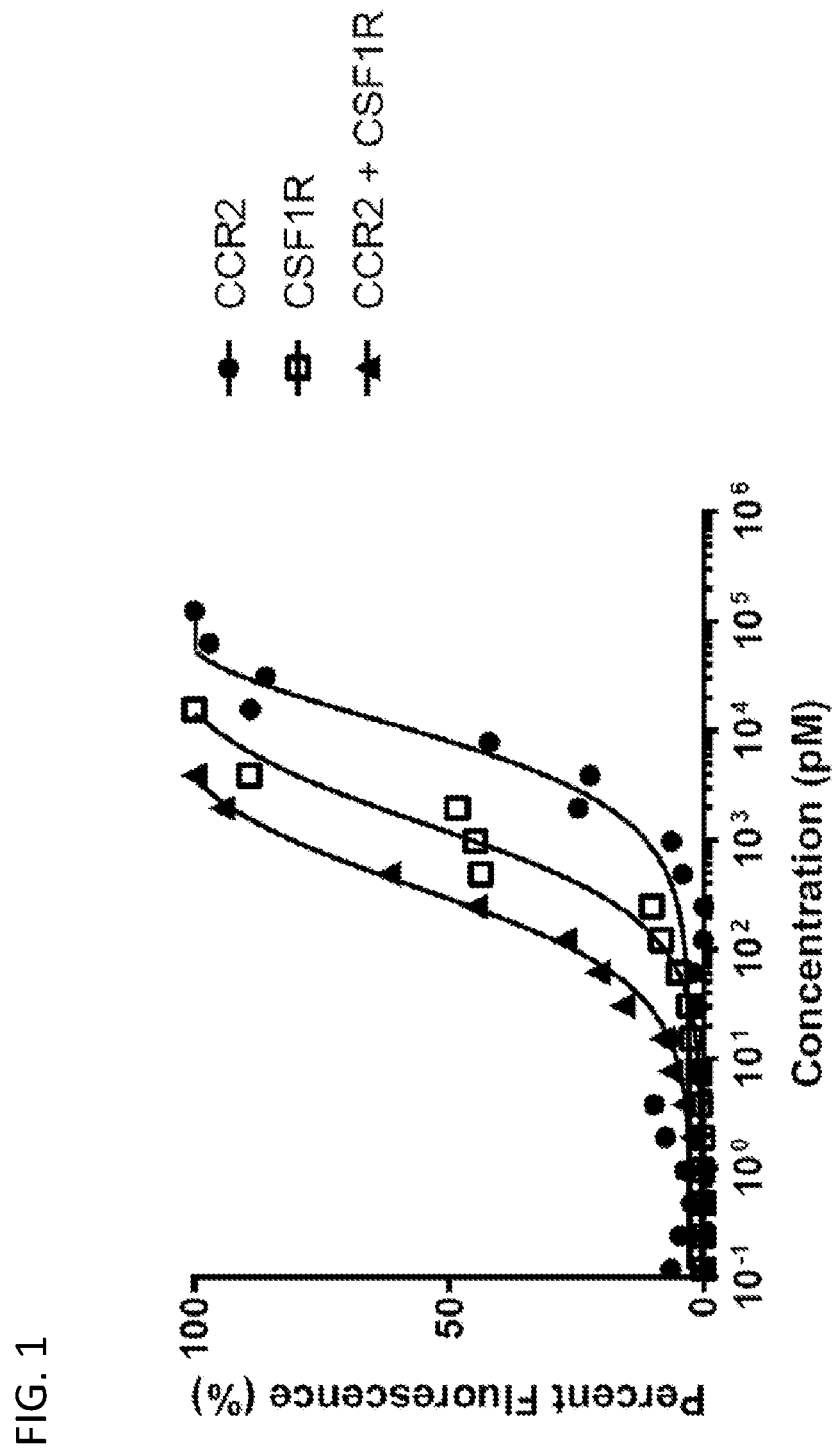
FIG. 1. In vitro binding of increasing concentrations of UniTI-01 to transiently transfected ExpiCHO cells expressing mCCR2 (circles), mCSF1R (squares), or both mCCR2 and mCSF1R (triangles), as determined by flow analysis.

TAMs originate from circulating monocytes and their recruitment into tumors is driven by tumor-derived chemotactic factors. TAMs can promote tumor cell proliferation and metastasis by causing such responses as inhibition of B and T cell activation, inhibition of tumor-associated antigen presentation, inhibition of cytotoxic granule release, increased angiogenesis, and secretion a wide range of growth and proangiogenic factors (see e.g., Liu et al Cellular & Molecular Immunology (2015) 12, 1-4; and Noy, Roy et al Immunity, Volume 41, Issue 1, 49-61; and Quatromoni et al. Am J Transl Res. 2012; 4(4): 376-389). Consequently, many tumors with a high number of TAMs have an increased tumor growth rate, local proliferation and distant metastasis. Thus, therapies that deplete TAMs or inhibit their activity would be useful.

Certain terms are defined below.

As used herein, the term "variant" of a parent sequence refers to a sequence that has a substantially identical amino acid sequence to the parent sequence, or a fragment thereof. In some embodiments, the variant is a functional variant.

As used herein, the articles "a" and "an" refer to one or more than one, e.g., to at least one, of the grammatical object of the article. The use of the words "a" or "an" when used in conjunction with the term "comprising" herein may mean "one," but it is also consistent with the meaning of "one or more," "at least one," and "one or more than one."

As used herein, "about" and "approximately" generally mean an acceptable degree of error for the quantity measured given the nature or precision of the measurements. Exemplary degrees of error are within 20 percent (%), typically, within 10%, and more typically, within 5% of a given range of values.

"Antibody molecule" as used herein refers to a protein, e.g., an immunoglobulin chain or fragment thereof, comprising at least one immunoglobulin variable region sequence. An antibody molecule encompasses antibodies (e.g., full-length antibodies) and antibody fragments. In an embodiment, an antibody molecule comprises an antigen binding or functional fragment of a full length antibody, or a full length immunoglobulin chain. For example, a full-length antibody is an immunoglobulin (Ig) molecule (e.g., an IgG antibody) that is naturally occurring or formed by normal immunoglobulin gene fragment recombinatorial processes). In embodiments, an antibody molecule refers to an immunologically active, antigen-binding portion of an immunoglobulin molecule, such as an antibody fragment. An antibody fragment, e.g., functional fragment, is a portion of an antibody, e.g., Fab, Fab', F(ab')$_2$, F(ab)$_2$, variable fragment (Fv), domain antibody (dAb), or single chain variable fragment (scFv). A functional antibody fragment binds to the same antigen as that recognized by the intact (e.g., full-length) antibody. The terms "antibody fragment" or "functional fragment" also include isolated fragments consisting of the variable regions, such as the "Fv" fragments consisting of the variable regions of the heavy and light chains or recombinant single chain polypeptide molecules in which light and heavy variable regions are connected by a peptide linker ("scFv proteins"). In some embodiments, an antibody fragment does not include portions of antibodies without antigen binding activity, such as Fc fragments or single amino acid residues. Exemplary antibody molecules include full length antibodies and antibody fragments, e.g., dAb (domain antibody), single chain, Fab, Fab', and F(ab')$_2$ fragments, and single chain variable fragments (scFvs).

As used herein, an "immunoglobulin variable region sequence" refers to an amino acid sequence which can form the structure of an immunoglobulin variable region. For example, the sequence may include all or part of the amino acid sequence of a naturally-occurring variable region. For example, the sequence may or may not include one, two, or more N- or C-terminal amino acids, or may include other alterations that are compatible with formation of the protein structure.

In embodiments, an antibody molecule is monospecific, e.g., it comprises binding specificity for a single epitope. In some embodiments, an antibody molecule is multispecific, e.g., it comprises a plurality of immunoglobulin variable region sequences, where a first immunoglobulin variable region sequence has binding specificity for a first epitope and a second immunoglobulin variable region sequence has binding specificity for a second epitope. In some embodiments, an antibody molecule is a bispecific antibody molecule. "Bispecific antibody molecule" as used herein refers to an antibody molecule that has specificity for more than one (e.g., two, three, four, or more) epitope and/or antigen.

"Antigen" (Ag) as used herein refers to a molecule that can provoke an immune response, e.g., involving activation of certain immune cells and/or antibody generation. Any macromolecule, including almost all proteins or peptides, can be an antigen. Antigens can also be derived from genomic recombinant or DNA. For example, any DNA comprising a nucleotide sequence or a partial nucleotide sequence that encodes a protein capable of eliciting an immune response encodes an "antigen." In embodiments, an antigen does not need to be encoded solely by a full length nucleotide sequence of a gene, nor does an antigen need to be encoded by a gene at all. In embodiments, an antigen can be synthesized or can be derived from a biological sample, e.g., a tissue sample, a tumor sample, a cell, or a fluid with other biological components. As used, herein a "tumor antigen" or interchangeably, a "cancer antigen" includes any molecule present on, or associated with, a cancer, e.g., a cancer cell or a tumor microenvironment that can provoke an immune response. As used, herein an "immune cell antigen" includes any molecule present on, or associated with, an immune cell that can provoke an immune response.

The "antigen-binding site," or "binding portion" of an antibody molecule refers to the part of an antibody molecule, e.g., an immunoglobulin (Ig) molecule, that participates in antigen binding. In embodiments, the antigen binding site is formed by amino acid residues of the variable (V) regions of the heavy (H) and light (L) chains. Three highly divergent stretches within the variable regions of the heavy and light chains, referred to as hypervariable regions, are disposed between more conserved flanking stretches called "framework regions," (FRs). FRs are amino acid sequences that are naturally found between, and adjacent to, hypervariable regions in immunoglobulins. In embodiments, in an antibody molecule, the three hypervariable regions of a light chain and the three hypervariable regions of a heavy chain are disposed relative to each other in three dimensional space to form an antigen-binding surface, which is complementary to the three-dimensional surface of a bound antigen. The three hypervariable regions of each of the heavy and light chains are referred to as "complementarity-determining regions," or "CDRs." The framework region and CDRs have been defined and described, e.g., in Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917. Each variable chain (e.g., variable heavy chain and variable light chain) is typically made up of three CDRs and four FRs, arranged from amino-terminus to carboxy-terminus in the amino acid order: FR1, CDR1, FR2, CDR2, FR3, CDR3, and FR4.

"Cancer" as used herein can encompass all types of oncogenic processes and/or cancerous growths. In embodiments, cancer includes primary tumors as well as metastatic tissues or malignantly transformed cells, tissues, or organs. In embodiments, cancer encompasses all histopathologies and stages, e.g., stages of invasiveness/severity, of a cancer. In embodiments, cancer includes relapsed and/or resistant cancer. The terms "cancer" and "tumor" can be used interchangeably. For example, both terms encompass solid and liquid tumors. As used herein, the term "cancer" or "tumor" includes premalignant, as well as malignant cancers and tumors.

The compositions and methods of the present invention encompass polypeptides and nucleic acids having the sequences specified, or sequences substantially identical or similar thereto, e.g., sequences at least 85%, 90%, 95% identical or higher to the sequence specified. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 85%, 90%. 91%, 92%, 93%, 94%, 95%, 96%, 97%, 98% or 99% identity to a reference sequence, e.g., a sequence provided herein.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 85%, 90%, 91%, 92%, 93%, 94%, 95%, 96%, 97%, 98% or 99% identity to a reference sequence, e.g., a sequence provided herein.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444-453) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) *CABIOS,* 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403-10. BLAST nucleotide searches can be performed with the NBLAST program, score=100, wordlength=12 to obtain nucleotide sequences homologous to a nucleic acid (e.g., SEQ ID NO: 1) molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) *Nucleic Acids Res.* 25:3389-3402. When utilizing BLAST and Gapped BLAST programs, the default parameters of the respective programs (e.g., XBLAST and NBLAST) can be used. See http://www.ncbi.nlm.nih.gov.

It is understood that the molecules of the present invention may have additional conservative or non-essential amino acid substitutions, which do not have a substantial effect on their functions.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing. As used herein the term "amino acid" includes both the D- or L-optical isomers and peptidomimetics.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The terms "polypeptide", "peptide" and "protein" (if single chain) are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. The polypeptide can be isolated from natural sources, can be a produced by recombinant techniques from a eukaryotic or prokaryotic host, or can be a product of synthetic procedures.

The terms "nucleic acid," "nucleic acid sequence," "nucleotide sequence," or "polynucleotide sequence," and "polynucleotide" are used interchangeably. They refer to a polymeric form of nucleotides of any length, either deoxyribonucleotides or ribonucleotides, or analogs thereof. The polynucleotide may be either single-stranded or double-stranded, and if single-stranded may be the coding strand or non-coding (antisense) strand. A polynucleotide may comprise modified nucleotides, such as methylated nucleotides and nucleotide analogs. The sequence of nucleotides may be interrupted by non-nucleotide components. A polynucleotide may be further modified after polymerization, such as by conjugation with a labeling component. The nucleic acid may be a recombinant polynucleotide, or a polynucleotide of genomic, cDNA, semisynthetic, or synthetic origin which either does not occur in nature or is linked to another polynucleotide in a non-natural arrangement.

The term "isolated," as used herein, refers to material that is removed from its original or native environment (e.g., the natural environment if it is naturally occurring). For example, a naturally-occurring polynucleotide or polypeptide present in a living animal is not isolated, but the same polynucleotide or polypeptide, separated by human intervention from some or all of the co-existing materials in the natural system, is isolated. Such polynucleotides could be part of a vector and/or such polynucleotides or polypeptides could be part of a composition, and still be isolated in that such vector or composition is not part of the environment in which it is found in nature.

As used herein, the term "immunosuppressive myeloid cell" or "IMC" generally refers to a cell of myeloid lineage that promotes immunosuppression (e.g., in a tumor microenvironment) (e.g., by inhibiting T cell activation, inhibiting T cell viability, promoting T regulatory cell induction and recruitment). Immunosuppressive myeloid cells include, e.g., tumor associated macrophages (TAMs) and myeloid derived suppressor cells (MDSCs).

As used herein, the term "tumor associated macrophage" or "TAM" generally refers to a macrophage that exists in the microenvironment of a cancer, for example, a tumor.

As used herein, the term "reducing TAMs" generally refers to decreasing the number of TAMs. Reducing includes decreasing the number of TAMs in a tumor or near a tumor (e.g., as compared to the number of TAMs prior to administration of a multispecific molecule described herein (e.g., prior to 1, 2, 3, 4, 5, 6, 7, 8, 9, 10 or more administrations of a multispecific molecule described herein). Reducing includes decreasing any number of TAMs (e.g., 1%, 5%, 10%, 20%, 30%, 40%, 50%, 60%, 70%, 80%, 90%, 95%, 99%, 100%, all, or substantially) (e.g., as compared to the number of TAMs prior to administration of a multispecific molecule described herein (e.g., prior to 1, 2, 3, 4, 5, 6, 7, 8, 9, 10 or more administrations of a multispecific molecule described herein).

As used herein, the term "myeloid derived suppressor cell" or "MDSC" generally refers to a cell of myeloid origin that is capable of promoting immunosuppression and commonly express CD33, CD11b and CD45. Various subpopulations of MDSCs have been defined, for example monocytic-MDSCs (M-MDSCs) are commonly associated with expression of CD14 and CD124 and low expression of HLA-DR. In some embodiments, the MDSC population is an MO-MDSC population. Polymorphonuclear MDSCs (PMN-MDSCs) are associated with expression of CD15, CD66b, and CD124, and no expression of HLA-DR. Immature MDSCs (I-MDSCs) are associated with expression of CD117 and CD34 and no expression of LIN and HLA-DR. See e.g., Ugel et al. (2015) JCI Vol 125 (9), page 3365.

As used herein, the term "a CSF1R-positive, CCR2-positive cell" refers to a cell expressing both CSF1R and CCR2 on the cell surface. The term "a CSF1R-positve, CCR2-negative cell" refers to a cell expressing CSF1R, but not CCR2 on the cell surface. The term "a CSF1R-negative, CCR2-positive cell" refers to a cell expressing CCR2, but not CSF1R on the cell surface.

As used herein, a binding moiety, e.g., an antibody molecule, binds to a target monovalently, when the binding moiety, e.g., the antibody molecule, binds to a single epitope on the target. In some embodiments, the binding moiety comprises only one antigen binding domain to the target. In some embodiments, one molecule of the binding moiety can only bind to one molecule of the target.

As used herein, a binding moiety, e.g., an antibody molecule, binds to a target bivalently, when the binding moiety, e.g., the antibody molecule, binds to two epitopes on the target. In some embodiments, the two epitopes are identical. In some embodiments, the two epitopes are different. In some embodiments, the binding moiety comprises two antigen binding domains to the target. In some embodiments, one molecule of the binding moiety can bind to two molecules of the target.

Various aspects of the invention are described in further detail below. Additional definitions are set out throughout the specification.

Antigens

TAM targeting antigens of the present disclosure include, e.g., CSF1R, CCR2, CXCR2, CD68, CD163, CX3CR1, MARCO, CD204, CD52, and folate receptor beta. Exemplary amino acid sequences of TAM targeting antigens are provided herein.

CSF1R

CSF1R (also known as Macrophage colony-stimulating factor 1 receptor) is a tyrosine-protein kinase that acts as cell-surface receptor for CSF1 and IL34 and plays an essential role in the regulation of survival, proliferation and differentiation of hematopoietic precursor cells, especially mononuclear phagocytes, such as macrophages and monocytes. CSF1R promotes the release of pro-inflammatory chemokines in response to IL34 and CSF1, and thereby plays an important role in innate immunity and in inflammatory processes. Exemplary CSF1R immature amino acid sequences are provided in SEQ ID NOs: 87 and 88.

CSF1R immature amino acid sequence isoform 1
(identifier: P07333-1):
SEQ ID NO: 87
MGPGVLLLLLVATAWHGQGIPVIEPSVPELVVKPGATVTLRCVGNGSVEW

DGPPSPHWTLYSDGSSSILSTNNATFQNTGTYRCTEPGDPLGGSAAIHLY

VKDPARPWNVLAQEVVVFEDQDALLPCLLTDPVLEAGVSLVRVRGRPLMR

HTNYSFSPWHGFTIHRAKFIQSQDYQCSALMGGRKVMSISIRLKVQKVIP

GPPALTLVPAELVRIRGEAAQIVCSASSVDVNFDVFLQHNNTKLAIPQQS

DFHNNRYQKVLTLNLDQVDFQHAGNYSCVASNVQGKHSTSMFFRVVESAY

LNLSSEQNLIQEVTVGEGLNLKVMVEAYPGLQGFNWTYLGPFSDHQPEPK

LANATTKDTYRHTFTLSLPRLKPSEAGRYSFLARNPGGWRALTFELTLRY

PPEVSVIWTFINGSGTLLCAASGYPQPNVTWLQCSGHTDRCDEAQVLQVW

DDPYPEVLSQEPFHKVTVQSLLTVETLEHNQTYECRAHNSVGSGSWAFIP

ISAGAHTHPPDEFLFTPVVVACMSIMALLLLLLLLLLYKYKQKPKYQVRW

KIIESYEGNSYTFIDPTQLPYNEKWEFPRNNLQFGKTLGAGAFGKVVEAT

AFGLGKEDAVLKVAVKMLKSTAHADEKEALMSELKIMSHLGQHENIVNLL

GACTHGGPVLVITEYCCYGDLLNFLRRKAEAMLGPSLSPGQDPEGGVDYK

NIHLEKKYVRRDSGFSSQGVDTYVEMRPVSTSSNDSFSEQDLDKEDGRPL

ELRDLLHFSSQVAQGMAFLASKNCIHRDVAARNVLLTNGHVAKIGDFGLA

RDIMNDSNYIVKGNARLPVKWMAPESIFDCVYTVQSDVWSYGILLWEIFS

LGLNPYPGILVNSKFYKLVKDGYQMAQPAFAPKNIYSIMQACWALEPTHR

PTFQQICSFLQEQAQEDRRERDYTNLPSSSRSGGSGSSSSELEEESSSEH

LTCCEQGDIAQPLLQPNNYQFC

CSF1R immature amino acid sequence isoform 2
(identifier: P07333-2):
SEQ ID NO: 88
MGPGVLLLLLVATAWHGQGIPVIEPSVPELVVKPGATVTLRCVGNGSVEW

```
DGPPSPHWTLYSDGSSSILSTNNATFQNTGTYRCTEPGDPLGGSAAIHLY

VKDPARPWNVLAQEVVVFEDQDALLPCLLTDPVLEAGVSLVRVRGRPLMR

HTNYSFSPWHGFTIHRAKFIQSQDYQCSALMGGRKVMSISIRLKVQKVIP

GPPALTLVPAELVRIRGEAAQIVCSASSVDVNFDVFLQHNNTKLAIPQQS

DFHNNRYQKVLTLNLDQVDFQHAGNYSCVASNVQGKHSTSMFFRVVGTPS

PSLCPA
```

CCR2

CCR2 (also known as C-C chemokine receptor type 2) is a G protein coupled receptor for the CCL2, CCL7 and CCL13 chemokines. CCR2 is known to function in the recruitment of monocytes/macrophages and T cells. CCR2 is expressed is expressed on monocytes and a small subpopulation of T cells and exhibits an almost identical expression pattern in mice and humans (Mack et al. J Immunol 2001; 166:4697-4704). Exemplary CCR2 amino acid sequences are provided in SEQ ID NOs: 89 and 90.

```
CCR2 amino acid sequence isoform A (Identifier:
P41597-1):
                                           SEQ ID NO: 89
MLSTSRSRFIRNTNESGEEVTTFFDYDYGAPCHKFDVKQIGAQLLPPLYS

LVFIFGFVGNMLVVLILINCKKLKCLTDIYLLNLAISDLLFLITLPLWAH

SAANEWVFGNAMCKLFTGLYHIGYFGGIFFIILLTIDRYLAIVHAVFALK

ARTVTFGVVTSVITWLVAVFASVPGIIFTKCQKEDSVYVCGPYFPRGWNN

FHTIMRNILGLVLPLLIMVICYSGILKTLLRCRNEKKRHRAVRVIFTIMI

VYFLFWTPYNIVILLNTFQEFFGLSNCESTSQLDQATQVTETLGMTHCCI

NPIIYAFVGEKFRSLFHIALGCRIAPLQKPVCGGPGVRPGKNVKVTTQGL

LDGRGKGKSIGRAPEASLQDKEGA

CCR2 amino acid sequence isoform B (Identifier:
P41597-2):
                                           SEQ ID NO: 90
MLSTSRSRFIRNTNESGEEVTTFFDYDYGAPCHKFDVKQIGAQLLPPLYS

LVFIFGFVGNMLVVLILINCKKLKCLTDIYLLNLAISDLLFLITLPLWAH

SAANEWVFGNAMCKLFTGLYHIGYFGGIFFIILLTIDRYLAIVHAVFALK

ARTVTFGVVTSVITWLVAVFASVPGIIFTKCQKEDSVYVCGPYFPRGWNN

FHTIMRNILGLVLPLLIMVICYSGILKTLLRCRNEKKRHRAVRVIFTIMI

VYFLFWTPYNIVILLNTFQEFFGLSNCESTSQLDQATQVTETLGMTHCCI

NPIIYAFVGEKFRRYLSVFFRKHITKRFCKQCPVFYRETVDGVTSTNTPS

TGEQEVSAGL
```

CXCR2

CXCR2 (also known as interleukin-8 receptor) is the G protein coupled receptor for IL8 which is a neutrophil chemotactic factor. Binding of IL8 to the receptor causes activation of neutrophils. This response is mediated via a G-protein that activates a phosphatidylinositol-calcium second messenger system. CXCR2 binds to IL-8 with high affinity, and also binds with high affinity to CXCL3, GRO/MGSA and NAP-2. CXCR2 is expressed at high levels on circulating neutrophils and is critical for directing their migration to sites of inflammation (J Clin Invest. 2012; 122(9):3127-3144). An exemplary CXCR2 amino acid sequence is provided in SEQ ID NO: 91.

```
CXCR2 amino acid sequence (Identifier: P25025-1):
                                           SEQ ID NO: 91
MEDFNMESDSFEDFWKGEDLSNYSYSSTLPPFLLDAAPCEPESLEINKYF

VVIIYALVFLLSLLGNSLVMLVILYSRVGRSVTDVYLLNLALADLLFALT

LPIWAASKVNGWIFGTFLCKVVSLLKEVNFYSGILLLACISVDRYLAIVH

ATRTLTQKRYLVKFICLSIWGLSLLLALPVLLFRRTVYSSNVSPACYEDM

GNNTANWRMLLRILPQSFGFIVPLLIMLFCYGFTLRTLFKAHMGQKHRAM

RVIPAVVLIFLLCWLPYNLVLLADTLMRTQVIQETCERRNHIDRALDATE

ILGILHSCLNPLIYAFIGQKFRHGLLKILAIHGLISKDSLPKDSRPSFVG

SSSGHTSTTL
```

Exemplary Antibodies

Exemplary antibodies binding TAM antigens are provided throughout the specification and below. Exemplary anti-CSF1R antibodies are described herein as well as in WO2009026303A1; WO2011123381A1; WO2016207312A1; WO2016106180A1; US20160220669A1; US20160326254A1; WO2013169264A1; WO2013087699A1; WO2011140249A2; WO2011131407A1; WO2011123381A1; WO2011107553A1; and WO2011070024A1, all of which are herein incorporated by reference in their entirety. Exemplary CCR2 antibodies are described herein as well as in WO2013192596A2; WO2010021697A2; WO2001057226A1; and WO1997031949A1, all of which are herein incorporated by reference in their entirety. Exemplary CXCR2 antibodies are described in WO2014170317A1 and US20160060347 (see e.g., a) SEQ ID NO: 14 (light chain) and SEQ ID NO: 15 (heavy chain); b) SEQ ID NO: 24 (light chain) and SEQ ID NO: 25 (heavy chain); c) SEQ ID NO: 34 (light chain) and SEQ ID NO: 35 (heavy chain); d) SEQ ID NO: 44 (light chain) and SEQ ID NO: 45 (heavy chain); e) SEQ ID NO: 54 (light chain) and SEQ ID NO: 55 (heavy chain); f) SEQ ID NO: 64 (light chain) and SEQ ID NO: 65 (heavy chain); g) SEQ ID NO: 74 (light chain) and SEQ ID NO: 75 (heavy chain); h) SEQ ID NO: 84 (light chain) and SEQ ID NO: 85 (heavy chain)), all of which are herein incorporated by reference in their entirety. Exemplary anti-CD163 antibodies are provided in US20120258107 (see e.g., MAC2158, MAC2-48), herein incorporated by reference in its entirety. Exemplary anti-CD52 antibodies are described in US20050152898, herein incorporated by reference in its entirety. Exemplary anti-folate antibodies are described in U.S. Pat. No. 9,522,196, herein incorporated by reference in its entirety. Exemplary anti-CD52 antibodies are described in US20050152898, herein incorporated by reference in its entirety. Exemplary anti-MARCO antibodies are described in WO2016196612, herein incorporated by reference in its entirety.

Antibody Molecules

In one embodiment, the multispecific molecule comprises an antibody molecule that binds to a first tumor associated macrophage (TAM) antigen; and an antibody molecule that binds to a second TAM antigen. In some embodiments, the first and/or second TAM antigen is, e.g., a mammalian, e.g., a human. For example, the antibody molecule binds specifically to an epitope, e.g., linear or conformational epitope, on the TAM antigen.

In one embodiment, the multispecific molecule comprises an antibody molecule that binds to a first myeloid derived suppressor cell (MDSC) antigen; and an antibody molecule that binds to a second MDSC antigen. In some embodiments, the first and/or second MDSC antigen is, e.g., a mammalian, e.g., a human. For example, the antibody molecule binds specifically to an epitope, e.g., linear or conformational epitope, on the MDSC antigen.

In an embodiment, an antibody molecule is a monospecific antibody molecule and binds a single epitope. E.g., a monospecific antibody molecule having a plurality of immunoglobulin variable region sequences, each of which binds the same epitope.

In an embodiment an antibody molecule is a multispecific antibody molecule, e.g., it comprises a plurality of immunoglobulin variable region sequences, wherein a first immunoglobulin variable region sequence of the plurality has binding specificity for a first epitope and a second immunoglobulin variable region sequence of the plurality has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., the different proteins (or different subunits of a multimeric protein). In an embodiment a multispecific antibody molecule comprises a third, fourth or fifth immunoglobulin variable region. In an embodiment, a multispecific antibody molecule is a bispecific antibody molecule, a trispecific antibody molecule, or a tetraspecific antibody molecule.

In an embodiment a multispecific antibody molecule is a bispecific antibody molecule. A bispecific antibody has specificity for no more than two antigens. A bispecific antibody molecule is characterized by a first immunoglobulin variable region sequence which has binding specificity for a first epitope and a second immunoglobulin variable region sequence that has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., the different proteins (or different subunits of a multimeric protein). In an embodiment a bispecific antibody molecule comprises a heavy chain variable region sequence and a light chain variable region sequence which have binding specificity for a first epitope and a heavy chain variable region sequence and a light chain variable region sequence which have binding specificity for a second epitope. In an embodiment a bispecific antibody molecule comprises a half antibody having binding specificity for a first epitope and a half antibody having binding specificity for a second epitope. In an embodiment a bispecific antibody molecule comprises a half antibody, or fragment thereof, having binding specificity for a first epitope and a half antibody, or fragment thereof, having binding specificity for a second epitope. In an embodiment a bispecific antibody molecule comprises a scFv or a Fab, or fragment thereof, have binding specificity for a first epitope and a scFv or a Fab, or fragment thereof, have binding specificity for a second epitope.

In an embodiment, an antibody molecule comprises a diabody, and a single-chain molecule, as well as an antigen-binding fragment of an antibody (e.g., Fab, F(ab')$_2$, and Fv). For example, an antibody molecule can include a heavy (H) chain variable region sequence (abbreviated herein as VH), and a light (L) chain variable region sequence (abbreviated herein as VL). In an embodiment an antibody molecule comprises or consists of a heavy chain and a light chain (referred to herein as a half antibody). In another example, an antibody molecule includes two heavy (H) chain variable region sequences and two light (L) chain variable region sequence, thereby forming two antigen binding sites, such as Fab, Fab', F(ab')$_2$, Fc, Fd, Fd', Fv, single chain antibodies (scFv for example), single variable region antibodies, diabodies (Dab) (bivalent and bispecific), and chimeric (e.g., humanized) antibodies, which may be produced by the modification of whole antibodies or those synthesized de novo using recombinant DNA technologies. These functional antibody fragments retain the ability to selectively bind with their respective antigen or receptor. Antibodies and antibody fragments can be from any class of antibodies including, but not limited to, IgG, IgA, IgM, IgD, and IgE, and from any subclass (e.g., IgG1, IgG2, IgG3, and IgG4) of antibodies. The a preparation of antibody molecules can be monoclonal or polyclonal. An antibody molecule can also be a human, humanized, CDR-grafted, or in vitro generated antibody. The antibody can have a heavy chain constant region chosen from, e.g., IgG1, IgG2, IgG3, or IgG4. The antibody can also have a light chain chosen from, e.g., kappa or lambda. The term "immunoglobulin" (Ig) is used interchangeably with the term "antibody" herein.

Examples of antigen-binding fragments of an antibody molecule include: (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a diabody (dAb) fragment, which consists of a VH domain; (vi) a camelid or camelized variable region; (vii) a single chain Fv (scFv), see e.g., Bird et al. (1988) *Science* 242:423-426; and Huston et al. (1988) *Proc. Natl. Acad. Sci. USA* 85:5879-5883); (viii) a single domain antibody. These antibody fragments are obtained using conventional techniques known to those with skill in the art, and the fragments are screened for utility in the same manner as are intact antibodies.

Antibody molecules include intact molecules as well as functional fragments thereof. Constant regions of the antibody molecules can be altered, e.g., mutated, to modify the properties of the antibody (e.g., to increase or decrease one or more of: Fc receptor binding, antibody glycosylation, the number of cysteine residues, effector cell function, or complement function).

Antibody molecules can also be single domain antibodies. Single domain antibodies can include antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, fish, shark, goat, rabbit, and bovine. According to another aspect of the invention, a single domain antibody is a naturally occurring single domain antibody known as heavy chain antibody devoid of light chains. Such single domain antibodies are disclosed in WO 9404678, for example. For clarity reasons, this variable region derived from a heavy chain antibody naturally devoid of light chain is known herein as a VHH or nanobody to distinguish it from the conventional VH of four chain immunoglobulins. Such a VHH molecule can be derived from antibodies raised in Camelidae species, for example in camel, llama, dromedary, alpaca and guanaco. Other species besides Camelidae may produce heavy chain antibodies naturally devoid of light chain; such VHHs are within the scope of the invention.

The VH and VL regions can be subdivided into regions of hypervariability, termed "complementarity determining regions" (CDR), interspersed with regions that are more conserved, termed "framework regions" (FR or FW).

The extent of the framework region and CDRs has been precisely defined by a number of methods (see, Kabat, E. A., et al. (1991) Sequences of Proteins of Immunological Interest, Fifth Edition, U.S. Department of Health and Human Services, NIH Publication No. 91-3242; Chothia, C. et al. (1987) *J. Mol. Biol.* 196:901-917; and the AbM definition used by Oxford Molecular's AbM antibody modeling software. See, generally, e.g., *Protein Sequence and Structure Analysis of Antibody Variable Domains*. In: Antibody Engineering Lab Manual (Ed.: Duebel, S. and Kontermann, R., Springer-Verlag, Heidelberg).

The terms "complementarity determining region," and "CDR," as used herein refer to the sequences of amino acids within antibody variable regions which confer antigen specificity and binding affinity. In general, there are three CDRs in each heavy chain variable region (HCDR1, HCDR2, HCDR3) and three CDRs in each light chain variable region (LCDR1, LCDR2, LCDR3).

The precise amino acid sequence boundaries of a given CDR can be determined using any of a number of known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) *JMB* 273,927-948 ("Chothia" numbering scheme). As used herein, the CDRs defined according the "Chothia" number scheme are also sometimes referred to as "hypervariable loops."

For example, under Kabat, the CDR amino acid residues in the heavy chain variable region (VH) are numbered 31-35 (HCDR1), 50-65 (HCDR2), and 95-102 (HCDR3); and the CDR amino acid residues in the light chain variable region (VL) are numbered 24-34 (LCDR1), 50-56 (LCDR2), and 89-97 (LCDR3). Under Chothia, the CDR amino acids in the VH are numbered 26-32 (HCDR1), 52-56 (HCDR2), and 95-102 (HCDR3); and the amino acid residues in VL are numbered 26-32 (LCDR1), 50-52 (LCDR2), and 91-96 (LCDR3).

Each VH and VL typically includes three CDRs and four FRs, arranged from amino-terminus to carboxy-terminus in the following order: FR1, CDR1, FR2, CDR2, FR3, CDR3, FR4.

The antibody molecule can be a polyclonal or a monoclonal antibody.

The terms "monoclonal antibody" or "monoclonal antibody composition" as used herein refer to a preparation of antibody molecules of single molecular composition. A monoclonal antibody composition displays a single binding specificity and affinity for a particular epitope. A monoclonal antibody can be made by hybridoma technology or by methods that do not use hybridoma technology (e.g., recombinant methods).

The antibody can be recombinantly produced, e.g., produced by phage display or by combinatorial methods.

Phage display and combinatorial methods for generating antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Hum Antibod Hybridomas* 3:81-85; Huse et al. (1989) *Science* 246:1275-1281; Griffths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, the contents of all of which are incorporated by reference herein).

In one embodiment, the antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. Preferably, the non-human antibody is a rodent (mouse or rat antibody). Methods of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368:856-859; Green, L. L. et al. 1994 *Nature Genet.* 7:13-21; Morrison, S. L. et al. 1994 *Proc. Natl. Acad. Sci. USA* 81:6851-6855; Bruggeman et al. 1993 *Year Immunol* 7:33-40; Tuaillon et al. 1993 *PNAS* 90:3720-3724; Bruggeman et al. 1991 *Eur J Immunol* 21:1323-1326).

An antibody molecule can be one in which the variable region, or a portion thereof, e.g., the CDRs, are generated in a non-human organism, e.g., a rat or mouse. Chimeric, CDR-grafted, and humanized antibodies are within the invention. Antibody molecules generated in a non-human organism, e.g., a rat or mouse, and then modified, e.g., in the variable framework or constant region, to decrease antigenicity in a human are within the invention.

An "effectively human" protein is a protein that does substantially not evoke a neutralizing antibody response, e.g., the human anti-murine antibody (HAMA) response. HAMA can be problematic in a number of circumstances, e.g., if the antibody molecule is administered repeatedly, e.g., in treatment of a chronic or recurrent disease condition. A HAMA response can make repeated antibody administration potentially ineffective because of an increased antibody clearance from the serum (see, e.g., Saleh et al., *Cancer Immunol. Immunother.*, 32:180-190 (1990)) and also because of potential allergic reactions (see, e.g., LoBuglio et al., *Hybridoma*, 5:5117-5123 (1986)).

Chimeric antibodies can be produced by recombinant DNA techniques known in the art (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No.

4,816,567; Cabilly et al., European Patent Application 125, 023; Better et al. (1988 Science 240:1041-1043); Liu et al. (1987) *PNAS* 84:3439-3443; Liu et al., 1987, *J. Immunol.* 139:3521-3526; Sun et al. (1987) *PNAS* 84:214-218; Nishimura et al., 1987, *Canc. Res.* 47:999-1005; Wood et al. (1985) *Nature* 314:446-449; and Shaw et al., 1988, *J. Natl Cancer Inst.* 80:1553-1559).

A humanized or CDR-grafted antibody will have at least one or two but generally all three recipient CDRs (of heavy and or light immuoglobulin chains) replaced with a donor CDR. The antibody may be replaced with at least a portion of a non-human CDR or only some of the CDRs may be replaced with non-human CDRs. It is only necessary to replace the number of CDRs required for binding to the antigen. Preferably, the donor will be a rodent antibody, e.g., a rat or mouse antibody, and the recipient will be a human framework or a human consensus framework. Typically, the immunoglobulin providing the CDRs is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody molecule can be humanized by methods known in the art (see e.g., Morrison, S. L., 1985, *Science* 229:1202-1207, by Oi et al., 1986, *BioTechniques* 4:214, and by Queen et al. U.S. Pat. Nos. 5,585,089, 5,693,761 and 5,693,762, the contents of all of which are hereby incorporated by reference).

Humanized or CDR-grafted antibody molecules can be produced by CDR-grafting or CDR substitution, wherein one, two, or all CDRs of an immunoglobulin chain can be replaced. See e.g., U.S. Pat. No. 5,225,539; Jones et al. 1986 *Nature* 321:552-525; Verhoeyan et al. 1988 *Science* 239:1534; Beidler et al. 1988 *J. Immunol.* 141:4053-4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibody molecules in which specific amino acids have been substituted, deleted or added. Criteria for selecting amino acids from the donor are described in U.S. Pat. No. 5,585,089, e.g., columns 12-16 of U.S. Pat. No. 5,585,089, e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

The antibody molecule can be a single chain antibody. A single-chain antibody (scFV) may be engineered (see, for example, Colcher, D. et al. (1999) *Ann N Y Acad Sci* 880:263-80; and Reiter, Y. (1996) *Clin Cancer Res* 2:245-52). The single chain antibody can be dimerized or multimerized to generate multivalent antibodies having specificities for different epitopes of the same target protein.

In yet other embodiments, the antibody molecule has a heavy chain constant region chosen from, e.g., the heavy chain constant regions of IgG1, IgG2, IgG3, IgG4, IgM, IgA1, IgA2, IgD, and IgE; particularly, chosen from, e.g., the (e.g., human) heavy chain constant regions of IgG1, IgG2, IgG3, and IgG4. In another embodiment, the antibody molecule has a light chain constant region chosen from, e.g., the (e.g., human) light chain constant regions of kappa or lambda. The constant region can be altered, e.g., mutated, to modify the properties of the antibody (e.g., to increase or decrease one or more of: Fc receptor binding, antibody glycosylation, the number of cysteine residues, effector cell function, and/or complement function). In one embodiment the antibody has: effector function; and can fix complement. In other embodiments the antibody does not; recruit effector cells; or fix complement. In another embodiment, the antibody has reduced or no ability to bind an Fc receptor. For example, it is a isotype or subtype, fragment or other mutant, which does not support binding to an Fc receptor, e.g., it has a mutagenized or deleted Fc receptor binding region.

Methods for altering an antibody constant region are known in the art. Antibodies with altered function, e.g. altered affinity for an effector ligand, such as FcR on a cell, or the C1 component of complement can be produced by replacing at least one amino acid residue in the constant portion of the antibody with a different residue (see e.g., EP 388,151 A1, U.S. Pat. Nos. 5,624,821 and 5,648,260, the contents of all of which are hereby incorporated by reference). Similar type of alterations could be described which if applied to the murine, or other species immunoglobulin would reduce or eliminate these functions.

An antibody molecule can be derivatized or linked to another functional molecule (e.g., another peptide or protein). As used herein, a "derivatized" antibody molecule is one that has been modified. Methods of derivatization include but are not limited to the addition of a fluorescent moiety, a radionucleotide, a toxin, an enzyme or an affinity ligand such as biotin. Accordingly, the antibody molecules of the invention are intended to include derivatized and otherwise modified forms of the antibodies described herein, including immunoadhesion molecules. For example, an antibody molecule can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate association of the antibody or antibody portion with another molecule (such as a streptavidin core region or a polyhistidine tag).

One type of derivatized antibody molecule is produced by cros slinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Multispecific Antibody Molecules

In embodiments, multispecific antibody molecules can comprise more than one antigen-binding site, where different sites are specific for different antigens. In embodiments, multispecific antibody molecules can bind more than one (e.g., two or more) epitopes on the same antigen. In embodiments, multispecific antibody molecules comprise an antigen-binding site specific for a target cell (e.g., cancer cell) and a different antigen-binding site specific for an immune effector cell. In one embodiment, the multispecific antibody molecule is a bispecific antibody molecule. Bispecific antibody molecules can be classified into five different structural groups: (i) bispecific immunoglobulin G (BsIgG); (ii) IgG appended with an additional antigen-binding moiety; (iii) bispecific antibody fragments; (iv) bispecific fusion proteins; and (v) bispecific antibody conjugates.

BsIgG is a format that is monovalent for each antigen. Exemplary BsIgG formats include but are not limited to crossMab, DAF (two-in-one), DAF (four-in-one), DutaMab, DT-IgG, knobs-in-holes common LC, knobs-in-holes assembly, charge pair, Fab-arm exchange, SEEDbody, triomab, LUZ-Y, Fcab, κλ-body, orthogonal Fab. See Spiess et al. Mol. Immunol. 67(2015):95-106. Exemplary BsIgGs include catumaxomab (Fresenius Biotech, Trion Pharma, Neopharm), which contains an anti-CD3 arm and an anti-EpCAM arm; and ertumaxomab (Neovii Biotech, Fresenius Biotech), which targets CD3 and HER2. In some embodiments, BsIgG comprises heavy chains that are engineered for heterodimerization. For example, heavy chains can be engineered for heterodimerization using a "knobs-into-holes" strategy, a SEED platform, a common heavy chain (e.g., in κλ-bodies), and use of heterodimeric Fc regions. See Spiess et al. Mol. Immunol. 67(2015):95-106. Strategies that have been used to avoid heavy chain pairing of homodimers in BsIgG include knobs-in-holes, duobody, azymetric, charge pair, HA-TF, SEEDbody, and differential protein A affinity. See Id. BsIgG can be produced by separate expression of the component antibodies in different host cells and subsequent purification/assembly into a BsIgG. BsIgG can also be produced by expression of the component antibodies in a single host cell. BsIgG can be purified using affinity chromatography, e.g., using protein A and sequential pH elution.

IgG appended with an additional antigen-binding moiety is another format of bispecific antibody molecules. For example, monospecific IgG can be engineered to have bispecificity by appending an additional antigen-binding unit onto the monospecific IgG, e.g., at the N- or C-terminus of either the heavy or light chain. Exemplary additional antigen-binding units include single domain antibodies (e.g., variable heavy chain or variable light chain), engineered protein scaffolds, and paired antibody variable regions (e.g., single chain variable fragments or variable fragments). See Id. Examples of appended IgG formats include dual variable domain IgG (DVD-Ig), IgG(H)-scFv, scFv-(H)IgG, IgG(L)-scFv, scFv-(L)IgG, IgG(L,H)-Fv, IgG(H)-V, V(H)-IgG, IgG(L)-V, V(L)-IgG, KIH IgG-scFab, 2scFv-IgG, IgG-2scFv, scFv4-Ig, zybody, and DVI-IgG (four-in-one). See Spiess et al. Mol. Immunol. 67(2015):95-106. An example of an IgG-scFv is MM-141 (Merrimack Pharmaceuticals), which binds IGF-1R and HERS. Examples of DVD-Ig include ABT-981 (AbbVie), which binds IL-1α and IL-1β; and ABT-122 (AbbVie), which binds TNF and IL-17A.

Bispecific antibody fragments (BsAb) are a format of bispecific antibody molecules that lack some or all of the antibody constant domains. For example, some BsAb lack an Fc region. In embodiments, bispecific antibody fragments include heavy and light chain regions that are connected by a peptide linker that permits efficient expression of the BsAb in a single host cell. Exemplary bispecific antibody fragments include but are not limited to nanobody, nanobody-HAS, BiTE, Diabody, DART, TandAb, scDiabody, scDiabody-CH3, Diabody-CH3, triple body, miniantibody, minibody, TriBi minibody, scFv-CH3 KIH, Fab-scFv, scFv-CH-CL-scFv, F(ab')2, F(ab')2-scFv2, scFv-KIH, Fab-scFv-Fc, tetravalent HCAb, scDiabody-Fc, Diabody-Fc, tandem scFv-Fc, and intrabody. See Id. For example, the BiTE format comprises tandem scFvs, where the component scFvs bind to CD3 on T cells and a surface antigen on cancer cells Bispecific fusion proteins include antibody fragments linked to other proteins, e.g., to add additional specificity and/or functionality. An example of a bispecific fusion protein is an immTAC, which comprises an anti-CD3 scFv linked to an affinity-matured T-cell receptor that recognizes HLA-presented peptides. In embodiments, the dock-and-lock (DNL) method can be used to generate bispecific antibody molecules with higher valency. Also, fusions to albumin binding proteins or human serum albumin can be extend the serum half-life of antibody fragments. See Id.

In embodiments, chemical conjugation, e.g., chemical conjugation of antibodies and/or antibody fragments, can be used to create BsAb molecules. See Id. An exemplary bispecific antibody conjugate includes the CovX-body format, in which a low molecular weight drug is conjugated site-specifically to a single reactive lysine in each Fab arm or an antibody or fragment thereof. In embodiments, the conjugation improves the serum half-life of the low molecular weight drug. An exemplary CovX-body is CVX-241 (NCT01004822), which comprises an antibody conjugated to two short peptides inhibiting either VEGF or Ang2. See Id.

The antibody molecules can be produced by recombinant expression, e.g., of at least one or more component, in a host system. Exemplary host systems include eukaryotic cells (e.g., mammalian cells, e.g., CHO cells, or insect cells, e.g., SF9 or S2 cells) and prokaryotic cells (e.g., E. coli). Bispecific antibody molecules can be produced by separate expression of the components in different host cells and subsequent purification/assembly. Alternatively, the antibody molecules can be produced by expression of the components in a single host cell. Purification of bispecific antibody molecules can be performed by various methods such as affinity chromatography, e.g., using protein A and sequential pH elution. In other embodiments, affinity tags can be used for purification, e.g., histidine-containing tag, myc tag, or streptavidin tag.

Multispecific Antibody Molecules Targeting CSF1R

In one aspect, disclosed herein is a multispecific antibody molecule comprising a CSF1R binding moiety. In some embodiments, the CSF1R binding moiety comprises an anti-CSF1R antibody molecule. Exemplary anti-CSF1R antibody molecule sequences are described in WO2009026303A1; WO2011123381A1; WO2016207312A1; WO2016106180A1; US20160220669A1; US20160326254A1; WO2013169264A1; WO2013087699A1; WO2011140249A2; WO2011131407A1; WO2011123381A1; WO2011107553A1; and WO2011070024A1, all of which are herein incorporated by reference in their entirety. In some embodiments, the CSF1R binding moiety comprises the CDR (e.g., one, two, three, four, five, or all six CDRs), VH, VL, heavy chain, or light chain sequences of emactuzumab, or a sequence substantially identical thereto (e.g., at least 95% identical thereto, e.g., 95% to 99.9% identical thereto, or having at least one amino acid alteration, but not more than five, ten or fifteen alterations (e.g., substitutions, deletions, or insertions, e.g., conservative substitutions)). In some embodiments, the CSF1R binding moiety comprises the CDR (e.g., one, two, three, four, five, or all six CDRs), VH, VL, heavy chain, or light chain sequences of cabiralizumab, or a sequence substantially identical thereto (e.g., at least 95% identical thereto, e.g., 95% to 99.9% identical thereto, or having at least one amino acid alteration, but not more than five, ten or fifteen alterations (e.g., substitutions, deletions, or insertions, e.g., conservative substitutions)). In some embodiments, the CSF1R binding moiety comprises the CDR (e.g., one, two, three, four, five, or all six CDRs), VH, VL, heavy chain, or light chain sequences of AMG820, or a sequence substantially identical thereto (e.g., at least 95% identical thereto, e.g., 95% to 99.9% identical thereto, or having at least one amino acid alteration, but not more than five, ten or fifteen alterations (e.g., substitutions, deletions, or insertions, e.g., conservative substitutions)). In some embodiments, the CSF1R binding moiety comprises the CDR (e.g., one, two, three, four, five, or all six CDRs), VH, VL, heavy chain, or light chain sequences of IMC-CS4, or a sequence substantially identical thereto (e.g., at least 95% identical thereto, e.g., 95% to 99.9% identical thereto, or having at least one amino acid alteration, but not more than five, ten or fifteen alterations (e.g., substitutions, deletions, or insertions, e.g., conservative substitutions)). In some embodiments, the CSF1R binding moiety comprises a VH or VL amino acid sequence disclosed in Table 8, a CDR of a VH or VL amino acid sequence disclosed in Table 8, or a sequence substantially identical thereto.

TABLE 8

Exemplary anti-CSF1R antibody molecule sequences

| SEQ ID NO | Description | Sequence |
|---|---|---|
| SEQ ID NO: 48 | αmCSF1R VH | QVQLQQSGAELVKPGSSVKISCKASGYTFTSNFMHWIKQQPGNGLE WIGWIYPGDGDTEYNQKFNGKATLTADKSSSTAYMQLSSLTSEDSA VYFCAVNYGGYVLDAWGQGASVTVSS |
| SEQ ID NO: 50 | αmCSF1R VL | EIVLTQSPTTMAASPGEKVTITCRASSSTNYMSWYQQKSGASPKPWI YETSKLASGVPDRFSGSGSGTSYSFTISSMETEDAATYYCHQWSSTP LTFGSGTKLEIK |
| SEQ ID NO: 66 | αhCSF1R emactuzumab VH | QVQLVQSGAEVKKPGASVKVSCKASGYTFTSYDISWVRQAPGQGL EWMGVIWTDGGTNYAQKLQGRVTMTTDTSTSTAYMELRSLRSDD TAVYYCARDQRLYFDVWGQGTTVTVSS |
| SEQ ID NO: 67 | αhCSF1R emactuzumab VL | DIQMTQSPSSLSASVGDRVTITCRASEDVNTYVSWYQQKPGKAPKL LIYAASNRYTGVPSRFSGSGSGTDFTLTISSLQPEDFATYYCQQSFSY PTFGQGTKLEIK |
| SEQ ID NO: 69 | αhCSF1R cabiralizumab VH | QVQLVQSGAEVKKPGSSVKVSCKASGYTFTDNYMIWVRQAPGQGL EWMGDINPYNGGTTFNQKFKGRVTITADKSTSTAYMELSSLRSEDT AVYYCARESPYFSNLYVMDYWGQGTLVTVSS |
| SEQ ID NO: 70 | αhCSF1R cabiralizumab VL | EIVLTQSPATLSLSPGERATLSCKASQSVDYDGDNYMNWYQQKPG QAPRLLIYAASNLESGIPARFSGSGSGTDFTLTISSLEPEDFAVYYCHL SNEDLSTFGGGTKVEIK |

Multispecific Antibody Molecules Targeting CCR2

In one aspect, disclosed herein is a multispecific antibody molecule comprising a CCR2 binding moiety. Exemplary CCR2 antibodies are described herein as well as in WO2013192596A2; WO2010021697A2; WO2001057226A1; and WO1997031949A1, all of which are herein incorporated by reference in their entirety. In some embodiments, the CCR2 binding moiety comprises the CDR (e.g., one, two, three, four, five, or all six CDRs), VH, VL, heavy chain, or light chain sequences of plozalizumab, or a sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions)). In some embodiments, the CCR2 binding moiety comprises a VH or VL amino acid sequence disclosed in Table 9, a CDR of a VH or VL amino acid sequence disclosed in Table 9, or a sequence substantially identical thereto.

TABLE 9

Exemplary anti-CCR2 antibody molecule sequences

| SEQ ID NO | Description | Sequence |
|---|---|---|
| SEQ ID NO: 44 | αCCR2 MC12 VH | QVQLQESGPGLVQPSQTLSLTCTVSGFSLTDFSVHWVRQPPGKGLE WMGRIRSEGNTDYNSALKSRLSISRDTSKSQVFLKMNSLQTEDTAIY FCTRGDILGFGYWGQGVMVTVSS |
| SEQ ID NO: 45 | αCCR2 MC12 VL | DIVMTQSPLSVSVTPGESASISCRSSKSLLHFKGITFVYWYLQKPGQS PQLLIFRMSSLASGVPDRFSGSGSETDFTLKISRVEAEDVGTYYCGQ LLENPYTFGAGTKLELK |

TABLE 9-continued

Exemplary anti-CCR2 antibody molecule sequences

| SEQ ID NO | Description | Sequence |
|---|---|---|
| SEQ ID NO: 54 | αhCCR2 plozalizumab VH | EVQLVESGGGLVKPGGSLRLSCAASGFTFSAYAMNWVRQAPGKGL EWVGRIRTKNNNYATYYADSVKDRFTISRDDSKNTLYLQMNSLKT EDTAVYYCTTFYGNGVWGQGTLVTVSS |
| SEQ ID NO: 57 | αhCCR2 plozalizumab VL | DVVMTQSPLSLPVTLGQPASISCKSSQSLLDSDGKTFLNWFQQRPGQ SPRRLIYLVSKLDSGVPDRFSGSGSGTDFTLKISRVEAEDVGVYYCW QGTHFPYTFGQGTRLEIK |
| SEQ ID NO: 59 | αhCCR2 D1 VH | EVQLVQSGAEVKKPGASVKVSCKASGYTFTGYHMHWVRQAPGQG LEWMGWINPNSGVTKYAQKFQGRVTMTRDTSINTAYMELSRLRFD DTDVYYCATGGFGYWGEGTLVTVSS |
| SEQ ID NO: 60 | αhCCR2 D1 VL | LPVLTQPPSVSKGLRQTATLTCTGNSNNVGNQGAAWLQQHQGQPP KLLSYRNHNRPSGVSERFSPSRSGDTSSLTITGLQPEDEADYYCLAW DSSLRAFVFGTGTKLTVL |
| SEQ ID NO: 62 | αhCCR2 42G7 VH | QVQLVQSGAEVKKPGASVKVSCKASGYTFSSYYMHWVRQAPGQG LEWMGIINPSGGNTSYAQKFQGRVTMTRDTSTSTVYMELSSLRSED TAVYYCARGGYQLPHGRARAFDMWGQGTMVTVSS |
| SEQ ID NO: 63 | αhCCR2 42G7 VL | AIRMTQSPLSLPVTLGQPASISCTSSQSLVYRDGTTYLNWFQQRPGQ SPRRLIYKVSNRDSGVPDRFTGSGSGTTFTLTISRVEAEDVGIYYCM QGTHWPLTFGQGTKVEIK |
| SEQ ID NO: 64 | αhCCR2 43G12 VH | EVQLVESGGGLVQPGGSLRLSCVASGFTFSDYWMSWVRQAPGKGL EWVANIKKDGSVNYYVDSVKGRFTISRDNAKNSLYLQMNSLRAED TAVYYCTRFDYWGQGTLVTVSS |
| SEQ ID NO: 65 | αhCCR2 43G12 VL | QAGLTQPPSVSKGLRQTATLTCTGNSNNVGNQGAAWLQQHQGHPP KLLFYRNNNRASGISERLSASRSGNTASLTITGLQPEDEADYYCLTW DSSLSVVVFGGGTKLTVL |

Multispecific Antibody Molecules Targeting PD-L1

In one aspect, disclosed herein is a multispecific antibody molecule comprising a PD-L1 binding moiety. In some embodiments, the PD-L1 binding moiety comprises an anti-PD-L1 antibody molecule. Exemplary anti-PD-L1 antibody molecule sequences are described in WO2013079174, WO 2010077634, WO2007/005874, and US20120039906, all of which are herein incorporated by reference in their entirety. In some embodiments, the PD-L1 binding moiety comprises the CDR (e.g., one, two, three, four, five, or all six CDRs), VH, VL, heavy chain, or light chain sequences of durvalumab, or a sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions)). In some embodiments, the PD-L1 binding moiety comprises the CDR (e.g., one, two, three, four, five, or all six CDRs), VH, VL, heavy chain, or light chain sequences of atezolizumab, or a sequence substantially identical thereto (e.g., at least 95% identical thereto, e.g., 95% to 99.9% identical thereto, or having at least one amino acid alteration, but not more than five, ten or fifteen alterations (e.g., substitutions, deletions, or insertions, e.g., conservative substitutions)). In some embodiments, the PD-L1 binding moiety comprises the CDR (e.g., one, two, three, four, five, or all six CDRs), VH, VL, heavy chain, or light chain sequences of avelumab, or a sequence substantially identical thereto (e.g., at least 95% identical thereto, e.g., 95% to 99.9% identical thereto, or having at least one amino acid alteration, but not more than five, ten or fifteen alterations (e.g., substitutions, deletions, or insertions, e.g., conservative substitutions)). In some embodiments, the PD-L1 binding moiety comprises a VH or VL amino acid sequence disclosed in Table 10, a CDR of a VH or VL amino acid sequence disclosed in Table 10, or a sequence substantially identical thereto.

TABLE 10

Exemplary anti-PD-L1 antibody molecule sequences

| SEQ ID NO | Description | Sequence |
|---|---|---|
| SEQ ID NO: 109 | αPD-L1 durvalumab VH | EVQLVESGGGLVQPGGSLRLSCAASGFTFSRYWMSWVRQAPGKGL EWVANIKQDGSEKYYVDSVKGRFTISRDNAKNSLYLQMNSLRAED TAVYYCAREGGWFGELAFDYWGQGTLVTVSS |
| SEQ ID NO: 110 | αPD-L1 durvalumab VL | EIVLTQSPGTLSLSPGERATLSCRASQRVSSSYLAWYQQKPGQAPRL LIYDASSRATGIPDRFSGSGSGTDFTLTISRLEPEDFAVYYCQQYGSL PWTFGQGTKVEIK |

TABLE 10-continued

Exemplary anti-PD-L1 antibody molecule sequences

| SEQ ID NO | Description | Sequence |
|---|---|---|
| SEQ ID NO: 111 | αPD-L1 atezolizumab VH | EVQLVESGGGLVQPGGSLRLSCAASGFTFSDSWIHWVRQAPGKGLE WVAWISPYGGSTYYADSVKGRFTISADTSKNTAYLQMNSLRAEDT AVYYCARRHWPGGFDYWGQGTLVTVSS |
| SEQ ID NO: 112 | αPD-L1 atezolizumab VL | DIQMTQSPSSLSASVGDRVTITCRASQDVSTAVAWYQQKPGKAPKL LIYSASFLYSGVPSRFSGSGSGTDFTLTISSLQPEDFATYYCQQYLYH PATFGQGTKVEIK |
| SEQ ID NO: 113 | αPD-L1 avelumab VH | EVQLLESGGGLVQPGGSLRLSCAASGFTFSSYIMMWVRQAPGKGLE WVSSIYPSGGITFYADTVKGRFTISRDNSKNTLYLQMNSLRAEDTAV YYCARIKLGTVTTVDYWGQGTLVTVSS |
| SEQ ID NO: 114 | αPD-L1 avelumab VL | QSALTQPASVSGSPGQSITISCTGTSSDVGGYNYVSWYQQHPGKAP KLMIYDVSNRPSGVSNRFSGSKSGNTASLTISGLQAEDEADYYCSSY TSSSTRVFGTGTKVTVL |

CDR-Grafted Scaffolds

In embodiments, the antibody molecule is a CDR-grafted scaffold domain. In embodiments, the scaffold domain is based on a fibronectin domain, e.g., fibronectin type III domain. The overall fold of the fibronectin type III (Fn3) domain is closely related to that of the smallest functional antibody fragment, the variable region of the antibody heavy chain. There are three loops at the end of Fn3; the positions of BC, DE and FG loops approximately correspond to those of CDR1, 2 and 3 of the VH domain of an antibody. Fn3 does not have disulfide bonds; and therefore Fn3 is stable under reducing conditions, unlike antibodies and their fragments (see, e.g., WO 98/56915; WO 01/64942; WO 00/34784). An Fn3 domain can be modified (e.g., using CDRs or hypervariable loops described herein) or varied, e.g., to select domains that bind to an antigen/marker/cell described herein.

In embodiments, a scaffold domain, e.g., a folded domain, is based on an antibody, e.g., a "minibody" scaffold created by deleting three beta strands from a heavy chain variable region of a monoclonal antibody (see, e.g., Tramontano et al., 1994, J Mol. Recognit. 7:9; and Martin et al., 1994, EMBO J. 13:5303-5309). The "minibody" can be used to present two hypervariable loops. In embodiments, the scaffold domain is a V-like domain (see, e.g., Coia et al. WO 99/45110) or a domain derived from tendamistatin, which is a 74 residue, six-strand beta sheet sandwich held together by two disulfide bonds (see, e.g., McConnell and Hoess, 1995, J Mol. Biol. 250:460). For example, the loops of tendamistatin can be modified (e.g., using CDRs or hypervariable loops) or varied, e.g., to select domains that bind to a marker/antigen/cell described herein. Another exemplary scaffold domain is a beta-sandwich structure derived from the extracellular domain of CTLA-4 (see, e.g., WO 00/60070).

Other exemplary scaffold domains include but are not limited to T-cell receptors; MHC proteins; extracellular domains (e.g., fibronectin Type III repeats, EGF repeats); protease inhibitors (e.g., Kunitz domains, ecotin, BPTI, and so forth); TPR repeats; trifoil structures; zinc finger domains; DNA-binding proteins; particularly monomeric DNA binding proteins; RNA binding proteins; enzymes, e.g., proteases (particularly inactivated proteases), RNase; chaperones, e.g., thioredoxin, and heat shock proteins; and intracellular signaling domains (such as SH2 and SH3 domains). See, e.g., US 20040009530 and U.S. Pat. No. 7,501,121, incorporated herein by reference.

In embodiments, a scaffold domain is evaluated and chosen, e.g., by one or more of the following criteria: (1) amino acid sequence, (2) sequences of several homologous domains, (3) 3-dimensional structure, and/or (4) stability data over a range of pH, temperature, salinity, organic solvent, oxidant concentration. In embodiments, the scaffold domain is a small, stable protein domain, e.g., a protein of less than 100, 70, 50, 40 or 30 amino acids. The domain may include one or more disulfide bonds or may chelate a metal, e.g., zinc.

Exemplary structures of the multifunctional molecules defined herein are described below. Exemplary structures are further described in: Weidle U et al. (2013) The Intriguing Options of Multispecific Antibody Formats for Treatment of Cancer. *Cancer Genomics & Proteomics* 10: 1-18 (2013); and Spiess C et al. (2015) Alternative molecular formats and therapeutic applications for bispecific antibodies. *Molecular Immunology* 67: 95-106; the full contents of each of which is incorporated by reference herein.

Heterodimerized Antibody Molecules

Heterodimerized bispecific antibodies are based on the natural IgG structure, wherein the two binding arms recognize different antigens. IgG derived formats that enable defined monovalent (and simultaneous) antigen binding are generated by forced heavy chain heterodimerization, combined with technologies that minimize light chain mispairing (e.g., common light chain). Forced heavy chain heterodimerization can be obtained using, e.g., knob-in-hole OR strand exchange engineered domains (SEED).

Knob-in-Hole

Knob-in-Hole as described in U.S. Pat. Nos. 5,731,116, 7,476,724 and Ridgway, J. et al. (1996) *Prot. Engineering* 9(7): 617-621, broadly involves: (1) mutating the CH3 domain of one or both antibodies to promote heterodimerization; and (2) combining the mutated antibodies under conditions that promote heterodimerization. "Knobs" or "protuberances" are typically created by replacing a small amino acid in a parental antibody with a larger amino acid (e.g., T366Y or T366W); "Holes" or "cavities" are created by replacing a larger residue in a parental antibody with a smaller amino acid (e.g., Y407T, T366S, 1368A and/or Y407V), numbered based on the Eu numbering system.

Strand Exchange Engineered Domains (SEED)

SEED is based on sequence exchanges between IgG1 and IgA to create non-identical chains which heterodimerize preferentially. Alternating sequences from human IgA and IgG in the SEED CH3 domains generate two asymmetric but complementary domains, designated AG and GA. The SEED design allows efficient generation of AG/GA heterodimers, while disfavoring homodimerization of AG and GA SEED CH3 domains.

Common Light Chain & CrossMab

Light chain mispairing must be avoided to generate homogenous preparations of bispecific IgGs. One way to achieve this is through the use of the common light chain principle, i.e. combining two binders that share one light chain but still have separate specificities. Another option is the CrossMab technology which avoids non-specific L chain mispairing by exchanging CH1 and CL domains in the Fab of one half of the bispecific antibody. Such crossover variants retain binding specificity and affinity, but make the two arms so different that L chain mispairing is prevented.

Antibody-Based Fusions

A variety of formats can be generated which contain additional binding entities attached to the N or C terminus of antibodies. These fusions with single chain or disulfide stabilized Fvs or Fabs result in the generation of tetravalent molecules with bivalent binding specificity for each antigen. Combinations of scFvs and scFabs with IgGs enable the production of molecules which can recognize three or more different antigens.

Antibody-Fab Fusion

Antibody-Fab fusions are bispecific antibodies comprising a traditional antibody to a first target and a Fab to a second target fused to the C terminus of the antibody heavy chain. Commonly the antibody and the Fab will have a common light chain. Antibody fusions can be produced by (1) engineering the DNA sequence of the target fusion, and (2) transfecting the target DNA into a suitable host cell to express the fusion protein. It seems like the antibody-scFv fusion may be linked by a (Gly)-Ser linker between the C-terminus of the CH3 domain and the N-terminus of the scFv, as described by Coloma, J. et al. (1997) *Nature Biotech* 15:159.

Antibody-scFv Fusion

Antibody-scFv Fusions are bispecific antibodies comprising a traditional antibody and a scFv of unique specificity fused to the C terminus of the antibody heavy chain. The scFv can be fused to the C terminus through the Heavy Chain of the scFv either directly or through a linker peptide. Antibody fusions can be produced by (1) engineering the DNA sequence of the target fusion, and (2) transfecting the target DNA into a suitable host cell to express the fusion protein. It seems like the antibody-scFv fusion may be linked by a (Gly)-Ser linker between the C-terminus of the CH3 domain and the N-terminus of the scFv, as described by Coloma, J. et al. (1997) *Nature Biotech* 15:159.

Variable Domain Immunoglobulin DVD

A related format is the dual variable domain immunoglobulin (DVD), which are composed of VH and VL domains of a second specificity place upon the N termini of the V domains by shorter linker sequences.

Fc-Containing Entities (Mini-Antibodies)

Fc-containing entities, also known as mini-antibodies, can be generated by fusing scFv to the C-termini of constant heavy region domain 3 (CH3-scFv) and/or to the hinge region (scFv-hinge-Fc) of an antibody with a different specificity. Trivalent entities can also be made which have disulfide stabilized variable regions (without peptide linker) fused to the C-terminus of CH3 domains of IgGs.

Fc-Less Bispecifics

Fc-less bispecifics are characterized by generally having smaller size than Fc-containing entities. Common bispecific of this class include Fab-scFv2 and Fab-scFv molecules. This class also includes, e.g., BiTEs (bispecific T-cell engagers), diabodies, TandAbs (tetravalent tandem antibodies), and DARTs (dual affinity retargeting molecules). BiTEs are created by fusing two scFvs via a flexible linker peptide. Diabodies consist of two VH and two VL domains from two different antibodies. Interaction only with complementary domains on another chain is achieved by attaching domains with short linker peptides which permits pairing only with VH and VL domains. VH of the first binder linked to the VL of the second binder is co-expressed with the VH of the second antibody linked to VL of the first antibody. TandAbs molecules are generated by functional dimerization of a protein consisting of four antibody variable H- and L-chains in an orientation that prevents intramolecular pairing. DARTs are entities that are stabilized by disulfide bonds which apply a similar design concept to that of diabodies.

Kappa/Lambda Formats

Multispecific molecules (e.g., multispecific antibody molecules) that include the lambda light chain polypeptide and a kappa light chain polypeptides, can be used to allow for heterodimerization. Methods for generating bispecific antibody molecules comprising the lambda light chain polypeptide and a kappa light chain polypeptides are disclosed in PCT/US2017/53053 filed on Sep. 22, 2017, incorporated herein by reference in its entirety.

In embodiments, the multispecific molecules include a multispecific antibody molecule, e.g., an antibody molecule comprising two binding specificities, e.g., a bispecific antibody molecule. The multispecific antibody molecule includes:

a lambda light chain polypeptide 1 (LLCP1) specific for a first epitope;

a heavy chain polypeptide 1 (HCP1) specific for the first epitope;

a kappa light chain polypeptide 2 (KLCP2) specific for a second epitope; and a heavy chain polypeptide 2 (HCP2) specific for the second epitope.

"Lambda light chain polypeptide 1 (LLCP1)", as that term is used herein, refers to a polypeptide comprising sufficient light chain (LC) sequence, such that when combined with a cognate heavy chain variable region, can mediate specific binding to its epitope and complex with an HCP1. In an embodiment it comprises all or a fragment of a CH1 region. In an embodiment, an LLCP1 comprises LC-CDR1, LC-CDR2, LC-CDR3, FR1, FR2, FR3, FR4, and CH1, or sufficient sequence therefrom to mediate specific binding of its epitope and complex with an HCP1. LLCP1, together with its HCP1, provide specificity for a first epitope (while KLCP2, together with its HCP2, provide specificity for a second epitope). As described elsewhere herein, LLCP1 has a higher affinity for HCP1 than for HCP2.

"Kappa light chain polypeptide 2 (KLCP2)", as that term is used herein, refers to a polypeptide comprising sufficient light chain (LC) sequence, such that when combined with a cognate heavy chain variable region, can mediate specific binding to its epitope and complex with an HCP2. In an embodiments it comprises all or a fragment of a CH1 region. In an embodiment, a KLCP2 comprises LC-CDR1, LC-CDR2, LC-CDR3, FR1, FR2, FR3, FR4, and CH1, or sufficient sequence therefrom to mediate specific binding of its epitope and complex with an HCP2. KLCP2, together with its HCP2, provide specificity for a second epitope (while LLCP1, together with its HCP1, provide specificity for a first epitope).

"Heavy chain polypeptide 1 (HCP1)", as that term is used herein, refers to a polypeptide comprising sufficient heavy chain (HC) sequence, e.g., HC variable region sequence, such that when combined with a cognate LLCP1, can mediate specific binding to its epitope and complex with an HCP1. In an embodiments it comprises all or a fragment of a CH1 region. In an embodiment, it comprises all or a fragment of a CH2 and/or CH3 region. In an embodiment an HCP1 comprises HC-CDR1, HC-CDR2, HC-CDR3, FR1, FR2, FR3, FR4, CH1, CH2, and CH3, or sufficient sequence therefrom to: (i) mediate specific binding of its epitope and complex with an LLCP1, (ii) to complex preferentially, as described herein to LLCP1 as opposed to KLCP2; and (iii) to complex preferentially, as described herein, to an HCP2, as opposed to another molecule of HCP1. HCP1, together with its LLCP1, provide specificity for a first epitope (while KLCP2, together with its HCP2, provide specificity for a second epitope).

"Heavy chain polypeptide 2 (HCP2)", as that term is used herein, refers to a polypeptide comprising sufficient heavy chain (HC) sequence, e.g., HC variable region sequence, such that when combined with a cognate LLCP1, can mediate specific binding to its epitope and complex with an HCP1. In an embodiments it comprises all or a fragment of a CH1 region. In an embodiments it comprises all or a fragment of a CH2 and/or CH3 region. In an embodiment an HCP1 comprises HC-CDR1, HC-CDR2, HC-CDR3, FR1, FR2, FR3, FR4, CH1, CH2, and CH3, or sufficient sequence therefrom to: (i) mediate specific binding of its epitope and complex with an KLCP2, (ii) to complex preferentially, as described herein to KLCP2 as opposed to LLCP1; and (iii) to complex preferentially, as described herein, to an HCP1, as opposed to another molecule of HCP2. HCP2, together with its KLCP2, provide specificity for a second epitope (while LLCP1, together with its HCP1, provide specificity for a first epitope).

In some embodiments of the multispecific antibody molecule disclosed herein:
LLCP1 has a higher affinity for HCP1 than for HCP2; and/or
KLCP2 has a higher affinity for HCP2 than for HCP1.

In embodiments, the affinity of LLCP1 for HCP1 is sufficiently greater than its affinity for HCP2, such that under preselected conditions, e.g., in aqueous buffer, e.g., at pH 7, in saline, e.g., at pH 7, or under physiological conditions, at least 75%, 80, 90, 95, 98, 99, 99.5, or 99.9% of the multispecific antibody molecule molecules have a LLCP1 complexed, or interfaced with, a HCP1.

In some embodiments of the multispecific antibody molecule disclosed herein:
the HCP1 has a greater affinity for HCP2, than for a second molecule of HCP1; and/or
the HCP2 has a greater affinity for HCP1, than for a second molecule of HCP2.

In embodiments, the affinity of HCP1 for HCP2 is sufficiently greater than its affinity for a second molecule of HCP1, such that under preselected conditions, e.g., in aqueous buffer, e.g., at pH 7, in saline, e.g., at pH 7, or under physiological conditions, at least 75%, 80, 90, 95, 98, 99 99.5 or 99.9% of the multispecific antibody molecule molecules have a HCP1 complexed, or interfaced with, a HCP2.

In another aspect, disclosed herein is a method for making, or producing, a multispecific antibody molecule. The method includes:

(i) providing a first heavy chain polypeptide (e.g., a heavy chain polypeptide comprising one, two, three or all of a first heavy chain variable region (first VH), a first CH1, a first heavy chain constant region (e.g., a first CH2, a first CH3, or both));

(ii) providing a second heavy chain polypeptide (e.g., a heavy chain polypeptide comprising one, two, three or all of a second heavy chain variable region (second VH), a second CH1, a second heavy chain constant region (e.g., a second CH2, a second CH3, or both));

(iii) providing a lambda chain polypeptide (e.g., a lambda light variable region (VLX), a lambda light constant chain (VLX), or both) that preferentially associates with the first heavy chain polypeptide (e.g., the first VH); and (iv) providing a kappa chain polypeptide (e.g., a lambda light variable region (VLK), a lambda light constant chain (VLK), or both) that preferentially associates with the second heavy chain polypeptide (e.g., the second VH), under conditions where (i)-(iv) associate.

In embodiments, the first and second heavy chain polypeptides form an Fc interface that enhances heterodimerization.

In embodiments, (i)-(iv) (e.g., nucleic acid encoding (i)-(iv)) are introduced in a single cell, e.g., a single mammalian cell, e.g., a CHO cell. In embodiments, (i)-(iv) are expressed in the cell.

In embodiments, (i)-(iv) (e.g., nucleic acid encoding (i)-(iv)) are introduced in different cells, e.g., different mammalian cells, e.g., two or more CHO cell. In embodiments, (i)-(iv) are expressed in the cells.

In one embodiments, the method further comprises purifying a cell-expressed antibody molecule, e.g., using a lambda- and/or- kappa-specific purification, e.g., affinity chromatography.

In embodiments, the method further comprises evaluating the cell-expressed multispecific antibody molecule. For example, the purified cell-expressed multispecific antibody molecule can be analyzed by techniques known in the art, include mass spectrometry. In one embodiment, the purified cell-expressed antibody molecule is cleaved, e.g., digested with papain to yield the Fab moieties and evaluated using mass spectrometry.

In embodiments, the method produces correctly paired kappa/lambda multispecific, e.g., bispecific, antibody molecules in a high yield, e.g., at least 75%, 80, 90, 95, 98, 99 99.5 or 99.9%.

In other embodiments, the multispecific, e.g., a bispecific, antibody molecule that includes:

(i) a first heavy chain polypeptide (HCP1) (e.g., a heavy chain polypeptide comprising one, two, three or all of a first heavy chain variable region (first VH), a first CH1, a first heavy chain constant region (e.g., a first CH2, a first CH3, or both)), e.g., wherein the HCP1 binds to a first epitope;

(ii) a second heavy chain polypeptide (HCP2) (e.g., a heavy chain polypeptide comprising one, two, three or all of a second heavy chain variable region (second VH), a second CH1, a second heavy chain constant region (e.g., a second CH2, a second CH3, or both)), e.g., wherein the HCP2 binds to a second epitope;

(iii) a lambda light chain polypeptide (LLCP1) (e.g., a lambda light variable region (VL1), a lambda light constant chain (VL1), or both) that preferentially associates with the first heavy chain polypeptide (e.g., the first VH), e.g., wherein the LLCP1 binds to a first epitope; and (iv) a kappa light chain polypeptide (KLCP2) (e.g., a lambda light variable region (VLk), a lambda light constant chain (VLk), or both) that preferentially associates with the second heavy chain polypeptide (e.g., the second VH), e.g., wherein the KLCP2 binds to a second epitope.

In embodiments, the first and second heavy chain polypeptides form an Fc interface that enhances heterodimerization. In embodiments, the multispecific antibody molecule has a first binding specificity that includes a hybrid VL1-CL1 heterodimerized to a first heavy chain variable region connected to the Fc constant, CH2-CH3 domain (having a knob modification) and a second binding specificity that includes a hybrid VLk-CLk heterodimerized to a second heavy chain variable region connected to the Fc constant, CH2-CH3 domain (having a hole modification).

Multispecific Molecules Comprising Non-Contiguous Polypeptides

In one embodiment, the multispecific molecule is not a single polypeptide chain.

In one embodiment, the antibody molecule includes two, complete heavy chains and two, complete light chains. In one embodiment, the multispecific molecules having at least two or at least three non-contiguous polypeptide chains include a first and second heavy chain constant regions (e.g., a first and second Fc region) in at least two non-contiguous polypeptide chains, e.g., as described herein.

In embodiments, the multispecific molecule is a bispecific or bifunctional molecule, wherein the first and second polypeptides (i) and (ii) are non-contiguous, e.g., are two separate polypeptide chains. In some embodiments, the first and second polypeptides (i) and (ii) include a paired amino acid substitution at a position chosen from one or more of 347, 349, 350, 351, 366, 368, 370, 392, 394, 395, 397, 398, 399, 405, 407, or 409, e.g., of the Fc region of human IgG1, numbered based on the Eu numbering system. For example, the first heavy chain constant region (e.g., the first Fc region) can include an amino acid substitution chosen from: T366S, L368A, or Y407V (e.g., corresponding to a cavity or hole), and the second heavy chain constant region (e.g., the second Fc region) includes a T366W (e.g., corresponding to a protuberance or knob), numbered based on the Eu numbering system. In some embodiments, the first and second polypeptides are a first and second member of a heterodimeric first and second Fc region.

In some embodiments, the first polypeptide has the following configuration from N-to-C:

(a) a first portion of a first antigen domain, e.g., a first VH-CH1 of a Fab molecule, that binds to a first antigen, e.g., CSF1R, connected, optionally via a linker to, the first heavy chain constant region (e.g., the CH2 connected to the CH3 region) (e.g., a first Fc region); (b) a first portion of a second antigen domain, e.g., a second VH-CH1 of a Fab molecule, that binds to a second antigen, e.g., CCR2 or CXCR2, connected, optionally via a linker to, the second heavy chain constant region (e.g., the CH2 connected to the CH3 region) (e.g., a first Fc region); (c) the third polypeptide has the following configuration from N-to-C: a second portion of the first antigen domain, e.g., a first VL-CL of the Fab, where the VL is of kappa subtype and binds to the first antigen, e.g., CSF1R (e.g., the same antigen bound by the first VH-CH1); (d) the fourth polypeptide has the following configuration from N-to-C: a second portion of the second antigen domain, e.g. a second VL-CL of the Fab, where the VL is of lambda subtype and binds to a second antigen, e.g., a cancer antigen, e.g., CCR2 or CXCR2 (e.g., the same antigen bound by the second VH-CH1).

In embodiments, the first heavy chain constant region (e.g., the first CH2-CH3 region) includes a protuberance or knob, e.g., as described herein. In embodiments, the second heavy chain constant region (e.g., the second CH2-CH3 region) includes a cavity or hole. In embodiments, the first and second heavy chain constant regions promote heterodimerization of the bispecific molecule.

Nucleic Acids

The invention also features nucleic acids comprising nucleotide sequences that encode heavy and light chain variable regions and CDRs or hypervariable loops of the antibody molecules, as described herein. For example, the invention features a first and second nucleic acid encoding heavy and light chain variable regions, respectively, of an antibody molecule chosen from one or more of the antibody molecules disclosed herein. The nucleic acid can comprise a nucleotide sequence as set forth in the tables herein, or a sequence substantially identical thereto (e.g., a sequence at least about 85%, 90%, 95%, 99% or more identical thereto, or which differs by no more than 3, 6, 15, 30, or 45 nucleotides from the sequences shown in the tables herein.

In certain embodiments, the nucleic acid can comprise a nucleotide sequence encoding at least one, two, or three CDRs or hypervariable loops from a heavy chain variable region having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions). In other embodiments, the nucleic acid can comprise a nucleotide sequence encoding at least one, two, or three CDRs or hypervariable loops from a light chain variable region having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions). In yet another embodiment, the nucleic acid can comprise a nucleotide sequence encoding at least one, two, three, four, five, or six CDRs or hypervariable loops from heavy and light chain variable regions having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions).

In certain embodiments, the nucleic acid can comprise a nucleotide sequence encoding at least one, two, or three CDRs or hypervariable loops from a heavy chain variable region having the nucleotide sequence as set forth in the tables herein, a sequence substantially homologous thereto (e.g., a sequence at least about 85%, 90%, 95%, 99% or more identical thereto, and/or capable of hybridizing under the stringency conditions described herein). In another embodiment, the nucleic acid can comprise a nucleotide sequence encoding at least one, two, or three CDRs or hypervariable loops from a light chain variable region having the nucleotide sequence as set forth in the tables herein, or a sequence substantially homologous thereto (e.g., a sequence at least about 85%, 90%, 95%, 99% or more identical thereto, and/or capable of hybridizing under the stringency conditions described herein). In yet another embodiment, the nucleic acid can comprise a nucleotide sequence encoding at least one, two, three, four, five, or six CDRs or hypervariable loops from heavy and light chain variable regions having the nucleotide sequence as set forth in the tables herein, or a sequence substantially homologous thereto (e.g., a sequence at least about 85%, 90%, 95%, 99% or more identical thereto, and/or capable of hybridizing under the stringency conditions described herein).

In another aspect, the application features host cells and vectors containing the nucleic acids described herein. The nucleic acids may be present in a single vector or separate vectors present in the same host cell or separate host cell, as described in more detail herein below.

Vectors

Further provided herein are vectors comprising the nucleotide sequences encoding an antibody molecule described herein. In one embodiment, the vectors comprise nucleotides encoding an antibody molecule described herein. In one embodiment, the vectors comprise the nucleotide sequences described herein. The vectors include, but are not limited to, a virus, plasmid, cosmid, lambda phage or a yeast artificial chromosome (YAC).

Numerous vector systems can be employed. For example, one class of vectors utilizes DNA elements which are derived from animal viruses such as, for example, bovine papilloma virus, polyoma virus, adenovirus, vaccinia virus, baculovirus, retroviruses (Rous Sarcoma Virus, MMTV or MOMLV) or SV40 virus. Another class of vectors utilizes RNA elements derived from RNA viruses such as Semliki Forest virus, Eastern Equine Encephalitis virus and Flaviviruses.

Additionally, cells which have stably integrated the DNA into their chromosomes may be selected by introducing one or more markers which allow for the selection of transfected host cells. The marker may provide, for example, prototropy to an auxotrophic host, biocide resistance (e.g., antibiotics), or resistance to heavy metals such as copper, or the like. The selectable marker gene can be either directly linked to the DNA sequences to be expressed, or introduced into the same cell by cotransformation. Additional elements may also be needed for optimal synthesis of mRNA. These elements may include splice signals, as well as transcriptional promoters, enhancers, and termination signals.

Once the expression vector or DNA sequence containing the constructs has been prepared for expression, the expression vectors may be transfected or introduced into an appropriate host cell. Various techniques may be employed to achieve this, such as, for example, protoplast fusion, calcium phosphate precipitation, electroporation, retroviral transduction, viral transfection, gene gun, lipid based transfection or other conventional techniques. In the case of protoplast fusion, the cells are grown in media and screened for the appropriate activity.

Methods and conditions for culturing the resulting transfected cells and for recovering the antibody molecule produced are known to those skilled in the art, and may be varied or optimized depending upon the specific expression vector and mammalian host cell employed, based upon the present description.

Cells

In another aspect, the application features host cells and vectors containing the nucleic acids described herein. The nucleic acids may be present in a single vector or separate vectors present in the same host cell or separate host cell. The host cell can be a eukaryotic cell, e.g., a mammalian cell, an insect cell, a yeast cell, or a prokaryotic cell, e.g., E. coli. For example, the mammalian cell can be a cultured cell or a cell line. Exemplary mammalian cells include lymphocytic cell lines (e.g., NSO), Chinese hamster ovary cells (CHO), COS cells, oocyte cells, and cells from a transgenic animal, e.g., mammary epithelial cell.

The invention also provides host cells comprising a nucleic acid encoding an antibody molecule as described herein.

In one embodiment, the host cells are genetically engineered to comprise nucleic acids encoding the antibody molecule.

In one embodiment, the host cells are genetically engineered by using an expression cassette. The phrase "expression cassette," refers to nucleotide sequences, which are capable of affecting expression of a gene in hosts compatible with such sequences. Such cassettes may include a promoter, an open reading frame with or without introns, and a termination signal. Additional factors necessary or helpful in effecting expression may also be used, such as, for example, an inducible promoter.

The invention also provides host cells comprising the vectors described herein.

The cell can be, but is not limited to, a eukaryotic cell, a bacterial cell, an insect cell, or a human cell. Suitable eukaryotic cells include, but are not limited to, Vero cells, HeLa cells, COS cells, CHO cells, HEK293 cells, BHK cells and MDCKII cells. Suitable insect cells include, but are not limited to, Sf9 cells.

Uses and Combination Therapies

The multispecific molecule described herein, alone or in combination with a second therapy or a second therapeutic agent, can be used to treat a hyperproliferative disorder, a cancer, or a fibrotic disorder.

Cancer

Methods described herein include treating a cancer in a subject by using a multispecific molecule described herein, e.g., using a pharmaceutical composition described herein. Also provided are methods for reducing or ameliorating a symptom of a cancer in a subject, as well as methods for inhibiting the growth of a cancer and/or killing one or more cancer cells. In embodiments, the methods described herein decrease the size of a tumor and/or decrease the number of cancer cells in a subject administered with a described herein or a pharmaceutical composition described herein.

In embodiments, the cancer is a hematological cancer. In embodiments, the hematological cancer is a leukemia or a lymphoma. As used herein, a "hematologic cancer" refers to a tumor of the hematopoietic or lymphoid tissues, e.g., a tumor that affects blood, bone marrow, or lymph nodes. Exemplary hematologic malignancies include, but are not limited to, leukemia (e.g., acute lymphoblastic leukemia (ALL), acute myeloid leukemia (AML), chronic lymphocytic leukemia (CLL), chronic myelogenous leukemia (CML), hairy cell leukemia, acute monocytic leukemia (AMoL), chronic myelomonocytic leukemia (CMML), juvenile myelomonocytic leukemia (JMML), or large granular lymphocytic leukemia), lymphoma (e.g., AIDS-related lymphoma, cutaneous T-cell lymphoma, Hodgkin lymphoma (e.g., classical Hodgkin lymphoma or nodular lymphocyte-predominant Hodgkin lymphoma), mycosis fungoides, non-Hodgkin lymphoma (e.g., B-cell non-Hodgkin lymphoma (e.g., Burkitt lymphoma, small lymphocytic lymphoma (CLL/SLL), diffuse large B-cell lymphoma, follicular lymphoma, immunoblastic large cell lymphoma, precursor B-lymphoblastic lymphoma, or mantle cell lymphoma) or T-cell non-Hodgkin lymphoma (mycosis fungoides, anaplastic large cell lymphoma, or precursor T-lymphoblastic lymphoma)), primary central nervous system lymphoma, Sézary syndrome, Waldenström macroglobulinemia), chronic myeloproliferative neoplasm, Langerhans cell histiocytosis, multiple myeloma/plasma cell neoplasm, myelodysplastic syndrome, or myelodysplastic/myeloproliferative neoplasm.

In embodiments, the cancer is a solid cancer. Exemplary solid cancers include, but are not limited to, ovarian cancer, rectal cancer, stomach cancer, testicular cancer, cancer of the anal region, uterine cancer, colon cancer, rectal cancer, renal-cell carcinoma, liver cancer, non-small cell carcinoma of the lung, cancer of the small intestine, cancer of the esophagus, melanoma, Kaposi's sarcoma, cancer of the endocrine system, cancer of the thyroid gland, cancer of the parathyroid gland, cancer of the adrenal gland, bone cancer, pancreatic cancer, skin cancer, cancer of the head or neck, cutaneous or intraocular malignant melanoma, uterine cancer, brain stem glioma, pituitary adenoma, epidermoid cancer, carcinoma of the cervix squamous cell cancer, carcinoma of the fallopian tubes, carcinoma of the endometrium, carcinoma of the vagina, sarcoma of soft tissue, cancer of the urethra, carcinoma of the vulva, cancer of the penis, cancer of the bladder, cancer of the kidney or ureter, carcinoma of the renal pelvis, spinal axis tumor, neoplasm of the central nervous system (CNS), primary CNS lymphoma, tumor angiogenesis, metastatic lesions of said cancers, or combinations thereof.

In certain embodiments, the cancer is an epithelial, mesenchymal or hematologic malignancy. In certain embodiments, the cancer treated is a solid tumor (e.g., carcinoid, carcinoma or sarcoma), a soft tissue tumor (e.g., a heme malignancy), and a metastatic lesion, e.g., a metastatic lesion of any of the cancers disclosed herein. In one embodiment, the cancer treated is a fibrotic or desmoplastic solid tumor, e.g., a tumor having one or more of: limited tumor perfusion, compressed blood vessels, fibrotic tumor interstitium, or increased interstitial fluid pressure. In one embodiment, the solid tumor is chosen from one or more of pancreatic (e.g., pancreatic adenocarcinoma or pancreatic ductal adenocarcinoma), breast, colon, colorectal, lung (e.g., small cell lung cancer (SCLC) or non-small cell lung cancer (NSCLC)), skin, ovarian, liver cancer, esophageal cancer, endometrial cancer, gastric cancer, head and neck cancer, kidney, or prostate cancer.

Examples of cancer include, but are not limited to, carcinoma, lymphoma, blastoma, sarcoma, and leukemia or lymphoid malignancies. More particular examples of such cancers are noted below and include: squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial cancer or uterine carcinoma, salivary gland carcinoma, kidney or renal cancer, prostate cancer, vulval cancer, thyroid cancer, hepatic carcinoma, anal carcinoma, penile carcinoma, as well as head and neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor).

Other examples of cancers or malignancies include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Disease, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Disease, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma During Pregnancy, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Purpura, Parathyroid Cancer, Penile Cancer, Pheochromocytoma, Pituitary Tumor, Plasma Cell Neoplasm/Multiple Myeloma, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, Wilms' Tumor, and any other hyperproliferative disease, besides neoplasia, located in an organ system listed above.

In other embodiements, the multispecific molecule, as described above and herein, is used to treat a hyperproliferative disorder, e.g., a hyperpoliferative connective tissue disorder (e.g., a hyperproliferative fibrotic disease). In one embodiment, the hyperproliferative fibrotic disease is multisystemic or organ-specific. Exemplary hyperproliferative fibrotic diseases include, but are not limited to, multisystemic (e.g., systemic sclerosis, multifocal fibrosclerosis, sclerodermatous graft-versus-host disease in bone marrow transplant recipients, nephrogenic systemic fibrosis, scleroderma), and organ-specific disorders (e.g., fibrosis of the eye, lung, liver, heart, kidney, pancreas, skin and other organs). In other embodiments, the disorder is chosen from liver cirrhosis or tuberculosis. In other embodiments, the disorder is leprosy.

In embodiments, the multispecific molecules (or pharmaceutical composition) are administered in a manner appropriate to the disease to be treated or prevented. The quantity and frequency of administration will be determined by such factors as the condition of the patient, and the type and severity of the patient's disease. Appropriate dosages may be determined by clinical trials. For example, when "an effective amount" or "a therapeutic amount" is indicated, the precise amount of the pharmaceutical composition (or multispecific molecules) to be administered can be determined by a physician with consideration of individual differences in tumor size, extent of infection or metastasis, age, weight, and condition of the subject. In embodiments, the pharmaceutical composition described herein can be administered at a dosage of $10^4$ to $10^9$ cells/kg body weight, e.g., $10^5$ to $10^6$ cells/kg body weight, including all integer values within those ranges. In embodiments, the pharmaceutical composition described herein can be administered multiple times at these dosages. In embodiments, the pharmaceutical composition described herein can be administered using infusion techniques described in immunotherapy (see, e.g., Rosenberg et al., New Eng. J. of Med. 319:1676, 1988).

In embodiments, the multispecific molecules or pharmaceutical composition is administered to the subject parenterally. In embodiments, the cells are administered to the subject intravenously, subcutaneously, intratumorally, intranodally, intramuscularly, intradermally, or intraperitoneally. In embodiments, the cells are administered, e.g., injected, directly into a tumor or lymph node. In embodiments, the cells are administered as an infusion (e.g., as described in Rosenberg et al., New Eng. J. of Med. 319: 1676, 1988) or an intravenous push. In embodiments, the cells are administered as an injectable depot formulation. In embodiments, the subject is a mammal. In embodiments, the subject is a human, monkey, pig, dog, cat, cow, sheep, goat, rabbit, rat, or mouse. In embodimnets, the subject is a human. In embodiments, the subject is a pediatric subject, e.g., less than 18 years of age, e.g., less than 17, 16, 15, 14, 13, 12, 11, 10, 9, 8, 7, 6, 5, 4, 3, 2, 1 or less years of age. In embodiments, the subject is an adult, e.g., at least 18 years of age, e.g., at least 19, 20, 21, 22, 23, 24, 25, 25-30, 30-35, 35-40, 40-50, 50-60, 60-70, 70-80, or 80-90 years of age.

Liver Conditions or Disorders

This invention also provides methods of treating liver conditions or disorders using the multispecific molecules or pharmaceutical compositions described herein.

As used herein, "liver disorder therapy" refers to therapies or therapeutic agents used to treat or prevent a liver disorder described herein, and therefore encompasses liver cancer therapies and other liver disorder therapies, e.g., therapies for fibrotic liver disorders, fatty liver diseases, liver inflammation disorders, autoimmune liver diseases, and liver disorders induced by genetic diseases, alcoholism, drug toxicity, infection, or injury.

Examples of liver cancers include: hepatocellular carcinoma (HCC), primary liver cell carcinoma, hepatoma, fibrolamellar carcinoma, focal nodular hyperplasia, cholangiosarcoma, intrahepatic bile duct cancer, angiosarcoma or hemangiosarcoma, hepatic adenoma, hepatic hemangiomas, hepatic hamartoma, hepatoblastoma, infantile hemangioendothelialoma, mixed tumors of the liver, tumors of mesenchymal tissue, sarcoma of the liver. Examples of cancers that may metastasize to the liver include: breast cancer, colorectal cancer, esophageal cancer, kidney or renal cancer, lung cancer, ovarian cancer, pancreatic cancer, rectal cancer, skin cancer (e.g., melanoma), gastric or stomach cancer (including gastrointestinal cancer), and uterine cancer.

In an embodiment, the liver disorder is a fibrotic disorder or connective tissue disorder affecting the function or physiology of the liver. In one embodiment, the fibrotic disorder or connective tissue disorder can be systemic (affecting the whole body), multi-organ, or organ-specific (e.g., liver-specific). Examples of fibrotic liver disorders include liver fibrosis (hepatic fibrosis), liver cirrhosis, and any disorder associated with accumulation of extracellular matrix proteins, e.g., collagen, in the liver, liver scarring, and/or abnormal hepatic vasculature. Liver fibrosis is caused by liver inflammation or damage which triggers the accumulation of extracellular matrix proteins, including collagens, and scar tissue in the liver. Liver cirrhosis is the end stage of liver fibrosis, involves regenerative nodules (as a result of repair processes), and is accompanied with the distortion of the hepatic vasculature. Liver fibrotic disorders are most commonly caused by chronic viral infection (e.g., hepatitis B, hepatitis C), alcoholism, and fatty liver disease.

Examples of fatty liver diseases include fatty liver (or FLD), alcoholic liver disease, non-alcoholic fatty liver disease (NAFLD), non-alcoholic steatohepatitis (NASH), alcoholic steatohepatitis, simple steatosis, Reye's syndrome, and any disorder associated with abnormal retention of lipids in liver cells.

In one embodiment, the liver disease is NASH.

Metabolic disorders can also affect the liver and cause liver damage. Examples of metabolic disorders of the liver or affecting the liver include hemachromatosis, diabetes, obesity, hypertension, dyslipidemia, galactosemia, and glycogen storage disease.

Autoimmune disorders of the liver or affecting the liver can include systemic disorders or disorders that primarily affect an organ other than the liver, but with secondary effects to liver cells or liver function. Examples of such autoimmune disorders include autoimmune hepatitis (AIH), autoimmune liver disease, lupoid hepatitis, systemic lupus erythematosus, primary biliary cirrhosis (PBC), scleroderma, and systemic scerlosis.

Fibrotic Conditions or Disorders

In another aspect, the invention features a method of treating or preventing a fibrotic condition or disorder in a subject. The method includes administering the multispecific molecule, as a single agent or in combination with another agent or therapeutic modality, to a subject in need thereof, in an amount sufficient to decrease or inhibit the fibrotic condition in the subject.

In certain embodiments, reducing fibrosis, or treatment of a fibrotic condition, includes reducing or inhibiting one or more of: formation or deposition of tissue fibrosis; reducing the size, cellularity (e.g., fibroblast or immune cell numbers), composition; or cellular content, of a fibrotic lesion; reducing the collagen or hydroxyproline content, of a fibrotic lesion; reducing expression or activity of a fibrogenic protein; reducing fibrosis associated with an inflammatory response; decreasing weight loss associated with fibrosis; or increasing survival.

In certain embodiments, the fibrotic condition is primary fibrosis. In one embodiment, the fibrotic condition is idiopathic. In other embodiments, the fibrotic condition is associated with (e.g., is secondary to) a disease (e.g., an infectious disease, an inflammatory disease, an autoimmune disease, a malignant or cancerous disease, and/or a connective disease); a toxin; an insult (e.g., an environmental hazard (e.g., asbestos, coal dust, polycyclic aromatic hydrocarbons), cigarette smoking, a wound); a medical treatment (e.g., surgical incision, chemotherapy or radiation), or a combination thereof.

In certain embodiments, the fibrotic condition is a fibrotic condition of the lung, a fibrotic condition of the liver (e.g., as described herein), a fibrotic condition of the heart or vasculature, a fibrotic condition of the kidney, a fibrotic condition of the skin, a fibrotic condition of the gastrointestinal tract, a fibrotic condition of the bone marrow or a hematopoietic tissue, a fibrotic condition of the nervous system, a fibrotic condition of the eye, or a combination thereof.

In certain embodiments, the fibrotic condition is a fibrotic condition of the lung. In certain embodiments, the fibrotic condition of the lung is chosen from one or more of: pulmonary fibrosis, idiopathic pulmonary fibrosis (IPF), usual interstitial pneumonitis (UIP), interstitial lung disease, cryptogenic fibrosing alveolitis (CFA), bronchiectasis, and scleroderma lung disease. In one embodiment, the fibrosis of the lung is secondary to a disease, a toxin, an insult, a medical treatment, or a combination thereof. For example, the fibrosis of the lung can be associated with (e.g., secondary to) one or more of: a disease process such as asbestosis and silicosis; an occupational hazard; an environmental pollutant; cigarette smoking; an autoimmune connective tissue disorders (e.g., rheumatoid arthritis, scleroderma and systemic lupus erythematosus (SLE)); a connective tissue disorder such as sarcoidosis; an infectious disease, e.g., infection, particularly chronic infection; a medical treatment, including but not limited to, radiation therapy, and drug therapy, e.g., chemotherapy (e.g., treatment with as bleomycin, methotrexate, amiodarone, busulfan, and/or nitrofurantoin). In one embodiment, the fibrotic condition of the lung treated with the methods of the invention is associated with (e.g., secondary to) a cancer treatment, e.g., treatment of a cancer (e.g., squamous cell carcinoma, testicular cancer, Hodgkin's disease with bleomycin). In one embodiment, the fibrotic condition of the lung is associated with an autoimmune connective tissue disorder (e.g., scleroderma or lupus, e.g., SLE).

Pulmonary fibrosis can occur as a secondary effect in disease processes such as asbestosis and silicosis, and is known to be more prevalent in certain occupations such as coal miner, ship workers and sand blasters where exposure to environmental pollutants is an occupational hazard (Green, F H et al. (2007) Toxicol Pathol. 35:136-47). Other factors that contribute to pulmonary fibrosis include cigarette smoking, and autoimmune connective tissue disorders, like rheumatoid arthritis, scleroderma and systemic lupus erythematosus (SLE) (Leslie, K O et al. (2007) Semin Respir Crit Care Med. 28:369-78; Swigris, J J et al. (2008) Chest. 133:271-80; and Antoniou, K M et al. (2008) Curr Opin Rheumatol. 20:686-91). Other connective tissue disorders such as sarcoidosis can include pulmonary fibrosis as part of the disease (Paramothayan, S et al. (2008) Respir Med. 102:1-9), and infectious diseases of the lung can cause fibrosis as a long term consequence of infection, particularly chronic infections.

Pulmonary fibrosis can also be a side effect of certain medical treatments, particularly radiation therapy to the chest and certain medicines like bleomycin, methotrexate, amiodarone, busulfan, and nitrofurantoin (Catane, R et al. (1979) Int J Radiat Oncol Biol Phys. 5:1513-8; Zisman, D A et al. (2001) Sarcoidosis Vasc Diffuse Lung Dis. 18:243-52; Rakita, L et al. (1983) Am Heart J. 106:906-16; Twohig, K J et al. (1990) Clin Chest Med. 11:31-54; and Witten C M. (1989) Arch Phys Med Rehabil. 70:55-7). In other embodiments, idiopathic pulmonary fibrosis can occur where no clear causal agent or disease can be identified. Genetic factors can play a significant role in these cases of pulmonary fibrosis (Steele, M P et al. (2007) Respiration 74:601-8; Brass, D M et al. (2007) Proc Am Thorac Soc. 4:92-100 and du Bois R M. (2006) Semin Respir Crit Care Med. 27:581-8).

In other embodiments, pulmonary fibrosis includes, but is not limited to, pulmonary fibrosis associated with chronic obstructive pulmonary disease (COPD), acute respiratory distress syndrome, scleroderma, pleural fibrosis, chronic asthma, acute lung syndrome, amyloidosis, bronchopulmonary dysplasia, Caplan's disease, Dressler's syndrome, histiocytosis X, idiopathic pulmonary haemosiderosis, lymphangiomyomatosis, mitral valve stenosis, polymyositis, pulmonary edema, pulmonary hypertension (e.g., idiopathic pulmonary hypertension (IPH)), pneumoconiosis, radiotherapy (e.g., radiation induced fibrosis), rheumatoid disease, Shaver's disease, systemic lupus erythematosus, systemic sclerosis, tropical pulmonary eosinophilia, tuberous sclerosis, Weber-Christian disease, Wegener's granulomatosis, Whipple's disease, or exposure to toxins or irritants (e.g., pharmaceutical drugs such as amiodarone, bleomycin, busulphan, carmustine, chloramphenicol, hexamethonium, methotrexate, methysergide, mitomycin C, nitrofurantoin, penicillamine, peplomycin, and practolol; inhalation of talc or dust, e.g., coal dust, silica). In certain embodiments, the pulmonary fibrosis is associated with an inflammatory disorder of the lung, e.g., asthma, and/or COPD.

In certain embodiments, the fibrotic condition is a fibrotic condition of the liver. In certain embodiments, the fibrotic condition of the liver is chosen from one or more of: fatty liver disease, steatosis (e.g., nonalcoholic steatohepatitis (NASH), cholestatic liver disease (e.g., primary biliary cirrhosis (PBC)), cirrhosis, alcohol induced liver fibrosis, biliary duct injury, biliary fibrosis, or cholangiopathies. In other embodiments, hepatic or liver fibrosis includes, but is not limited to, hepatic fibrosis associated with alcoholism, viral infection, e.g., hepatitis (e.g., hepatitis C, B or D), autoimmune hepatitis, non-alcoholic fatty liver disease (NAFLD), progressive massive fibrosis, exposure to toxins or irritants (e.g., alcohol, pharmaceutical drugs and environmental toxins). Additional examples of liver conditions and disorders are provided in the Sections entitled "Liver Conditions or Disorders," provided herein.

In certain embodiments, the fibrotic condition is a fibrotic condition of the kidney. In certain embodiments, the fibrotic condition of the kidney is chosen from one or more of: renal fibrosis (e.g., chronic kidney fibrosis), nephropathies associated with injury/fibrosis (e.g., chronic nephropathies associated with diabetes (e.g., diabetic nephropathy)), lupus, scleroderma of the kidney, glomerular nephritis, focal segmental glomerular sclerosis, IgA nephropathyrenal fibrosis associated with human chronic kidney disease (CKD), chronic progressive nephropathy (CPN), tubulointerstitial fibrosis, ureteral obstruction, chronic uremia, chronic interstitial nephritis, radiation nephropathy, glomerulosclerosis, progressive glomerulonephrosis (PGN), endothelial/thrombotic microangiopathy injury, HIV-associated nephropathy, or fibrosis associated with exposure to a toxin, an irritant, or a chemotherapeutic agent. In one embodiment, the fibrotic condition of the kidney is scleroderma of the kidney. In some embodiments, the fibrotic condition of the kidney is transplant nephropathy, diabetic nephropathy, lupus nephritis, focal segmental glomerulosclerosis (FSGS), endothelial/thrombotic microangiopathy injury, scleroderma of the kidney, HIV-associated nephropathy (HIVVAN), or exposure to toxins, irritants, chemotherapeutic agents.

In certain embodiments, the fibrotic condition is a fibrotic condition of the bone marrow or a hematopoietic tissue. In certain embodiments, the fibrotic condition of the bone marrow is an intrinsic feature of a chronic myeloproliferative neoplasm of the bone marrow, such as primary myelofibrosis (also referred to herein as agnogenic myeloid metaplasia or chronic idiopathic myelofibrosis). In other embodiments, the bone marrow fibrosis is associated with (e.g., is secondary to) a malignant condition or a condition caused by a clonal proliferative disease. In other embodiments, the bone marrow fibrosis is associated with a hematologic disorder (e.g., a hematologic disorder chosen from one or more of polycythemia vera, essential thrombocythemia, myelodysplasia, hairy cell leukemia, lymphoma (e.g., Hodgkin or non-Hodgkin lymphoma), multiple myeloma or chronic myelogeneous leukemia (CML)). In yet other embodiments, the bone marrow fibrosis is associated with (e.g., secondary to) a non-hematologic disorder (e.g., a non-hematologic disorder chosen from solid tumor metastasis to bone marrow, an autoimmune disorder (e.g., systemic lupus erythematosus, scleroderma, mixed connective tissue disorder, or polymyositis), an infection (e.g., tuberculosis or leprosy), or secondary hyperparathyroidism associated with vitamin D deficiency. In some embodiments, the fibrotic condition is idiopathic or drug-induced myelofibrosis. In some embodiments, the fibrotic condition of the bone marrow or hematopoietic tissue is associated with systemic lupus erythematosus or scleroderma.

In other embodiments, the fibrotic condition is associated with leprosy or tuberculosis.

In certain embodiments, the fibrotic condition is a fibrotic condition of the bone marrow. In certain embodiments, the fibrotic condition of the bone marrow is myelofibrosis (e.g., primary myelofibrosis (PMF)), myeloid metaplasia, chronic idiopathic myelofibrosis, or primary myelofibrosis. In other embodiments, bone marrow fibrosis is associated with a hematologic disorder chosen from one or more of hairy cell leukemia, lymphoma, or multiple myeloma.

In other embodiments, the bone marrow fibrosis is associated with one or more myeloproliferative neoplasms (MPN) chosen from: essential thrombocythemia (ET), polycythemia vera (PV), mastocytosis, chronic eosinophilic leukemia, chronic neutrophilic leukemia, or other MPN.

In one embodiment, the fibrotic condition is primary myelofibrosis. Primary myelofibrosis (PMF) (also referred to in the literature as idiopathic myeloid metaplasia, and Agnogenic myeloid metaplasia) is a clonal disorder of multipotent hematopoietic progenitor cells (reviewed in Abdel-Wahab, O. et al. (2009) Annu. Rev. Med. 60:233-45; Varicchio, L. et al. (2009) Expert Rev. Hematol. 2(3):315-334; Agrawal, M. et al. (2010) Cancer 1-15).

In certain embodiments, the fibrotic condition is a fibrotic condition of the heart. In certain embodiments, the fibrotic condition of the heart is myocardial fibrosis (e.g., myocardial fibrosis associated with radiation myocarditis, a surgical procedure complication (e.g., myocardial post-operative fibrosis), infectious diseases (e.g., Chagas disease, bacterial, trichinosis or fungal myocarditis)); granulomatous, metabolic storage disorders (e.g., cardiomyopathy, hemochromatosis); developmental disorders (e.g, endocardial fibroelastosis); arteriosclerotic, or exposure to toxins or irritants (e.g., drug induced cardiomyopathy, drug induced cardiotoxicity, alcoholic cardiomyopathy, cobalt poisoning or exposure). In certain embodiments, the myocardial fibrosis is associated with an inflammatory disorder of cardiac tissue (e.g., myocardial sarcoidosis). In some embodiments, the fibrotic condition is a fibrotic condition associated with a myocardial infarction. In some embodiments, the fibrotic condition is a fibrotic condition associated with congestive heart failure.

In some embodiments, the fibrotic condition is associated with an autoimmune disease selected from scleroderma or lupus, e.g., systemic lupus erythematosus.

In some embodiments, the fibrotic condition is systemic. In some embodiments, the fibrotic condition is systemic sclerosis (e.g., limited systemic sclerosis, diffuse systemic sclerosis, or systemic sclerosis sine scleroderma), nephrogenic systemic fibrosis, cystic fibrosis, chronic graft vs. host disease, or atherosclerosis.

In some embodiments, the fibrotic condition is scleroderma. In some embodiments, the scleroderma is localized, e.g., morphea or linear scleroderma. In some embodiments, the condition is a systemic sclerosis, e.g., limited systemic sclerosis, diffuse systemic sclerosis, or systemic sclerosis sine scleroderma.

In other embodiment, the fibrotic condition affects a tissue chosen from one or more of muscle, tendon, cartilage, skin (e.g., skin epidermis or endodermis), cardiac tissue, vascular tissue (e.g., artery, vein), pancreatic tissue, lung tissue, liver tissue, kidney tissue, uterine tissue, ovarian tissue, neural tissue, testicular tissue, peritoneal tissue, colon, small intestine, biliary tract, gut, bone marrow, hematopoietic tissue, or eye (e.g., retinal) tissue.

In some embodiments, the fibrotic condition is a fibrotic condition of the eye. In some embodiments, the fibrotic condition is glaucoma, macular degeneration (e.g., age-related macular degeneration), macular edema (e.g., diabetic macular edema), retinopathy (e.g., diabetic retinopathy), or dry eye disease.

In certain embodiments, the fibrotic condition is a fibrotic condition of the skin. In certain embodiments, the fibrotic condition of the skin is chosen from one or more of: skin fibrosis (e.g., hypertrophic scarring, keloid), scleroderma, nephrogenic systemic fibrosis (e.g., resulting after exposure to gadolinium (which is frequently used as a contrast substance for MRIs) in patients with severe kidney failure), and keloid.

In certain embodiments, the fibrotic condition is a fibrotic condition of the gastrointestinal tract. In certain embodiments, the fibrotic condition is chosen from one or more of: fibrosis associated with scleroderma; radiation induced gut fibrosis; fibrosis associated with a foregut inflammatory disorder such as Barrett's esophagus and chronic gastritis, and/or fibrosis associated with a hindgut inflammatory disorder, such as inflammatory bowel disease (IBD), ulcerative colitis and Crohn's disease. In some embodiments, the fibrotic condition of the gastrointestinal tract is fibrosis associated with scleroderma.

In one embodiment, the fibrotic condition is a chronic fibrotic condition or disorder. In certain embodiments, the fibrotic condition is associated with an inflammatory condition or disorder.

In some embodiments, the fibrotic and/or inflammatory condition is osteomyelitis, e.g., chronic osteomyelitis.

In some embodiments, the fibrotic condition is an amyloidosis. In certain embodiments, the amyloidosis is associated with chronic osteomyelitis.

In some embodiments, the one or more compositions described herein is administered in combination with one or more other therapeutic agents. Exemplary therapeutic agents include, but are not limited to, anti-fibrotics, corticosteroids, antiinflammatories, immunosuppressants, chemotherapeutic agents, anti-metabolites, and immunomodulators.

An example of suitable therapeutics for use in combination with the composition(s) for treatment of liver fibrosis includes, but is not limited to, adefovir dipivoxil, candesartan, colchicine, combined ATG, mycophenolate mofetil, and tacrolimus, combined cyclosporine microemulsion and tacrolimus, elastometry, everolimus, FG-3019, Fuzheng Huayu, GI262570, glycyrrhizin (monoammonium glycyrrhizinate, glycine, L-cysteine monohydrochloride), interferon gamma-1b, irbesartan, losartan, oltipraz, ORAL IMPACT®, peginterferon alfa-2a, combined peginterferon alfa-2a and ribavirin, peginterferon alfa-2b (SCH 54031), combined peginterferon alpha-2b and ribavirin, praziquantel, prazosin, raltegravir, ribavirin (REBETOL®, SCH 18908), ritonavir-boosted protease inhibitor, pentoxyphilline, tacrolimus, tauroursodeoxycholic acid, tocopherol, ursodiol, warfarin, and combinations thereof.

Combination Therapies

The multispecific molecules disclosed herein can be used in combination with a second therapeutic agent or procedure.

In embodiments, the multispecific molecule and the second therapeutic agent or procedure are administered/performed after a subject has been diagnosed with a cancer, e.g., before the cancer has been eliminated from the subject. In embodiments, the multispecific molecule and the second therapeutic agent or procedure are administered/performed simultaneously or concurrently. For example, the delivery of one treatment is still occurring when the delivery of the second commences, e.g., there is an overlap in administration of the treatments. In other embodiments, the multispecific molecule and the second therapeutic agent or procedure are administered/performed sequentially. For example, the delivery of one treatment ceases before the delivery of the other treatment begins.

In embodiments, combination therapy can lead to more effective treatment than monotherapy with either agent alone. In embodiments, the combination of the first and second treatment is more effective (e.g., leads to a greater reduction in symptoms and/or cancer cells) than the first or second treatment alone. In embodiments, the combination therapy permits use of a lower dose of the first or the second treatment compared to the dose of the first or second treatment normally required to achieve similar effects when administered as a monotherapy. In embodiments, the combination therapy has a partially additive effect, wholly additive effect, or greater than additive effect.

In one embodiment, the multispecific molecule is administered in combination with a therapy, e.g., a cancer therapy (e.g., one or more of anti-cancer agents, immunotherapy, photodynamic therapy (PDT), surgery and/or radiation). The terms "chemotherapeutic," "chemotherapeutic agent," and "anti-cancer agent" are used interchangeably herein. The administration of the multispecific molecule and the therapy, e.g., the cancer therapy, can be sequential (with or without overlap) or simultaneous. Administration of the multispecific molecule can be continuous or intermittent during the course of therapy (e.g., cancer therapy). Certain therapies described herein can be used to treat cancers and non-cancerous diseases. For example, PDT efficacy can be enhanced in cancerous and non-cancerous conditions (e.g., tuberculosis) using the methods and compositions described herein (reviewed in, e.g., Agostinis, P. et al. (2011) *CA Cancer J. Clin.* 61:250-281).

Anti-Cancer Therapies

In other embodiments, the multispecific molecule is administered in combination with a low or small molecular weight chemotherapeutic agent. Exemplary low or small molecular weight chemotherapeutic agents include, but not limited to, 13-cis-retinoic acid (isotretinoin, ACCUTANE®), 2-CdA (2-chlorodeoxyadenosine, cladribine, LEUSTATIN™), 5-azacitidine (azacitidine, VIDAZA®), 5-fluorouracil (5-FU, fluorouracil, ADRUCIL®), 6-mercaptopurine (6-MP, mercaptopurine, PURINETHOL®), 6-TG (6-thioguanine, thioguanine, THIOGUANINE TABLOID®), abraxane (paclitaxel protein-bound), actinomycin-D (dactinomycin, COSMEGEN®), alitretinoin (PANRETIN®), all-transretinoic acid (ATRA, tretinoin, VESANOID®), altretamine (hexamethylmelamine, HMM, HEXALEN®), amethopterin (methotrexate, methotrexate sodium, MTX, TREXALL™, RHEUMATREX®), amifostine (ETHYOL®), arabinosylcytosine (Ara-C, cytarabine, CYTOSAR-U®), arsenic trioxide (TRISENOX®), asparaginase (Erwinia L-asparaginase, L-asparaginase, ELSPAR®, KIDROLASE®), BCNU (carmustine, BiCNU®), bendamustine (TREANDA®), bexarotene (TARGRETIN®), bleomycin (BLENOXANE®), busulfan (BUSULFEX®, MYLERAN®), calcium leucovorin (Citrovorum Factor, folinic acid, leucovorin), camptothecin-11 (CPT-11, irinotecan, CAMPTOSAR®), capecitabine (XELODA®), carboplatin (PARAPLATIN®), carmustine wafer (prolifeprospan 20 with carmustine implant, GLIADEL® wafer), CCI-779 (temsirolimus, TORISEL®), CCNU (lomustine, CeeNU), CDDP (cisplatin, PLATINOL®, PLATINOL-AQ®), chlorambucil (leukeran), cyclophosphamide (CYTOXAN®, NEOSAR®), dacarbazine (DIC, DTIC, imidazole carboxamide, DTIC-DOME®), daunomycin (daunorubicin, daunorubicin hydrochloride, rubidomycin hydrochloride, CERUBIDINE®), decitabine (DACOGEN®), dexrazoxane (ZINECARD®), DHAD (mitoxantrone, NOVANTRONE®), docetaxel (TAXOTERE®), doxorubicin (ADRIAMYCIN®, RUBEX®), epirubicin (ELLENCE™), estramustine (EMCYT®), etoposide (VP-16, etoposide phosphate, TOPOSAR®, VEPESID®, ETOPOPHOS®), floxuridine (FUDR®), fludarabine (FLUDARA®), fluorouracil (cream) (CARAC™, EFUDEX®, FLUOROPLEX®), gemcitabine (GEMZAR®), hydroxyurea (HYDREA®, DROXIA™, MYLOCEL™), idarubicin (IDAMYCIN®), ifosfamide (IFEX®), ixabepilone (IXEMPRA™), LCR (leurocristine, vincristine, VCR, ONCOVIN®, VINCASAR PFS®), L-PAM (L-sarcolysin, melphalan, phenylalanine mustard, ALKERAN®), mechlorethamine (mechlorethamine hydrochloride, mustine, nitrogen mustard, MUSTARGEN®), mesna (MESNEX™), mitomycin (mitomycin-C, MTC, MUTAMYCIN®), nelarabine (ARRANON®), oxaliplatin (ELOXATIN™), paclitaxel (TAXOL®, ONXAL™), pegaspargase (PEG-L-asparaginase, ONCOSPAR®), PEMETREXED (ALIMTA®), pentostatin (NIPENT®), procarbazine (MATULANE®), streptozocin (ZANOSAR®), temozolomide (TEMODAR®), teniposide (VM-26, VUMON®), TESPA (thiophosphoamide, thiotepa, TSPA, THIOPLEX®), topotecan (HYCAMTIN®), vinblastine (vinblastine sulfate, vincaleukoblastine, VLB, ALKABAN-AQ®, VELBAN®), vinorelbine (vinorelbine tartrate, NAVELBINE®), and vorinostat (ZOLINZA®).

In another embodiment, the multispecific molecule is administered in conjunction with a biologic. Biologics useful in the treatment of cancers are known in the art and a binding molecule of the invention may be administered, for example, in conjunction with such known biologics. For example, the FDA has approved the following biologics for the treatment of breast cancer: HERCEPTIN® (trastuzumab, Genentech Inc., South San Francisco, Calif.; a humanized monoclonal antibody that has anti-tumor activity in HER2-positive breast cancer); FASLODEX® (fulvestrant, Astra7eneca Pharmaceuticals, LP, Wilmington, Del.; an estrogen-receptor antagonist used to treat breast cancer); ARIMIDEX® (anastrozole, Astra7eneca Pharmaceuticals, LP; a nonsteroidal aromatase inhibitor which blocks aromatase, an enzyme needed to make estrogen); Aromasin® (exemestane, Pfizer Inc., New York, N.Y.; an irreversible, steroidal aromatase inactivator used in the treatment of breast cancer); FEMARA® (letrozole, Novartis Pharmaceuticals, East Hanover, N.J.; a nonsteroidal aromatase inhibitor approved by the FDA to treat breast cancer); and NOLVADEX® (tamoxifen, AstraZeneca Pharmaceuticals, LP; a nonsteroidal antiestrogen approved by the FDA to treat breast cancer). Other biologics with which the binding molecules of the invention may be combined include: AVASTIN® (bevacizumab, Genentech Inc.; the first FDA-approved therapy designed to inhibit angiogenesis); and ZEVALIN® (ibritumomab tiuxetan, Biogen Idec, Cambridge, Mass.; a radiolabeled monoclonal antibody currently approved for the treatment of B-cell lymphomas).

In addition, the FDA has approved the following biologics for the treatment of colorectal cancer: AVASTIN®; ERBITUX® (cetuximab, ImClone Systems Inc., New York, N.Y., and Bristol-Myers Squibb, New York, N.Y.; is a monoclonal antibody directed against the epidermal growth factor receptor (EGFR)); GLEEVEC® (imatinib mesylate; a protein kinase inhibitor); and ERGAMISOL® (levamisole hydrochloride, Janssen Pharmaceutica Products, LP, Titusville, N.J.; an immunomodulator approved by the FDA in 1990 as an adjuvant treatment in combination with 5-fluorouracil after surgical resection in patients with Dukes' Stage C colon cancer).

For the treatment of lung cancer, exemplary biologics include TARCEVA® (erlotinib HCL, OSI Pharmaceuticals Inc., Melville, N.Y.; a small molecule designed to target the human epidermal growth factor receptor 1 (HER1) pathway).

For the treatment of multiple myeloma, exemplary biologics include VELCADE® Velcade (bortezomib, Millennium Pharmaceuticals, Cambridge Mass.; a proteasome inhibitor). Additional biologics include THALIDOMID® (thalidomide, Clegene Corporation, Warren, N.J.; an immunomodulatory agent and appears to have multiple actions, including the ability to inhibit the growth and survival of myeloma cells and anti-angiogenesis).

Additional exemplary cancer therapeutic antibodies include, but are not limited to, 3F8, abagovomab, adecatumumab, afutuzumab, alacizumab pegol, alemtuzumab (CAMPATH®, MABCAMPATH®), altumomab pentetate (HYBRI-CEAKER®), anatumomab mafenatox, anrukinzumab (IMA-638), apolizumab, arcitumomab (CEA-SCAN®), bavituximab, bectumomab (LYMPHOSCAN®), belimumab (BENLYSTA®, LYMPHOSTAT-B®), besilesomab (SCINTIMUN®), bevacizumab (AVASTIN®), bivatuzumab mertansine, blinatumomab, brentuximab vedotin, cantuzumab mertansine, capromab pendetide (PROSTASCINT®), catumaxomab (REMOVAB®), CC49, cetuximab (C225, ERBITUX®), citatuzumab bogatox, cixutumumab, clivatuzumab tetraxetan, conatumumab, dacetuzumab, denosumab (PROLIA®), detumomab, ecromeximab, edrecolomab (PANOREX®), elotuzumab, epitumomab cituxetan, epratuzumab, ertumaxomab (REXOMUN®), etaracizumab, farletuzumab, figitumumab, fresolimumab, galiximab, gemtuzumab ozogamicin (MYLOTARG®), girentuximab, glembatumumab vedotin, ibritumomab (ibritumomab tiuxetan, ZEVALIN®), igovomab (INDIMACIS-125®), intetumumab, inotuzumab ozogamicin, ipilimumab, iratumumab, labetuzumab (CEA-CIDE®), lexatumumab, lintuzumab, lucatumumab, lumiliximab, mapatumumab, matuzumab, milatuzumab, minretumomab, mitumomab, nacolomab tafenatox, naptumomab estafenatox, necitumumab, nimotuzumab (THERACIM®, THERALOC®), nofetumomab merpentan (VERLUMA®), ofatumumab (ARZERRA®), olaratumab, oportuzumab monatox, oregovomab (OVAREX®), panitumumab (VECTIBIX®), pemtumomab (THERAGYN®), pertuzumab (OMNITARG®), pintumomab, pritumumab, ramucirumab, ranibizumab (LUCENTIS®), rilotumumab, rituximab (MABTHERA®, RITUXAN®), robatumumab, satumomab pendetide, sibrotuzumab, siltuximab, sontuzumab, tacatuzumab tetraxetan (AFP-CIDE®), taplitumomab paptox, tenatumomab, TGN1412, ticilimumab (tremelimumab), tigatuzumab, TNX-650, tositumomab (BEXXAR®), trastuzumab (HERCEPTIN®), tremelimumab, tucotuzumab celmoleukin, veltuzumab, volociximab, votumumab (HUMASPECT®), zalutumumab (HUMAX-EGFR®), and zanolimumab (HUMAX-CD4®).

In other embodiments, the multispecific molecule is administered in combination with a viral cancer therapeutic agent. Exemplary viral cancer therapeutic agents include, but not limited to, vaccinia virus (vvDD-CDSR), carcinoembryonic antigen-expressing measles virus, recombinant vaccinia virus (TK-deletion plus GM-CSF), Seneca Valley virus-001, Newcastle virus, coxsackie virus A21, GL-ONC1, EBNA1 C-terminal/LMP2 chimeric protein-expressing recombinant modified vaccinia Ankara vaccine, carcinoembryonic antigen-expressing measles virus, G207 oncolytic virus, modified vaccinia virus Ankara vaccine expressing p53, OncoVEX GM-CSF modified herpes-simplex 1 virus, fowlpox virus vaccine vector, recombinant vaccinia prostate-specific antigen vaccine, human papillomavirus 16/18 L1 virus-like particle/ASO4 vaccine, MVA-EBNA1/LMP2 Inj. vaccine, quadrivalent HPV vaccine, quadrivalent human papillomavirus (types 6, 11, 16, 18)

recombinant vaccine (GARDASIL®), recombinant fowlpox-CEA(6D)/TRICOM vaccine; recombinant vaccinia-CEA(6D)-TRICOM vaccine, recombinant modified vaccinia Ankara-5T4 vaccine, recombinant fowlpox-TRICOM vaccine, oncolytic herpes virus NV1020, HPV L1 VLP vaccine V504, human papillomavirus bivalent (types 16 and 18) vaccine (CERVARIX®), herpes simplex virus HF10, Ad5CMV-p53 gene, recombinant vaccinia DF3/MUC1 vaccine, recombinant vaccinia-MUC-1 vaccine, recombinant vaccinia-TRICOM vaccine, ALVAC MART-1 vaccine, replication-defective herpes simplex virus type I (HSV-1) vector expressing human Preproenkephalin (NP2), wild-type reovirus, reovirus type 3 Dearing (REOLYSIN®), oncolytic virus HSV1716, recombinant modified vaccinia Ankara (MVA)-based vaccine encoding Epstein-Barr virus target antigens, recombinant fowlpox-prostate specific antigen vaccine, recombinant vaccinia prostate-specific antigen vaccine, recombinant vaccinia-B7.1 vaccine, rAd-p53 gene, Ad5-delta24RGD, HPV vaccine 580299, JX-594 (thymidine kinase-deleted vaccinia virus plus GM-CSF), HPV-16/18 L1/AS04, fowlpox virus vaccine vector, vaccinia-tyrosinase vaccine, MEDI-517 HPV-16/18 VLP AS04 vaccine, adenoviral vector containing the thymidine kinase of herpes simplex virus TK99UN, HspE7, FP253/Fludarabine, ALVAC(2) melanoma multi-antigen therapeutic vaccine, ALVAC-hB7.1, canarypox-hIL-12 melanoma vaccine, Ad-REIC/Dkk-3, rAd-IFN SCH 721015, TIL-Ad-INFg, Ad-ISF35, and coxsackievirus A21 (CVA21, CAVATAK®).

In other embodiments, the multispecific molecule is administered in combination with a nanopharmaceutical. Exemplary cancer nanopharmaceuticals include, but not limited to, ABRAXANE® (paclitaxel bound albumin nanoparticles), CRLX101 (CPT conjugated to a linear cyclodextrin-based polymer), CRLX288 (conjugating docetaxel to the biodegradable polymer poly (lactic-co-glycolic acid)), cytarabine liposomal (liposomal Ara-C, DEPOCYT™), daunorubicin liposomal (DAUNOXOME®), doxorubicin liposomal (DOXIL®, CAELYX®), encapsulated-daunorubicin citrate liposome (DAUNOXOME®), and PEG anti-VEGF aptamer (MACUGEN®).

In some embodiments, the multispecific molecule is administered in combination with paclitaxel or a paclitaxel formulation, e.g., TAXOL®, protein-bound paclitaxel (e.g., ABRAXANE®). Exemplary paclitaxel formulations include, but are not limited to, nanoparticle albumin-bound paclitaxel (ABRAXANE®, marketed by Abraxis Bioscience), docosahexaenoic acid bound-paclitaxel (DHA-paclitaxel, Taxoprexin, marketed by Protarga), polyglutamate bound-paclitaxel (PG-paclitaxel, paclitaxel poliglumex, CT-2103, XYOTAX, marketed by Cell Therapeutic), the tumor-activated prodrug (TAP), ANG105 (Angiopep-2 bound to three molecules of paclitaxel, marketed by ImmunoGen), paclitaxel-EC-1 (paclitaxel bound to the erbB2-recognizing peptide EC-1; see Li et al., *Biopolymers* (2007) 87:225-230), and glucose-conjugated paclitaxel (e.g., 2'-paclitaxel methyl 2-glucopyranosyl succinate, see Liu et al., *Bioorganic & Medicinal Chemistry Letters* (2007) 17:617-620).

Exemplary RNAi and antisense RNA agents for treating cancer include, but not limited to, CALAA-01, siG12D LODER (Local Drug EluteR), and ALN-VSP02.

Other cancer therapeutic agents include, but not limited to, cytokines (e.g., aldesleukin (IL-2, Interleukin-2, PROLEUKIN®), alpha Interferon (IFN-alpha, Interferon alfa, INTRON® A (Interferon alfa-2b), ROFERON-A® (Interferon alfa-2a)), Epoetin alfa (PROCRIT®), filgrastim (G-CSF, Granulocyte-Colony Stimulating Factor, NEUPOGEN®), GM-CSF (Granulocyte Macrophage Colony Stimulating Factor, sargramostim, LEUKINE™), IL-11 (Interleukin-11, oprelvekin, NEUMEGA®), Interferon alfa-2b (PEG conjugate) (PEG interferon, PEG-INTRON™), and pegfilgrastim (NEULASTA™)), hormone therapy agents (e.g., aminoglutethimide (CYTADREN®), anastrozole (ARIMIDEX®), bicalutamide (CASODEX®), exemestane (AROMASIN®), fluoxymesterone (HALOTESTIN®), flutamide (EULEXIN®), fulvestrant (FASLODEX®), goserelin (ZOLADEX®), letrozole (FEMARA®), leuprolide (ELIGARD™, LUPRON®, LUPRON DEPOT®, VIADUR™), megestrol (megestrol acetate, MEGACE®), nilutamide (ANANDRON®, NILANDRON®), octreotide (octreotide acetate, SANDOSTATIN®, SANDOSTATIN LAR®), raloxifene (EVISTA®), romiplostim (NPLATE®), tamoxifen (NOVALDEX®), and toremifene (FARESTON®)), phospholipase A2 inhibitors (e.g., anagrelide (AGRYLIN®)), biologic response modifiers (e.g., BCG (THERACYS®, TICE®), and Darbepoetin alfa (ARANESP®)), target therapy agents (e.g., bortezomib (VELCADE®), dasatinib (SPRYCEL™), denileukin diftitox (ONTAK®), erlotinib (TARCEVA®), everolimus (AFINITOR®), gefitinib (IRESSA®), imatinib mesylate (STI-571, GLEEVEC™), lapatinib (TYKERB®), sorafenib (NEXAVAR®), and SU11248 (sunitinib, SUTENT®)), immunomodulatory and antiangiogenic agents (e.g., CC-5013 (lenalidomide, REVLIMID®), and thalidomide (THALOMID®)), glucocorticosteroids (e.g., cortisone (hydrocortisone, hydrocortisone sodium phosphate, hydrocortisone sodium succinate, ALA-CORT®, HYDROCORT ACETATE®, hydrocortone phosphate LANACORT®, SOLU-CORTEF®), decadron (dexamethasone, dexamethasone acetate, dexamethasone sodium phosphate, DEXASONE®, DIODEX®, HEXADROL®, MAXIDEX®), methylprednisolone (6-methylprednisolone, methylprednisolone acetate, methylprednisolone sodium succinate, DURALONE®, MEDRALONE®, MEDROL®, M-PREDNISOL®, SOLU-MEDROL®), prednisolone (DELTA-CORTEF®, ORAPRED®, PEDIAPRED®, PRELONE®), and prednisone (DELTASONE®, LIQUID PRED®, METICORTEN®, ORASONE®)), and bisphosphonates (e.g., pamidronate (AREDIA®), and zoledronic acid (ZOMETA®))

In some embodiments, the multispecific molecule is used in combination with a tyrosine kinase inhibitor (e.g., a receptor tyrosine kinase (RTK) inhibitor). Exemplary tyrosine kinase inhibitor include, but are not limited to, an epidermal growth factor (EGF) pathway inhibitor (e.g., an epidermal growth factor receptor (EGFR) inhibitor), a vascular endothelial growth factor (VEGF) pathway inhibitor (e.g., an antibody against VEGF, a VEGF trap, a vascular endothelial growth factor receptor (VEGFR) inhibitor (e.g., a VEGFR-1 inhibitor, a VEGFR-2 inhibitor, a VEGFR-3 inhibitor)), a platelet derived growth factor (PDGF) pathway inhibitor (e.g., a platelet derived growth factor receptor (PDGFR) inhibitor (e.g., a PDGFR-β inhibitor)), a RAF-1 inhibitor, a KIT inhibitor and a RET inhibitor. In some embodiments, the anti-cancer agent used in combination with the multispecific molecule is selected from the group consisting of: axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZAC- TIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), alemtuzumab (CAMPATH®), gemtuzumab ozogamicin (MYLOTARG®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, XL228, AEE788, AG-490, AST-6, BMS-599626, CUDC-101, PD153035, pelitinib (EKB-569), vandetanib (zactima), WZ3146, WZ4002, WZ8040, ABT-869 (linifanib), AEE788, AP24534 (ponatinib), AV-951(tivozanib), axitinib, BAY 73-4506 (regorafenib), brivanib alaninate (BMS-582664), brivanib (BMS-540215), cediranib (AZD2171), CHIR-258 (dovitinib), CP 673451, CYC116, E7080, Ki8751, masitinib (AB1010), MGCD-265, motesanib diphosphate (AMG-706), MP-470, OSI-930, Pazopanib Hydrochloride, PD173074,nSorafenib Tosylate(Bay 43-9006), SU 5402, TSU-68(SU6668), vatalanib, XL880 (GSK1363089, EXEL-2880). Selected tyrosine kinase inhibitors are chosen from sunitinib, erlotinib, gefitinib, or sorafenib. In one embodiment, the tyrosine kinase inhibitor is sunitinib.

In one embodiment, the multispecific molecule is administered in combination with one of more of: an anti-angiogenic agent, or a vascular targeting agent or a vascular disrupting agent. Exemplary anti-angiogenic agents include, but are not limited to, VEGF inhibitors (e.g., anti-VEGF antibodies (e.g., bevacizumab); VEGF receptor inhibitors (e.g., itraconazole); inhibitors of cell proliferatin and/or migration of endothelial cells (e.g., carboxyamidotriazole, TNP-470); inhibitors of angiogenesis stimulators (e.g., suramin), among others. A vascular-targeting agent (VTA) or vascular disrupting agent (VDA) is designed to damage the vasculature (blood vessels) of cancer tumors causing central necrosis (reviewed in, e.g., Thorpe, P.E. (2004) *Clin. Cancer Res.* Vol. 10:415-427). VTAs can be small-molecule. Exemplary small-molecule VTAs include, but are not limited to, microtubule destabilizing drugs (e.g., combretastatin A-4 disodium phosphate (CA4P), ZD6126, AVE8062, Oxi 4503); and vadimezan (ASA404).

Immune Checkpoint Inhibitors

In other embodiments, methods described herein comprise use of an immune checkpoint inhibitor in combination with the multispecific molecule. The methods can be used in a therapeutic protocol in vivo.

In embodiments, an immune checkpoint inhibitor inhibits a checkpoint molecule. Exemplary checkpoint molecules include but are not limited to CTLA4, PD1, PD-L1, PD-L2, TIM3, LAG3, CD160, 2B4, CD80, CD86, B7-H3 (CD276), B7-H4 (VTCN1), HVEM (TNFRSF14 or CD270), BTLA, KIR, MHC class I, MHC class II, GALS, VISTA, BTLA, TIGIT, LAIR1, and A2aR. See, e.g., Pardoll. Nat. Rev. Cancer 12.4(2012):252-64, incorporated herein by reference.

In embodiments, the immune checkpoint inhibitor is a PD-1 inhibitor, e.g., an anti-PD-1 antibody such as Nivolumab, Pembrolizumab or Pidilizumab. Nivolumab (also called MDX-1106, MDX-1106-04, ONO-4538, or BMS-936558) is a fully human IgG4 monoclonal antibody that specifically inhibits PD1. See, e.g., U.S. Pat. No. 8,008,449 and WO2006/121168. Pembrolizumab (also called Lambrolizumab, MK-3475, MK03475, SCH-900475 or KEYTRUDA®; Merck) is a humanized IgG4 monoclonal antibody that binds to PD-1. See, e.g., Hamid, O. et al. (2013) *New England Journal of Medicine* 369 (2): 134-44, U.S. Pat. No. 8,354,509 and WO2009/114335. Pidilizumab (also called CT-011 or Cure Tech) is a humanized IgGlk monoclonal antibody that binds to PD1. See, e.g., WO2009/101611. In one embodiment, the inhibitor of PD-1 is an antibody molecule having a sequence substantially identical or similar thereto, e.g., a sequence at least 85%, 90%, 95% identical or higher to the sequence of Nivolumab, Pembrolizumab or Pidilizumab. Additional anti-PD1 antibodies, e.g., AMP 514 (Amplimmune), are described, e.g., in U.S. Pat. No. 8,609,089, US 2010028330, and/or US 20120114649.

In some embodiments, the PD-1 inhibitor is an immunoadhesin, e.g., an immunoadhesin comprising an extracellular/PD-1 binding portion of a PD-1 ligand (e.g., PD-L1 or PD-L2) that is fused to a constant region (e.g., an Fc region of a heavy chain). In embodiments, the PD-1 inhibitor is AMP-224 (B7-DCIg, e.g., described in WO2011/066342and WO2010/027827), a PD-L2 Fc fusion soluble receptor that blocks the interaction between B7-H1 and PD-1.

In embodiments, the immune checkpoint inhibitor is a PD-L1 inhibitor, e.g., an antibody molecule. In some embodiments, the PD-L1 inhibitor is YW243.55.570, MPDL3280A, MEDI-4736, MSB-0010718C, or MDX-1105. In some embodiments, the anti-PD-L1 antibody is MSB0010718C (also called A09-246-2; Merck Serono), which is a monoclonal antibody that binds to PD-L1. Exemplary humanized anti-PD-L1 antibodies are described, e.g., in WO2013/079174. In one embodiment, the PD-L1 inhibitor is an anti-PD-L1 antibody, e.g., YW243.55.570. The YW243.55.570 antibody is described, e.g., in WO 2010/077634. In one embodiment, the PD-L1 inhibitor is MDX-1105 (also called BMS-936559), which is described, e.g., in WO2007/005874. In one embodiment, the PD-L1 inhibitor is MDPL3280A (Genentech/Roche), which is a human Fc-optimized IgG1 monoclonal antibody against PD-L1. See, e.g., U.S. Pat. No. 7,943,743 and U.S Publication No.: 20120039906. In one embodiment, the inhibitor of PD-L1 is an antibody molecule having a sequence substantially identical or similar thereto, e.g., a sequence at least 85%, 90%, 95% identical or higher to the sequence of YW243.55.570, MPDL3280A, MEDI-4736, MSB-0010718C, or MDX-1105.

In embodiments, the immune checkpoint inhibitor is a PD-L2 inhibitor, e.g., AMP-224 (which is a PD-L2 Fc fusion soluble receptor that blocks the interaction between PD1 and B7-H1. See, e.g., WO2010/027827 and WO2011/066342.

In one embodiment, the immune checkpoint inhibitor is a LAG-3 inhibitor, e.g., an anti LAG-3 antibody molecule. In embodiments, the anti-LAG-3 antibody is BMS-986016 (also called BMS986016; Bristol-Myers Squibb). BMS-986016 and other humanized anti-LAG-3 antibodies are described, e.g., in US 2011/0150892, WO2010/019570, and WO2014/008218.

In embodiments, the immune checkpoint inhibitor is a TIM-3 inhibitor, e.g., anti-TIM3 antibody molecule, e.g., described in U.S. Pat. No. 8,552,156, WO 2011/155607, EP 2581113 and U.S Publication No.: 2014/044728.

In embodiments, the immune checkpoint inhibitor is a CTLA-4 inhibitor, e.g., anti-CTLA-4 antibody molecule. Exemplary anti-CTLA4 antibodies include Tremelimumab (IgG2 monoclonal antibody from Pfizer, formerly known as ticilimumab, CP-675,206); and Ipilimumab (also called MDX-010, CAS No. 477202-00-9). Other exemplary anti-CTLA-4 antibodies are described, e.g., in U.S. Pat. No. 5,811,097.

EXAMPLES

The following examples are intended to be illustrative, and are not meant in any way to be limiting.

Example 1

Generation of Multiple αCCR2αCSF1R Bispecific Antibody Molecules

1. Construction of the Plasmids.

The DNA encoding the protein sequences was optimized for expression in *Cricetulus griseus*, synthesized, and cloned into the pcDNA3.4-TOPO (Life Technologies A14697) using Gateway cloning. All constructs contained an Ig Kappa leader sequence (ATG-GAAACCGACACACTGCTGCTGTGGGTGCTGCTCTTGTGGGTGCCAGGATCTAC AGGA (SEQ ID NO: 115), METDTLLLWVLLLWVPGSTG (SEQ ID NO: 116)). The nucleic acid sequences used are shown in Table 1.

TABLE 1

| | | |
|---|---|---|
| \multicolumn{3}{c}{Exemplary nucleic acid sequences of antibodies} |
| SEQ ID NO | Description | Nucleic Acid Sequence |
| SEQ ID NO: 1 | αCCR2 MC12 VH | CAGGTCCAGCTGCAAGAGTCTGGCCCTGGACTGGTTCAG CCCTCTCAGACCCTGTCTCTGACCTGTACCGTGTCCGGCT TCTCCCTGACCGACTTCTCTGTGCACTGGGTCCGACAGCC TCCAGGCAAAGGACTGGAATGGATGGGCAGAATCAGATC CGAGGGCAACACCGACTACAACAGCGCCCTGAAGTCCCG GCTGTCTATCAGCAGAGACACCTCCAAGAGCCAGGTGTT CCTGAAGATGAACTCCCTGCAGACCGAGGACACCGCCAT CTATTTCTGCACCAGAGGCGACATCCTCGGCTTCGGCTAT TGGGGACAGGGCGTGATGGTCACCGTTAGCTCT |
| SEQ ID NO: 2 | αCCR2 MC12 VL | GACATCGTGATGACCCAGTCTCCACTGTCCGTGTCTGTGA CCCTGGCGAGTCTGCCTCCATCTCCTGCAGATCCTCCAA GAGCCTGCTGCACTTCAAGGGCATCACCTTCGTGTACTGG TATCTGCAGAAGCCCGGCCAGTCTCCTCAGCTGCTGATCT TCAGAATGTCCAGCCTGGCCTCTGGCGTGCCCGATAGATT TTCTGGCTCCGGCTCCGAGACAGACTTCACCCTGAAGATC TCCAGAGTGGAAGCCGAGGACGTGGGCACCTACTATTGT GGCCAGCTGCTGGAAAACCCCTACACCTTTGGCGCTGGC ACCAAGCTGGAACTGAAG |
| SEQ ID NO: 3 | R2b CH1 | GCTCAGACCACCGCTCCTAGCGTGTACCCTTTGGCTCCTG GCTGTGGCGACACCACCTCTTCTACAGTGACCCTGGGCTG TCTGGTCAAGGGCTACTTTCCTGAGCCTGTGACCGTGACC TGGAACTCTGGTGCCCTGTCCTCCGACGTGCACACCTTTC CAGCTGTGCTGCAGTCCGGCCTGTACACCCTGACATCCTC CGTGACCTCTTCCACCTGGCCTAGCCAGACCGTGACATGC AATGTGGCTCACCCTGCCTCCAGCACCAAGGTGGACAAG AAGGTGGAACGGCGG |
| SEQ ID NO: 4 | R2b CL | AGAGCTGACGCTGCCCCTACCGTGTCTATCTTCCCTCCAT CCATGGAACAGCTGACCTCTGGCGGAGCTACCGTCGTGT GCTTCGTGAACAACTTCTACCCTCGGGACATCTCCGTGAA GTGGAAGATCGACGGCTCTGAGCAGCGAGATGGCGTGCT GGATTCTGTGACCGACCAGGACTCCAAGGACAGCACCTA CTCCATGTCTAGCACCCTGAGCCTGACCAAGGTGGAATA CGAGCGGCACAACCTGTATACCTGCGAGGTGGTGCACAA GACCTCCAGCTCTCCCGTGGTCAAGTCCTTCAACCGGAAC GAGTGC |
| SEQ ID NO: 5 | αmCSF1R VH | CAGGTCCAGTTGCAGCAGTCTGGCGCTGAGCTGGTCAAG CCTGGATCCTCCGTGAAGATCTCCTGCAAGGCCTCCGGCT ACACCTTCACCTCCAACTTCATGCACTGGATCAAGCAGCA GCCCGGCAACGGCCTGGAATGGATCGGATGGATCTATCC TGGCGACGGCGACACCGAGTACAACCAGAAGTTCAACGG CAAGGCTACCCTGACCGCCGACAAGTCCTCTTCCACCGCT TACATGCAGCTGTCCAGCCTGACCTCTGAGGACTCCGCCG TGTACTTCTGCGCCGTGAATTATGGCGGCTACGTGCTGGA TGCTTGGGGCCAAGGCGCTTCTGTGACAGTGTCCTCT |
| SEQ ID NO: 6 | R2a CH1 | GCCGAGACAACCGCTCCTAGCGTTTACCCTCTGGCTCCTG GCACAGCCCTGAAGTCCAACTCTATGGTCACCCTGGGCT GCCTGGTCAAGGGCTACTTTCCTGAGCCTGTGACCGTGAC CTGGAACTCTGGTGCTCTGTCTAGCGGCGTGCACACCTTT CCAGCTGTGCTGCAGAGCGGCCTGTACACCCTGACATCT AGCGTGACCGTGCCTTCCAGCACCTGGTCTAGTCAGGCTG TGACCTGCAACGTGGCCCATCCTGCCTCTTCTACCAAGGT GGACAAGAAAATCGTGCCCAGAGAGTGCAAC |
| SEQ ID NO: 7 | αmC5F1R VL | GAGATCGTGCTGACCCAGTCTCCTACCACCATGGCTGCTA GCCCTGGCGAGAAAGTGACAATTACCTGCCGGGCCTCCT CCTCCACCAACTACATGTCCTGGTATCAGCAGAAGTCCG GCGCCTCTCCTAAGCTTGGATCTACGAGACATCCAAGCT GGCCTCTGGCGTGCCCGATAGATTTTCCGGCTCTGGCTCC GGCACCTCCTACAGCTTCACCATCTCCAGCATGGAAACA GAGGACGCCGCCACCTACTACTGCCACCAGTGGTCATCT |

TABLE 1-continued

Exemplary nucleic acid sequences of antibodies

| SEQ ID NO | Description | Nucleic Acid Sequence |
|---|---|---|
| | | ACCCCTCTGACCTTTGGCAGCGGCACCAAGCTGGAAATC<br>AAG |
| SEQ ID NO: 8 | R2a CL | AGAGCTGACGCCGCTCCTACCGTGTCTATCTTCCCTCCAT<br>CCATGGAACAGCTGACCTCCGGCGGAGCTACCGTCGTGT<br>GTTTCGTGAACAACTTCTACCCTCGGGACATCTCCGTGAA<br>GTGGAAGATCGACGGCTCTGAGCAGCGAGATGGCGTGCT<br>GGATTCTGTGACCGACCAGGACTCCAAGGACAGCACCTA<br>CTCCATGTCTAGCACCCTGAGCCTGACCAAGGTGGAATA<br>CGAGCGGCACAACCTGTATACCTGCGAGGTGGTGCACAA<br>GACCTCCAGCTCTCCCGTGGTCAAGTCCTTCAACCGGAAC<br>GAGTGC |
| SEQ ID NO: 9 | mFc Knob | ACCATTAAGCCTTGTCCTCCATGCAAGTGCCCCGCTCCTA<br>ATCTGCTCGGAGGCCCTTCCGTGTTCATCTTTCCACCTAA<br>GATCAAGGACGTGCTGATGATCTCCCTGTCTCCTATCGTG<br>ACCTGCGTGGTGGTGGACGTGTCCGAGGATGATCCTGAC<br>GTGCAGATCAGTTGGTTCGTGAACAACGTGGAAGTGCAC<br>ACCGCTCAGACCCAGACACACAGAGAGGACTACAACTCT<br>ACCCTGAGAGTGGTGTCTGCCCTGCCTATCCAGCATCAGG<br>ACTGGATGTCCGGCAAAGAATTCAAGTGCAAAGTGAACA<br>ACAAGGACCTGCCTGCTCCAATCGAGCGGACCATCTCTA<br>AGCCTAAGGGCTCTGTCAGGGCCCCTCAGGTGTACGTTCT<br>GCCTCCTTGCGAGGAAGAGATGACCAAGAAACAAGTGAC<br>ACTGTGGTGCATGGTCACAGACTTCATGCCCGAGGACAT<br>CTACGTGGAATGGACCAACAACGGCAAGACCGAGCTGAA<br>CTACAAGAACACCGAGCCTGTGCTGGACTCCGACGGCTC<br>CTACTTCATGTACTCCAAGCTGCGCGTCGAGAAGAAGAA<br>CTGGGTCGAGAGAAACTCCTACTCCTGCTCCGTGGTGCAC<br>GAGGGCCTGCACAATCACCACACCACCAAGTCCTTCTCTC<br>GGACCCCTGGCAAG |
| SEQ ID NO: 10 | mFc Hole | ACCATCAAGCCCTGTCCTCCATGCAAGTGCCCCGCTCCTA<br>ATCTGCTCGGAGGCCCTTCCGTGTTCATCTTCCCACCTAA<br>GATCAAGGACGTGCTGATGATCTCCCTGTCTCCTATCGTG<br>ACCTGCGTGGTGGTGGACGTGTCCGAGGATGATCCTGAC<br>GTGCAGATCAGTTGGTTCGTGAACAACGTGGAAGTGCAC<br>ACCGCTCAGACCCAGACACACAGAGAGGACTACAACAGC<br>ACCCTGAGAGTGGTGTCTGCCCTGCCAATCCAGCACCAG<br>GATTGGATGTCCGGCAAAGAATTCAAGTGCAAAGTGAAC<br>AACAAGGACCTGCCTGCTCCAATCGAGCGGACCATCTCT<br>AAGCCTAAGGGCTCTGTGCGGGCTCCCCAAGTTTGTGTTC<br>TGCCTCCACCTGAGGAAGAGATGACCAAGAAACAAGTGA<br>CCCTGTCTTGTGCCGTGACCGACTTCATGCCCGAGGACAT<br>CTACGTGGAATGGACCAACAATGGCAAGACCGAGCTGAA<br>CTACAAGAACACCGAGCCTGTGCTGGACTCCGACGGCTC<br>CTACTTCATGGTGTCTAAGCTGCGCGTCGAGAAGAAGAA<br>CTGGGTCGAGAGAAACTCCTACTCCTGCTCCGTGGTGCAC<br>GAGGGCCTGCACAATCACCACACCACCAAGTCCTTCTCTC<br>GGACCCCTGGCAAG |
| SEQ ID NO: 11 | αhCCR2<br>plozalizumab<br>VH | GAGGTGCAGCTGGTTGAATCTGGCGGAGGACTGGTTAAG<br>CCTGGCGGCTCTCTGAGACTGTCTTGTGCCCGCTTCTGGCT<br>TCACCTTCTCCGCTACGCCATGAACTGGGTCCGACAGGC<br>TCCTGGCAAAGGCCTGGAATGGGTCGGAAGAATCCGGAC<br>CAAGAACAACAACTACGCCACCTACTACGCCGACTCCGT<br>GAAGGACCGGTTCACCATCTCTCGGGACGACTCCAAGAA<br>CACCCTGTACCTGCAGATGAACTCCCTGAAAACCGAGGA<br>CACCGCCGTGTACTACTGCACCACCTTCTACGGCAATGGC<br>GTGTGGGGACAGGGCACACTGGTTACCGTTTCTTCCGCCT<br>CCACCAAGGGACCCTCTGTGTTTCCTCTGGCTCCCTCCAG<br>CAAGTCTACCTCTGGTGGAACAGCTGCCCTGGGCTGCCTG<br>GTCAAGGATTACTTTCCTGAGCCTGTGACCGTGTCCTGG |
| SEQ ID NO: 12 | hCH1 | GCTTCTACCAAGGGACCCAGCGTGTTCCCTCTGGCTCCTT<br>CCAGCAAGTCTACCTCTGGCGGAACAGCTGCTCTGGGCT<br>GCCTGGTCAAGGACTACTTTCCTGAGCCTGTGACCGTGTC<br>TTGGAACTCTGGCGCTCTGACATCCGGCGTGCACACATTT<br>CCAGCTGTGCTGCAGTCCTCCGGCCTGTACTCTCTGTCCT<br>CTGTCGTGACCGTGCCTTCCAGCTCTCTGGGAACCCAGAC<br>CTACATCTGCAATGTGAACCACAAGCCTTCCAACACCAA<br>GGTGGACAAGAGAGTGGAACCCAAGTCCTGC |
| SEQ ID NO: 13 | hFc Knob | GATAAGACCCACACATGTCCTCCATGCCCTGCCCCTGAGC<br>TGCTGGGCGGACCTTCCGTGTTCCTGTTCCCTCCAAAGCC<br>CAAGGACACCCTGATGATCAGCCGGACCCCTGAAGTGAC |

TABLE 1-continued

Exemplary nucleic acid sequences of antibodies

| SEQ ID NO | Description | Nucleic Acid Sequence |
|---|---|---|
| | | CTGCGTGGTGGTGGATGTGTCCCACGAGGATCCCGAAGT
GAAGTTCAATTGGTACGTGGACGGCGTGGAAGTGCACAA
CGCCAAGACCAAGCCCAGAGAGGAACAGTACAACAGCA
CCTACCGGGTGGTGTCCGTGCTGACCGTGCTGCATCAGGA
CTGGCTGAACGGCAAAGAGTACAAGTGCAAGGTGTCCAA
CAAGGCCCTGCCTGCCCCTATCGAGAAAACCATCAGCAA
GGCCAAGGGCCAGCCCCGCGAACCTCAGGTGTACACACT
GCCTCCCTGCCGGGAAGAGATGACCAAGAACCAGGTGTC
CCTGTGGTGCCTGGTCAAGGGCTTCTACCCCTCCGATATC
GCCGTGGAATGGGAGAGCAACGGCCAGCCCGAGAACAA
CTACAAGACCACCCCTCCCGTGCTGGACAGCGACGGCAG
CTTCTTCCTGTACTCCAAACTGACCGTGGACAAGAGCCGG
TGGCAGCAGGGCAATGTGTTCAGCTGTAGCGTGATGCAC
GAGGCCCTGCACAACCACTACACCCAGAAGTCCCTGAGC
CTGTCTCCTGGCAAA |
| SEQ ID NO: 14 | αhCCR2 plozalizumab VL | GACGTGGTCATGACACAGAGCCCTCTGTCTCTGCCCGTGA
CATTGGGACAGCCTGCCTCCATCTCCTGCAAGTCCTCTCA
GTCCCTGCTGGACTCTGACGGCAAGACCTTCCTGAACTGG
TTCCAGCAGCGGCCTGGCCAGTCTCCTAGAAGGCTGATCT
ACCTGGTGTCCAAGCTGGATTCTGGCGTGCCCGACAGATT
CTCCGGCTCTGGCTCTGGCACCGACTTCACCCTGAAGATC
TCCAGAGTGGAAGCCGAGGACGTGGGCGTGTACTACTGT
TGGCAGGGCACCCACTTTCCATACACCTTCGGCCAGGGC
ACCAGACTGGAAATCAAG |
| SEQ ID NO: 15 | hCL (kappa) | AGAACAGTGGCCGCTCCTTCCGTGTTCATCTTCCCACCCT
CCGACGAGCAGCTGAAGTCCGGCACCGCTTCTGTCGTGT
GCCTGCTCAACAACTTCTACCCTCGGGAAGCCAAGGTGC
AGTGGAAGGTGGACAACGCCCTGCAGTCCGGCAACTCCC
AGGAATCCGTCACCGAGCAGGACTCCAAGGACAGCACCT
ACTCCCTGTCCTCCACCCTGACCCTGTCCAAGGCCGACTA
CGAGAAGCACAAGGTGTACGCCTGCGAAGTGACCCACCA
GGGCCTGAGCAGCCCCGTGACCAAGTCCTTCAACCGGGG
CGAGTGC |
| SEQ ID NO: 16 | αhCCR2 D1 VH | GAAGTGCAGCTGGTTCAGTCTGGCGCCGAAGTGAAGAAA
CCTGGCGCCTCTGTGAAGGTGTCCTGCAAGGCTTCTGGCT
ACACCTTTACCGGCTACCACATGCACTGGGTCCGACAGG
CTCCAGGACAAGGCTTGGAATGGATGGGCTGGATCAACC
CCAACTCCGGCGTGACCAAATACGCCCAGAAATTCCAGG
GCAGAGTGACCATGACCAGAGACACCTCCATCAACACCG
CCTACATGGAACTGTCCCGGCTGAGATTCGACGACACCG
ACGTGTACTACTGTGCCACCGGCGGCTTTGGCTATTGGGG
AGAGGGAACACTGGTCACCGTGTCCTCC |
| SEQ ID NO: 17 | αhCCR2 D1 VL | CTGCCCGTGTTGACCCAGCCTCCTAGCGTTTCCAAGGGCC
TGAGACAGACCGCCACACTGACCTGTACCGGCAACTCTA
ACAACGTGGGCAATCAGGGCGCTGCCTGGTTGCAGCAGC
ATCAGGGACAGCCTCCAAAGCTGCTGTCCTACCGGAACC
ACAACAGACCTAGCGGCGTGTCCGAGCGGTTCAGCCCTT
CTAGATCTGGCGACACCTCCAGCCTGACCATCACTGGACT
GCAGCCTGAGGACGAGGCCGACTACTATTGTCTGGCCTG
GGACAGCTCCCTGCGGGCCTTTGTTTTTGGCACCGGCACC
AAGCTGACCGTGCTG |
| SEQ ID NO: 18 | hCL (lambda) | GGACAACCTAAGGCCAATCCTACCGTGACACTGTTCCCTC
CATCCTCCGAGGAACTGCAGGCCAACAAGGCTACCCTCG
TGTGCCTGATCTCCGACTTTTACCCTGGCGCTGTGACCGT
GGCCTGGAAGGCTGATGGATCTCCTGTGAAGGCTGGCGT
GGAAACCACCAAGCCTTCCAAGCAGTCCAACAACAAATA
CGCCGCCTCCTCCTACCTGTCTCTGACCCCTGAACAGTGG
AAGTCCCACCGGTCCTACAGCTGCCAAGTGACCCATGAG
GGCTCCACCGTGGAAAAGACCGTGGCTCCTACCGAGTGC
TCC |
| SEQ ID NO: 19 | αhCCR2 42G7 VH | CAGGTGCAGCTGGTTCAGTCTGGCGCCGAAGTGAAGAAA
CCTGGCGCCTCTGTGAAGGTGTCCTGCAAGGCTTCCGGCT
ACACCTTCTCCAGCTACATGCACTGGGTCCGACAGGC
CCCTGGACAAGGATTGGAGTGGATGGGCATCATCAACCC
CTCTGGCGGCAACACCTCTTACGCCCAGAAATTCCAGGG
CAGAGTGACCATGACCAGAGACACCTCCACCAGCACCGT
GTACATGGAACTGTCCAGCCTGAGATCCGAGGACACCGC
CGTGTACTACTGTGCCAGAGGCGGATACCAGCTGCCTCA
CGGTAGAGCCAGAGCCTTCGATATGTGGGGCCAGGGCAC
AATGGTCACCGTGTCCTCT |

TABLE 1-continued

Exemplary nucleic acid sequences of antibodies

| SEQ ID NO | Description | Nucleic Acid Sequence |
|---|---|---|
| SEQ ID NO: 20 | αhCCR2 42G7 VL | GCCATCAGAATGACCCAGTCTCCACTGAGCCTGCCTGTG ACATTGGGCCAGCCTGCCTCTATCTCCTGCACCTCCTCTC AGTCTCTGGTGTACAGAGATGGCACCACCTACCTGAACT GGTTCCAGCAGAGGCCTGGCCAGTCTCCTAGACGGCTGA TCTACAAGGTGTCCAACAGAGACTCTGGCGTGCCCGACA GATTCACCGGCTCTGGCTCTGGCACCACATTCACCCTGAC CATCTCCAGAGTGGAAGCCGAGGACGTGGGCATCTACTA CTGTATGCAGGGCACCCACTGGCCTCTGACCTTTGGCCAG GGAACAAAGGTGGAAATCAAG |
| SEQ ID NO: 21 | αhCCR2 43G12 VH | GAGGTGCAGCTGGTTGAATCTGGCGGAGGATTGGTTCAG CCTGGCGGTCTCTGAGACTGTCTTGTGTGGCCTCTGGCT TCACCTTCTCCGACTACTGGATGTCCTGGGTCCGACAGGC TCCTGGCAAAGGACTGGAATGGGTCGCCAACATCAAGAA AGACGGCTCCGTGAACTACTACGTGGACTCCGTGAAGGG CAGATTCACCATCTCTCGGGACAACGCCAAGAACTCCCT GTACCTGCAGATGAACAGCCTGAGAGCCGAGGACACCGC CGTGTACTACTGCACCAGATTCGATTACTGGGGCCAGGG CACCCTGGTCACAGTGTCCTCT |
| SEQ ID NO: 22 | αhCCR2 43G12 VL | CAGGCTGGCTTGACCCAGCCTCCTAGCGTTTCCAAGGGCC TGAGACAGACCGCCACACTGACCTGTACCGGCAACTCTA ACAACGTGGGCAATCAGGGCGCTGCCTGGTTGCAGCAGC ATCAGGGACATCCTCCAAAGCTGCTGTTCTACCGGAACA ACAACGAGAGCCTCCGGCATCTCCGAGCGGCTGTCTGCTTC TAGATCCGGCAATACCGCCAGCCTGACCATCACTGGACT GCAGCCTGAGGACGAGGCCGACTACTATTGCCTGACCTG GGACTCCTCTCTGTCCGTGGTGGTTTTTGGCGGAGGCACC AAGCTGACAGTGCTG |
| SEQ ID NO: 23 | αhCSF1R emactuzumab VH | CAGGTGCAGCTGGTTCAGTCTGGCGCCGAAGTGAAGAAA CCTGGCGCCTCTGTGAAGGTGTCCTGCAAGGCTTCCGGCT ACACCTTTACCAGCTACGACATCTCCTGGGTCCGACAGGC TCCTGGACAAGGCTTGGAATGGATGGGCGTGATCTGGAC CGATGGCGGCACCAATTACGCCCAGAAACTGCAGGGCAG AGTGACCATGACCACCGACACCTCTACCTCCACCGCCTAC ATGGAACTGCGGTCCCTGAGATCTGACGACACCGCCGTG TACTACTGCGCCAGAGATCAGCGGCTGTACTTCGATGTGT GGGGCCAGGGCACAACCGTGACAGTGTCCTCT |
| SEQ ID NO: 24 | αhCSF1R emactuzumab VL | GACATCCAGATGACCCAGTCTCCATCCTCTCTGTCCGCCT CTGTGGGCGACAGAGTGACCATCACCTGTAGAGCCTCCG AGGACGTGAACACCTACGTGTCCTGGTATCAGCAGAAGC CCGGCAAGGCTCCCAAGCTGCTGATCTACGCCGCCTCTA ACAGATACACCGGCGTGCCCTCTAGATTCTCCGGCTCTGG CTCTGGCACCGACTTTACCCTGACAATCTCCAGCCTGCAG CCTGAGGACTTCGCCACCTACTACTGCCAGCAGTCCTTCA GCTACCCCACCTTTGGCCAGGGCACCAAGCTGGAAATCA AG |
| SEQ ID NO: 25 | hFc Hole | GATAAGACCCACACCTGTCCTCCCTGCCCTGCCCCTGAAC TGCTGGGCGGACCTAGCGTGTTCCTGTTCCCTCCAAAGCC CAAGGACACCCTGATGATCAGCCGGACCCCTGAAGTGAC CTGCGTGGTGGTGGATGTGTCCCACGAGGATCCCGAAGT GAAGTTCAATTGGTACGTGGACGGCGTGGAAGTGCACAA CGCCAAGACCAAGCCCAGAGAGGAACAGTACAACAGCA CCTACCGGGTGGTGTCCGTGCTGACCGTGCTGCACCAGG ACTGGCTGAACGGCAAAGAGTACAAGTGCAAGGTGTCCA ACAAGGCCCTGCCAGCCCCTATCGAGAAAACCATCAGCA AGGCCAAGGGCCAGCCTAGAGAGCCTCAGGTCTGCACCC TGCCTCCCAGCCGGGAAGAGATGACCAAGAACCAGGTGT CCCTGAGCTGCGCCGTGAAGGGCTTCTACCCCTCCGATAT CGCCGTGGAATGGGAGAGCAACGGCCAGCCCGAGAACA ACTACAAGACCACCCCTCCCGTGCTGGACAGCGACGGCA GCTTCTTCCTGGTGTCCAAACTGACCGTGGACAAGAGCCG GTGGCAGCAGGGCAATGTGTTCAGCTGTAGCGTGATGCA CGAGGCCCTGCACAACCACTACACCCAGAAGTCTCTGAG CCTGAGCCCTGGCAAA |
| SEQ ID NO: 26 | αhCSF1R cabiralizumab VH | CAGGTGCAGCTGGTTCAGTCTGGCGCCGAAGTGAAGAAA CCTGGCTCCTCCGTGAAGGTGTCCTGCAAGGCTTCTGGCT ACACCTTTACCGACAACTACATGATCTGGGTCCGACAGG CTCCTGGACAGGGACTTGAGTGGATGGGCGACATCAACC CTTACAACGGCGGCACCACCTTCAACCAGAAATTCAAGG GCAGAGTGACCATCACCGCCGACAAGTCTACCTCCACCG |

… TABLE 1-continued

Exemplary nucleic acid sequences of antibodies

| SEQ ID NO | Description | Nucleic Acid Sequence |
|---|---|---|
|  |  | CCTACATGGAACTGTCCAGCCTGAGATCTGAGGACACCG CCGTGTACTACTGCGCCAGAGAGTCCCCTTACTTCTCCAA CCTGTACGTGATGGACTACTGGGGCCAGGGCACACTGGT CACAGTGTCCTCT |
| SEQ ID NO: 27 | αhCSF1R cabiralizumab VL | GAGATCGTGCTGACCCAGTCTCCTGCCACACTGTCACTGT CTCCAGGCGAGAGAGCTACCCTGTCCTGCAAGGCTTCTC AGTCCGTGGACTACGACGGCGACAACTACATGAACTGGT ATCAGCAGAAGCCCGGCCAGGCTCCTAGACTGCTGATCT ACGCCGCCTCCAACCTGGAATCTGGCATCCCCGCTAGATT CTCCGGCTCTGGCTCTGGCACAGACTTTACCCTGACCATC TCCAGCCTGGAACCTGAGGACTTCGCCGTGTACTACTGCC ACCTGTCCAACGAGGACCTGTCCACATTTGGCGGAGGCA CCAAGGTGGAAATCAAG |

TABLE 2

Sequences used to construct ORFs.

| Full length | Variable | Constant | Fc |
|---|---|---|---|
| SEQ ID NO: 28 | SEQ ID NO: 1 | SEQ ID NO: 3 | SEQ ID NO: 9 |
| SEQ ID NO: 29 | SEQ ID NO: 2 | SEQ ID NO: 4 |  |
| SEQ ID NO: 30 | SEQ ID NO: 5 | SEQ ID NO: 6 | SEQ ID NO: 10 |
| SEQ ID NO: 31 | SEQ ID NO: 7 | SEQ ID NO: 8 |  |
| SEQ ID NO: 32 | SEQ ID NO: 11 | SEQ ID NO: 12 | SEQ ID NO: 13 |
| SEQ ID NO: 33 | SEQ ID NO: 14 | SEQ ID NO: 15 |  |
| SEQ ID NO: 34 | SEQ ID NO: 16 | SEQ ID NO: 12 | SEQ ID NO: 13 |
| SEQ ID NO: 35 | SEQ ID NO: 17 | SEQ ID NO: 18 |  |
| SEQ ID NO: 36 | SEQ ID NO: 19 | SEQ ID NO: 12 | SEQ ID NO: 13 |
| SEQ ID NO: 37 | SEQ ID NO: 20 | SEQ ID NO: 15 |  |
| SEQ ID NO: 38 | SEQ ID NO: 21 | SEQ ID NO: 12 | SEQ ID NO: 13 |
| SEQ ID NO: 39 | SEQ ID NO: 22 | SEQ ID NO: 18 |  |
| SEQ ID NO: 40 | SEQ ID NO: 23 | SEQ ID NO: 12 | SEQ ID NO: 25 |
| SEQ ID NO: 41 | SEQ ID NO: 24 | SEQ ID NO: 15 |  |
| SEQ ID NO: 42 | SEQ ID NO: 26 | SEQ ID NO: 12 | SEQ ID NO: 25 |
| SEQ ID NO: 43 | SEQ ID NO: 27 | SEQ ID NO: 15 |  |

TABLE 3

Nucleic acid sequences of ORFs.

Nucleic Acid Sequence

SEQ ID NO: 28    ATGGAAACCGACACACTGCTGCTGTGGGTGCTGCTCTTGTGGGTGCCAG
GATCTACAGGACAGGTCCAGCTGCAAGAGTCTGGCCCTGGACTGGTTCA
GCCCTCTCAGACCCTGTCTCTGACCTGTACCGTGTCCGGCTTCTCCCTGAC
CGACTTCTCTGTGCACTGGGTCCGACAGCCTCCAGGCAAAGGACTGGAA
TGGATGGGCAGAATCAGATCCGAGGGCAACACCGACTACAACAGCGCCC
TGAAGTCCCGGCTGTCTATCAGCAGAGACACCTCCAAGAGCCAGGTGTT
CCTGAAGATGAACTCCCTGCAGACCGAGGACACCGCCATCTATTTCTGCA
CCAGAGGCGACATCCTCGGCTTCGGCTATTGGGGACAGGGCGTGATGGT
CACCGTTAGCTCTGCTCAGACCACCGCTCCTAGCGTGTACCCTTTGGCTC
CTGGCTGTGGCGACACCACCTCTTCTACAGTGACCCTGGGCTGTCTGGTC
AAGGGCTACTTTCCTGAGCCTGTGACCGTGACCTGGAACTCTGGTGCCCT
GTCCTCCGACGTGCACACCTTTCCAGCTGTGCTGCAGTCCGGCCTGTACA
CCCTGACATCCTCCGTGACCTCTTCCACCTGGCCTAGCCAGACCGTGACA
TGCAATGTGGCTCACCCTGCCTCCAGCACCAAGGTGGACAAGAAGGTGG
AACGGCGGACCATTAAGCTTGTCCTCCATGCAAGTGCCCCGCTCCTAAT
CTGCTCGGAGGCCCTTCCGTGTTCATCTTTCCACCTAAGATCAAGGACGT
GCTGATGATCTCCCTGTCTCCTATCGTGACCTGCGTGGTGGTGGACGTGT
CCGAGGATGATCCTGACGTGCAGATCAGTTGGTTCGTGAACAACGTGGA
AGTGCACACCGCTCAGACCCAGACACACAGAGAGGACTACAACTCTACC
CTGAGAGTGGTGTCTGCCCTGCCTATCCAGCATCAGGACTGGATGTCCGG
CAAAGAATTCAAGTGCAAAGTGAACAACAAGGACCTGCCTGCTCCAATC
GAGCGGACCATCTCTAAGCCTAAGGGCTCTGTCAGGGCCCCTCAGGTGT
ACGTTCTGCCTCCTTGCGAGGAAGAGATGACCAAGAAACAAGTGACACT
GTGGTGCATGGTCACAGACTTCATGCCCGAGGACATCTACGTGGAATGG
ACCAACAACGGCAAGACCGAGCTGAACTACAAGAACACCGAGCCTGTGC
TGGACTCCGACGGCTCCTACTTCATGTACTCCAAGCTGCGCGTCGAGAAG
AAGAACTGGGTCGAGAGAAACTCCTACTCCTGCTCCGTGGTGCACGAGG
GCCTGCACAATCACCACACCACCAAGTCCTTCTCTCGGACCCCTGGCAAG
TGATGA

SEQ ID NO: 29    ATGGAAACCGACACACTGCTGCTGTGGGTGCTGCTCTTGTGGGTGCCAG
GATCTACCGGCGACATCGTGATGACCCAGTCTCCACTGTCCGTGTCTGTG
ACCCCTGGCGAGTCTGCCTCCATCTCCTGCAGATCCTCCAAGAGCCTGCT
GCACTTCAAGGGCATCACCTTCGTGTACTGGTATCTGCAGAAGCCCGGCC
AGTCTCCTCAGCTGCTGATCTTCAGAATGTCCAGCCTGGCCTCTGGCGTG

TABLE 3-continued

Nucleic acid sequences of ORFs.

Nucleic Acid Sequence

CCCGATAGATTTTCTGGCTCCGGCTCCGAGACAGACTTCACCCTGAAGAT
CTCCAGAGTGGAAGCCGAGGACGTGGGCACCTACTATTGTGGCCAGCTG
CTGGAAAACCCCTACACCTTTGGCGCTGGCACCAAGCTGGAACTGAAGA
GAGCTGACGCTGCCCCTACCGTGTCTATCTTCCCTCCATCCATGGAACAG
CTGACCTCTGGCGGAGCTACCGTCGTGTGCTTCGTGAACAACTTCTACCC
TCGGGACATCTCCGTGAAGTGGAAGATCGACGGCTCTGAGCAGCGAGAT
GGCGTGCTGGATTCTGTGACCGACCAGGACTCCAAGGACAGCACCTACT
CCATGTCTAGCACCCTGAGCCTGACCAAGGTGGAATACGAGCGGCACAA
CCTGTATACCTGCGAGGTGGTGCACAAGACCTCCAGCTCTCCCGTGGTCA
AGTCCTTCAACCGGAACGAGTGCTGATGA

SEQ ID NO: 30   ATGGAAACCGACACACTGCTGCTGTGGGTGCTGCTCTTGTGGGTGCCAG
GATCTACAGGACAGGTCCAGTTGCAGCAGTCTGGCGCTGAGCTGGTCAA
GCCTGGATCCTCCGTGAAGATCTCCTGCAAGGCCTCCGGCTACACCTTCA
CCTCCAACTTCATGCACTGGATCAAGCAGCAGCCCGGCAACGGCCTGGA
ATGGATCGGATGGATCTATCCTGGCGACGGCGACACCGAGTACAACCAG
AAGTTCAACGGCAAGGCTACCCTGACCGCCGACAAGTCCTCTTCCACCG
CTTACATGCAGCTGTCCAGCCTGACCTCTGAGGACTCCGCCGTGTACTTC
TGCGCCGTGAATTATGGCGGCTACGTCTGGATGCTTGGGGCAAGGCG
CTTCTGTGACAGTGTCCTCTGCCGAGACAACCGCTCCTAGCGTTTACCCT
CTGGCTCCTGGCACAGCCCTGAAGTCCAACTCTATGGTCACCCTGGGCTG
CCTGGTCAAGGGCTACTTTCCTGAGCCTGTGACCGTGACCTGGAACTCTG
GTGCTCTGTCTAGCGGCGTGCACACCTTTCCAGCTGTGCTGCAGAGCGGC
CTGTACACCCTGACATCTAGCGTGACCGTGCCTTCCAGCACCTGGTCTAG
TCAGGCTGTGACCTGCAACGTGGCCCATCCTGCCTCTTCTACCAAGGTGG
ACAAGAAAATCGTGCCCAGAGAGTGCAACACCATCAAGCCCTGTCCTCC
ATGCAAGTGCCCCGCTCCTAATCTGCTCGGAGGCCCTTCCGTGTTCATCT
TCCCACCTAAGATCAAGGACGTGCTGATGATCTCCCTGTCTCCTATCGTG
ACCTGCGTGGTGGTGGACGTGTCCGAGGATGATCCTGACGTGCAGATCA
GTTGGTTCGTGAACAACGTGGAAGTGCACACCGCTCAGACCCAGACACA
CAGAGAGGACTACAACAGCACCCTGAGAGTGGTGTCTGCCCTGCCAATC
CAGCACCAGGATTGGATGTCCGGCAAAGAATTCAAGTGCAAAGTGAACA
ACAAGGACCTGCCTGCTCCAATCGAGCGGACCATCTCTAAGCCTAAGGG
CTCTGTGCGGGCTCCCCAAGTTTGTGTTCTGCCTCCACCTGAGGAAGAGA
TGACCAAGAAACAAGTGACCCTGTCTTGTGCCGTGACCGACTTCATGCCC
GAGGACATCTACGTGGAATGGACCAACAATGGCAAGACCGAGCTGAACT
ACAAGAACACCGAGCCTGTGCTGGACTCCGACGGCTCCTACTTCATGGT
GTCTAAGCTGCGCGTCGAGAAGAAGAACTGGGTCGAGAGAAACTCCTAC
TCCTGCTCCGTGGTGCACGAGGGCCTGCACAATCACCACACCACCAAGT
CCTTCTCTCGGACCCCTGGCAAGTGATGA

SEQ ID NO: 31   ATGGAAACCGACACACTGCTGCTGTGGGTGCTGCTCTTGTGGGTGCCAG
GATCTACAGGCGAGATCGTGCTGACCCAGTCTCCTACCACCATGGCTGCT
AGCCCTGGCGAGAAAGTGACAATTACCTGCCGGGCCTCCTCCTCCACCA
ACTACATGTCCTGGTATCAGCAGAAGTCCGGCGCCTCTCCTAAGCCTTGG
ATCTACGAGACATCCAAGCTGGCCTCTGGCGTGCCCGATAGATTTTCCGG
CTCTGGCTCCGGCACCTCCTACAGCTTCACCATCTCCAGCATGGAAACAG
AGGACGCCGCCACCTACTACTGCCACCAGTGGTCATCTACCCCTCTGACC
TTTGGCAGCGGCACCAAGCTGGAAATCAAGAGAGCTGACGCCGCTCCTA
CCGTGTCTATCTTCCCTCCATCCATGGAACAGCTGACCTCCGGCGGAGCT
ACCGTCGTGTGTTTCGTGAACAACTTCTACCCTCGGGACATCTCCGTGAA
GTGGAAGATCGACGGCTCTGAGCAGCGAGATGGCGTGCTGGATTCTGTG
ACCGACCAGGACTCCAAGGACAGCACCTACTCCATGTCTAGCACCCTGA
GCCTGACCAAGGTGGAATACGAGCGGCACAACCTGTATACCTGCGAGGT
GGTGCACAAGACCTCCAGCTCTCCCGTGGTCAAGTCCTTCAACCGGAAC
GAGTGCTGATGA

SEQ ID NO: 32   ATGGAAACCGACACACTGCTGCTGTGGGTGCTGCTCTTGTGGGTGCCAG
GATCTACAGGCGAGGTGCAGCTGGTTGAATCTGGCGGAGGACTGGTTAA
GCCTGGCGGCTCTCTGAGACTGTCTTGTGCCGCTTCTGGCTTCACCTTCTC
CGCCTACGCCATGAACTGGGTCCGACAGGCTCCTGGCAAAGGCCTGGAA
TGGGTCGGAAGAATCCGGACCAAGAACAACAACTACGCCACCTACTACG
CCGACTCCGTGAAGGACCGGTTCACCATCTCTCGGGACGACTCCAAGAA
CACCCTGTACCTGCAGATGAACTCCCTGAAAACCGAGGACACCGCCGTG
TACTACTGCACCACCTTCTACGGCAATGGCGTGTGGGGACAGGGCACAC
TGGTTACCGTTTCTTCCGCCTCCACCAAGGGACCCTCTGTGTTTCCTCTGG
CTCCCTCCAGCAAGTCTACCTCTGGTGGAACAGCTGCCCTGGGCTGCCTG
GTCAAGGATTACTTTCCTGAGCCTGTGACCGTGTCCTGGAACTCTGGCGC
TCTGACATCTGGCGTGCACACCTTTCCAGCTGTGCTGCAGTCCTCTGGCC
TGTACTCTCTGTCCTCCGTCGTGACCGTGCCTTCTAGCTCTCTGGGCACCC
AGACCTACATCTGCAATGTGAACCACAAGCCTTCCAACACCAAGGTGGA
CAAGAGAGTGGAACCCAAGTCCTGCGACAAGACCCACACCTGTCCTCCA
TGTCCTGCTCCAGAACTGCTCGGCGGACCTTCGTGTTCCTGTTTCCTCCA
AAGCCTAAGGACACCCTGATGATCTCTCGGACCCCTGAAGTGACCTGCG
TGGTGGTGGATGTGTCTCACGAGGATCCCGAAGTGAAGTTCAATTGGTA
CGTGGACGGCGTGGAAGTGCACAACGCCAAGACCAAGCCTAGAGAGGA

TABLE 3-continued

Nucleic acid sequences of ORFs.

Nucleic Acid Sequence

ACAGTACAACTCCACCTACAGAGTGGTGTCCGTGCTGACCGTGCTGCACC
AGGATTGGCTGAACGGCAAAGAGTACAAGTGCAAGGTGTCCAACAAGG
CCCTGCCTGCTCCTATCGAAAAGACCATCTCCAAGGCCAAGGGCCAGCC
TAGGGAACCCCAGGTTTACACCCTGCCTCCATGCCGGGAAGAGATGACC
AAGAATCAGGTGTCCCTGTGGTGCCTCGTGAAGGGCTTCTACCCTTCCGA
TATCGCCGTGGAATGGGAGAGCAATGGCCAGCCTGAGAACAACTACAAG
ACAACCCCTCCTGTGCTGGACTCCGACGGCTCATTCTTCCTGTACTCCAA
GCTGACAGTGGACAAGTCCAGATGGCAGCAGGGCAACGTGTTCTCCTGC
TCCGTGATGCACGAGGCCCTGCACAATCACTACACCCAGAAGTCCCTGTC
TCTGTCCCCTGGCAAGTGATGA

SEQ ID NO: 33  ATGGAAACCGACACACTGCTGCTGTGGGTGCTGCTCTTGTGGGTGCCAG
GATCTACAGGCGACGTGGTCATGACACAGAGCCCTCTGTCTCTGCCCGTG
ACATTGGGACAGCCTGCCTCCATCTCCTGCAAGTCCTCTCAGTCCCTGCT
GGACTCTGACGGCAAGACCTTCCTGAACTGGTTCCAGCAGCGGCCTGGC
CAGTCTCCTAGAAGGCTGATCTACCTGGTGTCCAAGCTGGATTCTGGCGT
GCCCGACAGATTCTCCGGCTCTGGCTCTGGCACCGACTTCACCCTGAAGA
TCTCCAGAGTGGAAGCCGAGGACGTGGGCGTGTACTACTGTTGGCAGGG
CACCCACTTTCCATACACCTTCGGCCAGGGCACCAGACTGGAAATCAAG
AGAACCGTGGCCGCTCCTTCCGTGTTCATCTTCCCACCTTCCGACGAGCA
GCTGAAGTCCGGCACAGCTTCTGTCGTGTGCCTGCTGAACAACTTCTACC
CTCGGGAAGCCAAGGTGCAGTGGAAGGTGGACAATGCCCTGCAGTCCGG
CAACTCCCAAGAGTCTGTGACCGAGCAGGACTCCAAGGACAGCACCTAC
AGCCTGTCCAGCACACTGACCCTGTCCAAGGCCGACTACGAGAAGCACA
AGGTGTACGCCTGCGAAGTGACCCATCAGGGCCTGTCTAGCCCTGTGAC
CAAGTCTTTCAACCGGGGCGAGTGCTGATGA

SEQ ID NO: 34  ATGGAAACCGACACACTGCTGCTGTGGGTGCTGCTCTTGTGGGTGCCAG
GATCTACAGGCGAAGTGCAGCTGGTTCAGTCTGGCGCCGAAGTGAAGAA
ACCTGGCGCCTCTGTGAAGGTGTCCTGCAAGGCTTCTGGCTACACCTTTA
CCGGCTACCACATGCACTGGGTCCGACAGGCTCCAGGACAAGGCTTGGA
ATGGATGGGCTGGATCAACCCCAACTCCGGCGTGACCAAATACGCCCAG
AAATTCCAGGGCAGAGTGACCATGACCAGAGACACCTCCATCAACACCG
CCTACATGGAACTGTCCCGGCTGAGATTCGACGACACCGACGTGTACTA
CTGTGCCACCGGCGGCTTTGGCTATTGGGGAGAGGGAACACTGGTCACC
GTGTCCTCCGCTTCTACCAAGGGACCCTCCGTGTTTCCTCTGGCTCCTTCC
AGCAAGTCTACCTCCGGTGGAACAGCTGCTCTGGGCTGCCTGGTCAAGG
ACTACTTTCCTGAGCCTGTGACCGTGTCTTGGAACTCTGGCGCTCTGACA
TCCGGCGTGCACACCTTTCCAGCTGTGCTGCAATCCTCCGGCCTGTACTC
TCTGTCCTCCGTCGTGACCGTGCCTTCTAGCTCTCTGGGCACCCAGACCT
ACATCTGCAATGTGAACCACAAGCCTTCCAACACCAAGGTGGACAAGAG
AGTGGAACCCAAGTCCTGCGACAAGACCCACACCTGTCCTCCATGTCCTG
CTCCAGAACTGCTCGGCGGACCTTCTGTGTTCCTGTTTCCTCCAAAGCCT
AAGGACACCCTGATGATCTCTCGGACCCCTGAAGTGACCTGCGTGGTGG
TGGATGTGTCTCACGAGGACCCAGAAGTGAAGTTCAATTGGTACGTGGA
CGGCGTGGAAGTGCACAACGCCAAGACCAAGCCTAGAGAGGAACAGTA
CAACTCCACCTACAGAGTGGTGTCCGTGCTGACCGTGCTGCACCAGGATT
GGCTGAACGGCAAAGAGTACAAGTGCAAGGTGTCCAACAAGGCCCTGCC
TGCTCCTATCGAAAAGACCATCTCCAAGGCCAAGGGCCAGCCTAGGGAA
CCCCAGGTTTACACCCTGCCTCCATGCCGGGAAGAGATGACCAAGAACC
AGGTGTCCCTGTGGTGCCTCGTGAAGGGCTTCTACCCTTCCGATATCGCC
GTGGAATGGGAGAGCAATGGCCAGCCTGAGAACAACTACAAGACAACC
CCTCCTGTGCTGGACTCCGACGGCTCATTCTTCCTGTACTCCAAGCTGAC
AGTGGACAAGTCCAGATGGCAGCAGGGCAACGTGTTCTCCTGCTCCGTG
ATGCACGAGGCCCTGCACAATCACTACACACAGAAGTCCCTGTCTCTGTC
CCCTGGCAAGTGATGA

SEQ ID NO: 35  ATGGAAACCGACACACTGCTGCTGTGGGTGCTGCTCTTGTGGGTGCCAG
GATCTACAGGACTGCCCGTGTTGACCCAGCCTCCTAGCGTTTCCAAGGGC
CTGAGACAGACCGCCACACTGACCTGTACCGGCAACTCTAACAACGTGG
GCAATCAGGGCGCTGCCTGGTTGCAGCAGCATCAGGGACAGCCTCCAAA
GCTGCTGTCCTACCGGAACCACAACAGACCTAGCGGCGTGTCCGAGCGG
TTCAGCCCCTTCTAGATCTGGCGACACCTCCAGCCTGACCATCACTGGACT
GCAGCCTGAGGACGAGGCCGACTACTATTGTCTGGCCTGGGACAGCTCC
CTGCGGGCCTTTGTTTTTGGCACCGGCACCAAGCTGACCGTGCTGGGACA
ACCTAAGGCCAATCCTACCGTGACACTGTTCCCTCCATCCTCCGAGGAAC
TGCAGGCCAACAAGGCTACCCTCGTGTGCCTGATCTCCGACTTTTACCCT
GGCGCTGTGACCGTGGCCTGGAAGGCTGATGGATCTCCTGTGAAGGCTG
GCGTGGAAACCACCAAGCCTTCCAAGCAGTCCAACAACAAATACGCCGC
CTCCTCCTACCTGTCTCTGACCCCTGAACAGTGGAAGTCCCACCGGTCCT
ACAGCTGCCAAGTGACCCATGAGGGCTCCACCGTGGAAAAGACCGTGGC
TCCTACCGAGTGCTCCTGATGA

SEQ ID NO: 36  ATGGAAACCGACACACTGCTGCTGTGGGTGCTGCTCTTGTGGGTGCCAG
GATCTACAGGACAGGTGCAGCTGGTTCAGTCTGGCGCCGAAGTGAAGAA
ACCTGGCGCCTCTGTGAAGGTGTCCTGCAAGGCTTCCGGCTACACCTTCT

TABLE 3-continued

Nucleic acid sequences of ORFs.

Nucleic Acid Sequence

```
CCAGCTACTACATGCACTGGGTCCGACAGGCCCCTGGACAAGGATTGGA
GTGGATGGGCATCATCAACCCCTCTGGCGGCAACACCTCTTACGCCCAG
AAATTCCAGGGCAGAGTGACCATGACCAGAGACACCTCCACCAGCACCG
TGTACATGGAACTGTCCAGCCTGAGATCCGAGGACACCGCCGTGTACTA
CTGTGCCAGAGGCGGATACCAGCTGCCTCACGGTAGAGCCAGAGCCTTC
GATATGTGGGGCCAGGGCACAATGGTCACCGTGTCCTCTGCTTCCACCAA
GGGACCCTCTGTGTTCCCTCTGGCTCCTTCCAGCAAGTCCACATCCGGTG
GAACAGCTGCTCTGGGCTGCCTGGTCAAGGACTACTTTCCTGAGCCTGTG
ACCGTGTCTTGGAACTCTGGCGCTCTGACATCCGGCGTGCACACATTTCC
AGCTGTGCTGCAGTCCTCCGGCCTGTACTCTCTGTCCTCTGTCGTGACCGT
GCCTTCCAGCTCTCTGGGAACCCAGACCTACATCTGCAATGTGAACCACA
AGCCTTCCAACACCAAGGTGGACAAGAGAGTGGAACCCAAGTCCTGCGA
CAAGACCCACACCTGTCCACCATGTCCTGCTCCAGAACTGCTCGGCGGAC
CTTCCGTGTTCCTGTTTCCTCCAAAGCCTAAGGACACCCTGATGATCTCTC
GGACCCCTGAAGTGACCTGCGTGGTGGTGGATGTGTCCCACGAGGACCC
AGAAGTGAAGTTCAATTGGTACGTGGACGGCGTGGAAGTGCACAACGCC
AAGACCAAGCCTAGAGAGGAACAGTACAACTCCACCTACAGAGTGGTGT
CCGTGCTGACCGTGCTGCACCAGGATTGGCTGAACGGCAAAGAGTACAA
GTGCAAGGTGTCCAACAAGGCCCTGCCTGCTCCTATCGAAAAGACCATC
TCCAAGGCCAAGGGCCAGCCTAGGGAACCCCAGGTTTACACCCTGCCTC
CATGCCGGGAAGAGATGACCAAGAACCAGGTGTCCCTGTGGTGCCTCGT
GAAGGGCTTCTACCCTTCCGATATCGCCGTGGAATGGGAGAGCAATGGC
CAGCCAGAGAACAACTACAAGACAACCCCTCCTGTGCTGGACTCCGACG
GCTCATTCTTCCTGTACTCCAAGCTGACAGTGGACAAGTCCAGATGGCAG
CAGGGCAACGTGTTCTCCTGCTCCGTGATGCACGAGGCCCTGCACAATCA
CTACACACAGAAGTCCCTGTCTCTGTCCCCTGGCAAGTGATGA
```

SEQ ID NO: 37
```
ATGGAAACCGACACACTGCTGCTGTGGGTGCTGCTCTTGTGGGTGCCAG
GATCTACCGGCGCCATCAGAATGACCCAGTCTCCACTGAGCCTGCCTGTG
ACATTGGGCCAGCCTGCCTCTATCTCCTGCACCTCCTCTCAGTCTCTGGTG
TACAGAGATGGCACCCACCTACCTGAACTGGTTCCAGCAGAGGCCTGGCC
AGTCTCCTAGACGGCTGATCTACAAGGTGTCCAACAGAGACTCTGGCGT
GCCCGACAGATTCACCGGCTCTGGCTCTGGCACCACATTCACCCTGACCA
TCTCCAGAGTGGAAGCCGAGGACGTGGGCATCTACTACTGTATGCAGGG
CACCCACTGGCCTCTGACCTTTGGCCAGGGAACAAAGGTGGAAATCAAG
CGGACCGTGGCCGCTCCTTCCGTGTTCATCTTCCCACCTTCCGACGAGCA
GCTGAAGTCTGGCACAGCCTCTGTCGTGTGCCTGCTGAACAACTTCTACC
CTCGGGAAGCCAAGGTGCAGTGGAAGGTGGACAATGCCCTGCAGTCCGG
CAACTCCCAAGAGTCTGTGACCGAGCAGGACTCCAAGGACAGCACCTAC
AGCCTGTCCTCCACACTGACCCTGTCCAAGGCCGACTACGAGAAGCACA
AGGTGTACGCCTGCGAAGTGACCCATCAGGGCCTGTCTAGCCCTGTGAC
CAAGTCTTTCAACCGGGGCGAGTGCTGATGA
```

SEQ ID NO: 38
```
ATGGAAACCGACACACTGCTGCTGTGGGTGCTGCTCTTGTGGGTGCCAG
GATCTACAGGCGAGGTGCAGCTGGTTGAATCTGGCGGAGGATTGGTTCA
GCCTGGCGGCTCTCTGAGACTGTCTTTGTGTGGCCTCTGGCTTCACCTTCTC
CGACTACTGGATGTCCTGGGTCCGACAGGCTCCTGGCAAAGGACTGGAA
TGGGTCGCCAACATCAAGAAAGACGGCTCCGTGAACTACTACGTGGACT
CCGTGAAGGGCAGATTCACCATCTCTCGGGACAACGCCAAGAACTCCCT
GTACCTGCAGATGAACAGCCTGAGAGCCGAGGACACCGCCGTGTACTAC
TGCACCAGATTCGATTACTGGGGCCAGGGCACCCTGGTCACAGTGTCCTC
TGCTTCTACCAAGGGACCCAGCGTGTTCCCTCTGGCTCCTTCCAGCAAGT
CTACCTCTGGCGGAACAGCTGCTCTGGGCTGCCTGGTCAAGGACTACTTT
CCTGAGCCTGTGACCGTGTCCTGGAACTCTGGCGCTCTGACATCTGGCGT
GCACACCTTTCCAGCTGTGCTGCAGTCCTCCGGCCTGTACTCTCTGTCCTC
TGTCGTGACCGTGCCTTCCAGCTCTCTGGGAACCCAGACCTACATCTGCA
ATGTGAACCACAAGCCTTCCAACACCAAGGTGGACAAGAGAGTGGAACC
CAAGTCCTGCGACAAGACCCACACCTGTCCTCCATGTCCTGCTCCAGAAC
TGCTCGGCGGACCTTCCGTGTTCCTGTTTCCTCCAAAGCCTAAGGACACC
CTGATGATCTCTCGGACCCCTGAAGTGACCTGCGTGGTGGTGGATGTGTC
TCACGAGGATCCCGAAGTGAAGTTCAATTGGTACGTGGACGGCGTGGAA
GTGCACAATGCCAAGACCAAGCCTAGAGAGGAACAGTACAACTCCACCT
ACAGAGTGGTGTCCGTGCTGACCGTGCTGCACCAGGATTGGCTGAACGG
CAAAGAGTACAAGTGCAAGGTGTCCAACAAGGCCCTGCCTGCTCCTATC
GAAAAGACCATCTCCAAGGCCAAGGGCCAGCCTAGGGAACCCCAGGTTT
ACACCCTGCCTCCATGCCGGGAAGAGATGACCAAGAACCAGGTGTCCCT
GTGGTGCCTGGTTAAGGGCTTCTACCCTTCCGATATCGCCGTGGAATGGG
AGTCTAATGGCCAGCCAGAGAACAACTACAAGACAACCCCTCCTGTGCT
GGACTCCGACGGCTCATTCTTCCTGTACTCCAAGCTGACAGTGGACAAGT
CCAGATGGCAGCAGGGCAACGTGTTCTCCTGCTCCGTGATGCACGAGGC
CCTGCACAATCACTACACCCAGAAGTCCCTGTCTCTGTCCCCTGGCAAGT
GATGA
```

SEQ ID NO: 39
```
ATGGAAACCGACACACTGCTGCTGTGGGTGCTGCTCTTGTGGGTGCCAG
GATCTACAGGACAGGCTGGCTTGACCCAGCCTCCTAGCGTTTCCAAGGG
CCTGAGACAGACCGCCACACTGACCTGTACCGGCAACTCTAACAACGTG
```

TABLE 3-continued

Nucleic acid sequences of ORFs.

Nucleic Acid Sequence

GGCAATCAGGGCGCTGCCTGGTTGCAGCAGCATCAGGGACATCCTCCAA
AGCTGCTGTTCTACCGGAACAACAACAGAGCCTCCGGCATCTCCGAGCG
GCTGTCTGCTTCTAGATCCGGCAATACCGCCAGCCTGACCATCACTGGAC
TGCAGCCTGAGGACGAGGCCGACTACTATTGCCTGACCTGGGACTCCTCT
CTGTCCGTGGTGGTTTTTGGCGGAGGCACCAAGCTGACAGTGCTGGGAC
AGCCTAAGGCCAATCCTACCGTGACACTGTTCCCTCCATCCTCCGAGGAA
CTGCAGGCCAACAAGGCTACCCTCGTGTGCCTGATCTCCGACTTTTACCC
TGGCGCTGTGACCGTGGCCTGGAAGGCTGATGGATCTCCTGTGAAGGCT
GGGCGTGGAAACCACCAAGCCTTCCAAGCAGTCCAACAACAAATACGCCG
CCTCCTCCTACCTGTCTCTGACCCCTGAACAGTGGAAGTCCCACCGGTCC
TACAGCTGCCAAGTGACCCATGAGGGCTCCACCGTGGAAAAGACCGTGG
CTCCTACCGAGTGCTCCTGATGA

SEQ ID NO: 40    ATGGAAACCGACACACTGCTGCTGTGGGTGCTGCTCTTGTGGGTGCCAG
GATCTACAGGACAGGTGCAGCTGGTTCAGTCTGGCGCCGAAGTGAAGAA
ACCTGGCGCCTCTGTGAAGGTGTCCTGCAAGGCTTCCGGCTACACCTTTA
CCAGCTACGACATCTCCTGGGTCCGACAGGCTCCTGGACAAGGCTTGGA
ATGGATGGGCGTGATCTGGACCGATGGCGGCACCAATTACGCCCAGAAA
CTGCAGGGCAGAGTGACCATGACCACCGACACCTCTACCTCCACCGCCT
ACATGGAACTGCGGTCCCTGAGATCTGACGACACCGCCGTGTACTACTG
CGCCAGAGATCAGCGGCTGTACTTCGATGTGTGGGGCCAGGGCACAACC
GTGACAGTGTCCTCTGCTTCCACCAAGGGACCCAGCGTTTTCCCTCTGGC
TCCATCCTCCAAGTCTACCTCTGGCGGAACAGCTGCTCTGGGCTGCCTGG
TCAAGGACTACTTTCCTGAGCCTGTGACCGTGTCCTGGAACTCTGGCGCT
CTGACATCTGGCGTGCACACATTCCCTGCTGTGCTGCAGTCCTCCGGCCT
GTACTCTCTGTCCTCTGTGGTTACCGTGCCTTCCTCTAGCCTGGGCACCCA
GACCTACATCTGCAATGTGAACCACAAGCCTTCCAACACCAAGGTGGAC
AAGAGAGTGGAACCCAAGTCCTGCGACAAGACCCACACCTGTCCACCAT
GTCCTGCTCCAGAACTGCTCGGCGGACCTTCCGTGTTCCTGTTTCCTCCA
AAGCCTAAGGACACCCTGATGATCTCTCGGACCCCTGAAGTGACCTGCG
TGGTGGTGGATGTGTCTCACGAGGACCCAGAAGTGAAGTTCAATTGGTA
CGTGGACGGCGTGGAAGTGCACAACGCCAAGACCAAGCCTAGAGAGGA
ACAGTACAACTCCACCTACAGAGTGGTGTCCGTGCTGACCGTGCTGCACC
AGGATTGGCTGAACGGCAAAGAGTACAAGTGCAAGGTGTCCAACAAGG
CCCTGCCTGCTCCTATCGAAAAGACCATCTCCAAGGCCAAGGGCCAGCC
TCGGGAACCTCAAGTCTGTACCCTGCCTCCTAGCCGGGAAGAGATGACC
AAGAACCAGGTGTCCCTGAGCTGCGCCGTGAAGGGCTTCTACCCTTCTGA
TATCGCCGTGGAATGGGAGAGCAACGGCCAGCCTGAGAACAACTACAAG
ACAACCCCTCCTGTGCTGGACTCCGACGGCTCATTCTTCCTGGTGTCCAA
GCTGACAGTGGACAAGTCCAGATGGCAGCAGGGCAACGTGTTCTCCTGC
TCCGTGATGCACGAGGCCCTGCACAATCACTACACACAGAAGTCCCTGT
CTCTGTCCCCTGGCAAGTGATGA

SEQ ID NO: 41    ATGGAAACCGACACACTGCTGCTGTGGGTGCTGCTCTTGTGGGTGCCAG
GATCTACCGGCGACATCCAGATGACCCAGTCTCCATCCTCTCTGTCCGCC
TCTGTGGGCGACAGAGTGACCATCACCTGTAGAGCCTCCGAGGACGTGA
ACACCTACGTGTCCTGGTATCAGCAGAAGCCCGGCAAGGCTCCCAAGCT
GCTGATCTACGCCGCCTCTAACAGATACACCGGCGTGCCCTCTAGATTCT
CCGGCTCTGGCTCTGGCACCGACTTTACCCTGACAATCTCCAGCCTGCAG
CCTGAGGACTTCGCCACCTACTACTGCCAGCAGTCCTTCAGCTACCCCAC
CTTTGGCCAGGGCACCAAGCTGGAAATCAAGCGGACAGTGGCCGCTCCT
TCCGTGTTCATCTTCCCACCTTCCGACGAGCAGCTGAAGTCCGGCACAGC
TTCTGTCGTGTGCCTGCTGAACAACTTCTACCCTCGGGAAGCCAAGGTGC
AGTGGAAGGTGGACAATGCCCTGCAGTCCGGCAACTCCCAAGAGTCTGT
GACCGAGCAGGACTCCAAGGACAGCACCTACAGCCTGTCCTCCACACTG
ACCCTGTCCAAGGCCGACTACGAGAAGCACAAGGTGTACGCCTGCGAAG
TGACCCATCAGGGCCTGTCTAGCCCTGTGACCAAGTCTTTCAACCGGGGC
GAGTGCTGATGA

SEQ ID NO: 42    ATGGAAACCGACACACTGCTGCTGTGGGTGCTGCTCTTGTGGGTGCCAG
GATCTACAGGACAGGTGCAGCTGGTTCAGTCTGGCGCCGAAGTGAAGAA
ACCTGGCTCCTCCGTGAAGGTGTCCTGCAAGGCTTCTGGCTACACCTTTA
CCGACAACTACATGATCTGGGTCCGACAGGCTCCTGGACAGGGACTTGA
GTGGATGGGCGACATCAACCCTTACAACGGCGGCACCACCTTCAACCAG
AAATTCAAGGGCAGAGTGACCATCACCGCCGACAAGTCTACCTCCACCG
CCTACATGGAACTGTCCAGCCTGAGATCTGAGGACACCGCCGTGTACTA
CTGCGCCAGAGAGTCCCCTTACTTCTCCAACCTGTACGTGATGGACTACT
GGGGCCAGGGCACACTGGTCACAGTGTCCTCTGCTTCCACCAAGGGACC
CAGCGTTTTCCCTCTGGCTCCATCCTCCAAGTCCACCTCTGGTGGAACAG
CTGCTCTGGGCTGCCTGGTCAAGGACTACTTTCCTGAGCCTGTGACCGTG
TCCTGGAACTCTGGCGCTCTGACATCTGGCGTGCACACCTTCCAGCTGT
GCTGCAGTCCTCCGGCCTGTACTCTCTGTCCTCTGTCGTGACCGTGCCTTC
CAGCTCTCTGGGAACCCAGACCTACATCTGCAATGTGAACCACAAGCCTT
CCAACACCAAGGTCGACAAGAGAGTGGAACCCAAGTCCTGCGACAAGA
CCCACACCTGTCCACCTTGTCCTGCTCCAGAACTGCTCGGCGGACCTTCC
GTGTTCCTGTTTCCTCCAAAGCCTAAGGACACCCTGATGATCTCTCGGAC

TABLE 3-continued

Nucleic acid sequences of ORFs.

| | Nucleic Acid Sequence |
|---|---|
| | CCCTGAAGTGACCTGCGTGGTGGTGGATGTGTCTCACGAGGACCCAGAA<br>GTGAAGTTCAATTGGTACGTGGACGGCGTGGAAGTGCACAACGCCAAGA<br>CCAAGCCTAGAGAGGAACAGTACAACTCCACCTACAGAGTGGTGTCCGT<br>GCTGACCGTGCTGCACCAGGATTGGCTGAACGGCAAAGAGTACAAGTGC<br>AAGGTGTCCAACAAGGCCCTGCCTGCTCCTATCGAAAAGACCATCTCCA<br>AGGCCAAGGGCCAGCCTCGGGAACCTCAAGTCTGTACCCTGCCTCCTAG<br>CCGGGAAGAGATGACCAAGAACCAGGTGTCCCTGAGCTGCGCCGTGAAG<br>GGCTTCTACCCTTCTGATATCGCCGTGGAATGGGAGAGCAACGGCCAGC<br>CAGAGAACAACTACAAGACAACCCCTCCTGTGCTGGACTCCGACGGCTC<br>ATTCTTCCTGGTGTCCAAGCTGACAGTGGACAAGTCCAGATGGCAGCAG<br>GGCAACGTGTTCTCCTGCTCCGTGATGCACGAGGCCCTGCACAATCACTA<br>CACACAGAAGTCTCTGTCTCTGAGCCCCGGCAAGTGATGA |
| SEQ ID NO: 43 | ATGGAAACCGACACACTGCTGCTGTGGGTGCTGCTCTTGTGGGTGCCAG<br>GATCTACAGGCGAGATCGTGCTGACCCAGTCTCCTGCCACACTGTCACTG<br>TCTCCAGGCGAGAGAGCTACCCTGTCCTGCAAGGCTTCTCAGTCCGTGGA<br>CTACGACGGCGACAACTACATGAACTGGTATCAGCAGAAGCCCGGCCAG<br>GCTCCTAGACTGCTGATCTACGCCGCCTCCAACCTGGAATCTGGCATCCC<br>CGCTAGATTCTCCGGCTCTGGCTCTGGCACAGACTTTACCCTGACCATCT<br>CCAGCCTGGAACCTGAGGACTTCGCCGTGTACTACTGCCACCTGTCCAAC<br>GAGGACCTGTCCACATTTGGCGGAGGCACCAAGGTGGAAATCAAGCGGA<br>CAGTGGCCGCTCCTTCCGTGTTCATCTTCCCACCTTCCGACGAGCAGCTG<br>AAGTCTGGCACCGCTTCTGTCGTGTGCCTGCTGAACAACTTCTACCCTCG<br>GGAAGCCAAGGTGCAGTGGAAGGTGGACAATGCCCTGCAGTCCGGCAAC<br>TCCCAAGAGTCTGTGACCGAGCAGGACTCCAAGGACAGCACCTACAGCC<br>TGTCCTCCACACTGACCCTGTCCAAGGCCGACTACGAGAAGCACAAGGT<br>GTACGCCTGCGAAGTGACCCATCAGGGCCTGTCTAGCCCTGTGACCAAG<br>TCTTTCAACCGGGGCGAGTGCTGATGA |

2. Expression and Purification.

The plasmids were co-transfected into either Expi293 cells (Life Technologies A14527) or ExpiCHO cells (Life Technologies A29127). Transfections were performed using 1 mg of total DNA for a multispecific construct with a 1:1 knob to hole heavy chain ratio and 3:2 light chain to heavy chain ratio. When biotinylation was required, 250 µg of BirA was added per liter in addition to the multispecific construct DNA. Transfection in Expi293 cells was done using linear 25,000 Da polyethylenimine (PEI, Polysciences Inc 23966) in a 3:1 ratio with the total DNA. The DNA and PEI were each added to 50 mL of OptiMem (Life Technologies 31985088) medium and sterile filtered. The DNA and PEI were combined for 10 minutes and added to the Expi293 cells with a cell density of 1.8-2.8×10⁶ cells/mL and a viability of at least 95%. The ExpiCHO transfection was performed according to the manufacturer's instructions. Expi293 cells were grown in a humidified incubator at 37° C. with 8% $CO_2$ for 5-7 days after transfection and ExpiCHO cells were grown for 14 days at 32° C. with 5% $CO_2$. The cells were pelleted by centrifugation at 4500×g and the supernatant was filtered through a 0.2 µm membrane. Protein A resin (GE 17-1279-03) was added to the filtered supernatant and incubated for 1-3 hours at room temperature. The resin was packed into a column, washed with 3×10 column volumes of Dulbecco's phosphate-buffered saline (DPBS, Life Technologies 14190-144). The bound protein was eluted from the column with 20 mM citrate, 100 mM NaCl, pH 2.9. When necessary, the proteins were further purified using ligand affinity and/or size exclusion chromatography on a Superdex 200 column with a running buffer of DPBS.

TABLE 4

Amino Acid Sequences.

| SEQ ID NO | Description | Amino Acid Sequence |
|---|---|---|
| SEQ ID NO: 44 | αCCR2 MC12 VH | QVQLQESGPGLVQPSQTLSLTCTVSGFSLTDFSVHWVRQPP<br>GKGLEWMGRIRSEGNTDYNSALKSRLSISRDTSKSQVFLKM<br>NSLQTEDTAIYFCTRGDILGFGYWGQGVMVTVSS |
| SEQ ID NO: 45 | αCCR2 MC12 VL | DIVMTQSPLSVSVTPGESASISCRSSKSLLHFKGITFVYWYLQ<br>KPGQSPQLLIFRMSSLASGVPDRFSGSGSETDFTLKISRVEAE<br>DVGTYYCGQLLENPYTFGAGTKLELK |
| SEQ ID NO: 46 | R2b CH1 | AQTTAPSVYPLAPGCGDTTSSTVTLGCLVKGYFPEPVTVTW<br>NSGALSSDVHTFPAVLQSGLYTLSSVTSSTWPSQTVTCNV<br>AHPASSTKVDKKVERR |
| SEQ ID NO: 47 | R2b CL | RADAAPTVSIFPPSMEQLTSGGATVVCFVNNFYPRDISVKW<br>KIDGSEQRDGVLDSVTDQDSKDSTYSMSSTLSLTKVEYERH<br>NLYTCEVVHKTSSSPVVKSFNRNEC |
| SEQ ID NO: 48 | αmCSF1R VH | QVQLQQSGAELVKPGSSVKISCKASGYTFTSNFMHWIKQQP<br>GNGLEWIGWIYPGDGDTEYNQKFNGKATLTADKSSSTAYM<br>QLSSLTSEDSAVYFCAVNYGGYVLDAWGQGASVTVSS |

TABLE 4-continued

Amino Acid Sequences.

| SEQ ID NO | Description | Amino Acid Sequence |
|---|---|---|
| SEQ ID NO: 49 | R2a CH1 | AETTAPSVYPLAPGTALKSNSMVTLGCLVKGYFPEPVTVTW NSGALSSGVHTFPAVLQSGLYTLTSSVTVPSSTWSSQAVTC NVAHPASSTKVDKKIVPRECN |
| SEQ ID NO: 50 | αmCSF1R VL | EIVLTQSPTTMAASPGEKVTITCRASSSTNYMSWYQQKSGA SPKPWIYETSKLASGVPDRFSGSGSGTSYSFTISSMETEDAAT YYCHQWSSTPLTFGSGTKLEIK |
| SEQ ID NO: 51 | R2a CL | RADAAPTVSIFPPSMEQLTSGGATVVCFVNNFYPRDISVKW KIDGSEQRDGVLDSVTDQDSKDSTYSMSSTLSLTKVEYERH NLYTCEVVHKTSSSPVVKSFNRNEC |
| SEQ ID NO: 52 | mFc Knob | TIKPCPPCKCPAPNLLGGPSVFIFPPKIKDVLMISLSPIVTCVV VDVSEDDPDVQISWFVNNVEVHTAQTQTHREDYNSTLRVV SALPIQHQDWMSGKEFKCKVNNKDLPAPIERTISKPKGSVR APQVYVLPPCEEEMTKKQVTLWCMVTDFMPEDIYVEWTN NGKTELNYKNTEPVLDSDGSYFMYSKLRVEKKNWVERNSY SCSVVHEGLHNHHTTKSFSRTPGK |
| SEQ ID NO: 53 | mFc Hole | TIKPCPPCKCPAPNLLGGPSVFIFPPKIKDVLMISLSPIVTCVV VDVSEDDPDVQISWFVNNVEVHTAQTQTHREDYNSTLRVV SALPIQHQDWMSGKEFKCKVNNKDLPAPIERTISKPKGSVR APQVCVLPPPEEEMTKKQVTLSCAVTDFMPEDIYVEWTNN GKTELNYKNTEPVLDSDGSYFMVSKLRVEKKNWVERNSYS CSVVHEGLHNHHTTKSFSRTPGK |
| SEQ ID NO: 54 | αhCCR2 plozalizumab VH | EVQLVESGGGLVKPGGSLRLSCAASGFTFSAYAMNWVRQA PGKGLEWVGRIRTKNNNYATYYADSVKDRFTISRDDSKNTL YLQMNSLKTEDTAVYYCTTFYGNGVWGQGTLVTVSS |
| SEQ ID NO: 55 | hCH1 | ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKRVEPKSC |
| SEQ ID NO: 56 | hFc Knob | DKTHTCPPCPAPELLGGPSVFLFPPKPKDTLMISRTPEVTCV VVDVSHEDPEVKFNWYVDGVEVHNAKTKPREEQYNSTYR VVSVLTVLHQDWLNGKEYKCKVSNKALPAPIEKTISKAKG QPREPQVYTLPPCREEMTKNQVSLWCLVKGFYPSDIAVEWE SNGQPENNYKTTPPVLDSDGSFFLYSKLTVDKSRWQQGNVF SCSVMHEALHNHYTQKSLSLSPGX, wherein X is K or absent |
| SEQ ID NO: 57 | αhCCR2 plozalizumab VL | DVVMTQSPLSLPVTLGQPASISCKSSQSLLDSDGKTFLNWFQ QRPGQSPRRLIYLVSKLDSGVPDRFSGSGSGTDFTLKISRVE AEDVGVYYCWQGTHFPYTFGQGTRLEIK |
| SEQ ID NO: 58 | hCL (kappa) | RTVAAPSVFIFPPSDEQLKSGTASVVCLLNNFYPREAKVQW KVDNALQSGNSQESVTEQDSKDSTYSLSSTLTLSKADYEKH KVYACEVTHQGLSSPVTKSFNRGEC |
| SEQ ID NO: 59 | αhCCR2 D1 VH | EVQLVQSGAEVKKPGASVKVSCKASGYTFTGYHMHWVRQ APGQGLEWMGWINPNSGVTKYAQKFQGRVTMTRDTSINTA YMELSRLRFDDTDVYYCATGGFGYWGEGTLVTVSS |
| SEQ ID NO: 60 | αhCCR2 D1 VL | LPVLTQPPSVSKGLRQTATLTCTGNSNNVGNQGAAWLQQH QGQPPKLLSYRNHNRPSGVSERFSPSRSGDTSSLTITGLQPED EADYYCLAWDSSLRAFVFGTGTKLTVL |
| SEQ ID NO: 61 | hCL (lambda) | GQPKANPTVTLFPPSSEELQANKATLVCLISDFYPGAVTVA WKADGSPVKAGVETTKPSKQSNNKYAASSYLSLTPEQWKS HRSYSCQVTHEGSTVEKTVAPTECS |
| SEQ ID NO: 62 | αhCCR2 42G7 VH | QVQLVQSGAEVKKPGASVKVSCKASGYTFSSYYMHWVRQ APGQGLEWMGIINPSGGNTSYAQKFQGRVTMTRDTSTSTV YMELSSLRSEDTAVYYCARGGYQLPHGRARAFDMWGQGT MVTVSS |
| SEQ ID NO: 63 | αhCCR2 42G7 VL | AIRMTQSPLSLPVTLGQPASISCTSSQSLVYRDGTTYLNWFQ QRPGQSPRRLIYKVSNRDSGVPDRFTGSGSGTTFTLTISRVE AEDVGIYYCMQGTHWPLTFGQGTKVEIK |
| SEQ ID NO: 64 | αhCCR2 43G12 VH | EVQLVESGGGLVQPGGSLRLSCVASGFTFSDYWMSWVRQA PGKGLEWVANIKKDGSVNYYVDSVKGRFTISRDNAKNSLY LQMNSLRAEDTAVYYCTRFDYWGQGTLVTVSS |

TABLE 4-continued

Amino Acid Sequences.

| SEQ ID NO | Description | Amino Acid Sequence |
|---|---|---|
| SEQ ID NO: 65 | αhCCR2 43G12 VL | QAGLTQPPSVSKGLRQTATLTCTGNSNNVGNQGAAWLQQH QGHPPKLLFYRNNNRASGISERLSASRSGNTASLTITGLQPE DEADYYCLTWDSSLSVVVFGGGTKLTVL |
| SEQ ID NO: 66 | αhCSF1R emactuzumab VH | QVQLVQSGAEVKKPGASVKVSCKASGYTFTSYDISWVRQA PGQGLEWMGVIWTDGGTNYAQKLQGRVTMTTDTSTSTAY MELRSLRSDDTAVYYCARDQRLYFDVWGQGTTVTVSS |
| SEQ ID NO: 67 | αhCSF1R emactuzumab VL | DIQMTQSPSSLSASVGDRVTITCRASEDVNTYVSWYQQKPG KAPKLLIYAASNRYTGVPSRFSGSGSGTDFTLTISSLQPEDFA TYYCQQSFSYPTFGQGTKLEIK |
| SEQ ID NO: 68 | hFc Hole | DKTHTCPPCPAPELLGGPSVFLFPPKPKDTLMISRTPEVTCV VVDVSHEDPEVKFNWYVDGVEVHNAKTKPREEQYNSTYR VVSVLTVLHQDWLNGKEYKCKVSNKALPAPIEKTISKAKG QPREPQVCTLPPSREEMTKNQVSLSCAVKGFYPSDIAVEWE SNGQPENNYKTTPPVLDSDGSFFLVSKLTVDKSRWQQGNVF SCSVMHEALHNHYTQKSLSLSPGX, wherein X is K or absent |
| SEQ ID NO: 69 | αhCSF1R cabiralizumab VH | QVQLVQSGAEVKKPGSSVKVSCKASGYTFTDNYMIWVRQA PGQGLEWMGDINPYNGGTTFNQKFKGRVTITADKSTSTAY MELSSLRSEDTAVYYCARESPYFSNLYVMDYWGQGTLVTV SS |
| SEQ ID NO: 70 | αhCSF1R cabiralizumab VL | EIVLTQSPATLSLSPGERATLSCKASQSVDYDGDNYMNWYQ QKPGQAPRLLIYAASNLESGIPARFSGSGSGTDFTLTISSLEPE DFAVYYCHLSNEDLSTFGGGTKVEIK |

TABLE 5

Protein sequences for full heavy and light chains.

| Full length | Variable | Constant | Fc |
|---|---|---|---|
| SEQ ID NO: 71 | SEQ ID NO: 44 | SEQ ID NO: 46 | |
| SEQ ID NO: 72 | SEQ ID NO: 45 | SEQ ID NO: 47 | |
| SEQ ID NO: 73 | SEQ ID NO: 48 | SEQ ID NO: 49 | SEQ ID NO: 53 |
| SEQ ID NO: 74 | SEQ ID NO: 50 | SEQ ID NO: 51 | |
| SEQ ID NO: 75 | SEQ ID NO: 54 | SEQ ID NO: 55 | SEQ ID NO: 56 |
| SEQ ID NO: 76 | SEQ ID NO: 57 | SEQ ID NO: 58 | |
| SEQ ID NO: 77 | SEQ ID NO: 59 | SEQ ID NO: 55 | SEQ ID NO: 56 |
| SEQ ID NO: 78 | SEQ ID NO: 60 | SEQ ID NO: 61 | |
| SEQ ID NO: 79 | SEQ ID NO: 62 | SEQ ID NO: 55 | SEQ ID NO: 56 |
| SEQ ID NO: 80 | SEQ ID NO: 63 | SEQ ID NO: 58 | |
| SEQ ID NO: 81 | SEQ ID NO: 64 | SEQ ID NO: 55 | SEQ ID NO: 56 |
| SEQ ID NO: 82 | SEQ ID NO: 65 | SEQ ID NO: 58 | |
| SEQ ID NO: 83 | SEQ ID NO: 66 | SEQ ID NO: 55 | SEQ ID NO: 68 |
| SEQ ID NO: 84 | SEQ ID NO: 67 | SEQ ID NO: 58 | |
| SEQ ID NO: 85 | SEQ ID NO: 69 | SEQ ID NO: 55 | SEQ ID NO: 68 |
| SEQ ID NO: 86 | SEQ ID NO: 70 | SEQ ID NO: 58 | |

TABLE 6

Amino acid sequences of the chains used to construct multispecific molecules.

| SEQ ID NO | Amino Acid Sequence |
|---|---|
| SEQ ID NO: 71 | QVQLQESGPGLVQPSQTLSLTCTVSGFSLTDFSVHWVRQPPGKGLEWMGRI RSEGNTDYNSALKSRLSISRDTSKSQVFLKMNSLQTEDTAIYFCTRGDILGFG YWGQGVMVTVSSAQTTAPSVYPLAPGCGDTTSSTVTLGCLVKGYFPEPVTV TWNSGALSSDVHTFPAVLQSGLYTLTSSVTSSTWPSQTVTCNVAHPASSTKV DKKVERRTIKPCPPCKCPAPNLLGGPSVFIFPPKIKDVLMISLSPIVTCVVVDV SEDDPDVQISWFVNNVEVHTAQTQTHREDYNSTLRVVSALPIQHQDWMSG KEFKCKVNNKDLPAPIERTISKPKGSVRAPQVYVLPPCEEEMTKKQVTLWC MVTDFMPEDIYVEWTNNGKTELNYKNTEPVLDSDGSYFMYSKLRVEKKN WVERNSYSCSVVHEGLHNHHTTKSFSRTPGK |
| SEQ ID NO: 72 | DIVMTQSPLSVSVTPGESASISCRSSKSLLHFKGITFVYWYLQKPGQSPQLLIF RMSSLASGVPDRFSGSGSETDFTLKISRVEAEDVGTYYCGQLLENPYTFGAG TKLELKRADAAPTVSIFPPSMEQLTSGGATVVCFVNNFYPRDISVKWKIDGS EQRDGVLDSVTDQDSKDSTYSMSSTLSLTKVEYERHNLYTCEVVHKTSSSP VVKSFNRNEC |
| SEQ ID NO: 73 | QVQLQQSGAELVKPGSSVKISCKASGYTFTSNFMHWIKQQPGNGLEWIGWI YPGDGDTEYNQKFNGKATLTADKSSSTAYMQLSSLTSEDSAVYFCAVNYG GYVLDAWGQGSVTVSSAETTAPSVYPLAPGTALKSNSMVTLGCLVKGYF PEPVTVTWNSGALSSGVHTFPAVLQSGLYTLTSSVTVPSSTWSSQAVTCNVA HPASSTKVDKKIVPRECNTIKPCPPCKCPAPNLLGGPSVFIFPPKIKDVLMISLS |

TABLE 6-continued

Amino acid sequences of the chains used to construct multispecific molecules.

| SEQ ID NO | Amino Acid Sequence |
|---|---|
| | PIVTCVVVDVSEDDPDVQISWFVNNVEVHTAQTQTHREDYNSTLRVVSALPI<br>QHQDWMSGKEFKCKVNNKDLPAPIERTISKPKGSVRAPQVCVLPPPEEEMT<br>KKQVTLSCAVTDFMPEDIYVEWTNNGKTELNYKNTEPVLDSDGSYFMVSK<br>LRVEKKNWVERNSYSCSVVHEGLHNHHTTKSFSRTPGK |
| SEQ ID NO: 74 | EIVLTQSPTTMAASPGEKVTITCRASSSTNYMSWYQQKSGASPKPWIYETSK<br>LASGVPDRFSGSGSGTSYSFTISSMETEDAATYYCHQWSSTPLTFGSGTKLEI<br>KRADAAPTVSIFPPSMEQLTSGGATVVCFVNNFYPRDISVKWKIDGSEQRDG<br>VLDSVTDQDSKDSTYSMSSTLSLTKVEYERHNLYTCEVVHKTSSSPVVKSFN<br>RNEC |
| SEQ ID NO: 75 | EVQLVESGGGLVKPGGSLRLSCAASGFTFSAYAMNWVRQAPGKGLEWVGR<br>IRTKNNNYATYYADSVKDRFTISRDDSKNTLYLQMNSLKTEDTAVYYCTTF<br>YGNGVWGQGTLVTVSSASTKGPSVFPLAPSSKSTSGGTAALGCLVKDYFPE<br>PVTVSWNSGALTSGVHTFPAVLQSSGLYSLSSVVTVPSSSLGTQTYICNVNH<br>KPSNTKVDKRVEPKSCDKTHTCPPCPAPELLGGPSVFLFPPKPKDTLMISRTP<br>EVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPCREEM<br>TKNQVSLWCLVKGFYPSDIAVEWESNGQPENNYKTTPPVLDSDGSFFLYSK<br>LTVDKSRWQQGNVFSCSVMHEALHNHYTQKSLSLSPGX, wherein X is K or<br>absent |
| SEQ ID NO: 76 | DVVMTQSPLSLPVTLGQPASISCKSSQSLLDSDGKTFLNWFQQRPGQSPRRLI<br>YLVSKLDSGVPDRFSGSGSGTDFTLKISRVEAEDVGVYYCWQGTHFPYTFG<br>QGTRLEIKRTVAAPSVFIFPPSDEQLKSGTASVVCLLNNFYPREAKVQWKVD<br>NALQSGNSQESVTEQDSKDSTYSLSSTLTLSKADYEKHKVYACEVTHQGLS<br>SPVTKSFNRGEC |
| SEQ ID NO: 77 | EVQLVQSGAEVKKPGASVKVSCKASGYTFTGYHMHWVRQAPGQGLEWM<br>GWINPNSGVTKYAQKFQGRVTMTRDTSINTAYMELSRLRFDDTDVYYCAT<br>GGFGYWGEGTLVTVSSASTKGPSVFPLAPSSKSTSGGTAALGCLVKDYFPEP<br>VTVSWNSGALTSGVHTFPAVLQSSGLYSLSSVVTVPSSSLGTQTYICNVNHK<br>PSNTKVDKRVEPKSCDKTHTCPPCPAPELLGGPSVFLFPPKPKDTLMISRTPE<br>VTCVVVDVSHEDPEVKFNWYVDGVEVHNAKTKPREEQYNSTYRVVSVLTV<br>LHQDWLNGKEYKCKVSNKALPAPIEKTISKAKGQPREPQVYTLPPCREEMT<br>KNQVSLWCLVKGFYPSDIAVEWESNGQPENNYKTTPPVLDSDGSFFLYSKL<br>TVDKSRWQQGNVFSCSVMHEALHNHYTQKSLSLSPGX, wherein X is K or<br>absent |
| SEQ ID NO: 78 | LPVLTQPPSVSKGLRQTATLTCTGNSNNVGNQGAAWLQQHQGQPPKLLSYR<br>NHNRPSGVSERFSPSRSGDTSSLTITGLQPEDEADYYCLAWDSSLRAFVFGT<br>GTKLTVLGQPKANPTVTLFPPSSEELQANKATLVCLISDFYPGAVTVAWKA<br>DGSPVKAGVETTKPSKQSNNKYAASSYLSLTPEQWKSHRSYSCQVTHEGST<br>VEKTVAPTECS |
| SEQ ID NO: 79 | QVQLVQSGAEVKKPGASVKVSCKASGYTFSSYYMHWVRQAPGQGLEWMG<br>IINPSGGNTSYAQKFQGRVTMTRDTSTSTVYMELSSLRSEDTAVYYCARGG<br>YQLPHGRARAFDMWGQGTMVTVSSASTKGPSVFPLAPSSKSTSGGTAALGC<br>LVKDYFPEPVTVSWNSGALTSGVHTFPAVLQSSGLYSLSSVVTVPSSSLGTQ<br>TYICNVNHKPSNTKVDKRVEPKSCDKTHTCPPCPAPELLGGPSVFLFPPKPK<br>DTLMISRTPEVTCVVVDVSHEDPEVKFNWYVDGVEVHNAKTKPREEQYNS<br>TYRVVSVLTVLHQDWLNGKEYKCKVSNKALPAPIEKTISKAKGQPREPQVY<br>TLPPCREEMTKNQVSLWCLVKGFYPSDIAVEWESNGQPENNYKTTPPVLDS<br>DGSFFLYSKLTVDKSRWQQGNVFSCSVMHEALHNHYTQKSLSLSPGX,<br>wherein X is K or absent |
| SEQ ID NO: 80 | AIRMTQSPLSLPVTLGQPASISCTSSQSLVYRDGTTYLNWFQQRPGQSPRRLI<br>YKVSNRDSGVPDRFTGSGSGTTFTLTISRVEAEDVGIYYCMQGTHWPLTFGQ<br>GTKVEIKRTVAAPSVFIFPPSDEQLKSGTASVVCLLNNFYPREAKVQWKVDN<br>ALQSGNSQESVTEQDSKDSTYSLSSTLTLSKADYEKHKVYACEVTHQGLSSP<br>VTKSFNRGEC |
| SEQ ID NO: 81 | EVQLVESGGGLVQPGGSLRLSCVASGFTFSDYWMSWVRQAPGKGLEWVA<br>NIKKDGSVNYYVDSVKGRFTISRDNAKNSLYLQMNSLRAEDTAVYYCTRFD<br>YWGQGTLVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNT<br>KVDKRVEPKSCDKTHTCPPCPAPELLGGPSVFLFPPKPKDTLMISRTPEVTCV<br>VVDVSHEDPEVKFNWYVDGVEVHNAKTKPREEQYNSTYRVVSVLTVLHQ<br>DWLNGKEYKCKVSNKALPAPIEKTISKAKGQPREPQVYTLPPCREEMTKNQ<br>VSLWCLVKGFYPSDIAVEWESNGQPENNYKTTPPVLDSDGSFFLYSKLTVD<br>KSRWQQGNVFSCSVMHEALHNHYTQKSLSLSPGX, wherein X is K or absent |
| SEQ ID NO: 82 | QAGLTQPPSVSKGLRQTATLTCTGNSNNVGNQGAAWLQQHQGHPPKLLFY<br>RNNNRASGISERLSASRSGNTASLTITGLQPEDEADYYCLTWDSSLSVVVFG<br>GGTKLTVLGQPKANPTVTLFPPSSEELQANKATLVCLISDFYPGAVTVAWK |

TABLE 6-continued

Amino acid sequences of the chains used to construct multispecific molecules.

| SEQ ID NO | Amino Acid Sequence |
|---|---|
|  | ADGSPVKAGVETTKPSKQSNNKYAASSYLSLTPEQWKSHRSYSCQVTHEGS<br>TVEKTVAPTECS |
| SEQ ID NO: 83 | QVQLVQSGAEVKKPGASVKVSCKASGYTFTSYDISWVRQAPGQGLEWMGV<br>IWTDGGTNYAQKLQGRVTMTTDTSTSTAYMELRSLRSDDTAVYYCARDQR<br>LYFDVWGQGTTVTVSSASTKGPSVFPLAPSSKSTSGGTAALGCLVKDYFPEP<br>VTVSWNSGALTSGVHTFPAVLQSSGLYSLSSVVTVPSSSLGTQTYICNVNHK<br>PSNTKVDKRVEPKSCDKTHTCPPCPAPELLGGPSVFLFPPKPKDTLMISRTPE<br>VTCVVVDVSHEDPEVKFNWYVDGVEVHNAKTKPREEQYNSTYRVVSVLTV<br>LHQDWLNGKEYKCKVSNKALPAPIEKTISKAKGQPREPQVCTLPPSREEMT<br>KNQVSLSCAVKGFYPSDIAVEWESNGQPENNYKTTPPVLDSDGSFFLVSKLT<br>VDKSRWQQGNVFSCSVMHEALHNHYTQKSLSLSPGX, wherein X is K or<br>absent |
| SEQ ID NO: 84 | DIQMTQSPSSLSASVGDRVTITCRASEDVNTYVSWYQQKPGKAPKLLIYAAS<br>NRYTGVPSRFSGSGSGTDFTLTISSLQPEDFATYYCQQSFSYPTFGQGTKLEIK<br>RTVAAPSVFIFPPSDEQLKSGTASVVCLLNNFYPREAKVQWKVDNALQSGN<br>SQESVTEQDSKDSTYSLSSTLTLSKADYEKHKVYACEVTHQGLSSPVTKSFN<br>RGEC |
| SEQ ID NO: 85 | QVQLVQSGAEVKKPGSSVKVSCKASGYTFTDNYMIWVRQAPGQGLEWMG<br>DINPYNGGTTFNQKFKGRVTITADKSTSTAYMELSSLRSEDTAVYYCARESP<br>YFSNLYVMDYWGQGTLVTVSSASTKGPSVFPLAPSSKSTSGGTAALGCLVK<br>DYFPEPVTVSWNSGALTSGVHTFPAVLQSSGLYSLSSVVTVPSSSLGTQTYIC<br>NVNHKPSNTKVDKRVEPKSCDKTHTCPPCPAPELLGGPSVFLFPPKPKDTLM<br>ISRTPEVTCVVVDVSHEDPEVKFNWYVDGVEVHNAKTKPREEQYNSTYRV<br>VSVLTVLHQDWLNGKEYKCKVSNKALPAPIEKTISKAKGQPREPQVCTLPPS<br>REEMTKNQVSLSCAVKGFYPSDIAVEWESNGQPENNYKTTPPVLDSDGSFFL<br>VSKLTVDKSRWQQGNVFSCSVMHEALHNHYTQKSLSLSPGX, wherein X is<br>K or absent |
| SEQ ID NO: 86 | EIVLTQSPATLSLSPGERATLSCKASQSVDYDGDNYMNWYQQKPGQAPRLL<br>IYAASNLESGIPARFSGSGSGTDPTLTISSLEPEDFAVYYCHLSNEDLSTFGGG<br>TKVEIKRTVAAPSVFIFPPSDEQLKSGTASVVCLLNNFYPREAKVQWKVDNA<br>LQSGNSQESVTEQDSKDSTYSLSSTLTLSKADYEKHKVYACEVTHQGLSSPV<br>TKSFNRGEC |

TABLE 7

Sequences used to generate αCCR2/αCSF1R multispecific molecules.

| Multispecific Molecule | Heavy Chain 1 | Light Chain 1 | Heavy Chain 2 | Light Chain 2 |
|---|---|---|---|---|
| 1 | SEQ ID NO: 71 | SEQ ID NO: 72 | SEQ ID NO: 73 | SEQ ID NO: 74 |
| 2 | SEQ ID NO: 75 | SEQ ID NO: 76 | SEQ ID NO: 83 | SEQ ID NO: 84 |
| 3 | SEQ ID NO: 75 | SEQ ID NO: 76 | SEQ ID NO: 85 | SEQ ID NO: 86 |
| 4 | SEQ ID NO: 77 | SEQ ID NO: 78 | SEQ ID NO: 83 | SEQ ID NO: 84 |
| 5 | SEQ ID NO: 77 | SEQ ID NO: 78 | SEQ ID NO: 85 | SEQ ID NO: 86 |
| 6 | SEQ ID NO: 79 | SEQ ID NO: 80 | SEQ ID NO: 83 | SEQ ID NO: 84 |
| 7 | SEQ ID NO: 79 | SEQ ID NO: 80 | SEQ ID NO: 85 | SEQ ID NO: 86 |
| 8 | SEQ ID NO: 81 | SEQ ID NO: 82 | SEQ ID NO: 83 | SEQ ID NO: 84 |
| 9 | SEQ ID NO: 81 | SEQ ID NO: 82 | SEQ ID NO: 85 | SEQ ID NO: 86 |

Example 2

UniTI-01 Binding to Cells Expressing mCCR2 Alone, mCSF1R Alone, or Both mCCR2 and mCSF1R In this and the next few examples, multispecific molecule #1 (also referred to as UniTI-01) shown in Table 7 was characterized. UniTI-01 is an anti-CCR2/anti-CSF1R bispecific antibody. The variable region and full length sequences of UniTI-01 are also provided in Table 11. In a few examples, the bispecific antibody UniTI-01 was compared against an anti-CCR2 bivalent monospecific antibody or an anti-CSF1R bivalent monospecific antibody.

TABLE 11

Sequences of an anti-CCR2/anti-CSF1R bispecific antibody molecule

| SEQ ID NO | Description | Sequence |
|---|---|---|
| SEQ ID NO: 44 | αCCR2 MC12 VH | QVQLQESGPGLVQPSQTLSLTCTVSGFSLTDFSVHWVRQPPG<br>KGLEWMGRIRSEGNTDYNSALKSRLSISRDTSKSQVFLKMNS<br>LQTEDTAIYFCTRGDILGFGYWGQGVMVTVSS |

TABLE 11-continued

Sequences of an anti-CCR2/anti-CSF1R bispecific antibody molecule

| SEQ ID NO | Description | Sequence |
|---|---|---|
| SEQ ID NO: 45 | αCCR2 MC12 VL | DIVMTQSPLSVSVTPGESASISCRSSKSLLHFKGITFVYWYLQ KPGQSPQLLIFRMSSLASGVPDRFSGSGSETDFTLKISRVEAED VGTYYCGQLLENPYTFGAGTKLELK |
| SEQ ID NO: 71 | Full length αCCR2 MC12 heavy chain | QVQLQESGPGLVQPSQTLSLTCTVSGFSLTDFSVHWVRQPPG KGLEWMGRIRSEGNTDYNSALKSRLSISRDTSKSQVFLKMNS LQTEDTAIYFCTRGDILGFGYWGQGVMVTVSSAQTTAPSVYP LAPGCGDTTSSTVTLGCLVKGYFPEPVTVTWNSGALSSDVHT FPAVLQSGLYTLTSSVTSSTWPSQTVTCNVAHPASSTKVDKK VERRTIKPCPPCKCPAPNLLGGPSVFIFPPKIKDVLMISLSPIVT CVVVDVSEDDPDVQISWFVNNVEVHTAQTQTHREDYNSTLR VVSALPIQHQDWMSGKEFKCKVNNKDLPAPIERTISKPKGSV RAPQVYVLPPCEEEMTKKQVTLWCMVTDFMPEDIYVEWTN NGKTELNYKNTEPVLDSDGSYFMYSKLRVEKKNWVERNSYS CSVVHEGLHNHHTTKSFSRTPGK |
| SEQ ID NO: 72 | Full length αCCR2 MC12 light chain | DIVMTQSPLSVSVTPGESASISCRSSKSLLHFKGITFVYWYLQ KPGQSPQLLIFRMSSLASGVPDRFSGSGSETDFTLKISRVEAED VGTYYCGQLLENPYTFGAGTKLELKRADAAPTVSIFPPSMEQ LTSGGATVVCFVNNFYPRDISVKWKIDGSEQRDGVLDSVTD QDSKDSTYSMSSTLSLTKVEYERHNLYTCEVVHKTSSSPVVK SFNRNEC |
| SEQ ID NO: 48 | αmCSF1R VH | QVQLQQSGAELVKPGSSVKISCKASGYTFTSNFMHWIKQQPG NGLEWIGWIYPGDGDTEYNQKFNGKATLTADKSSSTAYMQL SSLTSEDSAVYFCAVNYGGYVLDAWGQGASVTVSS |
| SEQ ID NO: 50 | αmCSF1R VL | EIVLTQSPTTMAASPGEKVTITCRASSSTNYMSWYQQKSGAS PKPWIYETSKLASGVPDRFSGSGSGTSYSFTISSMETEDAATY YCHQWSSTPLTFGSGTKLEIK |
| SEQ ID NO: 73 | Full length αmCSF1R heavy chain | QVQLQQSGAELVKPGSSVKISCKASGYTFTSNFMHWIKQQPG NGLEWIGWIYPGDGDTEYNQKFNGKATLTADKSSSTAYMQL SSLTSEDSAVYFCAVNYGGYVLDAWGQGASVTVSSAETTAP SVYPLAPGTALKSNSMVTLGCLVKGYFPEPVTVTWNSGALSS GVHTFPAVLQSGLYTLTSSVTVPSSTWSSQAVTCNVAHPASS TKVDKKIVPRECNTIKPCPPCKCPAPNLLGGPSVFIFPPKIKDV LMISLSPIVTCVVVDVSEDDPDVQISWFVNNVEVHTAQTQTH REDYNSTLRVVSALPIQHQDWMSGKEFKCKVNNKDLPAPIE RTISKPKGSVRAPQVCVLPPPEEEMTKKQVTLSCAVTDFMPE DIYVEWTNNGKTELNYKNTEPVLDSDGSYFMVSKLRVEKKN WVERNSYSCSVVHEGLHNHHTTKSFSRTPGK |
| SEQ ID NO: 74 | Full length αmCSF1R light chain | EIVLTQSPTTMAASPGEKVTITCRASSSTNYMSWYQQKSGAS PKPWIYETSKLASGVPDRFSGSGSGTSYSFTISSMETEDAATY YCHQWSSTPLTFGSGTKLEIKRADAAPTVSIFPPSMEQLTSGG ATVVCFVNNFYPRDISVKWKIDGSEQRDGVLDSVTDQDSKD STYSMSSTLSLTKVEYERHNLYTCEVVHKTSSSPVVKSFNRN EC |

ExpiCHO cells were transiently transfected with mouse CCR2, mouse CSF1R, or both mouse CCR2 and CSF1R, according to the manufacturer's instructions. In brief, the transfections were performed with ExpiCHO cells at a cell density of 5.6-6.3×10$^6$ cells/mL and at least 95% viability. For each transfection, 25 µg of DNA was diluted with 1 mL of OptiPro SFM (Gibco 12309050) and filtered using spin-X centrifuge tube filters (Corning 8160). A solution of 920 µL of OptiPro and 80 µL of expifectamine was added to the filtered DNA, incubated for 1 minute at room temperature, and then added to the cells. On day 1 of the transfection, the cells were enhanced using 150 µL of ExpiCHO enhancer.

On day 2 of the transfection, the cells were washed with PBS containing 1% BSA (Sigma) and used to set 96-well V-bottom plates (Biotix AP-0350-9CVS) with 100,000 cells/well. UniTI-01 was added to the cells in serial dilutions and incubated for 1 hour at 4° C. The plates were washed twice with PBS containing 1% BSA. The secondary antibody was a 1:500 dilution of goat anti-mouse Fc biotin antibody (Invitrogen Cat. No. 31805), and incubated with the cells for 45 minutes at 4° C. The plates were washed twice with PBS containing 1% BSA. For detection, 1.56×10$^{-3}$ µg of streptavidin-PE (eBioscience Cat. No. 12-4317-87) was used, per well, and incubated for 1 hour at 4° C. The plates were read on a CytoFLEX S (Beckman Coulter). Data were calculated as the median fluorescence intensity of the PE-positive population vs. the median fluorescence intensity of the PE-negative population. The data was normalized for the percent of total median fluorescence intensity.

Without wishing to be bound by theory, UniTI-01 may preferentially bind cells expressing both CCR2 and CSF1R relative to cells that express either CCR2 or CSF1R. Consistent with the hypothesis that dual target binding increases the avidity of UniTI-01 for the target cell, UniTI-01 exhibited enhanced binding to CCR2 and CSF1R double positive cells, relative to single positive cells (FIG. 1). UniTI-01 showed binding with an $EC_{50}$ of 15 nM to cells expressing only CCR2. For cells expressing only CSF1R, UniTI-01 had an EC$_{50}$ of 1 nM. UniTI-01 displayed an EC50 of 400 pM to cells that expressed both CCR2 and CSF1R.

Example 3

UniTI-01 Inhibits MCP1-Induced Migration of Bone Marrow Derived Monocytes In Vitro Mouse bone marrow cells were isolated from femurs of healthy Balb/c mice and differentiated into monocytes in the presence of mCSF1 for four days. Monocyte differentiation was assessed by flow-cytometric analysis of CCR2 and CSF1R expression on hematopoietic cells. The differentiated cells were counted, and cultured with different concentrations of Isotype (mIgG2a), anti-CCR2 and UniTI-01 respectively for 30 minutes at 37° C. Antibody treated cells were subsequently added on the upper chamber in the transwell insert plates, which contained MCP1 (CCL2) in the bottom chamber. MCP1 induced migration was assessed after collecting the media from bottom chamber of transwell plates and cell number enumeration was performed by flow-cytometric analysis.

Figure 2:
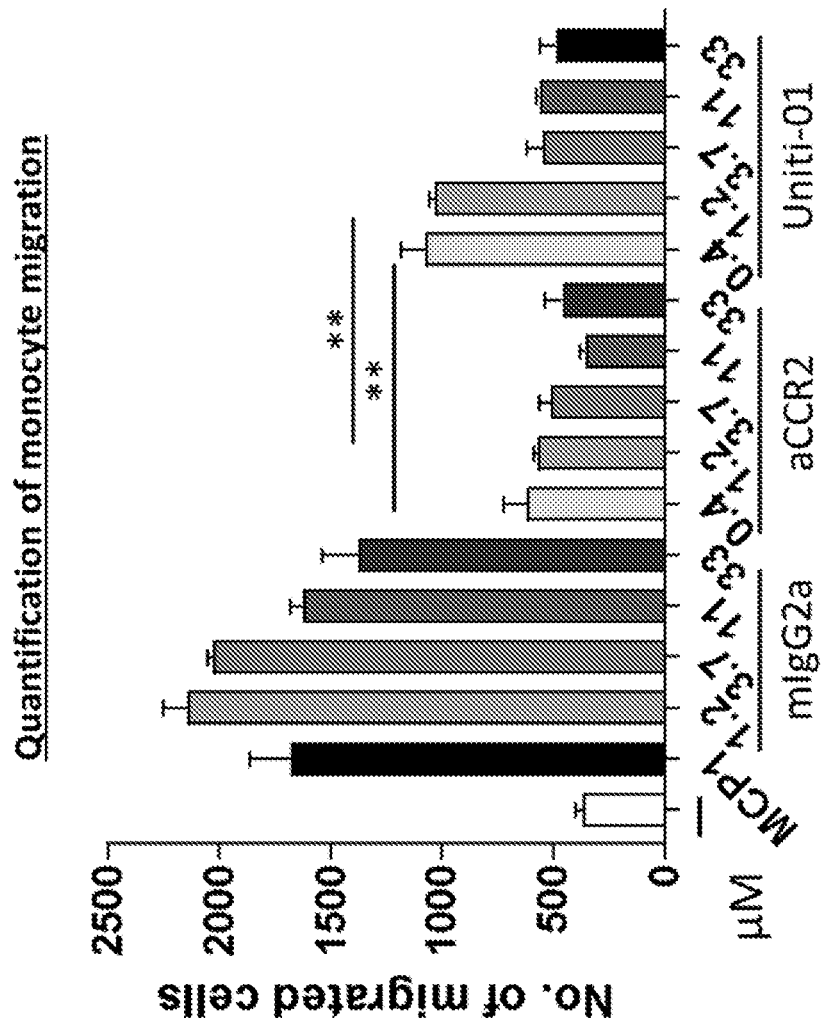
FIG. 2. Effect of increasing concentrations of isotype control (mIgG2a), anti-mouse CCR2 monoclonal antibody (aCCR2) or UniTI-01 on MCP-1-dependent cell migration of bone marrow-derived monocytes in a trans-well cell culture system.

The anti-CCR2/anti-CSF1R bispecific antibody UniTI-01 inhibited the MCP1 induced migration of monocytes across the transwell in a dose dependent manner (FIG. 2). At doses 3.7 µM and above, monocyte migration was reduced to the levels observed in the absence of chemokine (FIG. 2). Similar results were obtained with anti-CCR2 antibody treatment, while treatment of cells with IgG2a did not influence migration (FIG. 2).

Example 4

Figure 3B:
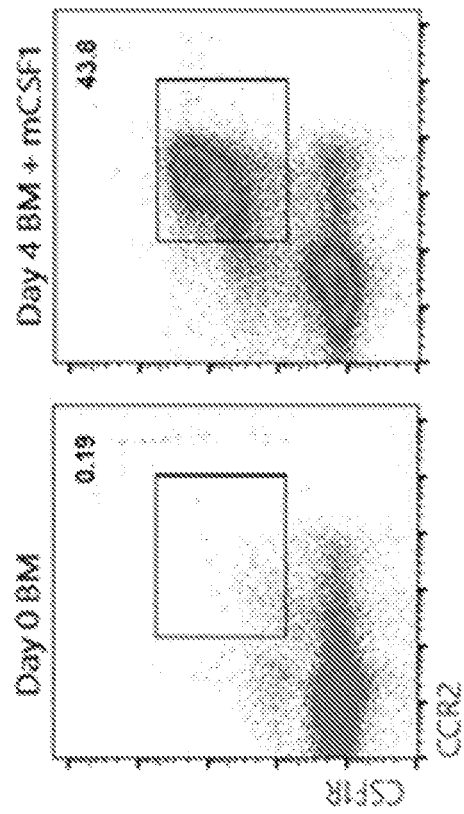
FIGS. 3A and 3B. Effect of increasing concentrations of UniTI-01, anti-mouse CSF1R monoclonal antibody (aCSF1R), or isotype control (mIgG2a) on mCSF-1-dependent differentiation and proliferation of bone marrow-derived monocytes into macrophages in vitro.
Figure 3A:
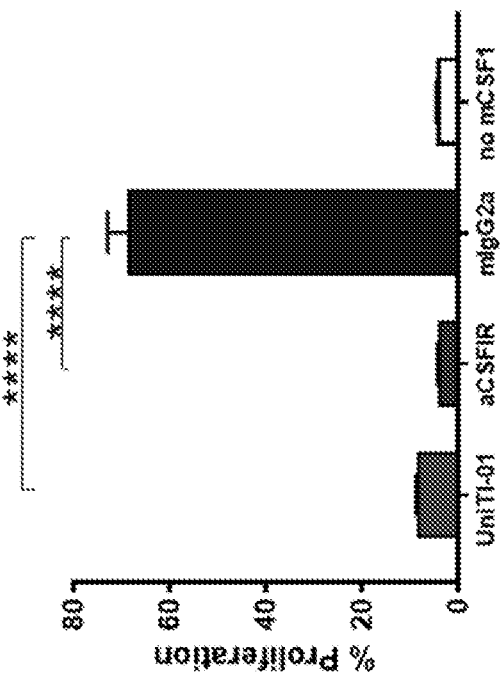

UniTI-01 Inhibits mCSF-1-Dependent Proliferation of Bone Marrow-Derived Macrophages In Vitro Mouse bone marrow cells were isolated from femurs of healthy Balb/c mice and differentiated into monocytes in the presence of mCSF1 for four days. Flow cytometry analysis showed bone marrow cells did not appreciably express CCR2 (FIG. 3A; left panel) at day 0. However, after 4 days of cell culture in the presence of mCSF1, a significant portion of bone marrow cell differentiated into monocytes which displayed CCR2 and CSF1R expression (FIG. 3A; right panel). Monocytes were counted and plated in 96 well plates in the presence of mCSF1. UniTI-01, anti-CSF1R or mIgG2a antibody was added to the cells containing mCSF1. After 72 hours of incubation at 37° C., cell proliferation metabolic activity was assessed by colorimetric reading at OD570 following manufacturer's protocol for the MTT assay kit.

mCSF1 induced differentiation of monocytes to macrophages, visualized as long fibroblastic cells under the microscope. UniTI-01 and anti-CSF1R antibodies prevented the proliferation of macrophages in the presence of mCSF1 (FIG. 3B).

Example 5

UniTI-01 Does Not Inhibit mCSF-1-Dependent Bone Marrow-Derived Monocyte Differentiation In Vitro Bone marrow cells were extracted from both femur and tibia of a naive (non-tumor bearing) Balb/c mouse. UniTI-01, anti-CSF1R or mIgG2 antibodies were pre-incubated with freshly isolated bone marrow cells for 30 minutes at 37° C. before the addition of mCSF-1 to allow monocyte differentiation. After 4 days of incubation at 37° C., cells were collected for flow cytometry staining to identify differentiated monocytes. Cells were stained with fluorescent-labeled antibodies for 15 minutes at 4° C. followed by flow cytometry analysis. Monocytes are gated as Live, CD45+, CD11b+, Ly6C+, Ly6G− cells.

Figure 4:
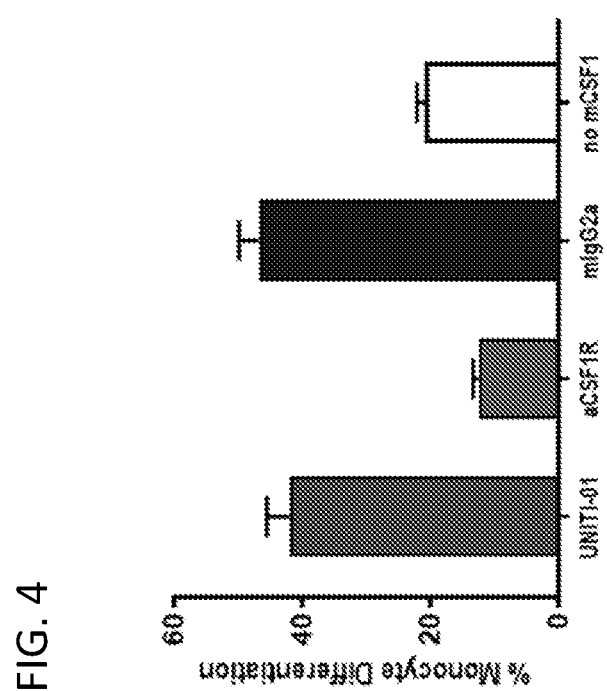
FIG. 4. Effect of UniTI-01, anti-mouse CSF1R monoclonal antibody (aCSF1R), or isotype control (mIgG2a) on mCSF-1-dependent differentiation and proliferation of bone marrow-derived monocytes. All antibodies were tested at 15 µg/ml.

Consistent with the observation that bone marrow precursor cells did not significantly express CCR2 at day 0 (FIG. 3A), the anti-CCR2/anti-CSF1R bispecific antibody UniTI-01 did not inhibit mCSF-1-dependent bone marrow-derived monocyte differentiation in vitro after 4 days of cell culture (FIG. 4). In contrast, the anti-CSF1R bivalent monospecific antibody significantly inhibited mCSF-1-dependent bone marrow-derived monocyte differentiation in vitro (FIG. 4).

Example 6

UniTI-01 Specifically Binds to Primary Intratumoral M-MDSCs and M2-Like Macrophages In Vitro LLC tumors, grown in B6− albino mice, were harvested at a volume of 500-800 mm$^3$ and dissociated using liberase DL+Dnase I for 30 minutes at 37° C., followed by the dissociation program m_imptumor_01 on the GentleMacs. Single cell suspensions were filtered through a 70 µm strainer and total cells were stained with fluorescently labeled antibodies. For this binding study, 100 µg of UniTI-01 was labeled using the Alexa Fluor 647 Antibody Labeling Kit (ThermoFisher Scientific), the concentration of labeled antibody was determined by Nanodrop, and the indicated serial dilutions (5 uM, 1 uM, 0.1 uM, 0.01 uM) were made in Facs buffer. M-MDSCs were gated by live CD45+ CD11b+Ly6ChighLy6G−, M2 macrophages were gated by live CD45+CD11b+F4/80+CD206+, CD3+ T cells were gated by live CD45+CD3+, and neutrophils were gated by live CD45+CD11b+Ly6G+. The cells were stained for 15 minutes on ice in the dark, stained with zombie violet for viability, and immediately acquired on the cytometer.

Figure 5:
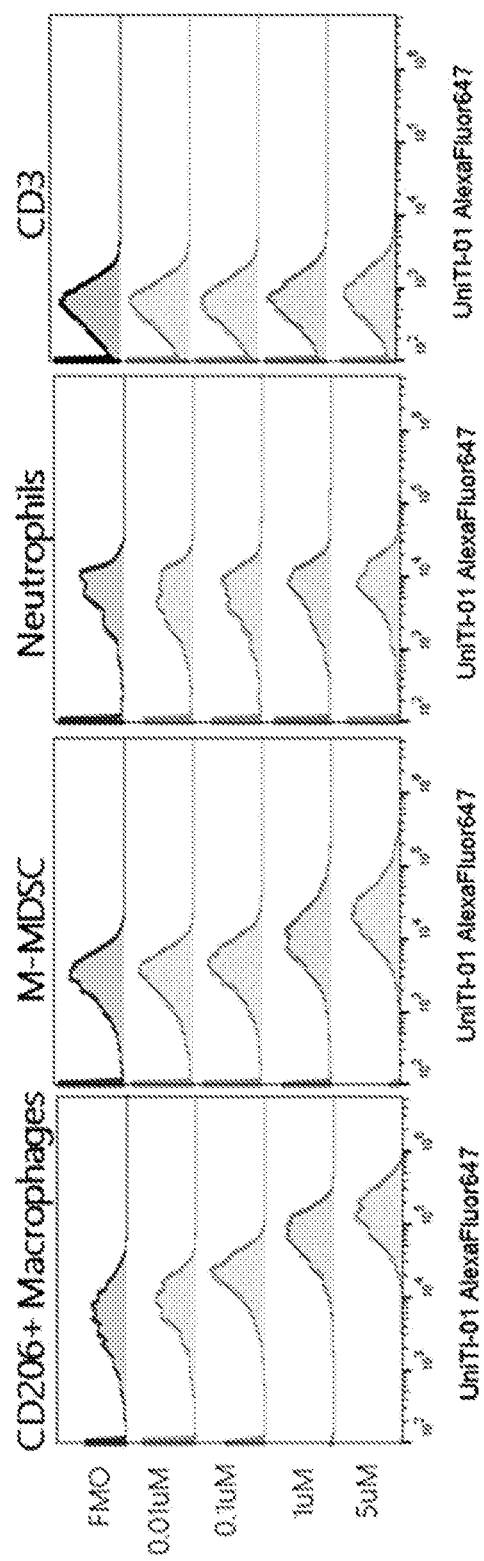
FIG. 5. In vitro binding of increasing concentrations of UniTI-01 to primary intratumoral M-MDSCs and M2-like macrophages, as determined by flow analysis.

Concentration-dependent binding of UniTI-01 to M2 macrophages and M-MDSCs is shown in FIG. 5.

Example 7

UniTI-01 Depletes Suppressive Myeloid Cells in Several Mouse Models In Vivo

Mice were injected either with MC38 colon cancer cell line (B6 albino mice) or EMT6 breast cancer cell line (BALB/c mice) and once tumors reached a volume of 150-200 mm$^3$, the same mice were randomized and grouped into two arms. One arm received a treatment of 20 mg/kg UniTI-01 via ip route at a dose of 20 mg/kg on day 1, 4, 7 and 10 and the other received PBS (vehicle) at the same schedule. Twenty-four hours after the 4$^{th}$ dose, tumors were harvested for flow cytometry analysis. Tumors were minced into ~2 mm pieces and dissociated with liberase+dnase I for 30 minutes at 37° C., followed by using a 1 minute tumor blend program on the gentleMACs. Single cell suspensions were made by filtering through a 70 µM filter and counted. Cells were then stained for flow cytometry analysis. TAMs were gated by live CD45+CD11b+Ly6G−Ly6C−F4/80+ and M-MDSCs were gated by live CD45+CD11b+Ly6G− Ly6C$^{high}$. Each point represents a single mouse. Error bars represent the mean and standard error between individual mice. Statistics were calculated using Student's t test.

Figure 6:
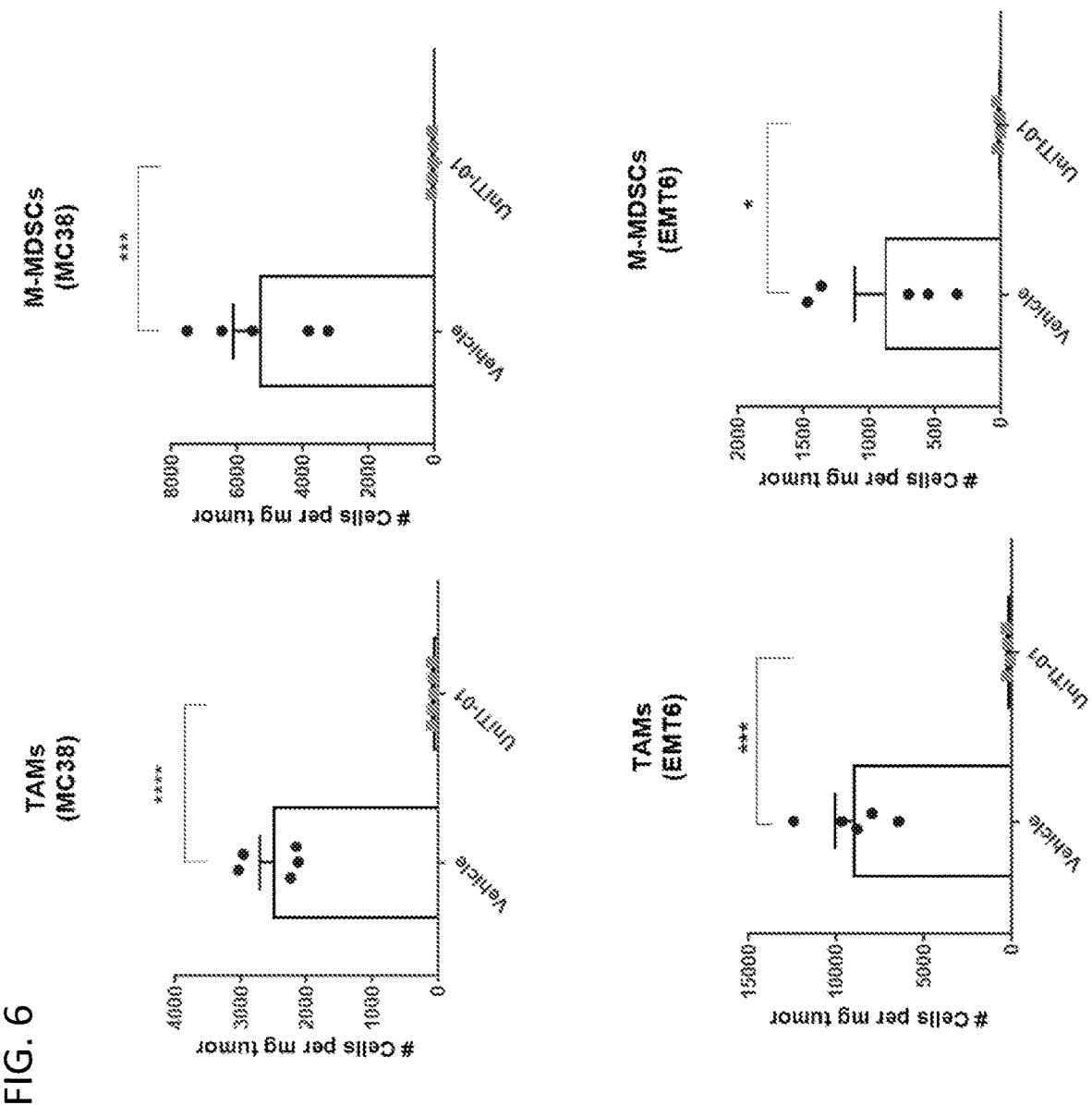
FIG. 6. Effect of in vivo administration of UniTI-01 on intratumoral myeloid cell populations in EMT6 and MC38 syngeneic tumor models.

Consistent with the binding to M2 macrophages and M-MDSCs observed in Example 6, the anti-CCR2/anti-CSF1R bispecific antibody UniTI-01 reduced TAMs and M-MDSCs in both EMT6 and MC38 syngeneic tumor models (FIG. 6).

Example 8

UniTI-01 Depletes Tumor-Associated Macrophages but Spares Kupffer Cells In Vivo

Balb/c mice were injected with EMT6 syngeneic breast cell line and once tumors reached a volume of 150-200 mm$^3$, were randomized and grouped into three arms. One arm received a treatment of 20 mg/kg UniTI-01 via ip route at a dose of 20 mg/kg, the second arm received a treatment of 10 mg/kg anti-CSF1R antibody and the third arm received PBS on day 1, 4, 7 and 10. Twenty-four hours after the 4$^{th}$ dose, mice were sacrificed and tumors and livers were harvested and formalin fixed and paraffin embedded. To detect the macrophage populations in liver and tumors, tissue sections were immunohistochemically stained with F4/80 antibody (Cell Signaling) and detected by Envision system. Approximately 10 regions of interest per tumor or liver section were analyzed by ImageJ software.

Without wishing to be bound by theory, UniTI-01 may preferentially bind to cells expressing both CCR2 and CSF1R relative to cells expressing either CCR2 or CSF1R, and may have less an effect on tissue-resident macrophages, such as the liver-resident Kupffer cells, which do not express CCR2, relative to tumor-associated macrophages which express both CCR2 and CSF1R.

Figure 7C:
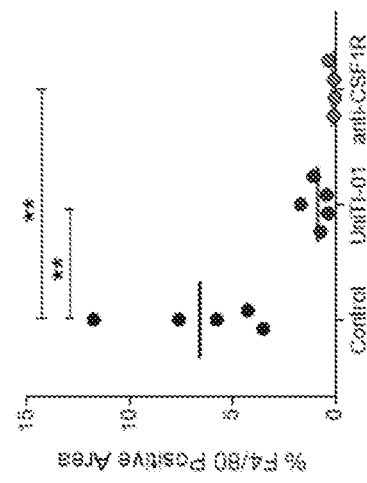
FIGS. 7A-7D. Effect of in vivo administration of UniTI-01 on Kupffer cells in EMT6 syngeneic tumor model.
Figure 7D:
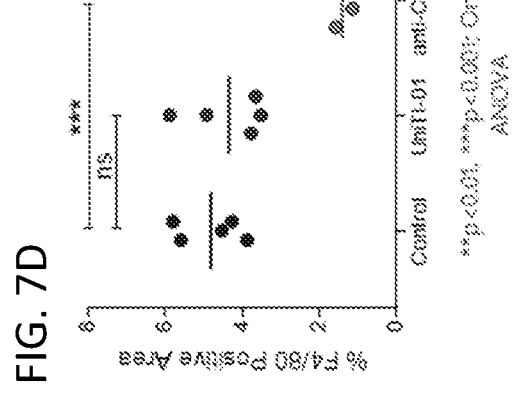
Figure 7A:
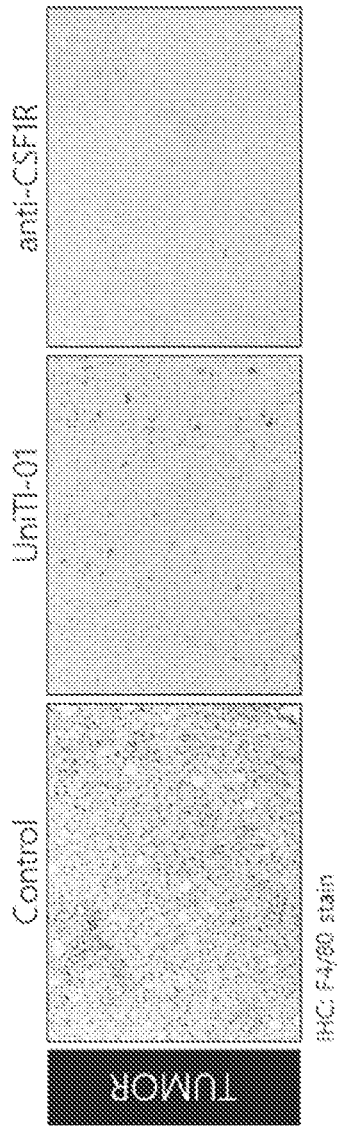
Figure 7B:
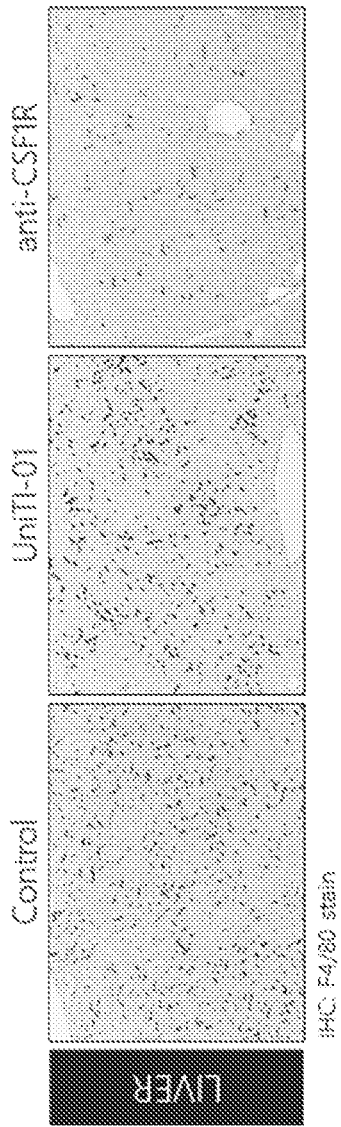

Consistent with the data described earlier (FIG. 6), the anti-CCR2/anti-CSF1R bispecific antibody UniTI-01 markedly depleted tumor-associated macrophages (FIGS. 7A and 7C). In contrast, UniTI-01 did not appreciably deplete tissue-resident macrophages in the liver (FIGS. 7B and 7D), whereas the anti-CSF1R bivalent monospecific antibody significantly reduced macrophages in both compartments (FIGS. 7A-7D).

Example 9

UniTI-01 Does Not Inhibit CSF-1 Dependent Cell Survival in CCR2-Negative NFS-60 Cells In Vitro CCR2-negative, CSF1R-positive NFS-60 cells were cultured in phenol-red-free media in the presence of UniTI-01, a monovalent monospecific anti-CSF1R antibody, a bivalent monospecific anti-CSF1R antibody, or a mIgG2 antibody for 30 minutes at 37° C. followed by the addition of mCSF-1 for cell survival. After 48 hours of incubation at 37° C., cell viability metabolic activity was assessed by colorimetric reading at OD570 following manufacturer's protocol for the MTT assay kit.

Figure 8B:
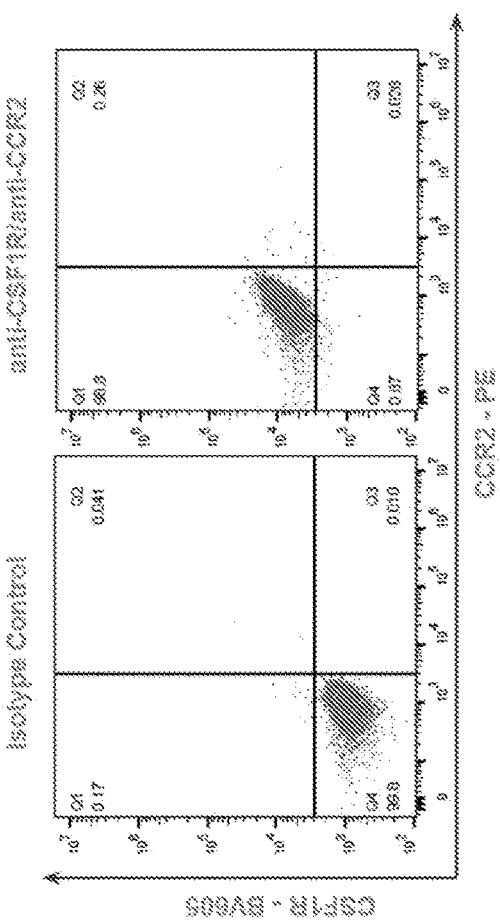
FIGS. 8A and 8B. Effect of UniTI-01 on CSF-1 dependent cell survival in CCR2-negative NFS-60 cells in vitro.
Figure 8A:
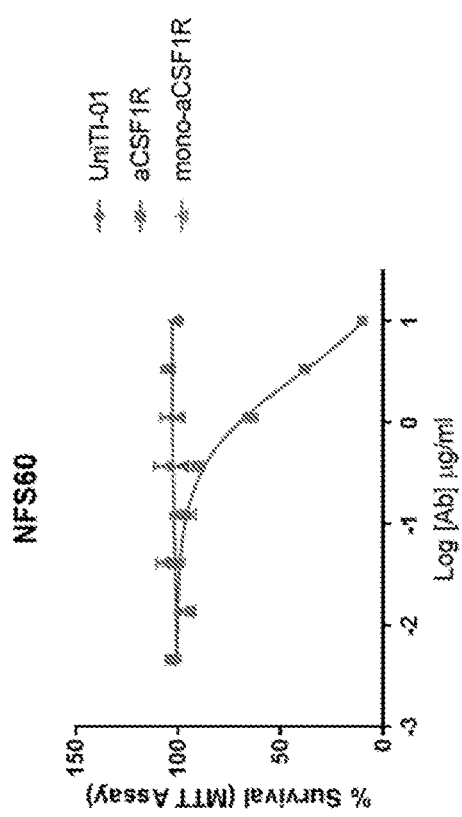

As shown in FIG. 8A, the anti-CSF1R bivalent monospecific antibody (aCSF1R) markedly reduced viability of NFS-60 cells at high antibody concentrations. In contrast, the anti-CCR2/anti-CSF1R bispecific antibody UniTI-01 or the monovalent monospecific anti-CSF1R antibody (mono-aCSF1R) did not inhibit CSF-1 dependent cell survival in CCR2-negative NFS-60 cells in vitro (FIG. 8A). Without wishing to be bound by theory, this data suggests that the anti-CCR2/anti-CSF1R bispecific antibody UniTI-01 may be less likely to inhibit CCR2-negative, CSF1R-positive cells, compared with an anti-CSF1R bivalent monospecific antibody, which is consistent with the results described in FIGS. 7B and 7D. To confirm NFS-60 did not express CCR2, cells were washed with BSA containing PBS buffer and fluorescent-labeled antibodies for CSF1R and CCR2 for 20 minutes at 4° C. followed by flow cytometry analysis. As shown in FIG. 8B, NFS-60 expressed CSF1R but not CCR2.

Example 10

UniTI-01 Promotes CD8+ T Cell Infiltration in EMT6 Tumors In Vivo

Balb/c mice were injected with EMT6 syngeneic breast cell line and once tumors reached a volume of 150-200 mm$^3$, were randomized and grouped into three arms. One arm received a treatment of 20 mg/kg UniTI-01 via ip route at a dose of 20 mg/kg, the second arm received a treatment of 10 mg/kg anti-PDL1 and the third arm received PBS on day 1, 4, 7 and 10. Twenty-four hours after the 4$^{th}$ dose, mice were sacrificed and tumors were harvested for flow cytometry analysis. Tumors were minced into ~2 mm pieces and dissociated with liberase+dnase I for 30 minutes at 37° C., followed by using a 1 minute tumor blend program on the gentleMACS. Single cell suspensions were made by filtering through a 70 μM filter and counted. Cells were then stained for flow cytometry analysis. CD8 T cells were gated by staining on live CD8 cells that expressed CD45 and CD3. Each point represents a single mouse tumor. Error bars represent the mean and standard error between individual mice. Statistics were calculated using one way ANOVA analysis.

Figure 9:
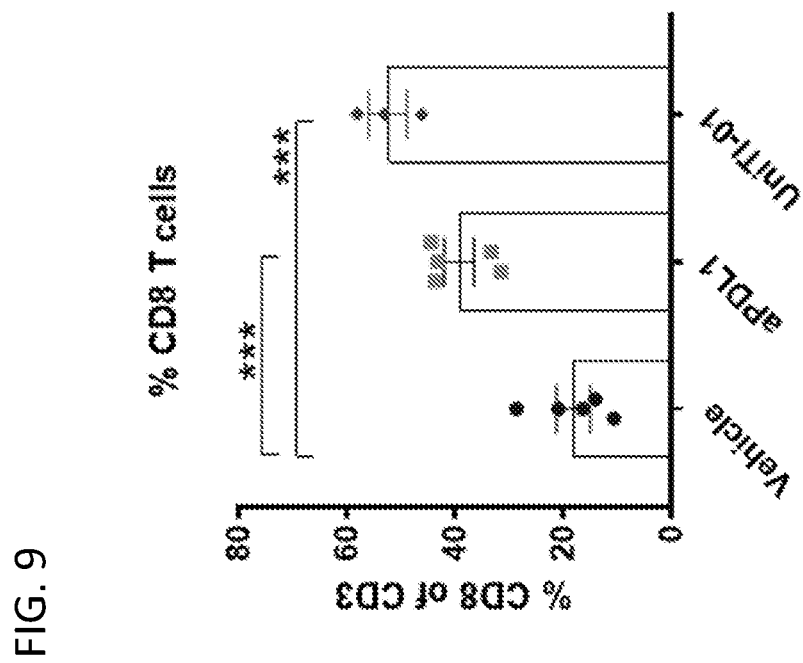
FIG. 9. Effect of in vivo administration of UniTI-01 on CD8+ T cell infiltration in the tumor of EMT6 model.

The anti-CCR2/anti-CSF1R bispecific antibody UniTI-01 significantly increased CD8+ T cell infiltration in EMT6 tumors in vivo (FIG. 9).

Example 11

UniTI-01 Reduces Treg Frequency and Increases CD8 T Cells/Treg Ratio in EMT6 Tumors In Vivo B6 albino mice were injected with MC38 syngeneic colon cell line and once tumors reached a volume of 150-200 mm$^3$, were randomized and grouped into three arms. One arm received a treatment of 20 mg/kg UniTI-01 via ip route at a dose of 20 mg/kg, the second arm received a treatment of 10 mg/kg anti-PDL1 and the third arm received PBS on day 1, 4, 7 and 10. Twenty-four hours after the 4$^{th}$ dose, mice were sacrificed and tumors were harvested for immune profiling by Flow cytometry. Tumors were minced into ~2 mm pieces and dissociated with liberase+dnase I for 30 minutes at 37° C., followed by using a 1 minute tumor blend program on the gentleMACs. Single cell suspensions were made by filtering through a 70 μM filter and counted. Cells were then stained for flow cytometry analysis. T regulatory cells were analyzed by gating on live CD4+ Foxp3+ T cells. In addition, CD8 T cells were gated by staining on live CD8 cells that expressed CD45 and CD3. Each point represents a single mouse tumor. Error bars represent the mean and standard error between individual mice. Statistics were calculated using one way ANOVA analysis.

Figure 10A:
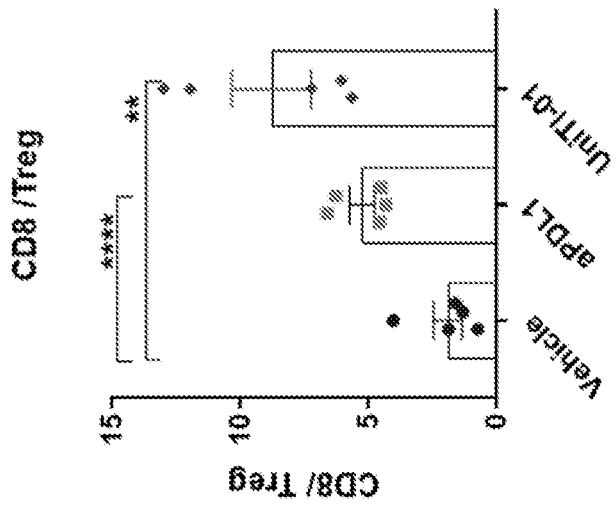
FIGS. 10A and 10B. Effect of in vivo administration of UniTI-01 on Treg frequency in the tumor of MC38 model.
Figure 10B:
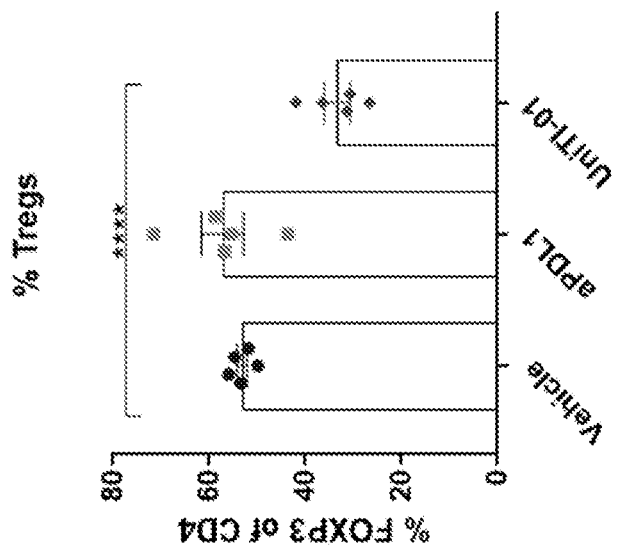

Treatment with UniTI-01 led to a greater reduction in Treg frequency and a greater increase in the CD8+ T cell/Treg ratio in the tumor, compared with treatment with the anti-PDL1 antibody (FIGS. 10A and 10B).

Example 12

UniTI-01 Shows Antitumor Efficacy, Tumor Regressions and Enhanced Survival When Used in Combination with Anti-PDL1 Antibody Tumor growth inhibition of UniTI-01 in combination with anti-PDL1 antibody was tested in a subcutaneous mouse syngeneic EMT6 breast cancer model. ~8 week old female BALB/c (Jackson Labs) were acclimatized for 3 days prior to start of the studies. Mice were housed 5 animals per cage, and the disposable cages were placed in Innovive IVC mouse racks. EMT6 cells previously tested to be free from mouse pathogens (mouse CLEAR panel, Charles River Labs) were implanted subcutaneously on day 0 at a density of $0.5 \times 10^6$ cells in the right flanks of BALB/c mice. Tumors were measured and recorded in two dimensions twice weekly using a digital caliper. Tumor volumes ($mm^3$) were calculated using the formula width×width×length×0.52. Following tumor volume measurements on day 7 post implantation, mice were randomized and grouped into four arms according to a mean tumor volume of 77 $mm^3$. One arm was treated with PBS, the second arm was treated with anti-PDL1 antibody at a dose of 10 mg/kg, the third arm treated with UniTI-01 at a dose of 20 mg/kg, and the fourth arm treated with a combination of anti-PDL1 antibody and UniTI-01. All treatments were via ip route and the schedules were twice weekly for up to four weeks of dosing. All the agents were formulated freshly in PBS prior to dosing. Tumor volume measurements continued up to 80 days. Tumor volume data is plotted as Mean±SEM. In addition, survival is recorded based on the time to reach the study endpoint of a TV of 2000 $mm^3$ and plotted as a Kaplan Meier curve. Statistics were determined by Log-rank test and p-values are plotted.

Figure 11A:
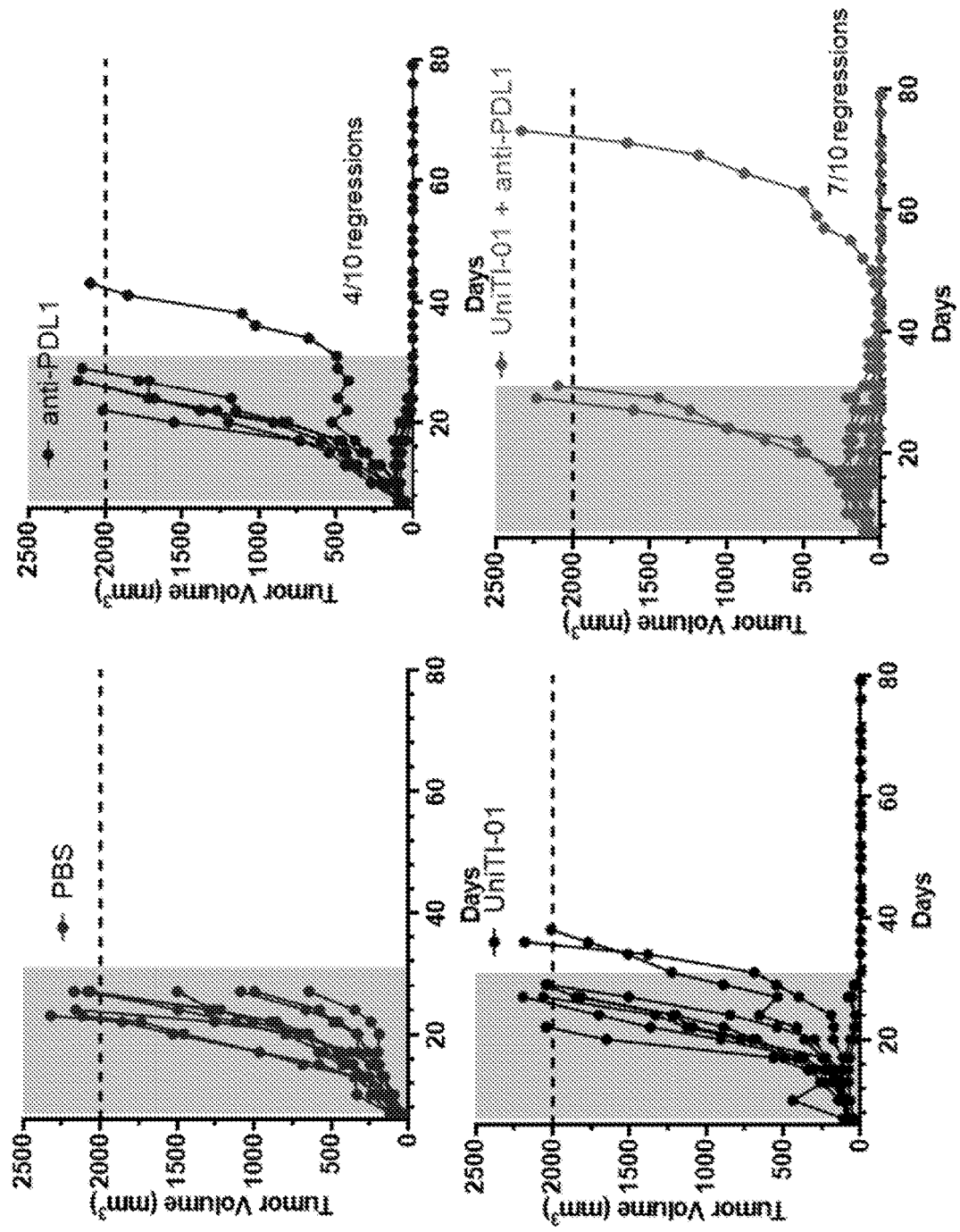
FIGS. 11A and 11B. UniTI-01 shows antitumor efficacy, tumor regressions and enhanced survival when treated in combination with anti-PDL1 antibody in EMT6 tumor model.
Figure 11B:
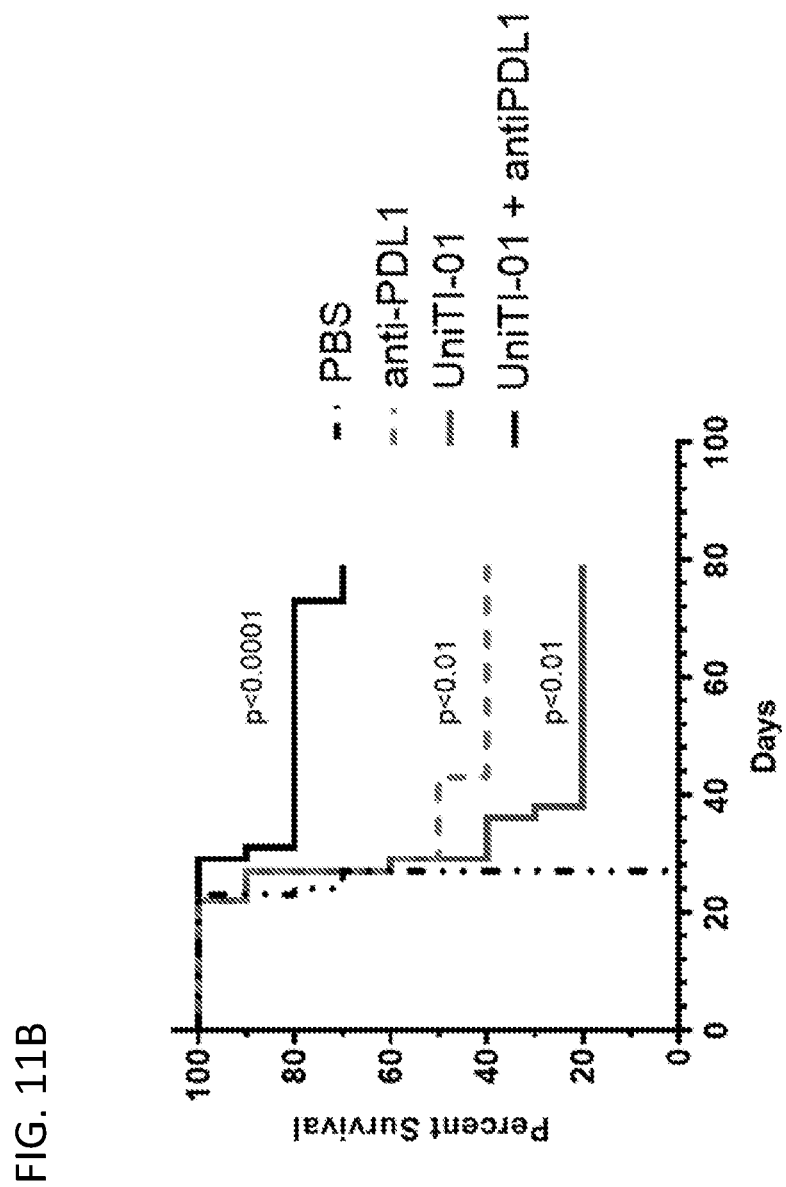

As shown in FIGS. 11A and 11B, treatment with UniTI-01 improved the survival of tumor-bearing animals. Combining UniTI-01 and an anti-PDL1 antibody further improved the antitumor efficacy, tumor regressions and survival in vivo (FIGS. 11A and 11B).

INCORPORATION BY REFERENCE

All publications and patents mentioned herein are hereby incorporated by reference in their entirety as if each individual publication or patent was specifically and individually indicated to be incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

---

We claim:
1. A multispecific antibody molecule comprising:
  (i) a single anti-CSF1R binding moiety, wherein the anti-CSF1R binding moiety comprises three complementarity-determining regions (CDRs) from a heavy chain variable region sequence of: SEQ ID NO: 48, SEQ ID NO: 66, or SEQ ID NO: 69; and three CDRs from a light chain variable region sequence of: SEQ ID NO: 50, SEQ ID NO: 67, or SEQ ID NO: 70; and
  (ii) an anti-CCR2 binding moiety, wherein the anti-CCR2 binding moiety comprise comprises three CDRs from a heavy chain variable region sequence of: SEQ ID NO: 44, SEQ ID NO: 54, SEQ ID NO: 59, SEQ ID NO: 62, or SEQ ID NO: 64; and three CDRs from a light chain variable region sequence of: SEQ ID NO: 45, SEQ ID NO: 57, SEQ ID NO: 60, SEQ ID NO: 63, or SEQ ID NO: 65;
  wherein the multispecific antibody molecule:
    binds to CSF1R monovalently,
    does not reduce CSF1-dependent bone marrow-derived monocyte differentiation in vitro by more than 10%, and
    does not reduce the number of tissue-resident macrophages in vivo by more than 15% when administered to a mammalian subject.

2. The multispecific antibody molecule of claim 1, wherein the anti-CCR2 binding moiety is a full antibody, or an antigen-binding fragment, wherein the antigen-binding fragment comprises a Fab, F(ab')2, Fv, a scFv, a single domain antibody, or a diabody (dAb); and wherein the anti-CSFIR binding moiety is an antigen-binding fragment, and wherein the antigen-binding fragment comprises a Fab, Fv, a scFv, or a single domain antibody.

3. The multispecific antibody molecule of claim 1, wherein the multispecific antibody molecule binds to CCR2 monovalently.

4. A pharmaceutical composition comprising the multispecific antibody molecule of claim 1, and a pharmaceutically acceptable carrier, excipient, or stabilizer.

5. The multispecific antibody molecule of claim 1, wherein the anti-CSF1R binding moiety, the anti-CCR2 binding moiety, or a combination thereof comprises a heavy chain constant region selected from the group consisting of IgG1 or a fragment thereof, IgG2 or a fragment thereof, IgG3 or a fragment thereof, and IgG4 or a fragment thereof.

6. The multispecific antibody molecule of claim 1, wherein the multispecific antibody molecule comprises a heavy chain constant region that can mediate antibody-dependent cellular cytotoxicity (ADCC) or complement-dependent cytotoxicity (CDC).

7. The multispecific antibody molecule of claim 1, wherein the anti-CSF1R binding moiety comprises a first heavy chain constant region and the anti-CCR2 binding moiety comprises a second heavy chain constant region, wherein the first heavy chain constant region comprises one or more mutations that increase heterodimerization of the first heavy chain constant region and the second heavy chain constant region, relative to a naturally-existing heavy chain constant region; the second heavy chain constant region comprises one or more mutations that increase heterodimerization of the second heavy chain constant region and the first heavy chain constant region, relative to a naturally-existing heavy chain constant region; or a combination thereof.

8. The multispecific antibody molecule of claim 1, wherein the anti-CSFIR binding moiety and the anti-CCR2 binding moiety comprises a kappa light chain constant region or a fragment thereof; the anti-CSFIR binding moiety and the anti-CCR2 binding moiety comprises a lambda light chain constant region or a fragment thereof; the anti-CSFIR binding moiety comprises a kappa light chain constant region or a fragment thereof, and the anti-CCR2 binding moiety comprises a lambda light chain constant region or a fragment thereof; or the anti-CSFIR binding moiety comprises a lambda light chain constant region or a fragment thereof, and the anti-CCR2 binding moiety comprises a kappa light chain constant region or a fragment thereof.

9. The multispecific antibody molecule of claim 1, wherein the anti-CSF1R binding moiety comprises an anti-CSFIR antibody molecule comprising a first polypeptide and a second polypeptide, wherein the first polypeptide comprises a first light chain variable region (VL) and a first light chain constant region (CL), and the second polypeptide comprises a first heavy chain variable region (VH), and a first heavy chain constant region 1 (CH1); and the anti-CCR2 binding moiety comprises an anti-CCR2 antibody molecule comprising a third polypeptide and a fourth polypeptide, wherein the third polypeptide comprises a second VL and a second CL, and the fourth polypeptide comprises a second VH, and a second CH1.

10. The multispecific antibody molecule of claim 9, wherein the second polypeptide further comprises a first CH2 and a first CH3, the fourth polypeptide further comprises a second CH2 and a second CH3, or a combination thereof.

11. The multispecific antibody molecule of claim 1, further comprising a cytokine molecule, wherein the cytokine molecule is selected from the group consisting of interleukin-2 (IL-2) or a functional variant thereof, interleukin-7 (IL-7) or a functional variant thereof, interleukin-12 (IL-12) or a functional variant thereof, interleukin-15 (IL-15) or a functional variant thereof, interleukin-18 (IL-18) or a functional variant thereof, interleukin-21 (IL-21) or a functional variant thereof, interferon gamma or a functional variant thereof, or any combination thereof.

12. The multispecific antibody molecule of claim 1,
  wherein the anti-CSFIR binding moiety comprises a heavy chain variable region sequence at least 95% identical to the heavy chain variable region sequence of: SEQ ID NO: 48, SEQ ID NO: 66, or SEQ ID NO: 69; and a light chain variable region sequence at least 95% identical to the light chain variable region sequence of: SEQ ID NO: 50, SEQ ID NO: 67, or SEQ ID NO: 70, and
  wherein the anti-CCR2 binding moiety comprises a heavy chain variable region sequence at least 95% identical to the heavy chain variable region sequence of: SEQ ID NO: 44, SEQ ID NO: 54, SEQ ID NO: 59, SEQ ID NO: 62, or SEQ ID NO: 64; and a light chain variable region sequence at least 95% identical to the light chain variable region sequence of: SEQ ID NO: 45, SEQ ID NO: 57, SEQ ID NO: 60, SEQ ID NO: 63, or SEQ ID NO: 65.

* * * * *